US008940294B2

(12) United States Patent
Tseng et al.

(10) Patent No.: US 8,940,294 B2
(45) Date of Patent: Jan. 27, 2015

(54) METHODS OF ISOLATING AND CULTURING STEM CELLS

(71) Applicant: TissueTech, Inc., Miami, FL (US)

(72) Inventors: Scheffer Tseng, Pinecrest, FL (US); Szu-Yu Chen, Miami, FL (US); Suzhen Zhang, Miami, FL (US)

(73) Assignee: Tissuetech, Inc., Doral, FL (US)

( * ) Notice: Subject to any disclaimer, the term of this patent is extended or adjusted under 35 U.S.C. 154(b) by 0 days.

(21) Appl. No.: 13/782,968

(22) Filed: Mar. 1, 2013

(65) Prior Publication Data

US 2013/0251684 A1 Sep. 26, 2013

Related U.S. Application Data

(60) Provisional application No. 61/606,309, filed on Mar. 2, 2012, provisional application No. 61/767,223, filed on Feb. 20, 2013.

(51) Int. Cl.

| | |
|---|---|
| ***A01N 63/00*** | (2006.01) |
| ***C12N 5/00*** | (2006.01) |
| ***C12N 5/074*** | (2010.01) |
| ***C12N 5/0775*** | (2010.01) |

(52) U.S. Cl.

CPC ............ *C12N 5/0607* (2013.01); *C12N 5/0665* (2013.01); *C12N 5/0667* (2013.01); *C12N 2533/80* (2013.01); *C12N 2533/90* (2013.01)

USPC .......................................... 424/93.7; 435/325

(58) Field of Classification Search

USPC .......................................... 424/93.7; 435/325

See application file for complete search history.

(56) References Cited

U.S. PATENT DOCUMENTS

| | | | |
|---|---|---|---|
| 5,399,493 | A | 3/1995 | Emerson et al. |
| 5,435,151 | A | 7/1995 | Han |
| 5,612,211 | A | 3/1997 | Wilson et al. |
| 5,728,581 | A | 3/1998 | Schwartz et al. |
| 7,015,037 | B1 | 3/2006 | Furcht et al. |
| 7,067,316 | B2 | 6/2006 | Pykett et al. |
| 7,101,710 | B2 | 9/2006 | Tsai et al. |
| 7,297,539 | B2 | 11/2007 | Mandalam et al. |
| 7,312,078 | B2 | 12/2007 | Peled et al. |
| 7,547,546 | B2 | 6/2009 | Davies et al. |
| 7,582,477 | B2 | 9/2009 | Han et al. |
| 7,592,174 | B2 | 9/2009 | Sylvester et al. |
| 7,682,828 | B2 | 3/2010 | Jaenisch et al. |
| 7,704,739 | B2 | 4/2010 | Han et al. |
| 7,736,892 | B2 | 6/2010 | Weiss et al. |
| 7,939,323 | B2 | 5/2011 | Auger et al. |
| 8,268,302 | B2 | 9/2012 | Weiss et al. |
| 2006/0078993 | A1 | 4/2006 | Phan et al. |
| 2006/0171930 | A1 | 8/2006 | Seyda et al. |
| 2006/0199263 | A1 | 9/2006 | Auger et al. |
| 2006/0205071 | A1 | 9/2006 | Hasson et al. |
| 2006/0223177 | A1 | 10/2006 | Harris et al. |
| 2007/0036767 | A1 | 2/2007 | Mistry et al. |
| 2007/0092967 | A1 | 4/2007 | Han et al. |
| 2007/0110727 | A1 | 5/2007 | Kang |
| 2007/0122902 | A1 | 5/2007 | Lee et al. |
| 2007/0292910 | A1 | 12/2007 | Heidaran et al. |
| 2008/0102522 | A1 | 5/2008 | Auger et al. |
| 2008/0152630 | A1 | 6/2008 | Ginis et al. |
| 2008/0181967 | A1 | 7/2008 | Liu et al. |
| 2008/0226595 | A1 | 9/2008 | Edinger et al. |
| 2008/0241171 | A1 | 10/2008 | Gentry et al. |
| 2008/0248005 | A1 | 10/2008 | Phan |
| 2008/0292597 | A1 | 11/2008 | Steenblock |
| 2008/0299090 | A1 | 12/2008 | Weiss et al. |
| 2009/0124007 | A1 | 5/2009 | Cho |
| 2009/0169597 | A1 | 7/2009 | Brown et al. |
| 2009/0175832 | A1 | 7/2009 | Zhao et al. |
| 2009/0269318 | A1 | 10/2009 | Davies et al. |
| 2009/0280093 | A1 | 11/2009 | Friedlander |
| 2009/0305413 | A1 | 12/2009 | Kang |
| 2009/0305415 | A1 | 12/2009 | Huang |
| 2010/0184218 | A1 | 7/2010 | Ha et al. |
| 2010/0184221 | A1 | 7/2010 | Yokoo et al. |
| 2010/0210013 | A1 | 8/2010 | Mistry et al. |
| 2010/0266553 | A1 | 10/2010 | Ra et al. |

(Continued)

FOREIGN PATENT DOCUMENTS

| | | | |
|---|---|---|---|
| EP | 1099754 | A1 | 5/2001 |
| EP | 1226233 | B1 | 7/2002 |

(Continued)

OTHER PUBLICATIONS

Nishikawa et al. (Progressive lineage analysis by cell sorting and culture identifies FLK1+VE-cadherin cells at a diverging point of endothelial and hematopoietic lineages. Development 1998) 125, 1747-1757.*

Acera et al., "Inflammatory markers in the tears of patients with ocular surface disease." (2008) *Ophthalmic Res*. 40:315-321.

Can et al., "Isolation, culture, and characterization of human umbilical cord stroma-derived mesenchymal stem cells." *Methods Mol Biol* 2011;698:51-62.

Chiriac et al., (2010) "Cardiogenic Induction of Pluripotent Stem Cells Streamlined Through a Conserved SDF-1/VEGF/BMP2 Integrated Network." *PLoS One*, 5:e9943.

Chong et al., (2011) "Adult Cardiac-Resident MSC-like Stem Cells with a Proepicardial Origin." *Cell Stem Cell* 9:527-540.

(Continued)

*Primary Examiner* — Karen Cochrane Carlson
*Assistant Examiner* — Natalie Moss
(74) *Attorney, Agent, or Firm* — Wilson Sonsini Goodrich & Rosati

(57) ABSTRACT

Provided herein are methods of isolating and expanding a plurality of multipotent stem cells. Also described are methods of expanding stem cells on a substrate comprising an HC-HA complex. Also described are isolated and expanded stem cells produced by the methods and uses thereof, including stem cell therapy, as niche cells for supporting other types of stem cells, or as bioreactors for the production of HC-HA complexes. Also described are uses of HC-HA complexes as a carrier for stem cells.

24 Claims, 68 Drawing Sheets

(56) References Cited

U.S. PATENT DOCUMENTS

| | | | |
|---|---|---|---|
| 2010/0323027 | A1 | 12/2010 | Lim et al. |
| 2011/0151556 | A1 | 6/2011 | Kallis et al. |
| 2011/0182866 | A1 | 7/2011 | Mcniece |
| 2012/0021509 | A1 | 1/2012 | Kang et al. |
| 2012/0034195 | A1 | 2/2012 | Hariri |
| 2012/0058089 | A1 | 3/2012 | Hariri |
| 2012/0083445 | A1 | 4/2012 | Tseng et al. |
| 2012/0122215 | A1 | 5/2012 | Edinger et al. |
| 2012/0129256 | A1 | 5/2012 | Kiselev et al. |
| 2012/0142102 | A1 | 6/2012 | Chen et al. |
| 2012/0196312 | A1 | 8/2012 | Sato et al. |
| 2014/0106448 | A1 | 4/2014 | Chen et al. |

FOREIGN PATENT DOCUMENTS

| | | |
|---|---|---|
| WO | WO2009/144008 | 12/2009 |
| WO | WO2010/011352 | 1/2010 |
| WO | WO2010/085751 | 7/2010 |
| WO | WO2010/107392 | 9/2010 |
| WO | WO2012/149574 | 11/2012 |
| WO | WO 2012/170905 | 12/2012 |

OTHER PUBLICATIONS

Erdogan-Poyraz et al., (2009) "Elevated tear interleukin-6 and interleukin-8 levels in patients with conjunctivochalasis." *Cornea* 28:189-193.

Feng et al., (2004) "Ultrastructural Localization of Platelet Endothelial Cell Adhesion Molecule (PECAM-1, CD31) in Vascular Endithelium." *J Histochem Cytochem*. 52:87-101.

Gargett et al., (2000) "Isolation, characterization and long-term culture of human myometrial microvascular endothelial cells." *Hum Reprod*. 15:293-301.

Gonzalez et al., "An Efficient Approach to Isolation and Characterization of Pre- and Postnatal Umbilical Cord Lining Stem Cells for Clinical Applications." *Cell Transplantation*, vol. 19, pp. 1439-1449, (2010).

Guo et al., (2012) "PTX3 Controls Activation of Matrix Metalloproteinase 1 and Apoptosis in Conjunctivochalasis Fibroblasts." *Invest Ophthalmol Vis Sci*. 53(7): 3414-23.

He et al., (Jul. 24, 2009) "Biochemical Characterization and Function of Complexes formed by Hyaluronan and the Heavy Chains of Inter-α-inhibitor (HC-HA) Purified from Extracts of Human Amniotic Membrane." *J. Biol. Chem*., 284 (30):20136-20146.

Huang, et al., "Umbilical Cord Versus Bone Marrow-Derived Mesenchymal Stromal Cells." *Stem Cells and Development*, vol. 21, No. 15, (2012).

Ieronimakis et al., (2008) "Direct Isolation, Culture and Transplant of Mouse Skeletal Muscle Derived Endothelial Cells with Angiogenic Potential." *PLoS One* 3:e0001753.

Koliakos et al., (2011) "Mesenchymal cells isolation from Wharton's jelly, in perspective to clinical applications." *Journal of Biological Research—Thessaloniki* 16:194-201.

Konski et al., "Stem Cell patents: a landscape analysis." *Nature Biotechnology*, vol. 27, No. 8, Aug. 2009, pp. 722-726.

Lee et al., (2012) "Spherical Bullet Formation via E-cadherin Promotes Therapeutic Potency of Mesenchymal Stem Cells Derived from Human Umbilical Cord Blood for Myocardial Infarction." *Mol. Ther*. 20:1424-1433.

Li et al., (2000) "Overexpression of MMP-1 and MMP-3 by Cultured Conjunctivochalsis Fibroblasts." *Invest Ophthalmol Vis Sci*. 41:404-410.

Li et al., (2012) "Mesenchymal Stem Cells Derived from Human Limbal Niche Cells." *Invest Ophthalmol Vis Sci*. 53(9):5686-97.

Li et al., (2012) "Angiogenesis Potential of Human Limbal Stromal Niche Cells." *Invest Ophthalmol Vis Sci*. 53(7):3357-67.

Lin, et al., "A chemical platform for improved induction of human iPSCs." *Nature Methods*, vol. 6, No. 11, Nov. 2009, pp. 805-808.

Lindenmair et al., "Mesenchymal Stem or Stromal Cells from Amnion and Umbilical Cord Tissue and Their Potential for Clinical Applications." *Cells*, 2012, 1, 1061-1088.

Lindner et al., (2010) "Improved proliferation and differentiation capacity of human mesenchymal stromal cells cultured with Basement-membrane extracellular matrix proteins." *Cytotherapy* 12:992-1005.

Loureiro et al.. "Comparison of culture media for ex vivo cultivation of limbal epithelial progenitor cells." *Molecular Vision*, Jan. 2013; 19:69-77.

Lu et al., (2006) "Isolation and characterization of human umbilical cord mesenchymal stem cells with hematopoiesis-supportive function and other potentials." *Haematologica* 91:1017-1026.

Maherali et al., "Tgfβ signal inhibition cooperates in the induction of iPSCs and replaces Sox2 and cMyc." *Curr. Biol*., Nov. 3, 2009; 19(20): 1718-1723.

Matsubara et al., (2004) "Expression of α-catenin in α-catenin-deficient cells results in a reduced proliferation in three-dimensional multicellular spheroids but not in two-dimensional monolayer cultures." *Oncogene* 23:2694-2702.

Meller et al, (2000) "Regulation of Collagenase, Stromelysin, and Gelatinase B in Human Conjunctival and Conjunctivochalasis Fibroblasts by Interleukin-1β and Tumor Necrosis Factor-a." *Invest Ophthalmol Vis Sci*. 41:2922-2929.

Miki et al. (2005) "Stem Cell Characteristics of Amniotic Epithelial Cells." *Stem Cells* 23:1549-1559.

Montanucci et al., (2011) "New simple and rapid methods for purification of mesenchymal stem cells from the human umbilical cord Wharton jelly." *Tissue Eng* Part A. 2011;17:2651-2661.

Park et al. (2010) "Green tea consumption improves endothelial function but not circulating endothelial progenitor cells in patients with chronic renal failure." *Int J Cardiol* 145:261-262.

Salehinejad et al., "Comparison of different methods for the isolation of mesenchymal stem cells from human umbilical cord Wharton's jelly." *In Vitro Cell Dev Biol Anim* Feb. 2012; 48(2):75-83.

Samavarchi-Tehrani et al., "Functional Genomics Reveals a BMP-Driven Mesenchymal-to-Epithelial Transition in the Initiation of Somatic Cell Reprogramming." *Cell Stem Cell* 7, Jul. 2, 2010, pp. 64-77.

Sarugaser et al., (2005) "Human Umbilical Cord Perivascular (HUCPV) Cells: A Source of Mesenchymal Progenitors." *Stem Cells* 23:220-229.

Schugar et al., (2009) "High Harvest Yield, High Expansion, and Phenotype Stability of CD146 Mecenchymal Stromal Cells from Whole Primitive Human Umbilical Cord Tissue." *J Biomed Biotechnol*. 2009:789526.

Sehareddy et al., (2008) "Method to isolate mesenchymal-like cells from Wharton's Jelly of umbilical cord." *Methods Cell Biol* 86:101-119.

Soncin (2011) "The Function of E-Cadherin in Stem Cell Pluripotency and Self-Renewal." *Genes* 2(1):229-259.

Song (2005) "Transplantation of human limbal cells cultivated on amniotic membrane for reconstruction of rat corneal epithelium after alkaline burn." *Chin Med J* (Engl) 118:927-935.

Stratman et al., (2009) "Pericyte recruitment during vasculogenic tube assembly stimulates endothelial basement membrane matrix formation." *Blood* 114:5091-5101.

Tong et al., (2011) "Generation of mesenchymal stem cell from human umbilical cord tissue using a combination enzymatic and mechanical disassociation method." *Cell Biol Int*. 35:221-226.

Traktuev et al., (2008) "Isolation of mesenchymal stem cells using the total length of umbilical cord for transplantation purposes." *Circ Res*. 102:77-85.

Tsagias et al., (2011) "Isolation of mesenchymal stem cells using the total length of umbilical cord for transplantation purposes." *Transfus Med*. 21:253-261.

Voyta et al., (1984) "Identification and Isolation of Endothelial Calls based on Their Increased Uptake of Acetylated-Low Density Lipoprotein." *J Cell Biol*. 99:2034-2040.

Wang, et al., 2004, "Mesenchymal Stem Cells in the Wharton's Jelly of the Human Umbilical Cord." *Stem Cells* 22:1330-1337.

Ward et al., (2010) "The Role of Oxidative Stress and Inflammation in Conjunctivochalasis." *Invest Ophthalmol Vis Sci*. 51:1994-2002.

Weiss, et al., (2006) "Human Umbilical Cord Matrix Stem Cells: Preliminary Characterization and Effect of Transplantation in a Rodent Model of Parkinson's Disease." *Stem Cells* 24:781-792.

(56) References Cited

OTHER PUBLICATIONS

Woltjen et al , "Inhibition of Tgf-β Signaling Improves Mouse Fibroblast Reprogramming." *Cell Stem Cell* 5, Nov. 6, 2009, pp. 457-458.
Xie et al. (2011) "Limbal Epithelial Stem/Progenitor Cells Attract Stromal Niche Cells by SDF-1/CXXR4 Signaling to Prevent Differentiation." *Stem Cells* 29(11):1874-85.
Xie et al. (2012) "Isolation and Expansion of Human Limbal Stromal Niche Cells." *Invest Ophthalmol Vis Sci*. 53:279-286.
Zhao et al., (2011) "Osteogenic Media and rhBMP-2-Induced Differentiation of Umbilical Cord Mesenchymal Stem Cells Encapsulated in Alginate Microbeads and Integrated in an Injectable Calcium Phosphate-Chitosan Fibrous Scaffold." *Tissue Eng Part A*. 17:969-979.
Bilic et al, In Vitro Lesion Repair by Human Amnion Epithelial and Mesenchymal Cells, Am J of Obstet Gynecol, 190:87-92 (2004).
PCT/US2012/035897 International Search Report and Written Opinion dated Jul. 31, 2012.

* cited by examiner

| **ECM** | hAMEC | hAMSC (compact) | hAMSC (spongy) | Zone 1 | Zone 2 | Zone 3 | Zone 4 | Zone 5 |
|---|---|---|---|---|---|---|---|---|
| Collagen Type IV | -- | ± | + | + | + | + | ++ | + |
| Lumican | + | + | + | + | ± | ± | ± | ± |
| Keratan Sulfate | -- | + | + | + | + | + | + | + |
| PTX3 | ++ | ++ | + | -- | + | + | ++ | -- |
| TSG6 | ++ | + | + | + | + | + | + | + |
| HA | + | + | + | + | + | + | + | + |
| HC1 | + | + | + | ± | + | + | + | -- |
| HC2 | + | + | + | -- | -- | -- | -- | -- |
| HC3 | + | + | -- | ± | -- | -- | -- | -- |
| Bikunin | + | + | + | + | + | + | + | + |
| PCK | + | -- | -- | ++ | + | + | + | +/- |
| E-cadherin | | | | ++ | + | + | + | +/- |
| Vimentin | + | + | + | + | + | + | + | + |
| **ESC** | | | | | | | | |
| Oct4 | + | + | -- | + | + | + | + | + |
| Nanog | -- | + | -- | -- | -- | -- | -- | -- |
| Sox2 | + | + | + | + | + | + | + | + |
| Nestin | + | + | + | -- | -- | -- | -- | + |
| SSEA4 | + | -- | -- | + | + | ± | -- | -- |
| Rex1 | + | + | + | + | + | + | + | + |
| **Angiogenesis** | | | | | | | | |
| FLK1 | + | + | -- | -- | -- | -- | -- | -- |
| CD31 | nd | + | -- | -- | -- | -- | -- | + |
| CD34 | + | -- | -- | + | + | + | ± | -- |
| PDGFR-b | + | + | -- | ± | + | + | + | ++ |
| NG2 | + | + | + | + | + | + | + | ++ |
| a-SMA | -- | + | -- | + | + | + | + | ++ |
| CD146 | -- | -- | + | -- | -- | -- | + | ++ |
| vWF | + | + | -- | + | ± | ± | ± | + |
| S100A4 | ++ | + | -- | + | + | + | + | ++ |
| SMMHC | -- | -- | -- | + | + | + | + | ++ |
| SDF-1 | ++ | -- | -- | -- | ++ | ± | ± | ++ |
| CXCR4 | | | | + | ± | ± | ± | + |

FIG. 15

Current Methods of Isolation, Characterization and Expansion of MSCs/SCs from Human Umbilical cord (subamniotic region) and Wharton's jelly

| | Wang 2004 | Weiss 2005 | Sarugasar 2005 | Lu-Lu 2006 | Seshareddy 2008 | Schugar 2009 | Koliakos 2010 | Zhao 2010 | Montanucci 2011 | Tong 2011 | Tsagias 2011 |
|---|---|---|---|---|---|---|---|---|---|---|---|
| Zone 1 | -- | + | -- | + | + | + | + | -- | + | -- | + |
| Zone 2 | -- | -- | -- | + | + | + | + | + | + | May be | + |
| Zone 3 | + | + | + | + | + | + | + | + | + | + | + |
| Zone 4 | May be | May be | + | + | May be | + | May be | + | + | May be | + |
| Zone 5 | -- | -- | + | + | -- | + | -- | + | + | -- | + |
| Final size | Scrap | 2-4 cm | 4-5cm | 1-2 mm3 | 3-5 cm | small sections | 2-5mm3 | M | 10cm | M | Whole UC |
| Remove vessels | + | + | -- | Not removed | + | Not removed | + | -- | -- | + | Not removed |
| before enzyme | | | | | | | | | | | |
| Enzymes | | | | | | | | | | | |
| Dispase | -- | -- | -- | -- | -- | 6hrs or | -- | -- | -- | -- | -- |
| Collagenase | 16hrs | 1hr | 18-24hrs | 30min | 1hr | 6hrs | 1hr | 30min | Liberase 30min | 30min | 3hrs |
| HAase | -- | 1hr | -- | -- | 1hr | -- | 1hr | 30min | 30min | -- | 3hrs |
| Trypsin | + | + | -- | + | + | -- | + | -- | -- | -- | + |
| DNase I | -- | -- | -- | -- | -- | -- | -- | -- | -- | 30min | -- |
| Crush tissue | -- | + | -- | -- | + | -- | -- | -- | -- | Homogenized | + |

FIG. 16

| | Wang 2004 | Weiss 2005 | Sarugasar 2005 | Lu-Lu 2006 | Seshareddy 2008 | Schugar 2009 | Koliakos 2010 | Zhao 2010 | Montanucci 2011 | Tong 2011 | Tsagias 2011 |
|---|---|---|---|---|---|---|---|---|---|---|---|
| Filtration | -- | -- | Magnetic beads | 100 µm | -- | 100µm | 70 mm | -- | -- | 70- & 40-mm | 40-mm |
| Centrifuge | + | + | to remove CD45 cells | -- | + | -- | + | -- | + | + | + |
| Polysterene | + | HA-coated | + | + | + | + | + | Alginate microbeads | HA-coated | + | + |
| Medium | | | | | | | | | | | |
| Basal | DMEM-HG | DMEM, MCDB | α-MEM | DMEM-LG | DMEM-LG, MCDB | DMEM | DMEM-LG | DMEM-LG | DMEM, MCDB | DMEM | HES |
| FBS | 10% | 2% | 15% | 5% | 2% | 10% | 20% | 10% | 2% | 10% | (hydroxyethyl |
| Growth factors | | PDGF-bb, EGF | | VEGF, EGF | PDGF-bb, EGF | | | | PDGF-bb, EGF | bFGF | starch) |
| Others | | Dexa, | | L-glut | Dexa, | 10% horse | L-Glut, AA | ALBUMax | | Glutamax | H allumin, |
| | | AA, BSA | | | AA, ITS | serum | | | | | CPD-A |
| | | ITS, ALBUMax | | | ALBUMax, Glut | | | | | | |

FIG. 16 (CONT.)

Markers Expressed cultured MSCs isolated from UC

FIG. 17

| Markers | Wang 2004 | Weiss 2005 | Sarugasar 2005 | Lu-Lu 2006 | Seshareddy 2008 | Schugar 2009 | Koliakos 2010 | Zhao 2010 | Montanucci 2011 | Tong 2011 | Tsagias 2011 |
|---|---|---|---|---|---|---|---|---|---|---|---|
| CD105 | + | ND | + | + | + | + | + | + | ND | + | + |
| CD73 | + | ND | + | + | ND | + | ND | + | ND | + | ND |
| CD90 | ND | + | + | + | + | + | + | + | ND | + | + |
| CD51 | + | ND | ND | ND | ND | ND | ND | ND | ND | ND | ND |
| CD44 | + | + | + | + | + | ND | ND | ND | ND | ND | + |
| CD29 | + | + | ND | + | ND | ND | + | + | ND | + | + |
| Other positives | | FGFR4,LIFR, | CD117, | CD13 | CD13, | CD144, | | CD49e | CD117,SCF, ABCG2 | | |
| | | FLK-1, ABCG2 | MHC-1 | CD166 | CD49e | CD146 | | | actin,vimentin | | |
| | | PDGFb, bmp1, | | HLA-ABC | | | | | E-cad,N-cadh | | |
| | | Cxcr4,Glut-1 | | | | | | | c-myc | | |
| | | CD10,CD13 | | | | | | | Tub-3, CK19 | | |
| Oct-4 | ND | + | -- | ND | ND | ND | ND | ND | + | + | ND |
| Nanog | ND | + | ND | ND | ND | ND | ND | ND | + | + | ND |
| Nestin | ND | + | ND | ND | ND | ND | ND | ND | + | ND | ND |
| Rex-1 | ND | ND | ND | ND | ND | ND | ND | ND | ND | + | ND |
| Sox-2 | ND | ND | ND | ND | ND | ND | ND | ND | + | + | ND |
| SSEA-4 | ND | ND | -- | ND | ND | ND | ND | ND | ND | ND | ND |
| CD14 | ND | -- | ND | ND | ND | ND | ND | ND | ND | ND | ND |
| CD31 | ND | -- | ND | -- | ND | ND | ND | ND | -- | ND | ND |
| CD33 | ND | -- | ND | ND | ND | ND | ND | ND | ND | ND | ND |
| CD34 | -- | -- | -- | -- | ND | -- | ND | ND | ND | -- | -- |
| CD45 | -- | -- | -- | -- | ND | -- | -- | ND | -- | -- | -- |
| Other | | CD56, CD133 | CD235a, CD106, | CD38, | | | | | | | |
| negatives | | | CD123, STRO-1 | HLA-DR | | | | | | | |
| | | | HLA-DR, DP,DQ | | | | | | | | |

* P < 0.05 vs PL

CCh Fibs. on immobilized HC-HA after cultured in DMEM+ 0.5% FBS for 48 h

SEQUENCE LISTING

```
<160> NUMBER OF SEQ ID NOS: 21

<210> SEQ ID NO 1
<211> LENGTH: 16
<212> TYPE: PRT
<213> ORGANISM: Homo sapiens

<400> SEQUENCE: 1

Thr Ser Thr Gly Asn Lys Asn Phe Leu Ala Gly Arg Phe Ser His Leu
1               5                   10                  15


<210> SEQ ID NO 2
<211> LENGTH: 10
<212> TYPE: PRT
<213> ORGANISM: Homo sapiens

<400> SEQUENCE: 2

Ser Leu Pro Gly Glu Ser Glu Glu Met Met
1               5                   10


<210> SEQ ID NO 3
<211> LENGTH: 10
<212> TYPE: PRT
<213> ORGANISM: Homo sapiens

<400> SEQUENCE: 3

Ser Leu Pro Glu Gly Val Ala Asn Gly Ile
1               5                   10


<210> SEQ ID NO 4
<211> LENGTH: 12
<212> TYPE: PRT
<213> ORGANISM: Homo sapiens

<400> SEQUENCE: 4

Glu Ser Thr Pro Pro Pro His Val Met Arg Val Glu
1               5                   10


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5

uaauguucug aggagucact t                                              21


<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

uugacuaucu gcacguugcc a                                              21


<210> SEQ ID NO 7
<211> LENGTH: 25
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 7
gguuuccaaa ucaaauaugu ugcaa 25

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 8
ggaucaaaua gagagcguua ucacg 25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 9
gguauuucua uaaugguaca uccat 25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
ccaccccatc ggttttgaag tgtct 25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
tgccacgggt ccttgctgta gtct 24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
atgaaaagac tcacgtgctt tttc 24

<210> SEQ ID NO 13

```
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

atttgcctgg ggccagt                                                17


<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

tgaggaggtg gccaacccac t                                           21


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

cgcttctcca gcagctgctc                                             20


<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

gtccggaggg ctgtgctacc                                             20


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

gatgaaggct cggcaggggc                                             20


<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

ccaggcttcc caaatgagta                                             20


<210> SEQ ID NO 19
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

ttgatttgga aacctccagc                                                20


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

accacagtcc atgccatcac                                                20


<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

tccaccaccc tgttgctgta                                                20
```

METHODS OF ISOLATING AND CULTURING STEM CELLS

CROSS-REFERENCE

This application claims the benefit under 35 U.S.C. §119 (e) of U.S. Provisional Patent Application No. 61/606,309, filed Mar. 2, 2012, and U.S. Provisional Patent Application No. 61/767,223, filed Feb. 20, 2013, which are both expressly incorporated herein by reference.

STATEMENT AS TO FEDERALLY SPONSORED RESEARCH

This invention was made with government support under award by RO1EY06819. The government has certain rights in the invention.

SEQUENCE LISTING

The present application contains a Sequence Listing which has been submitted in ASCII format via EFS-Web and is hereby incorporated by reference in its entirety. Said ASCII copy, created May 7, 2013, is named "34157731201" and is 5,075 bytes in size.

BACKGROUND OF THE INVENTION

Stem cells have the ability to differentiate into multiple diverse cell types and self-renew to produce more stem cells. In mammals, there are two broad types of stem cells: embryonic stem cells, which are isolated from the inner cell mass of blastocysts, and adult stem cells, which are found in various tissues, including fetal tissues. Generally, adult stem cells are lineage-restricted (multipotent) and are generally referred to by their tissue origin. Multipotent stem cells have been isolated from several tissues including bone marrow, peripheral blood, adipose tissue, liver, skin, amniotic fluid, placenta and umbilical cord. Included among such cells are mesenchymal stem cells, adipose-derived stem cells, and endothelial stem cells. Human mesenchymal stem cells (MSC) have been shown to differentiate into multiple mesoderm-type lineages, including chondrocytes, osteoblasts, and adipocytes and into ectodermal and endodermal origin. Because of their ability for self-renewal and multilineage differentiation potential, multipotent stem cells are useful for cell-based therapies and tissue engineering applications. Multipotent stem cells also exhibit immunomodulatory and paracrine effects.

SUMMARY OF THE INVENTION

Provided herein are methods for the isolation and expansion of stem cells.

Described herein, in certain embodiments, are methods for isolating an E-cadherin positive stem cell, comprising contacting a mixed cell population comprising one or more stem cells with an agent that binds to E-cadherin, thereby isolating an E-cadherin positive stem cell. In some embodiments, the mixed cell population is substantially free of epithelial cells. In some embodiments, the methods further comprise removing one or more epithelial cells from the mixed cell population. In some embodiments, the methods further comprise removing one or more epithelial cells from the mixed cell population prior to contacting the mixed cell population with the agent. In some embodiments, the agent is an antibody. In some embodiments, the methods further comprise isolating the E-cadherin positive stem cell by fluorescence activated cell sorting or magnetic activated cell sorting. In some embodiments, the mixed cell population comprises an embryonic stem cell, an adult stem cell, a fetal stem cell, or an induced pluripotent stem cell. In some embodiments, the mixed cell population comprises a limbal stromal niche cell, an umbilical cord stem cell, an amniotic membrane stem cell or an adipose stem cell. In some embodiments, the methods further comprise deriving the mixed cell population from an umbilical cord. In some embodiments, the umbilical cord is a human, non-human primate, cow or pig umbilical cord. In some embodiments, the methods further comprise (a) mechanically or enzymatically removing the amniotic membrane epithelial cells from an umbilical cord, thereby producing remaining umbilical cord tissue; and (b) contacting the remaining umbilical cord tissue with collagenase for a period of time sufficient to separate one or more stem cells from other bound cells and components of the stromal matrix of the remaining umbilical cord tissue. In some embodiments, the methods further comprise removing an umbilical cord blood vessel from the remaining umbilical cord tissue prior to digestion of the remaining umbilical cord tissue. In some embodiments, the methods further comprise deriving the mixed cell population from adipose tissue. In some embodiments, the methods further comprise digesting the adipose tissue with collagenase, thereby producing collagenase-digested adipose tissue. In some embodiments, the methods further comprise digesting the adipose tissue in modified ESC medium. In some embodiments, the methods further comprise fractionating the collagenase-digested adipose tissue by centrifugation, thereby producing a floating cell fraction (FC) and a sedimented stromal vascular fraction (SVF). In some embodiments, the methods further comprise selecting the FC as the mixed cell population. In some embodiments, the methods further comprise selecting the sedimented SVF as the mixed cell population. In some embodiments, the methods further comprise filtering the sedimented SVF on a mesh filter, thereby producing a filtered SVF and a remaining cell fraction (RC) remaining on the filter. In some embodiments, the methods further comprise selecting the filtered SVF as the mixed cell population. In some embodiments, the methods further comprise selecting the RC as the mixed cell population. In some embodiments, the filter has a pore size of about 40 μm to about 250 μm. In some embodiments, the methods further comprise deriving the mixed cell population from amniotic membrane. In some embodiments, the methods further comprise (a) contacting the amniotic membrane with collagenase, thereby producing collagenase-digested amniotic membrane; and (b) contacting the collagenase-digested amniotic membrane with dispase. In some embodiments, the methods further comprise (a) contacting the amniotic membrane with dispase, thereby producing dispase-digested amniotic membrane; and (b) contacting the dispase-digested amniotic membrane with collagenase.

Described herein, in certain embodiments are methods for expanding a stem cell population comprising: expanding one or more isolated stem cells of any of the methods provided herein in a culture comprising a two-dimensional substrate, thereby forming a plurality of expanding stem cells. In some embodiments, at least one of the expanding stem cells does not pass the Hayflick limit. In some embodiments, the two-dimensional substrate comprises Matrigel, laminin, fibronectin, collagen or entactin. In some embodiments, the two-dimensional substrate comprises an HC-HA complex. In some embodiments, the HC-HA complex is immobilized. In some embodiments, the HC-HA complex is a native HC-HA complex or is a reconstituted HC-HA complex. In some embodiments, the native HC-HA complex is an amniotic membrane HC-HA complex. In some embodiments, the native HC-HA complex is an umbilical cord HC-HA complex. In some embodiments, the HC-HA complex comprises TSG-6. In some embodiments, the HC-HA complex comprises PTX3. In some embodiments, the HC-HA complex comprises a small leucine rich proteoglycan (SLRP). In some embodiments, the HC-HA complex comprises TSG-6, PTX3, and a small leucine rich proteoglycan (SLRP). In some embodiments, the small leucine-rich proteoglycan is selected from among decorin, biglycan, fibromodulin, lumican, PRELP (proline arginine rich end leucine-rich protein), keratocan, osteoadherin, epipycan, and osteoglycin. In some embodiments, the HC-HA complex comprises TSG-6, PTX3, and a small leucine rich proteoglycan (SLRP). In some embodiments, the culture comprises supplemental hormonal epithelial media or embryonic stem cell media. In some embodiments, the culture comprises bFGF or LIF. In some embodiments, the culture comprises an inhibitor of Rho-associated kinase (ROCK). In some embodiments, the methods further comprise (a) isolating at least one expanding stem cell from the plurality of expanding stem cells, thereby producing an isolated expanded stem cell; and (b) culturing the isolated expanded stem cell in a second culture comprising a three-dimensional substrate. In some embodiments, the three-dimensional substrate comprises Matrigel, laminin, fibronectin, collagen or entactin. In some embodiments, the second culture comprises supplemental hormonal epithelial media or embryonic stem cell media.

Described herein, in certain embodiments are methods for expanding a stem cell population comprising: expanding one or more stem cells in a culture comprising a two-dimensional substrate comprising an HC-HA complex, thereby forming a plurality of expanding stem cells. In some embodiments, at least one of the expanding stem cells does not pass the Hayflick limit. In some embodiments, the HC-HA complex is immobilized. In some embodiments, the HC-HA complex is a native HC-HA complex or is a reconstituted HC-HA complex. In some embodiments, the native HC-HA complex is an amniotic membrane HC-HA complex. In some embodiments, the native HC-HA complex is an umbilical cord HC-HA complex. In some embodiments, the methods further comprise purifying the native HC-HA complex by performing ultracentrifugation on an amniotic membrane extract. In some embodiments, the methods further comprise purifying the native HC-HA complex by performing ultracentrifugation on an umbilical cord extract. In some embodiments, the umbilical cord extract comprises umbilical cord stroma and/or Wharton's jelly. In some embodiments, the methods further comprise performing two, three or four rounds of ultracentifugation. In some embodiments, the methods further comprise performing four rounds of ultracentifugation. In some embodiments, the HC-HA complex comprises TSG-6. In some embodiments, the HC-HA complex comprises PTX3. In some embodiments, the HC-HA complex comprises PTX3. In some embodiments, the HC-HA complex comprises a small leucine rich proteoglycan (SLRP). In some embodiments, the HC-HA complex comprises TSG-6, PTX3, and a small leucine rich proteoglycan (SLRP). In some embodiments, the small leucine-rich proteoglycan is selected from among decorin, biglycan, fibromodulin, lumican, PRELP (proline arginine rich end leucine-rich protein), keratocan, osteoadherin, epipycan, and osteoglycin. In some embodiments, the HC-HA complex comprises TSG-6, PTX3, and a small leucine rich proteoglycan (SLRP). In some embodiments, the stem cell is an embryonic stem cell, an adult stem cell, a fetal stem cell, or an induced progenitor cell. In some embodiments, the stem cell is a limbal stromal niche cell, an umbilical cord stem cell, an amniotic membrane stem cell or an adipose stem cell. In some embodiments, the stem cell is a mesenchymal stem cell. In some embodiments, the stem cell is an induced pluripotent stem cell derived from an adult differentiated cell. In some embodiments, the stem cell is an induced pluripotent stem cell derived from a fibroblast. In some embodiments, the stem cell is an induced pluripotent stem cell derived from a conjunctivochalasis fibroblast. In some embodiments, the methods further comprise deriving the mixed cell population from an umbilical cord. In some embodiments, the umbilical cord is a human, non-human primate, cow or pig umbilical cord. In some embodiments, the methods further comprise (a) mechanically or enzymatically removing the amniotic membrane epithelial cells from an umbilical cord, thereby producing remaining umbilical cord tissue; and (b) contacting the remaining umbilical cord tissue with collagenase for a period of time sufficient to separate one or more stem cells from other bound cells and components of the stromal matrix of the remaining umbilical cord tissue. In some embodiments, the methods further comprise removing an umbilical cord blood vessel from the remaining umbilical cord tissue prior to digestion of the remaining umbilical cord tissue. In some embodiments, the methods further comprise deriving the mixed cell population from adipose tissue. In some embodiments, the methods further comprise digesting the adipose tissue with collagenase, thereby producing collagenase-digested adipose tissue. In some embodiments, the methods further comprise digesting the adipose tissue in modified ESC medium. In some embodiments, the methods further comprise fractionating the collagenase-digested adipose tissue by centrifugation, thereby producing a floating cell fraction (FC) and a sedimented stromal vascular fraction (SVF). In some embodiments, the methods further comprise selecting the FC as the mixed cell population. In some embodiments, the methods further comprise selecting the sedimented SVF as the mixed cell population. In some embodiments, the methods further comprise filtering the sedimented SVF on a mesh filter, thereby producing a filtered SVF and a remaining cell fraction (RC) remaining on the filter. In some embodiments, the methods further comprise selecting the filtered SVF as the mixed cell population. In some embodiments, the methods further comprise selecting the RC as the mixed cell population. In some embodiments, the filter has a pore size of about 40 μm to about 250 μm. In some embodiments, the methods further comprise deriving the mixed cell population from amniotic membrane. In some embodiments, the methods further comprise (a) contacting the amniotic membrane with collagenase, thereby producing collagenase-digested amniotic membrane; and (b) contacting the collagenase-digested amniotic membrane with dispase. In some embodiments, the methods further comprise (a) contacting the amniotic membrane with dispase, thereby producing dispase-digested amniotic membrane; and (b) contacting the dispase-digested amniotic membrane with collagenase. In some embodiments, the two-dimensional substrate comprises Matrigel, laminin, fibronectin, collagen or entactin. In some embodiments, the culture comprises supplemental hormonal epithelial media or embryonic stem cell media. In some embodiments, the culture comprises bFGF or LIF. In some embodiments, the culture comprises an inhibitor of Rho-associated kinase (ROCK). In some embodiments, the methods further comprise (a) isolating at least one expanding stem cell from the plurality of expanding stem cells, thereby producing an isolated expanded stem cell; and (b) culturing the isolated expanded stem cell in a second culture comprising a three-dimensional substrate. In some embodiments, the three-dimensional substrate comprises Matrigel, laminin, fibronectin, collagen or entactin. In some embodiments, the second culture comprises supplemental hormonal epithelial media or embryonic stem cell media. In some embodiments, the methods further comprise (a) separating a plurality of cells of a tissue sample from components of an extracellular matrix in the tissue sample, to form a mixed cell population; (b) culturing the mixed cell population in a first culture comprising supplemented hormonal epithelial medium (SHEM) on a plastic tissue culture dish, thereby producing a population of non-adherent cells; (c) isolating the population of non-adherent cells; and (d) expanding at least one cell of the population of non-adherent cells in a second culture comprising a two-dimensional substrate, thereby forming a plurality of expanding stem cells. In some embodiments, at least one of the expanding stem cells does not pass the Hayflick limit. In some embodiments, the tissue is an amniotic membrane, an umbilical cord, a limbal tissue or an adipose tissue. In some embodiments, the stem cell is a limbal stromal niche cell, an umbilical cord stem cell, an amniotic membrane stem cell or an adipose stem cell. In some embodiments, the stem cell is a mesenchymal stem cell. In some embodiments, the two-dimensional substrate comprises Matrigel, laminin, fibronectin, collagen or entactin. In some embodiments, the two-dimensional substrate comprises an HC-HA complex. In some embodiments, the HC-HA complex is a native HC-HA complex or is a reconstituted HC-HA complex. In some embodiments, the native HC-HA complex is an amniotic membrane HC-HA complex. In some embodiments, the native HC-HA complex is an umbilical cord HC-HA complex. In some embodiments, the methods further comprise purifying the native HC-HA complex by performing ultracentrifugation on an amniotic membrane extract. In some embodiments, the methods further comprise purifying the native HC-HA complex by performing ultracentrifugation on an umbilical cord extract. In some embodiments, the umbilical cord extract comprises umbilical cord stroma and/or Wharton's jelly. In some embodiments, the methods further comprise performing two, three or four rounds of ultracentifugation. In some embodiments, the methods further comprise performing four rounds of ultracentifugation. In some embodiments, the HC-HA complex comprises TSG-6. In some embodiments, the HC-HA complex comprises PTX3. In some embodiments, the HC-HA complex comprises PTX3. In some embodiments, the HC-HA complex comprises a small leucine rich proteoglycan (SLRP). In some embodiments, the HC-HA complex comprises TSG-6, PTX3, and a small leucine rich proteoglycan (SLRP). In some embodiments, the small leucine-rich proteoglycan is selected from among decorin, biglycan, fibromodulin, lumican, PRELP (proline arginine rich end leucine-rich protein), keratocan, osteoadherin, epipycan, and osteoglycin. In some embodiments, the HC-HA complex comprises TSG-6, PTX3, and a small leucine rich proteoglycan (SLRP). In some embodiments, the second culture comprises supplemental hormonal epithelial media or embryonic stem cell media. In some embodiments, the second culture comprises bFGF or LIF. In some embodiments, the second culture comprises an inhibitor of Rho-associated kinase (ROCK). In some embodiments, the tissue is an amniotic membrane. In some embodiments, the methods further comprise (i) contacting the amniotic membrane with collagenase, thereby producing collagenase-digested amniotic membrane; and (ii) contacting the collagenase-digested amniotic membrane with dispase. In some embodiments, the methods further comprise (i) contacting the amniotic membrane with dispase, thereby producing dispase-digested amniotic membrane; and (ii) contacting the dispase-digested amniotic membrane with collagenase. In some embodiments, the methods further comprise (a) isolating at least one expanding stem cell from the plurality of expanding stem cells, thereby producing an isolated expanding stem cell; and (b) culturing the isolated expanding stem cell in a second culture comprising a three-dimensional substrate. In some embodiments, the three-dimensional substrate comprises Matrigel, laminin, fibronectin, collagen or entactin. In some embodiments, the methods of producing an isolated or expanding stem cell provided herein further comprise the method further comprises isolating an HC-HA complex from the stem cell.

Described herein, in certain embodiments, are methods for inducing or maintaining pluripotency in a cell, comprising culturing the cell with an HC-HA complex, thereby inducing or maintaining pluripotency in a cell. In some embodiments, the cell heterogeneously expresses a protein selected from among Sox2, myc, Oct4 and KLF4. In some embodiments, the cell heterogeneously expresses one, two, or three proteins selected from among Sox2, myc, Oct4 and KLF4. In some embodiments, the HC-HA complex is immobilized. In some embodiments, the cell is an adult differentiated cell. In some embodiments, the cell is a fibroblast. In some embodiments, the cell is a conjunctivochalasis fibroblast. In some embodiments, the cell is an embryonic stem cell, an adult stem cell, a fetal stem cell, or an induced pluripotent stem cell. In some embodiments, the cell is a limbal epithelial progenitor cell, a limbal stromal niche cell, an umbilical cord stem cell, an amniotic membrane stem cell or an adipose stem cell. In some embodiments, the HC-HA complex is a native HC-HA complex or is a reconstituted HC-HA complex. In some embodiments, the native HC-HA complex is an amniotic membrane HC-HA complex. In some embodiments, the native HC-HA complex is an umbilical cord HC-HA complex. In some embodiments, the methods further comprise purifying the native HC-HA complex by performing ultracentrifugation on an amniotic membrane extract. In some embodiments, the methods further comprise purifying the native HC-HA complex by performing ultracentrifugation on an umbilical cord extract. In some embodiments, the umbilical cord extract comprises umbilical cord stroma and/or Wharton's jelly. In some embodiments, the methods further comprise performing two, three or four rounds of ultracentifugation. In some embodiments, the methods further comprise performing four rounds of ultracentifugation. In some embodiments, the HC-HA complex comprises TSG-6. In some embodiments, the HC-HA complex comprises PTX3. In some embodiments, the HC-HA complex comprises PTX3. In some embodiments, the HC-HA complex comprises a small leucine rich proteoglycan (SLRP). In some embodiments, the HC-HA complex comprises TSG-6, PTX3, and a small leucine rich proteoglycan (SLRP). In some embodiments, the small leucine-rich proteoglycan is selected from among decorin, biglycan, fibromodulin, lumican, PRELP (proline arginine rich end leucine-rich protein), keratocan, osteoadherin, epipycan, and osteoglycin. In some embodiments, the HC-HA complex comprises TSG-6, PTX3, and a small leucine rich proteoglycan (SLRP).

Described herein, in certain embodiments, are methods for producing an isolated native HC-HA complex comprising: (a) culturing an amniotic membrane stem cell, thereby producing a cultured amniotic membrane stem cell; and (b) isolating an HC-HA complex from the cultured stem cell, thereby producing an isolated native HC-HA complex. In some embodiments, the amniotic membrane is from a placenta or an umbilical cord. In some embodiments, the stem cell is an amniotic stem cell or an umbilical cord stem cell. In some embodiments, the umbilical cord stem cell is from the umbilical cord stromal layer or Wharton's jelly layer.

Described herein, in certain embodiments, are methods for treating an individual in need of a stem cell therapy, comprising administering to the individual a plurality of isolated or expanded stem cells produced by any of the methods provided herein for isolating and expanding stem cells. In some embodiments, the individual has a disease or condition selected from among non-healing wounds, diabetes, arthritis, inflammatory bowel disease, Crohn's disease, myocardial infarction, stroke, traumatic brain injury, spinal cord injury, learning defects, Alzheimer's disease, Parkinson's disease, baldness, missing teeth, osteoarthritis, rheumatoid arthritis, muscular dystrophy, cancer, amyotrophic lateral sclerosis. In some embodiments, the methods comprise transplanting the isolated or expanded stem cells into the bone marrow of the individual.

Described herein, in certain embodiments, are methods for expanding a stem cell comprising culturing the stem cell in the presence of one or more isolated or expanded stem cells produced by any of the methods provided herein for isolating and expanding stem cells.

Described herein, in certain embodiments, are compositions comprising a plurality of expanded stem cells produced by any of the methods provided herein for isolating and expanding stem cells and a pharmaceutically acceptable excipient.

Described herein, in certain embodiments, are compositions comprising (a) a stem cell; (b) an HC-HA complex; and (c) a tissue culture plate. In some embodiments, HC-HA complex is immobilized to the tissue culture plate. In some embodiments, the stem cell is an isolated or expanded stem cell produced by any of the methods provided herein for isolating and expanding stem cells. In some embodiments, the stem cell is an embryonic stem cell, an adult stem cell, a fetal stem cell, or an induced progenitor cell. In some embodiments, the stem cell is a limbal stromal niche cell, an umbilical cord stem cell, an amniotic membrane stem cell or an adipose stem cell. In some embodiments, the stem cell is a mesenchymal stem cell. In some embodiments, the stem cell is an induced pluripotent stem cell derived from an adult differentiated cell. In some embodiments, stem cell is an induced pluripotent stem cell derived from a fibroblast. In some embodiments, stem cell is an induced pluripotent stem cell derived from a conjunctivochalasis fibroblast. In some embodiments, HC-HA complex is a native HC-HA complex or is a reconstituted HC-HA complex. In some embodiments, HC-HA complex comprises TSG-6. In some embodiments, HC-HA complex comprises PTX3. In some embodiments, the HC-HA complex comprises PTX3. In some embodiments, the HC-HA complex comprises a small leucine rich proteoglycan (SLRP). In some embodiments, the HC-HA complex comprises TSG-6, PTX3, and a small leucine rich proteoglycan (SLRP). In some embodiments, the small leucine-rich proteoglycan is selected from among decorin, biglycan, fibromodulin, lumican, PRELP (proline arginine rich end leucine-rich protein), keratocan, osteoadherin, epipycan, and osteoglycin. In some embodiments, the HC-HA complex comprises TSG-6, PTX3, and a small leucine rich proteoglycan (SLRP).

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings.

BRIEF DESCRIPTION OF THE DRAWINGS

FIG. 15 provides a table of comparison of the ECM and ESC and Angiogenic Markers between AM versus UC in vivo.

FIG. 16 provides a table of published methods of isolation, characterization, and expansion of MSCs/SCs from human umbilical cord. (Wang et al. (2004) *Stem Cells* 22:1330-1337, Weiss et al. (2006) *Stem Cells* 24:781-792, Sarugasar et al. (2005) *Stem Cells* 23:220-229, Lu et al. (2006) *Haematologica* 91:1017-1026, Seshareddy et al. (2008) *Methods Cell Biol* 86:101-119, Schugar et al. (2009) *J Biomed Biotechnol.* 2009:789526, Koliakos et al. (2011) *Journal of Biological Research-Thessaloniki* 16:194-201, Zhao et al. (2011) *Tissue Eng Part A.* 17:969-979, Montanucci et al. (2011) *Tissue Eng Part A.* 2011; 17:2651-2661, Tong et al. (2011) *Cell Biol Int.* 35:221-226, and Tsagias et al. (2011) *Transfus Med.* 21:253-261).

FIG. 17 provides a table of ES, MSC markers expressed in cultured UC according to published methods (references provided above).

DETAILED DESCRIPTION

Certain Terminology

Figure 1:
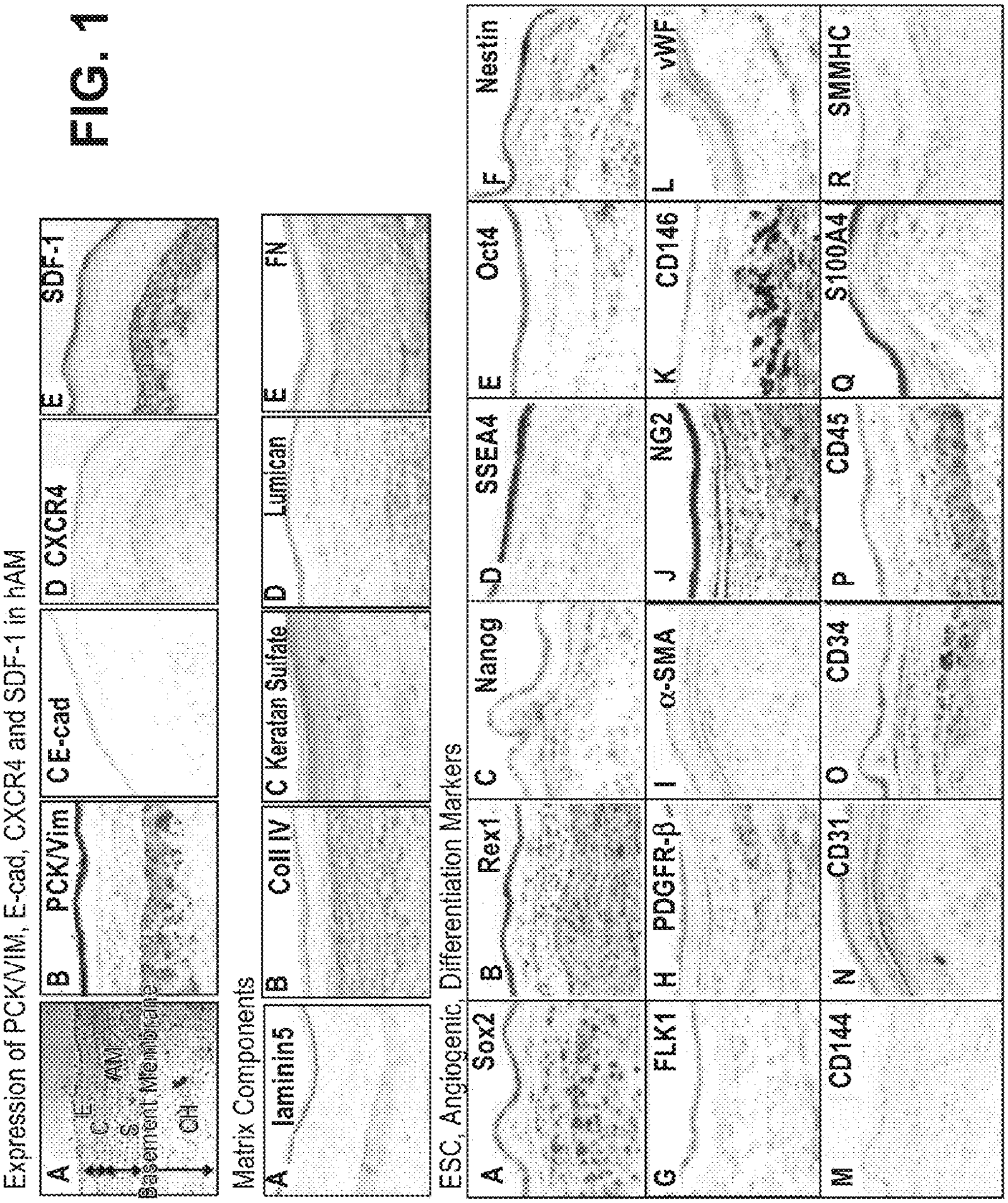
FIG. 1 illustrates a cross section of anatomy of the amniotic membrane (AM) demonstrating expression of PCK/VIM, E-cad, CXCR4/SDF1, matrix components, embryonic stem cell (ESC), angiogenic and differentiation markers.

As used herein, “amniotic membrane” (AM), and/or amnion, means the thin, tough membrane that encloses the embryo and/or fetus. It is the innermost layer of the placenta. AM is also found in the umbilical cord. AM has multiple layers, including an epithelial layer, a basement membrane; a compact layer; a fibroblast layer; and a spongy layer.

As used herein, “basement membrane” means a thin sheet of fibers that underlies epithelium and/or endothelium. The primary function of the basement membrane is to anchor the epithelium and endothelium to tissue. This is achieved by cell-matrix adhesions through substrate adhesion molecules (SAMs). The basement membrane is the fusion of two lamina, the basal lamina and the lamina reticularis. The basal lamina layer is divided into two layers—the lamina lucida and the lamina densa. The lamina densa is made of reticular collagen (type IV) fibrils coated in perlecan. The lamina lucida is made up of laminin, integrins, entactins, and dystroglycans. The lamina reticularis is made of type III collagen fibers. Basement membrane is found in, amongst other locations, amniotic membrane, adipose tissue, and the corneal limbus.

As used herein, the term “stem cell niche” means the microenvironment in which stem cells are found. The stem cell niche regulates stem cell fate. It generally maintains stem cells in a quiescent state to avoid their depletion. However, signals from stem cell niches also signal stem cells to differentiate. Control over stem cell fate results from, amongst other factors, cell-cell interactions, adhesion molecules, extracellular matrix components, oxygen tension, growth factors, cytokines, and the physiochemical nature of the niche.

As used herein, a stem cell encompasses any type of stem cell, including embryonic stem cells, adult stem cell and stem cells derived from fetal tissues.

As used herein, a multipotent stem cell refers to a stem cell derived from an adult or fetal tissue that can differentiate into a number of cell types.

As used herein, an embryonic stem cell refers to a stem cell isolated from the inner cell mass of a blastocyst that is pluripotent (i.e. can differentiate into almost all cell types).

As used herein, a mesenchymal stem cell refers to a multipotent stem cell capable of differentiating into the mesenchymal cell lineages (i.e., osteoblasts, chondroblasts and adipocytes).

As used herein, multipotent stem cells isolated from adipose tissue are referred to as adipose-derived stem cells (ASC).

As used herein, mechanical removal of amniotic membrane from an umbilical cord refers to physical manipulation, such as peeling, to separate the amniotic layer of the umbilical cord from the underlying umbilical cord stroma and blood vessels.

As used herein, the term “HC-HA complex” refers to a complex comprising hyaluronan (HA) and the heavy chain of inter-α-inhibitor (IαI). The term HC-HA complex encompasses native HC-HA complexes (also called nHC-HA) or reconstituted HC-HA complexes comprising native or recombinant proteins. The term HC-HA complex is not limiting and includes HC-HA complexes comprising one or more additional components, such as pentraxin 3 (PTX3), Tumor necrosis factor α-stimulated gene 6 (TSG-6), or a small leucine-rich proteoglycan (SLRP). In some examples, HC-HA complex complexes comprising PTX3 are referred to herein as HC-HA/PTX3.

As used herein, a purified native HC-HA (nHC-HA) complex refers to an HC-HA complex that is purified from a biological source such as a cell, a tissue or a biological fluid. Such complexes are generally assembled in vivo in a subject or ex vivo in cells, tissues, or biological fluids from a subject, including a human or other animal. In some examples, native HC-HA complexes are purified by successive rounds of ultracentrifugation of an amniotic membrane extract (AME) an umbilical cord extract and are referred to herein by the round in which the complex was purified (e.g. nHC-HA $2^{nd}$ or nHC-HA $4^{th}$). In some embodiments, the umbilical cord extract comprises umbilical cord stroma and/or Wharton’s jelly. In some embodiments, ultracentrifugation is performed on a extract obtained by homogenization of a tissue in PBS and isolation of the soluble fraction by centrifugation. As used herein, nHC-HA complexes purified by ultracentrifugation of a PBS-extracted tissue are referred to herein as nHC-HA soluble complexes. In some embodiments, ultracentrifugation is performed on a extract obtained by homogenization of a tissue in PBS, removal of the soluble fraction and further extraction of the insoluble fraction in guanidine HCl. As used herein, nHC-HA complexes purified by ultracentrifugation of a guanidine HCl-extracted tissue are referred to herein as nHC-HA insoluble complexes.

As used herein, a reconstituted HC-HA complex or rcHC-HA is an HC-HA complex that is formed by assembly of the component molecules of the complex in vitro. The process of assembling the rcHC-HA includes reconstitution with purified native proteins or molecules from biological source, recombinant proteins generated by recombinant methods, or synthesis of molecules by in vitro synthesis. In some instances, the purified native proteins used for assembly of the rcHC-HA are proteins in a complex with other proteins (i.e. a multimer, a multichain protein or other complex).

The terms “patient”, “subject” and “individual” are used interchangeably. As used herein, both terms mean any animal, preferably a mammal, including a human and/or non-human. None of the terms are to be interpreted as requiring the supervision of a medical professional (e.g., a doctor, nurse, physician’s assistant, orderly, hospice worker).

The terms “treat,” “treating” or “treatment,” as used herein, include alleviating, abating and/or ameliorating a disease and/or condition symptoms, preventing additional symptoms, ameliorating and/or preventing the underlying metabolic causes of symptoms, inhibiting the disease and/or condition, e.g., arresting the development of the disease and/or condition, relieving the disease and/or condition, causing regression of the disease and/or condition, relieving a condition caused by the disease and/or condition, and/or stopping the symptoms of the disease and/or condition either prophylactically or therapeutically.

Overview

Described herein, in certain embodiments, are methods for the isolation and expansion a variety of stem cells, including, but not limited to, adult stem cells derived from fetal tissues (e.g. placenta and umbilical cord), adipose tissue, limbal tissue and other tissue sources. Such stem cells can be employed to regenerate tissues and restore physiologic and anatomic functionality.

Mesenchymal Stem Cells (MSCs) are multipotent stem cells that have the ability to differentiate into a variety of cell types, including: osteoblasts, chondrocytes, adipocytes, pericytes. MSCs have a large capacity for self-renewal while maintaining their multipotency. MSCs have been isolated from placenta, umbilical cord tissue, namely Wharton’s jelly and the umbilical cord blood, amniotic membrane (AM), amniotic fluid, adipose tissue, the corneal limbus, bone marrow, peripheral blood, liver, skin, and the corneal limbus. Currently, efforts to isolate MSCs focus on the perivascular space and the pericytes. Described herein, in certain embodiments, cells adjacent to basement membranes are an alternative source of MSCs. For example, in the limbus, an excellent source of MSCs is not the perivascular area but the basement membrane subadjacent to the limbal epithelium. MSCs also have been isolated from the avascular stroma of the amniotic membrane.

Human AM contains two different cell types derived from two different embryological origins: amniotic membrane epithelial cells (hAMEC) are derived from the embryonic ectoderm, while human amniotic membrane stromal cells (hAMSC) are derived from the embryonic mesoderm and are sparsely distributed in the stroma underlying the amnion epithelium. Phenotypically, hAMEC uniformly express epithelial markers, for example CK 8, CK14, CK17, CK18, CK19, SSEA3, SSEA4, Tra-1-60, Tra-1-81, Oct4, Nanog, and Sox2. hAMECs also express the mesenchymal marker vimentin (Vim) in some scattered clusters. hAMSCs express the mesenchymal cell marker vimentin (Vim) but not pancytokeratins (PCK), α-smooth muscle actin (α-SMA) and/or desmin. MSCs also express Oct4, Sox2, Nanog, Rex1, SSEA4, Nestin, N-cadherin, and CD34. Little is known whether the avascular property of AM contain angiogenic expressing cells in hAMEC and/or hAMSC in vivo and whether the AM expressing ESC markers might represent a subset that might be different from those not expressing ESC markers and angiogenic markers, and if so, whether they can be separately isolated. It also remains unclear whether these markers were also expressed in AM stroma. MSCs have been expanded from both hAMEC and hAMSC.

Current isolation and culturing techniques for adult stem cells are crude and result in low yields of stem cells. For example, hAMECs have been isolated from the AM stroma by use of trypsin/EDTA (T/E) and/or dispase (D), and collagenase digestion has been used later to release hAMSC. However, protocols have not clearly defined nor documented whether stem cells are derived from hAMECs or hAMSCs during isolation or both. Further, these methods result in high yield of hAMEC (<2% vim+ cells) and low epithelial contamination of hAMSC (<1% of cytokeratin+). Current isolation and expansion methods for stem cells are carried out in a basal nutrient medium supplemented with fetal bovine serum. There is a need for new methods of preferentially isolating and expanding stem cells.

In some embodiments, the methods provided herein are performed for the isolation and expansion of a variety of stem cell types and for the induction of pluripotency in differentiated cells. In some embodiments, the isolated stems cells are embryonic stem cells. In some embodiments, the isolated stems cells are adult or fetal stem cells. As described herein and in the examples provided herein, methods are provided for the isolation and expansion of stem cells from a variety of exemplary tissues including, but not limited to, amniotic membrane, umbilical cord, adipose tissue, and limbal tissues.

Among the methods provided herein are methods of isolation of multipotent cells from a cell population using a cell surface marker, such as E-cadherin, which is expressed in a subpopulation of stem cells. In exemplary methods, stem cells are isolated from the stroma of the umbilical cord by mechanical or enzymatic removal of amniotic membrane (AM) prior to digestion of the stroma and subsequent purification of the cells. In an exemplary method, mechanical removal or enzymatic digestion of the AM epithelium prior to digestion of the stroma reduces the epithelial cell contamination of the sample and permits isolation of multipotent cells by targeting specific cell surface markers, such as E-cadherin.

Also among the methods provided herein are methods of enriching or selecting stem cells from a mixed cell population by removal of cells that adhere to plastic followed by culturing of the remainder cells (i.e. non-adherent) on a suitable two dimensional substrate. In some embodiments, the suitable two dimensional substrate is 5% Matrigel. In exemplary embodiments, a mixed cell population is first prepared by enzymatic digestion of a tissue. In exemplary embodiments, a mixed cell population is plated on plastic following enzymatic digestion of a tissue. In exemplary embodiments, the non-adherent cells of such cultures are enriched for stem cell markers. In some embodiments, the non-adherent cells are subsequently cultured on a suitable substrate for expansion of the isolated stem cell population. The methods thus provide for an enriched stem cell population.

Also among the methods provided herein are improved methods of expanding and maintaining stem cells by culturing the stem cells on a substrate containing a complex of hyaluronan (HA) and the heavy chain of inter-α-inhibitor HCl (HC-HA). In certain instances, the expansion of stem cells on a substrate comprising a HC-HA complex promotes aggregation, prevents differentiation of the stem cells, and preserves the expression of stem cell markers.

Further, in some embodiments, HC-HA promotes pluripotency in differentiated or partially differentiated cells, such as adult fibroblasts. Accordingly, in some embodiments, methods are provided herein for the induction of pluripotency in differentiated or partially differentiated cells, such as adult fibroblasts.

Methods of Isolation Stem Cells and Enrichment of Stem Cell Populations

Described herein, in certain embodiments, are methods for isolating and enriching a stem cell from a mixed cell population to generate an isolated stem cell. In some embodiments, the mixed cell population comprises one or more stem cells. In some embodiments, the mixed cell population comprises one or more stem cells and one or more non-stem cells. In some embodiments, the mixed cell population is obtained from an adult tissue or a fetal tissue. In non-limiting examples, the mixed cell population is obtained from an amniotic membrane tissue, an umbilical cord tissue, a limbal tissue or an adipose tissue. In some embodiments, culturing of the mixed cell population in a supplemented hormonal epithelial medium (SHEM) prior to plating on a substrate enriches for cells expressing stem cell markers. In some embodiments, a stem cell is isolated from the mixed cell population by cell sorting based on E-cadherin expression. E-cadherin marker expression in multipotent stem cells promotes 3D aggregation, which is important for maintaining multipotency of the stem cells.

In some embodiments, the methods further comprise expanding the isolated stem cell using any of the methods of expansion provided herein. For example, in some embodiments, the methods comprise expanding the isolated stem cells in a first culture comprising a suitable two-dimensional substrate without passing the Hayflick limit to form a plurality of expanding stem cells. In some embodiments, the two-dimensional substrate comprises an HC-HA complex. In some embodiments, the methods comprise expanding the isolated stem cell using a conventional method of stem cell expansion, such as culturing on feeder cells and/or use of modified media comprising various growth factors (see, e.g. U.S. Pat. Nos. 5,399,493, 5,612,211, 5,435,151, 5,728,581, 7,297,539, 7,067,316, and 7,312,078).

In some embodiments, the isolated stem cell is an embryonic stem cell. In some embodiments, the isolated stem cell is an adult stem cell. In some embodiments, the isolated stem cell is a fetal stem cell. In some embodiments, the isolated stem cell is an induced pluripotent cell (iPS).

In some embodiments, the isolated stem cell is a mesenchymal stem cell (MSC). In some embodiments, the isolated stem cell is an adipose stem cell (ASC). In some embodiments, the isolated stem cell is an umbilical cord stem cell. In some embodiments, the isolated stem cell is an amniotic membrane stem cell. In some embodiments, the isolated stem cell is a limbal cell, such as a limbal niche cell or a limbal epithelial progenitor cell. In some embodiments, the isolated stem cell is an endothelial stem cell. In some embodiments, the isolated stem cell is a hematopoietic stem cell. In some embodiments, the isolated stem cell is a bone marrow stem cell. In some embodiments, the isolated stem cell is a neural stem cell. In some embodiments, the isolated stem cell is an endothelial progenitor cell. In some embodiments, the isolated stem cell is a skeletal muscle stem cell. In some embodiments, the isolated stem cell is a mammary stem cell. In some embodiments, the isolated stem cell is an intestinal stem cell.

In some embodiments, the isolated stem cell is an induced pluripotent stem cell (iPS). In some embodiments, the isolated stem cell is an induced pluripotent stem cell derived from a an adult differentiated or partially differentiated cell. In some embodiments, the isolated stem cell is an induced pluripotent stem cell derived from a fibroblast. In some embodiments, the isolated stem cell is an induced pluripotent stem cell derived from a Conjunctivochalasis (CCh) fibroblast.

In some embodiments, the mixed cell population is derived from a fetal tissue, such as placental tissue or an umbilical cord tissue. In some embodiments, the mixed cell population is derived from amniotic membrane. In some embodiments, the mixed cell population is derived from adipose tissue. In some embodiments, the mixed cell population is derived from limbal tissue. In some embodiments, the mixed cell population is derived from bone marrow. In some embodiments, the mixed cell population is derived from limbal tissue. In some embodiments, the mixed cell population is derived from endothelial tissue. In some embodiments, the mixed cell population is derived from limbal tissue. In some embodiments, the mixed cell population is derived from neural tissue. In some embodiments, the mixed cell population is derived from skeletal muscle. In some embodiments, the mixed cell population is derived from the skin. In some embodiments, the mixed cell population is derived from the digestive system. In some embodiments, the mixed cell population is derived from the pancreas. In some embodiments, the mixed cell population is derived from the liver. In some embodiments, the mixed cell population is derived from the olfactory mucosa. In some embodiments, the mixed cell population is derived from a germ cell population. In some embodiments, the mixed cell population is derived from blood. In some embodiments, the mixed cell population is derived from umbilical cord blood.

Isolation Based on Expression of E-Cadherin (E-cad)

Described herein, in certain embodiments are stem cell populations that express the cell surface marker E-cadherin. In some embodiments, methods are provided for isolating a stem cell from a mixed cell population comprising selecting cells that express E-cadherin.

In some embodiments, isolation comprises contacting the mixed cell population with an agent that binds to E-cadherin. In some embodiments, isolation comprises contacting the mixed cell population with an agent that binds to the extracellular portion of E-cadherin. In some embodiments, isolation comprises contacting the mixed cell population with an agent that binds to one or more of the five extracellular cadherin repeats of E-cadherin.

In some embodiments, the agent is an E-cadherin antibody. In some embodiments, the antibody is conjugated to a moiety permits identification and/or sorting of cells bound to a primary antibody. In some embodiments, the moiety is a fluorophore, radioactive isotope, chromophore or magnetic particle.

In some embodiments, a secondary antibody that binds to a primary E-cadherin antibody is employed to identify and/or permit cell sorting of cells bound to the E-cadherin antibody. In some embodiments, the secondary antibody is conjugated to a moiety permits identification and/or sorting of cells bound to a primary antibody. In some embodiments, the moiety is a fluorophore, radioactive isotope, chromophore or magnetic particle.

In some embodiments, the agent is an E-cadherin ligand (e.g. an integrin or a subunit thereof or portion thereof that binds to E-cadherin). In some embodiments, the ligand is conjugated to a moiety that permits identification and/or sorting of cells bound to the ligand. In some embodiments, the moiety a fluorophore, radioactive isotope, chromophore or magnetic particle.

In some embodiments, the stem cells are isolated from the mixed cell population by flow cytometry, for example, fluorescence activated cell sorting (FACS), or magnetic activated cell sorting (MACS). In some embodiments, magnetic activated cell sorting is performed using Dynabeads.

In exemplary isolation methods, the methods comprise mixing the mixed cell population with paramagnetic beads, which exhibit magnetic properties when placed within a magnetic field and are coated with an antibody (e.g. an anti-E-cadherin antibody). In an exemplary tube-based method, target-bead complexes are removed from the cell suspension using an external magnet that draws the complexes to the inner edge of the tube, allowing supernatant to be removed. Removing the tube from the magnetic field enables resuspension of the target-bead complexes. Separation is gentle and does not require centrifugation or columns.

In the another exemplary method, a column-based method is used where target-bead complexes pass through a separation column, which is placed in a strong, permanent magnet. The column matrix serves to create a high-gradient magnetic field that retains bead-bound complexes while non-labeled cells flow through. Following removal of the column from the magnetic field, the retained cells may be eluted.

Media Based Enrichment

In certain embodiments, as described herein, culturing cells in a mixed cell population separated from a tissue in supplemented hormonal epithelial medium (SHEM) and selection of non-adherent cells for re-plating on diluted Matrigel enriches a population of stem cells that express embryonic stem cell (ESC) markers and angiogenesis markers as compared to plating on diluted Matrigel directly. Such methods enrich for cells that preferentially adhere to a two dimensional substrate, such as Matrigel.

In some embodiments, the methods comprise (a) culturing the mixed cell population in a first culture comprising supplemented hormonal epithelial medium (SHEM) on a plastic tissue culture dish for a period of time; (b) isolating non-adherent cells of the first culture to form a plurality of isolated non-adherent cells; and (c) expanding the plurality of isolated non-adherent cells in a second culture, to form a plurality of expanding stem cells. In some embodiments the second culture comprises a suitable two-dimensional substrate. In some embodiments, the expanding stem cells do not pass the Hayflick limit. In some embodiments, the substrate comprises an HC-HA complex. In some embodiments, the second culture comprises embryonic stem cell medium (ESCM) or modified embryonic stem cell medium (MESCM, ESCM supplemented with bFGF and LIF).

In some embodiments, the methods further comprise culturing the expanded stem cells of the first culture in a second culture comprising a suitable three-dimensional substrate. In some embodiments, the methods comprise (a) expanding an isolated stem cell in a first culture comprising a suitable two-dimensional substrate without passing the Hayflick limit to form a plurality of expanding stem cells; and (b) isolating and expanding at least one expanding stem cell from the plurality of expanding stem cells in a second culture comprising a suitable three-dimensional substrate. In some examples, the two dimensional substrate comprises an HC-HA complex.

In some embodiments, the methods comprise (a) separating a plurality of cells from other components of an extracellular matrix in a tissue sample, to form a mixed cell population; (b) culturing the mixed cell population in a first culture comprising supplemented hormonal epithelial medium (SHEM) on a plastic tissue culture dish for a period of time; (c) isolating non-adherent cells of the first culture, to form a plurality of isolated non-adherent cells; and (d) expanding the plurality of isolated non-adherent cells in a second culture comprising a suitable two-dimensional substrate to form a plurality of expanding stem cells. In some embodiments, the expanding stem cells do not pass the Hayflick limit. In some embodiments, the second culture comprises embryonic stem cell medium (ESCM) or modified embryonic stem cell medium (MESCM, ESCM supplemented with bFGF and LIF). In some embodiments, the method further comprises isolating and expanding at least one expanding stem cell from the plurality of expanding stem cells in a second culture comprising a suitable three-dimensional substrate.

Preparation of Mixed Cell Populations from Tissues

Provide herein are methods of preparing mixed cell populations from tissues for use in the isolation methods provided herein. The methods provided herein are exemplary and not intended to limit the types of tissues that can be used for the production of mixed cell populations for use in the methods provided herein. Any of a variety of tissues and methods of preparation of a mixed cell population may be employed in combination with the methods provided herein. In some embodiments, the mixed cell population comprises at least one stem cell and at least one non-stem cell. In some embodiments, the mixed cell population comprises about 5%, 10%, 15%, 20%, 25%, 30%, 35%, 40%, 45%, 50%, 55%, 60%, 65%, 70%, 75%, 80%, 85%, 90%, or 95% stem cells of the total number of cells in the mixed cell population.

In some embodiments, the mixed cell population is substantially free of epithelial cells. In some embodiments, the mixed cell population is less than 10%, less than 9%, less than 8%, less than 7%, less than 6%, less than 5%, less than 4%, less than 3%, less than 2%, less than 1%, or fewer epithelial cells. In some embodiments, the epithelial cells are removed from a mixed cell population. In some embodiments, the epithelial cells are removed from a mixed cell population prior to application of an isolation or expansion method provided herein. In some embodiments, the epithelial cells are removed from a mixed cell population by cell sorting method such as flow cytometry or magnetic sorting.

In some embodiments, the mixed cell population for use in the methods is derived from cells found in contact with a basement membrane of a tissue. In some embodiments, the mixed cell population for use in the methods is derived from cells found in the stroma. In some embodiments, the mixed cell population for use in the methods is derived from cells found in the umbilical cord stroma. In some embodiments, the mixed cell population for use in the methods is derived from cells found in the amniotic membrane, for example in the avascular stroma. In some embodiments, the mixed cell population for use in the methods is derived from cells found in adipose stromal tissue. In some embodiments, the mixed cell population for use in the methods is derived from cells found in the corneal limbus.

In some embodiments, the preparation of the mixed cell population is performed in a suitable medium. In some embodiments, the medium is embryonic stem cell medium, modified embryonic stem cell medium, supplemented hormonal epithelial medium, and/or a combination thereof. In some embodiments, the medium is supplemented with one or more growth factors. In some embodiments, the medium is supplemented with EGF, bFGF and/or LIF. In some embodiments, the medium is supplemented with an inhibitor of Rho-associated kinase (ROCK inhibitor).

In some embodiments, the mixed cell population is separated from a tissue sample by contacting the tissue sample with a protease. In some embodiments, the protease degrades and/or hydrolyzes components of the basement membrane (e.g., collagens, heparan sulfate proteoglycans, laminin, and nidogen-1/2 (entactin)), but not components of the interstitial space (e.g., stroma). In some embodiments, the protease is a dispase. In some embodiments, the dispase is added to the tissue sample for a period of time, such as for example, about 10, 20, 30, 40, 50, 60, 70, 80, 90, 100, 110, 120 minutes or longer. In some embodiments, the tissue is digested at 37° C. In some embodiments, dispase is used in combination with a hyaluronidase.

In some embodiments, the mixed cell population is separated from a tissue sample by contacting the tissue sample with an enzyme that hydrolyzes and/or degrades interstitial (e.g., stromal) collagen but not basement membrane collagen. In some embodiments, the mixed cell population is separated from a tissue sample by contacting the tissue sample with a collagenase. In some embodiments, the mixed cell population is separated from a tissue sample by contacting the tissue sample with collagenase A, collagenase B, collagenase D, and/or a combination thereof. In some embodiments, the mixed cell population is separated from a tissue sample by contacting the tissue sample with collagenase A. In some embodiments, the collagenase is used in combination with hyaluronidase. In some embodiments, the collagenase is added to the tissue sample for a period of time, such as for example, about 10, 20, 30, 40, 50, 60, 70, 80, 90, 100, 110, 120 minutes or longer. In some embodiments, the tissue is digested at 37° C. In some embodiments, the cells of the mixed cell sample are further separated from one another by contacting the cells with a protease, such as trypsin.

In some embodiments, the mixed cell population is isolated from a tissue sample by contacting the tissue sample with a collagenase and dispase. In some embodiments, the mixed cell population is isolated from a tissue sample by contacting the tissue sample with dispase and collagenase A. In some embodiments the collagenase and dispase are added sequentially. For example, in some embodiments, the mixed cell population is isolated from a tissue sample by contacting the tissue sample with a collagenase for a period of time and then contacting the tissue sample with dispase for a period of time. In some embodiments the dispase and collagenase are added sequentially. For example, in some embodiments, the mixed cell population is isolated from a tissue sample by contacting the tissue sample with a dispase for a period of time and then contacting the tissue sample with collagenase for a period of time. In some embodiments, the dispase is used in combination with a hyaluronidase. In some embodiments, the loose cells are removed following collagenase digestion and prior to dispase digestion. In some embodiments, the loose cells are not removed following collagenase digestion and prior to dispase digestion. In some embodiments, the collagenase is added to the tissue sample for a period of time, such as for example, about 10, 20, 30, 40, 50, 60, 70, 80, 90, 100, 110, 120 minutes or longer. In some embodiments, the tissue is digested at 37° C. In some embodiments, the dispase is added to the tissue sample for a period of time, such as for example, about 10, 20, 30, 40, 50, 60, 70, 80, 90, 100, 110, 120 minutes or longer. In some embodiments, the tissue is digested at 37°

C. In some embodiments, the cells of the mixed cell sample are further separated from one another by contacting the cells with a protease, such as trypsin.

Described herein, in certain embodiments, are methods of separating a mixed cell population from an umbilical cord tissue. In exemplary methods, the mixed cell population is separated from an umbilical cord by: (a) mechanically or enzymatically removing the amniotic membrane epithelial cells from an umbilical cord; and (b) contacting the remaining umbilical cord tissue with collagenase for a period of time sufficient to separate mixed cell population from the tissue. In some embodiments, the methods further comprise isolating stem cells from the mixed cell population by selecting cells that express E-cadherin. In some embodiments, the blood vessels of the umbilical cord are removed prior to digestion. In exemplary methods, enzymatic removal of the amniotic membrane is performed by digesting the tissue with dispase. In exemplary methods, enzymatic removal of the remaining amniotic membrane stroma is performed by digesting the tissue with collagenase and hyaluronidase. In some embodiments, the cells of the mixed cell sample are further separated from one another by contacting the cells with a protease, such as trypsin.

As described herein, in certain embodiments, the mixed cell population from the stroma of the umbilical cord can be isolated with minimal epithelial cell contamination by mechanical removal of the epithelial layer of the amniotic membrane (AM) of the umbilical cord and digestion of the underlying stromal tissue. In addition, because the epithelial tissue has been removed, isolation of stem cells by selecting E-cadherin positive stromal cells can be achieved by cell sorting. Thus, in certain embodiments, the epithelial layer of the AM is mechanically removed without enzymatic digestion.

Described herein, in certain embodiments, are methods of separating a mixed cell population from an adipose tissue. As described herein, fractionation collagenase-digested adipose tissue by centrifugation and filtration results in adipose stem cell (ASC) populations that differ in their ability to express stem cell markers. Conventional methods of separation methods of isolating ASCs involves the following steps: (1) digesting adipose tissue with collagenase I in DMEM/10% FBS, (2) separating the stromal vascular fraction (SVF) cells, and discarding the floating cells that contain mature adipose cells, and (3) filtering the SVF via a 250 μm mesh filter and collecting cell flow through. Problematically, collecting the cell flow through results in the loss of any cells attached to basement membrane. As discussed above, many multipotent stem cells are attached to basement membrane. Thus, the current methods of isolating ASCs results in the loss of a significant fraction of ASCs. In some embodiments, the cells remaining on the filter (RC fraction) are enriched for the expression of ESC and angiogenic markers and are thus can be an additional source of ASCs. Similarly, in some embodiments, the cells in FC that is normally discarded can also be another source of ASCs.

In some embodiments, cell aggregation during expansion is maintained when ASCs are isolated in human embryonic stem cell medium supplemented with bFGF and LIF MESCM. In some embodiments, cell aggregation during expansion is maintained when ASCs are cultured on a substrate comprising an HC-HA complex.

In exemplary methods, the mixed cell population is separated from an adipose tissue by: (1) digesting adipose tissue with collagenase, to create digested adipose tissue; (2) separating the stromal vascular fraction (SVF) cells of the digested adipose tissue from other cells (e.g., floating cells that contain mature adipose cells and other cells, some of which include stem-like cells (FC fraction)), to create isolated SVF; and (3) isolating ASCs attached to basement membrane other bound cells and components of an extracellular matrix in the isolated SVF. In some embodiments, isolation of the ASCs is performed in human embryonic stem cell medium supplemented with bFGF and LIF (MESCM). In some embodiments, isolating ASCs attached to basement membrane comprises filtering the SVF via a mesh filter and collecting the non-cell flow through (remaining cell or RC fraction). In some embodiments, the mesh filter has pore size of about 40 μm to about 250 μm. In some embodiments, the mesh filter has pore size of about 40, 50, 60, 70, 80, 90, 100, 110, 120, 130, 140, 150, 160, 170, 180, 190, 200, 210, 220, 230, 240, or 250 μm.

The methods provide herein for the isolation and expansion of stem cells are not limited to application to the RC. The methods provide herein for the isolation and expansion of stem cells are not limited to application to the RC. In some embodiments, one or more stem cells are isolated and/or expanded from the RC fraction. In some embodiments, one or more stem cells are isolated and/or expanded from the SVF fraction. In some embodiments, one or more stem cells are isolated and/or expanded from the FC fraction.

In some embodiments, the methods for isolating stem cells provided herein are performed using the FC fraction as the mixed cell population. In some embodiments, the methods for isolating stem cells provided herein are performed using the SVF fraction as the mixed cell population. In some embodiments, the methods for isolating stem cells provided herein are performed using the RC fraction as the mixed cell population. In some embodiments, the methods further comprise isolating stem cells from the mixed cell population by selecting cells that express E-cadherin. In some embodiments, the methods further comprised expanding the stem cells using a conventional method or a method of expansion provided herein.

In some embodiments, separating the mixed cell population from adipose tissue comprises contacting the adipose tissue with a protease. In some embodiments, separating the mixed cell population from adipose tissue comprises contacting the adipose tissue with a protease that does degrade and/or hydrolyze components of the basement membrane (e.g., collagens, heparan sulfate proteoglycans, laminin, and nidogen-1/2 (entactin)). In some embodiments, the protease is collagenase.

Methods of Expanding Isolated Stem Cells

Described herein are methods for expanding a stem cell, such as, but not limited to, a stem cell isolated by a method provided herein or any other suitable method. Exemplary methods of expansion include, but are not limited to, expansion of the isolated stem cells on a substrate comprising HC-HA and/or matrigel.

Expansion on HC-HA

Disclosed herein, in certain embodiments, are methods of expanding an isolated stem cell on a substrate that comprises a complex comprising hyaluronan (HA) and the heavy chain 1 (HC1) of inter-α-inhibitor (IαI), (i.e. HC-HA). As described herein, HC-HA complexes promote the aggregation of stem cells, prevent differentiation of the cells and preserve expression of stem cell markers.

In some embodiments, the expansion on HC-HA preserves expression of one or more of embryonic stem cell (ESC) markers (e.g. Oct4, Nanog, Sox2 (SRY (sex determining region Y)-box 2), Rex1 (Zfp42), SSEA4 (stage-specific embryonic antigen-4), MYC/c-Myc and KLF4, pericyte markers (e.g. NG2 (neuron-glial antigen 2/Chondroitin sulfate proteoglycan 4(CSPG4)), PDGFR-β (Platelet-derived growth factor receptor B), and α-SMA (α-smooth muscle actin)), and angiogenic markers (e.g. CD133/2, FLK-1 (VEGF-R2, Ly-73), vWF (von Willebrand factor), CD34, CD31 (PECAM-1) and CD146). In some embodiments, the expression of the stem cell marker is determined by conventional methods, such as for example, protein expression analysis (e.g. Western blotting, immunofluorescence, immunohistochemistry, fluorescence activated cell sorting) or mRNA analysis (e.g. polymerase chain reaction (PCR) or Northern).

In some embodiments, the isolated stem cell cultured on HC-HA is an embryonic stem cell. In some embodiments, the isolated stem cell cultured on HC-HA is an adult stem cell. In some embodiments, the isolated stem cell cultured on HC-HA is a fetal stem cell. In some embodiments, the isolated stem cell cultured on HC-HA is an induced pluripotent cell (iPS).

In some embodiments, the isolated stem cell cultured on HC-HA is a mesenchymal stem cell. In some embodiments, the isolated stem cell cultured on HC-HA is an adipose stem cell (ASC). In some embodiments, the isolated stem cell cultured on HC-HA is an umbilical cord stem cell. In some embodiments, the isolated stem cell cultured on HC-HA is an amniotic membrane stem cell. In some embodiments, the isolated stem cell cultured on HC-HA is a limbal cell, such as a limbal niche cell or a limbal epithelial progenitor cell. In some embodiments, the isolated stem cell cultured on HC-HA is an endothelial stem cell. In some embodiments, the isolated stem cell cultured on HC-HA is a hematopoietic stem cell. In some embodiments, the isolated stem cell is a bone marrow stem cell. In some embodiments, the isolated stem cell cultured on HC-HA is a neural stem cell. In some embodiments, the isolated stem cell cultured on HC-HA is an endothelial progenitor cell. In some embodiments, the isolated stem cell cultured on HC-HA is a skeletal muscle stem cell. In some embodiments, the isolated stem cell cultured on HC-HA is a mammary stem cell. In some embodiments, the isolated stem cell cultured on HC-HA is an intestinal stem cell.

In some embodiments, the isolated stem cell cultured on HC-HA is an induced pluripotent stem cell (iPS). In some embodiments, the isolated stem cell cultured on HC-HA is an induced pluripotent stem cell derived from an adult differentiated or partially differentiated cell. In some embodiments, the isolated stem cell cultured on HC-HA is an induced pluripotent stem cell derived from a fibroblast. In some embodiments, the isolated stem cell cultured on HC-HA is an induced pluripotent stem cell derived from a Conjunctivochalasis (CCh) fibroblast.

In some embodiments, the isolated stem cell cultured on HC-HA is derived from a fetal tissue, such as placental tissue or an umbilical cord tissue. In some embodiments, the isolated stem cell cultured on HC-HA is derived from amniotic membrane. In some embodiments, the isolated stem cell cultured on HC-HA is derived from adipose tissue. In some embodiments, the isolated stem cell cultured on HC-HA is derived from limbal tissue. In some embodiments, the isolated stem cell cultured on HC-HA is derived from bone marrow. In some embodiments, the isolated stem cell cultured on HC-HA is derived from endothelial tissue. In some embodiments, the isolated stem cell cultured on HC-HA is derived from limbal tissue. In some embodiments, the isolated stem cell cultured on HC-HA is derived from neural tissue, In some embodiments, the isolated stem cell cultured on HC-HA is derived from limbal tissue. In some embodiments, the isolated stem cell cultured on HC-HA is derived from skeletal muscle. In some embodiments, the isolated stem cell cultured on HC-HA is derived from the skin. In some embodiments, the isolated stem cell cultured on HC-HA is derived from the digestive system. In some embodiments, the isolated stem cell cultured on HC-HA is derived from the pancreas. In some embodiments, the isolated stem cell cultured on HC-HA is derived from the liver. In some embodiments, the isolated stem cell cultured on HC-HA is derived from the olfactory mucosa. In some embodiments, the isolated stem cell cultured on HC-HA is derived from a germ cell population. In some embodiments, the isolated stem cell cultured on HC-HA is derived from blood. In some embodiments, the isolated stem cell cultured on HC-HA is derived from umbilical cord blood.

In some embodiments, the HC-HA complex is a native HC-HA complex (nHC-HA) isolated from amniotic membrane or umbilical cord. In some embodiments, the HC-HA complex is a reconstituted HC-HA complex. In some embodiments, HA is covalently linked to HC. In some embodiments, the HC of IαI is heavy chain 1 (HC1). In some embodiments, the HC-HA complex comprises Tumor necrosis factor α-stimulated gene 6 (TSG-6). In some embodiments, the HC-HA complex comprises pentraxin 3 (PTX3) (also called HC-HA/PTX3). In some embodiments, the HC-HA complex comprises TSG-6 and PTX3. In some embodiments, the HC-HA complex is a native HC-HA complex comprising PTX3, or nHC-HA/PTX3. In some embodiments, the HC-HA complex is a reconstituted HC-HA complex comprising PTX3, or rcHC-HA/PTX3.

In some embodiments, the HC-HA complex comprises a small leucine rich proteoglycan (SLRP). In some embodiments, the HC-HA complex comprises a class I, class II or class II SLRP. In some embodiments, the HC-HA complex comprises TSG-6, PTX3, and a small leucine rich proteoglycan (SLRP). In some embodiments, the small leucine-rich proteoglycan is selected from among class I SLRPs, such as decorin and biglycan. In some embodiments, the small leucine-rich proteoglycan is selected from among class II SLRPs, such as fibromodulin, lumican, PRELP (proline arginine rich end leucine-rich protein), keratocan, and osteoadherin. In some embodiments, the small leucine-rich proteoglycan is selected from among class III SLRPs, such as epipycan and osteoglycin. In some embodiments, the HC-HA complex comprises TSG-6, PTX3, and a small leucine rich proteoglycan (SLRP).

In some embodiments, the isolated stem cell is expanded on a substrate comprising immobilized HC-HA. In some embodiments, the isolated stem cell is expanded in a culture medium comprising HC-HA complex. In some embodiments, the medium is embryonic stem cell medium, modified embryonic stem cell medium, supplemented hormonal epithelial medium, and/or a combination thereof. In some embodiments, the medium is supplemented with one or more growth factors. In some embodiments, the medium is supplemented with EGF, bFGF and/or LIF. In some embodiments, the medium is supplemented with an inhibitor of Rho-associated kinase (ROCK inhibitor).

Sources of HC-HA

Isolated HC-HA complexes for use in the methods provided are described in, including methods of isolation and preparation of, for example in U.S. Patent Pub. Nos. US2012-0083445, US2012-0083445, and International PCT Pub. No. WO 2012/170905, all of which are expressly incorporated herein by reference. In some embodiments, the isolated HC-HA complex is derived from fresh, frozen or previously frozen placental amniotic membrane (PAM), fresh, frozen or previously frozen umbilical cord amniotic membrane (UCAM), fresh, frozen or previously frozen placenta, fresh, frozen or previously frozen umbilical cord, fresh, frozen or previously frozen chorion, fresh, frozen or previously frozen amnion-chorion, or any combinations thereof. Such tissues can be obtained from any mammal, such as, for example, but not limited to a human, non-human primate, cow or pig.

In some embodiments, the HC-HA is purified by any suitable method. In some embodiments, the HC-HA complex is purified by centrifugation (e.g., ultracentrifugation, gradient centrifugation), chromatography (e.g., ion exchange, affinity, size exclusion, and hydroxyapatite chromatography), gel filtration, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, the HC-HA complex is purified by immunoaffinity chromatography. In some embodiments, anti HC1 antibodies, anti-HC2 antibodies, or both are generated and affixed to a stationary support. In some embodiments, the unpurified HC-HA complex (i.e., the mobile phase) is passed over the support. In certain instances, the HC-HA complex binds to the antibodies (e.g., via interaction of (a) an HC1 antibody and HC1, (b) an HC2 antibody and HC2, or (c) both). In some embodiments the support is washed (e.g., with PBS) to remove any unbound or loosely bound molecules. In some embodiments, the support is then washed with a solution that enables elution of the HC-HA complex from the support (e.g., 1% SDS, 6M guanidine-HC1, or 8M urea).

In some embodiments, the HC-HA complex is purified by affinity chromatography. In some embodiments, HABP is generated and affixed to a stationary support. In some embodiments, the unpurified HC-HA complex (i.e., the mobile phase) is passed over the support. In certain instances, the HC-HA complex binds to the HABP. In some embodiments the support is washed (e.g., with PBS) to remove any unbound or loosely bound molecules. In some embodiments, the support is then washed with a solution that enables elution of the HC-HA complex from the support.

In some embodiments, the HC-HA complex is purified by a combination of HABP affinity chromatography, and immunoaffinity chromatography using anti HC1 antibodies, anti-HC2 antibodies, or both.

In some embodiments, the extract is prepared from an amniotic membrane extract. In some embodiments, the extract is prepared from an umbilical cord extract. In some embodiments, the umbilical cord extract comprises umbilical cord stroma and/or Wharton's jelly. In some embodiments, the HC-HA complex is contained in an extract that is prepared by ultracentrifugation. In some embodiments, the HC-HA complex is contained in an extract that is prepared by ultracentrifugation using a CsCl/4-6M guanidine HCl gradient. In some embodiments, the extract is prepared by at least 2 rounds of ultracentrifugation. In some embodiments, the extract is prepared by more than 2 rounds of ultracentrifugation (i.e. nHC-HA $2^{nd}$). In some embodiments, the extract is prepared by at least 4 rounds of ultracentrifugation (i.e. nHC-HA $4^{th}$). In some embodiments, the nHC-HA complex comprises TSG-6, PTX3 and/or a small leucine-rich proteoglycan. In some embodiments, the nHC-HA insoluble complex comprises TSG-6, PTX3 and/or a small leucine-rich proteoglycan.

In some embodiments, ultracentrifugation is performed on an extract prepared by PBS extraction. For example, in some embodiments the tissue is homogenized in PBS to produce a homogenized sample. The homogenized sample is then separated into a soluble portion and insoluble portion by centrifugation. In some embodiments, ultracentrifugation is performed on the soluble portion of the PBS-extracted tissue. In such embodiments, the nHC-HA purified by ultracentrifugation of the PBS-extracted tissue called an nHC-HA soluble complex.

In some embodiments, ultracentrifugation is performed on an extract prepared by further guanidine HCl extraction of the insoluble portion of the PBS-extracted tissue. For example, in some embodiments the tissue is homogenized in PBS to produce a homogenized sample. The homogenized sample is then separated into a soluble portion and insoluble portion by centrifugation. The insoluble portion is then further extracted in guanidine HCl (e.g. 4 M GnHCl) and centrifuged to produce a guanidine HCl soluble and insoluble portions. In some embodiments, ultracentrifugation is performed on the guanidine HCl soluble portion. In such embodiments, the nHC-HA purified by ultracentrifugation of the guanidine HCl-extracted tissue is called an nHC-HA insoluble complex.

In some embodiments, the method of purifying the isolated HC-HA extract comprises: (a) dissolving the isolated extract (e.g. prepared by the soluble or insoluble method described herein) in CsCl/4-6M guanidine HCl at the initial density of 1.35 g/ml, to generate a CsCl mixture, (b) centrifuging the CsCl mixture at 125,000×g for 48 h at 15° C., to generate a first purified extract, (c) extracting the first purified extract and dialyzing it against distilled water to remove CsCl and guanidine HCl, to generate a dialysate. In some embodiments, the method of purifying the isolated extract further comprises (d) mixing the dialysate with 3 volumes of 95% (v/v) ethanol containing 1.3% (w/v) potassium acetate at 0° C. for 1 h, to generate a first dialysate/ethanol mixture, (e) centrifuging the first dialysate/ethanol mixture at 15,000×g, to generate a second purified extract, and (f) extracting the second purified extract. In some embodiments, the method of purifying the isolated extract further comprises: (g) washing the second purified extract with ethanol (e.g., 70% ethanol), to generate a second purified extract/ethanol mixture; (h) centrifuging the second purified extract/ethanol mixture, to generate a third purified extract; and (i) extracting the third purified extract. In some embodiments, the method of purifying the isolated extract further comprises: (j) washing the third purified extract with ethanol (e.g., 70% ethanol), to generate a third purified extract/ethanol mixture; (k) centrifuging the third purified extract/ethanol mixture, to generate a forth purified extract; and (1) extracting the forth purified extract. In some embodiments, the purified extract comprises an HC-HA complex.

In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the HC-HA complex is formed by incubating the mixture for at least 6 hours, at least 12 hours, at least 24 hours, at least 36 hours, at least 48 hours, at least 60 hours, or at least 72 hours.

In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; (iv) PTX3, wherein the PTX3 is optionally recombinant and (v) one or more small leucine-rich proteoglycans; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the HC-HA complex is formed by incubating the mixture for at least 6 hours, at least 12 hours, at least 24 hours, at least 36 hours, at least 48 hours, at least 60 hours, or at least 72 hours. In some embodiments, the one or more small leucine-rich proteoglycans is selected from among decorin, biglycan, fibromodulin, lumican, PRELP (proline arginine rich end leucine-rich protein), keratocan, osteoadherin, epipycan, and osteoglycin.

In some embodiments, the method further comprises immobilizing HA (e.g., HMW HA) to a stationary support (e.g., by cross-linking) In some embodiments, the stationary support comprising HA (e.g., HMW HA) is contacted with IαI (e.g., IαI purified from serum, IαI in serum), TSG-6 (or, recombinant TSG-6), and PTX3 (or, recombinant PTX3). In some embodiments, the contacting occurs for at least 6 hours, at least 12 hours, at least 24 hours, at least 36 hours, at least 48 hours, at least 60 hours, or at least 72 hours. In some embodiments, the stationary support is washed to remove any unbound components.

Additional Methods of Expansion

In some embodiments, isolated stem cells are subjected to a first expansion on a substrate. In some embodiments, the first expansion occurs on a coated and/or two-dimensional substrate. In some embodiments, the substrate is coated in composition that mimics the basement membrane and/or comprises components of the basement membrane, such as such as laminin, type IV collagen and heparan sulfate proteoglycan. In some embodiments, the substrate is coated in a gelatinous protein mixture secreted by Engelbreth-Holm-Swarm (EHS) mouse sarcoma cells. In some embodiments, the substrate is coated in Matrigel. In some embodiments, the two-dimensional substrate mimics the basement membrane and/or comprises components of the basement membrane, such as such as laminin, type IV collagen and heparan sulfate proteoglycan. In some embodiments, the two-dimensional substrate is a gelatinous protein mixture secreted by Engelbreth-Holm-Swarm (EHS) mouse sarcoma cells. In some embodiments, the two-dimensional substrate is Matrigel. In some embodiments, expansion on a coated and/or two-dimensional substrate (e.g., a Matrigel coated and/or 2D substrate) results in proliferation of isolated stem cells. In some embodiments, expansion on a coated and/or two-dimensional substrate (e.g., a Matrigel coated and/or 2D substrate) results in proliferation of isolated stem cells and transient loss of expression of embryonic stem cell (ESC) markers. In some embodiments, the two-dimensional substrate comprises an HC-HA complex.

In some embodiments, the first expansion of the isolated stem cells is performed in the presence of a substrate that prevents differentiation. In some embodiments, the first expansion of the isolated stem cells is performed in the presence of a substrate that preserves expression of one or more stem cell markers. In some embodiments, the first expansion occurs in the presence of a substrate that preserves expression of one or more of embryonic stem cell (ESC) markers (e.g. Oct4, Nanog, Sox2 (SRY (sex determining region Y)-box 2), Rex1 (Zfp42) and SSEA4 (stage-specific embryonic antigen-4), pericyte markers (e.g. NG2 (neuron-glial antigen 2/Chondroitin sulfate proteoglycan 4(CSPG4)), PDGFR-β (Platelet-derived growth factor receptor B), and α-SMA (α-smooth muscle actin)), and angiogenic markers (e.g. CD133/2, FLK-1 (VEGF-R2, Ly-73), vWF (von Willebrand factor), CD34, CD31 (PECAM-1) and CD146). In some embodiments, the expression of the stem cell marker is determined by conventional methods, such as for example, protein expression analysis (e.g. Western blotting, immunofluorescence, immunohistochemistry, fluorescence activated cell sorting) or mRNA analysis (e.g. polymerase chain reaction (PCR) or Northern).

In some embodiments, the expanded stem cell is an embryonic stem cell. In some embodiments, the expanded stem cell is an adult stem cell. In some embodiments, the expanded stem cell is a fetal stem cell. In some embodiments, the expanded stem cell is an induced pluripotent cell (iPS).

In some embodiments, the expanded stem cell is a mesenchymal stem cell. In some embodiments, the expanded stem cell is an adipose stem cell (ASC). In some embodiments, the expanded stem cell is an umbilical cord stem cell. In some embodiments, the expanded stem cell is an amniotic membrane stem cell. In some embodiments, the expanded stem cell is a limbal cell, such as a limbal niche cell or a limbal epithelial progenitor cell. In some embodiments, the expanded stem cell is an endothelial stem cell. In some embodiments, the expanded stem cell is a hematopoietic stem cell. In some embodiments, the isolated stem cell is a bone marrow stem cell. In some embodiments, the expanded stem cell is a neural stem cell. In some embodiments, the expanded stem cell is an endothelial progenitor cell. In some embodiments, the expanded stem cell is a skeletal muscle stem cell. In some embodiments, the expanded stem cell is a mammary stem cell. In some embodiments, the expanded stem cell is an intestinal stem cell.

In some embodiments, the expanded stem cell is an induced pluripotent stem cell (iPS). In some embodiments, the expanded stem cell is an induced pluripotent stem cell derived from an adult differentiated or partially differentiated cell. In some embodiments, the expanded stem cell is an induced pluripotent stem cell derived from a fibroblast. In some embodiments, the expanded stem cell is an induced pluripotent stem cell derived from a Conjunctivochalasis (CCh) fibroblast.

In some embodiments, the expanded stem cell is derived from a fetal tissue, such as placental tissue or an umbilical cord tissue. In some embodiments, the expanded stem cell is derived from amniotic membrane. In some embodiments, the expanded stem cell is derived from adipose tissue. In some embodiments, the expanded stem cell is derived from limbal tissue. In some embodiments, the expanded stem cell is derived from bone marrow. In some embodiments, the expanded stem cell is derived from endothelial tissue. In some embodiments, the expanded stem cell is derived from limbal tissue. In some embodiments, the expanded stem cell is derived from neural tissue, In some embodiments, the expanded stem cell is derived from limbal tissue. In some embodiments, the expanded stem cell is derived from skeletal muscle. In some embodiments, the expanded stem cell is derived from the skin. In some embodiments, the expanded stem cell is derived from the digestive system. In some embodiments, the expanded stem cell is derived from the pancreas. In some embodiments, the expanded stem cell is derived from the liver. In some embodiments, the expanded stem cell is derived from the olfactory mucosa. In some embodiments, the expanded stem cell is derived from a germ cell population. In some embodiments, the expanded stem cell is derived from blood. In some embodiments, the expanded stem cell is derived from umbilical cord blood.

In some embodiments, expanded stem cells are subjected to a second expansion following the first expansion. In some embodiments, the second expansion occurs on a three-dimensional substrate. In the exemplary methods, a first expansion on Matrigel coated substrate and/or 2D Matrigel, followed by a second expansion in 3D Matrigel enables optimal expansion of isolated stem cells. In some embodiments, the three-dimensional substrate mimics the basement membrane and/or comprises components of the basement membrane, such as such as laminin, type IV collagen and heparan sulfate proteoglycan. In some embodiments, the three-dimensional substrate is a gelatinous protein mixture secreted by Engelbreth-Holm-Swarm (EHS) mouse sarcoma cells. In some embodiments, the three-dimensional substrate is Matrigel. In some embodiments, expansion on a three-dimensional substrate (e.g., a Matrigel 3D substrate) results in the isolated stem cells from the first expansion regaining expression of ESC markers. In some embodiments, expansion of isolated stem cells on a three-dimensional substrate (e.g., a Matrigel 3D substrate) in the presence epithelial cells of results in the formation of epithelial/stem cells spheres/aggregates.

In some embodiments, the expansion of the isolated stem cells is performed in a suitable medium. In some embodiments, the medium is embryonic stem cell medium, modified embryonic stem cell medium (ESCM supplemented with bFGF and LIF), supplemented hormonal epithelial medium, and/or a combination thereof. In some embodiments, the medium is supplemented with one or more growth factors. In some embodiments, the medium is supplemented with EGF, bFGF and/or LIF. In some embodiments, the medium is supplemented with an inhibitor of Rho-associated kinase (i.e. a ROCK inhibitor). In some embodiments, kinase activity is inhibited by the intramolecular binding between the C-terminal cluster of RBD domain and the PH domain to the N-terminal kinase domain of ROCK. Thus, the kinase activity is off when ROCK is intramolecularly folded.

In some embodiments, the methods comprise (a) expanding at least one of the plurality of isolated stem cells in a first culture comprising a suitable two-dimensional substrate without passing the Hayflick limit to form a plurality of expanding stem cells; and (b) isolating and expanding at least one expanding stem cell from the plurality of expanding stem cell in a second culture comprising a suitable three-dimensional substrate.

In some embodiments, the methods comprise (a) expanding at least one of the plurality of isolated stem cells in a first culture comprising a suitable two-dimensional substrate without passing the Hayflick limit to form a plurality of expanding stem cells, wherein the substrate comprises an HC-HA complex; and (b) isolating and expanding at least one expanding multipotent cell from the plurality of expanding stem cell in a second culture comprising a suitable three-dimensional substrate.

Methods of Inducing and Maintaining Pluripotency

Disclosed herein, in certain embodiments, are methods of inducing pluripotency in a cell or maintaining pluripotency of a stem cell on a substrate that comprises an HC-HA complex. As described herein, HC-HA complexes assist in the maintenance of stem cell marker expression and prevent differentiation of the cells over successive passages of a stem cell population. In addition, as described herein, HC-HA complexes promote the induction of stem cell properties in a differentiated or partially differentiated population of cells.

In certain embodiments, an HC-HA complex promotes or induces pluripotency of a differentiated or partially differentiated cell. In certain embodiments, an HC-HA complex promotes or induces pluripotency of a differentiated or partially differentiated cell compared to a differentiated or partially differentiated cell cultured in the absence of an HC-HA complex. In an exemplary method, a differentiated cell or partially differentiated cell is cultured on a substrate comprising HC-HA, whereby pluripotency is induced in the cell.

In certain embodiments, an HC-HA complex further promotes or induces pluripotency of a stem cell. In certain embodiments, an HC-HA complex further promotes or induces pluripotency of a stem cell compared to a stem cultured in the absence of an HC-HA complex. In an exemplary method, a stem cell is cultured on a substrate comprising HC-HA, whereby pluripotency is maintained in the stem cell. In an exemplary method, a stem cell is cultured on a substrate comprising HC-HA, whereby pluripotency is further induced in the stem cell.

Using genetic reprogramming with protein transcription factors, pluripotent stem cells equivalent to embryonic stem cells have been derived from human adult skin tissue. iPS cells are typically derived by transfection of certain stem cell-associated genes into non-pluripotent cells, such as adult fibroblasts. Transfection is typically achieved through viral vectors, such as retroviruses. Four key pluripotency genes essential for the production of pluripotent stem cells are Oct-3/4 (Pou5fl), Sox2, c-Myc, and Klf4. Other genes can enhance the efficiency of induction. In some studies, Oct4, Sox2, Nanog, and Lin28 have been employed to induce pluripotency. In certain instances, after 3-4 weeks, small numbers of transfected cells begin to become morphologically and biochemically similar to pluripotent stem cells, and are typically isolated through morphological selection, doubling time, or through a reporter gene and antibiotic selection.

In some embodiments, methods are provided for inducing pluripotency in a differentiated or partially differentiated cell using heterologous expression of fewer than four of the essential transcription factors Oct-3/4 (Pou5fl), Sox2, c-Myc, and Klf4. In some embodiments, a method for inducing pluripotency is provided where use of an HC-HA enhances the induction of pluripotency of a differentiated or partially differentiated cell that expresses at least one of Oct-3/4 (Pou5fl), Sox2, c-Myc, and/or Klf4 by heterologous gene transfer. In some embodiments, a method for inducing pluripotency is provided where use of an HC-HA enhances the induction of pluripotency of a differentiated or partially differentiated cell that expresses one, two or three factors selected from among Oct-3/4 (Pou5fl), Sox2, c-Myc, and/or Klf4 by heterologous gene transfer.

In some embodiments, a differentiated or partially differentiated cell is transduced to express one or more of Oct-3/4 (Pou5fl), SOX2, c-Myc, and Klf4; and the transduced cell is cultured on a substrate comprising an HC-HA complex. In some embodiments, a differentiated or partially differentiated cell is transduced to express at least one of Oct-3/4 (Pou5fl), SOX2, c-Myc, and Klf4; and the transduced cell is cultured on a substrate comprising an HC-HA complex. In some embodiments, a differentiated or partially differentiated cell is transduced to express one, two or three of Oct-3/4 (Pou5fl), SOX2, c-Myc, and Klf4; and the transduced cell is cultured on a substrate comprising an HC-HA complex. In some embodiments, a differentiated or partially differentiated cell is transduced to express Oct-3/4 (Pou5fl), SOX2, c-Myc, and Klf4; and the transduced cell is cultured on a substrate comprising an HC-HA complex.

In some embodiments, a differentiated or partially differentiated cell is transduced with a viral vector containing one or more genes encoding one or more of Oct-3/4 (Pou5fl), SOX2, c-Myc, and Klf4. In some embodiments, a differentiated or partially differentiated cell is transduced with two or more viral vectors containing one or more genes encoding one or more of Oct-3/4 (Pou5fl), SOX2, c-Myc, and Klf4.

In some embodiments, the HC-HA complex reduces to time of induction of pluripotency in the transduced cell compared to a transduced cell cultured in the absence of HC-HA. In some embodiments, the HC-HA complex increases the percentage of transduced cells that are induced to pluripotency in a population of transduced cells compared to transduced cells cultured in the absence of HC-HA compared to a transduced cell cultured in the absence of HC-HA. In some embodiments, the HC-HA complex enhances the level of pluripotency in the transduced cell. In some embodiments, the HC-HA complex decreases the number of heterologous transcription factors required for induction of pluripotency in the transduced cell.

Uses of Multipotent Stem Cells

Therapeutic Uses

For any or all of the following uses, the isolated or expanded stem cells obtained by any of the methods provided herein are administered by any suitable means. For example, they are administered by infusion (e.g., into an organ or bone marrow) or they are administered by a wound covering or bandage. Exemplary methods for the transplantation of stem cells are known in the art, including combination therapies to limit the rejection of the administered stem cells. In some embodiments, such methods are employed in combination with the therapeutic uses provided herein.

In some embodiments, the isolated or expanded stem cells are administered in combination with a pharmaceutically acceptable excipient. In some embodiments, the isolated or expanded stem cells are administered in combination with a carrier. In some embodiments, the isolated or expanded stem cells are administered in combination with an HC-HA complex as a carrier. In some embodiment the HC-HA complex is a native HC-HA complex or is a reconstituted HC-HA complex. Exemplary HC-HA complexes are described elsewhere herein. In some embodiments, such HC-HA complexes are administered in combination with an isolated of expanded stem cell provided herein.

In some embodiments, the isolated or expanded stem cells obtained by any of the methods described herein are used for transplantation into an individual in need thereof. In some embodiments, the isolated or expanded stem cells obtained by any of the methods described herein are used for transplantation into an individual in need of a stem cell therapy. In some embodiments, the isolated or expanded stem cells obtained by any of the methods described herein are used for transplantation into an individual in need of a stem cell therapy to regenerated a damaged tissue.

In some embodiments, the cells are isolated from one individual and transplanted into another individual. In some embodiments, such transplantation is used to regenerate a damaged tissue.

In some embodiments, the isolated or expanded stem cells disclosed herein are transplanted into the bone marrow of an individual whose bone marrow does not produce an adequate supply of stem cells. In some embodiments, the isolated or expanded stem cells disclosed herein are transplanted into an individual whose bone marrow does not produce an adequate supply of white blood cells. In some embodiments, the isolated or expanded stem cells disclosed herein are transplanted into an individual whose bone marrow does not produce an adequate supply of red blood cells. In some embodiments, the isolated or expanded stem cells disclosed herein are transplanted into an individual whose bone marrow does not produce an adequate supply of platelets. In some embodiments, the isolated or expanded stem cells disclosed herein are transplanted into an individual that suffers from anemia. In some embodiments, the isolated or expanded stem cells disclosed herein are transplanted into the bone marrow of an individual following chemotherapy and/or radiation therapy.

In some embodiments, the isolated or expanded stem cells disclosed herein are transplanted into an individual suffering from neurological damage. In some embodiments, the isolated or expanded stem cells disclosed herein are transplanted into an individual to regenerate neurons.

In some embodiments, the isolated or expanded stem cells disclosed herein are transplanted into an individual suffering from a neurodegenerative disease. In some embodiments, the isolated or expanded stem cells disclosed herein are transplanted into an individual to treat Parkinson's disease. In some embodiments, the isolated or expanded stem cells disclosed herein are transplanted into an individual to treat Alzheimer's disease.

In some embodiments, the isolated or expanded stem cells disclosed herein are transplanted into an individual to treat a stroke.

In some embodiments, the isolated or expanded stem cells disclosed herein are transplanted into an individual to treat traumatic brain injury.

In some embodiments, the isolated or expanded stem cells disclosed herein are transplanted into the spinal cord of an individual suffering from a spinal cord injury. In some embodiments, the isolated or expanded stem cells disclosed herein are transplanted into the spinal cord of an individual to treat paralysis (e.g., due to a spinal cord injury). In some embodiments, the isolated or expanded stem cells disclosed herein are transplanted into an individual to treat amyotrophic lateral sclerosis (ALS). In some embodiments, the isolated or expanded stem cells disclosed herein are transplanted into an individual to treat multiple sclerosis.

In some embodiments, the isolated or expanded stem cells disclosed herein are transplanted into an individual to treat heart damage. In some embodiments, the isolated or expanded stem cells disclosed herein are transplanted into an individual to treat/regenerate damaged heart muscle. In some embodiments, the isolated or expanded stem cells disclosed herein are transplanted into an individual to treat/regenerate damaged blood vessels (i.e., to promote angiogenesis).

In some embodiments, the isolated or expanded stem cells disclosed herein are transplanted into an individual to treat deafness. In some embodiments, the isolated or expanded stem cells disclosed herein are transplanted into an individual to regenerate hair cells of the auditory system.

In some embodiments, the isolated or expanded stem cells disclosed herein are transplanted into an individual to treat blindness.

In some embodiments, the isolated or expanded stem cells disclosed herein are transplanted into an individual to treat a skin wound. In some embodiments, the isolated or expanded stem cells disclosed herein are transplanted into an individual to treat a chronic skin wound. In some embodiments, the isolated or expanded stem cells disclosed herein are administered to the individual via a wound covering or bandage.

In some embodiments, the isolated or expanded stem cells disclosed herein are used to treat an autoimmune disease. In some embodiments, the isolated or expanded stem cells disclosed herein are administered to an individual with an autoimmune disease. In some embodiments, the autoimmune disease is selected from diabetes mellitus, psoriasis, Crohn's disease, or any combination thereof.

In some embodiments, the isolated or expanded stem cells disclosed herein are used to treat or prevent transplant rejection, for example they are administered to an individual receiving a bone marrow transplant, a kidney transplant, a liver transplant, a lung transplant. In some embodiments, the isolated or expanded stem cells disclosed herein are administered to the individual with psoriasis via a wound covering or bandage. In some embodiments, the isolated or expanded stem cells disclosed herein are used to treat or prevent Graft-versus-Host disease.

In some embodiments, the isolated or expanded stem cells disclosed herein are transplanted into an individual to treat idiopathic pulmonary fibrosis.

In some embodiments, the isolated or expanded stem cells disclosed herein are transplanted into an individual to treat a cancer.

In some embodiments, the isolated or expanded stem cells disclosed herein are transplanted into an individual to treat aplastic anemia.

In some embodiments, the isolated or expanded stem cells disclosed herein are transplanted into an individual to reconstitute the immune system of an HIV positive individual.

In some embodiments, the isolated or expanded stem cells disclosed herein are transplanted into an individual to treat liver cirrhosis.

In some embodiments, the isolated or expanded stem cells disclosed herein are transplanted into an individual to treat an inflammatory disorder.

In some embodiments, the isolated or expanded stem cells disclosed herein are transplanted into an individual to generate or regenerate epithelial tissue. In some embodiments, the isolated or expanded stem cells disclosed herein are transplanted into an individual to generate or regenerate skin, bone, teeth or hair. In some embodiments, the isolated or expanded stem cells disclosed herein are transplanted into an individual to treat baldness. In some embodiments, the isolated or expanded stem cells disclosed herein are transplanted into an individual to regenerate missing teeth.

Niche for Stem Cell Culture

In some embodiments, the isolated or expanded stem cells disclosed herein are used as niche cells to support the growth of epithelial progenitor cells. In some embodiments, the isolated or expanded stem cells disclosed herein are used as niche cells in vivo to support the growth of epithelial progenitor cells, for example to treat a disease, disorder and/or condition characterized by epithelial progenitor cell failure. In some embodiments, the isolated or expanded stem cells disclosed herein are used as niche cells to support the growth of epithelial progenitor cells in vitro (i.e., in cell culture). In some embodiments, the isolated or expanded stem cells disclosed herein are used as niche cells to support the growth of epithelial progenitor cells into tissue grafts.

Bioreactor for Generation of HC-HA Complex Containing TSG-6, PTX3, and/or Small Leucine-Rich Proteins (SLRPS)

In some embodiments, the isolated or expanded stem cells disclosed herein are used as a bioreactor source for the isolation of HC-HA complexes. As described herein, the amniotic membrane epithelial cells (hAMEC) and amniotic membrane stromal cells (hAMSC) express both IαI and TSG-6 to produce HC-HA complexes. In some embodiments, stem cells are isolated from the amniotic membrane and employed for the production of HC-HA complexes. In some embodiments, the amniotic membrane is derived from the placental or the umbilical cord. In some embodiments, the stem employed for the production of HC-HA complexes is an amniotic membrane stem cell. In some embodiments, the stem employed for the production of HC-HA complexes is an umbilical cord stem cell derived from the umbilical cord stroma and/or Wharton's jelly.

Non-limiting examples of methods of isolation of HC-HA complexes are disclosed herein and, for example, in U.S. Patent Pub. Nos. US2012-0083445, US2012-0083445, and International PCT Pub. No. WO 2012/170905, all of which are expressly incorporated herein by reference. In some embodiments, the isolated HC-HA complexes are employed for in vitro or in vivo methods. In some embodiments, the isolated HC-HA complexes are employed for treatment of a disease or disorder. Methods comprising administration of an HC-HA complexes for therapy are disclosed, for example, in U.S. Patent Pub. Nos. US2012-0083445, US2012-0083445, and International PCT Pub. No. WO 2012/170905, all of which are expressly incorporated herein by reference. In some embodiments, an HC-HA complex isolated from an isolated or expanded stem cell disclosed herein is used to inhibit at least one of the following: scarring, inflammation, immune reaction leading to autoimmune or immune rejection, adhesion, angiogenesis or is used to treat conditions requiring cell or tissue regeneration.

In some embodiments, the isolated HC-HA complexes comprise TSG-6. In some embodiments, the isolated HC-HA complexes comprise PTX3. In some embodiments, the isolated HC-HA complex comprises a small leucine rich proteoglycan (SLRP). In some embodiments, the isolated HC-HA complex comprises TSG-6, PTX3, and a small leucine rich proteoglycan (SLRP). In some embodiments, the small leucine-rich proteoglycan is selected from among decorin, biglycan, fibromodulin, lumican, PRELP (proline arginine rich end leucine-rich protein), keratocan, osteoadherin, epipycan, and osteoglycin. In some embodiments, the isolated HC-HA complex comprises TSG-6, PTX3, and a small leucine rich proteoglycan (SLRP).

EXAMPLES

Example 1

Expression of Markers of ESC and Angiogenesis Progenitors in AM In Vivo

Isolation of multi-potent stem cells (SCs) with highest purity and cell numbers from a given tissue is the first step toward cell expansion in vitro. Before devising a method for isolation and expansion of amniotic membrane (AM) cells, it was important to identify key factors for maintaining SCs in order to gauge the success of such expansion. The conventional method of isolating and expanding functional mesenchymal stem cells (MSCs) are defined by the International Society for Cellular Therapy (ISCT) as meeting the following set of minimal criteria: (1) adherent to plastic (PL) in a basal medium containing serum, while non-adherent cells are normally discarded, (2) expression of surface marker profile comprising $CD105^+$, $CD73^+$, CD90+, $CD45^-$, $CD34^-$, $CD14^-$ or $CD11b^-$, $CD79a^-$ or $CD19^-$, and HLA-DW, and (3) tri-lineage differentiation potential to osteoblast, adipocyte, or chondrocyte developmental pathways. Isolation of MSCs from different parts of organs and tissues has been demonstrated based on the above criteria. Several other studies have demonstrated that cells isolated from tissue such as limbus, placenta, and bone marrow can be expanded on coated substrate in serum-free medium or in reduced serum containing medium, yet such cells demonstrated more differential potential for vascular endothelial cells, neuronal cells or hepatocytes. Perivascular pericytes have been regarded as a key source of MSC in different tissues and in in vitro studies have demonstrated potential to differentiate into vascular endothelial cells. Although AM is transparent and avascular, cells isolated from human AM (hAM) have previously been shown with differential potential into endothelial cells. In this experiment, the expression of embryonic stem cell (ESC) and angiogenic markers in the AM was examined.

AM consists of a single layer of epithelial cells (hAMEC), and a compacted and a spongy stromal layer. 1×1 $cm^2$ square pieces of intact human amnion/chorion tissue from at least two different donors were embedded and sectioned to 6 μm thickness. Immunohistochemistry was performed using standard protocols on the cross sectioned tissue using antibodies against embryonic stem cell (ESC) markers (Oct4, Nanog, Sox2 (SRY (sex determining region Y)-box 2), Rex1 (Zfp42) and SSEA4 (stage-specific embryonic antigen-4), pericyte markers (NG2 (neuron-glial antigen 2/Chondroitin sulfate proteoglycan 4(CSPG4)), PDGFR-β (Platelet-derived growth factor receptor B), and α-SMA (α-smooth muscle actin)), and angiogenic markers (CD133/2, FLK-1 (VEGF-R2, Ly-73), vWF (von Willebrand factor), CD34, CD31 (PE-CAM-1) and CD146. Staining with pan-cytokeratin (PCK) and vimentin (vim) was used to distinguish the hAMEC from the stromal layer.

hAMECs uniformly express embryonic markers, Oct4, Sox2, Rex1, and heterogeneously express Nanog (FIG. 1). hAMECs also uniformly express pericyte markers, NG2 and PDGF-β but heterogeneously express α-SMA. Positive expression of angiogenic markers FLK-1, vWF, CD34, and CD31 but negative expression of CD133 and CD146 also was observed. The data suggest that native hAMECs express ESC, angiogenic markers in vivo.

Presence of ESC and Angiogenic Expressing Cells in hAMEC by Cytospin.

Figure 2:
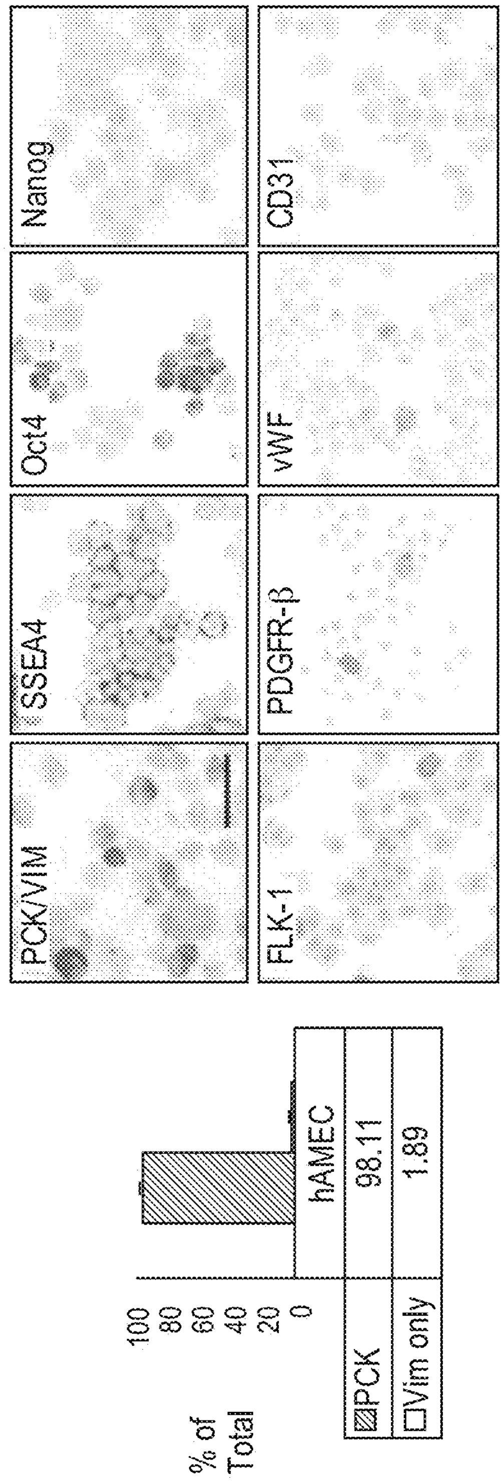
FIG. 2 illustrates the percentage of cell purity (left) and the presence of ESC and angiogenesis markers (right) in isolated hAMECs after collagenase followed by dispase digestion method.
Figure 3A:
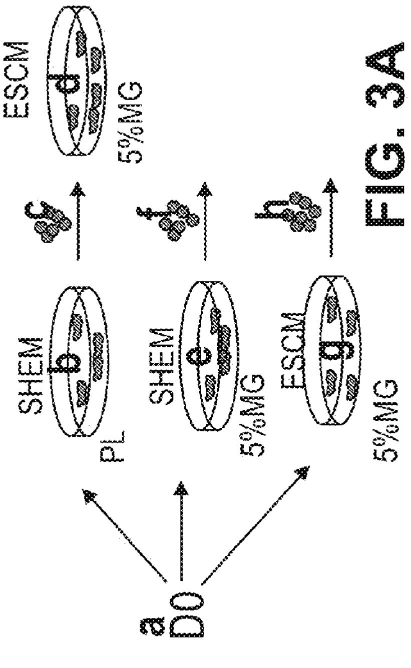
FIG. 3 illustrates the effects of different culture conditions on hAMEC, SHEM versus ESCM on percentage of cell attachment (A-F).
Figure 3B:
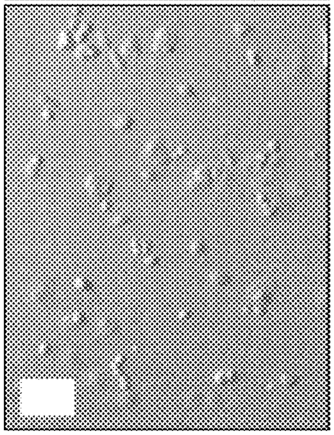
Figure 3C:
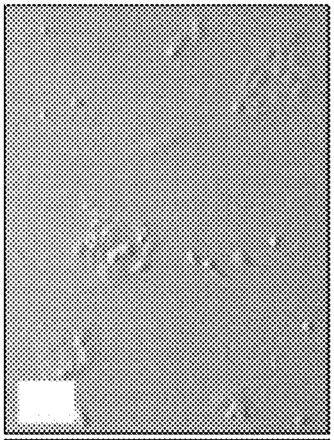
Figure 3D:
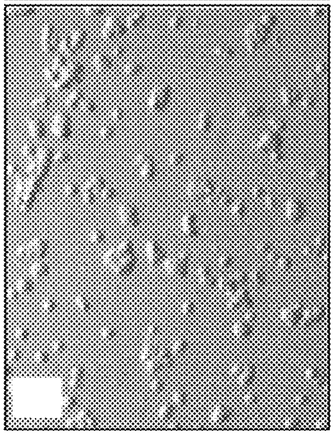
Figure 3E:
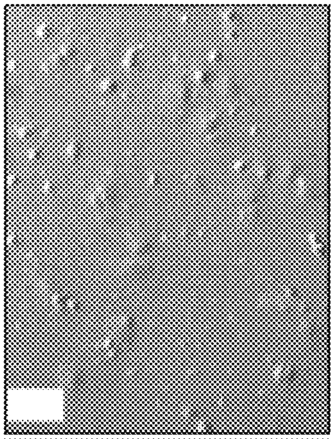
Figure 3F:
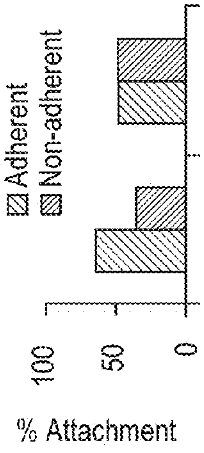

The purity of hAMEC from collagenase follow by dispase method was confirmed by cytospin, double immunostaining and showed that the percentage of PCK+ expression was 98.11±0.53% and Vim+/PCK− expressing cells was 1.89±0.53% (FIG. 2). Cytospin confirmed PCK positive cells coexpress uniformly with SSEA4, occasionally express Oct4 and weakly express Nanog, very few PCK positive cells coexpress with FLK-1+, very few cells expressing in PDGFR-β, vWF and negative expression to CD31.

Example 2

Populations of hAMEC Expressing ESC and Angiogenesis Markers Preferentially Isolated on 5% Matrigel The extracellular matrix (ECM), once thought to function only as a scaffold to maintain tissue and organ structure, regulates many aspects of cell behavior, including cell proliferation and growth, survival, change in cell shape, migration, and differentiation. The ECM serves directly as a stem cell niche or indirectly in conjunction with niche cells in regulating ESC and other adult stem cells (SCs). In vitro, isolated limbal SCs along with niche cells can be maintained on 3D Matrigel (MG). In addition, studies have shown that bone marrow derived mesenchymal stem cells co-cultured on ECM improves proliferation and differentiation capacity compare to plastic alone. In this experiment, whether MG selectively preserves not only mesenchymal stem cells (MSC) but also other progenitor cells was examined.

Our previous data demonstrated that isolated limbal SCs along with its niche cells can be maintained on 3D matrigel (Xie et al. (2012) *Invest Ophthalmol V is Sci.* 53:279-286). Other studies also reported bone marrow derived mesenchymal stem cells co-cultured on ECM improves proliferation and differentiation capacity compared to plastic (see Lindner et al. (2010) *Cytotherapy* 12:992-1005; Matsubara et al. (2004) *Oncogene* 23:2694-2702). It remains unclear whether MG selectively preserves not only MSC but also other progenitor cells as a result. Isolation of hAMEC from placenta in the past has followed the MSC standard protocol with modification of addition of different growth factors such as EGF. We speculated that the discarded fraction of non-adherent cells, may contain progenitors that prefer to adhere to some matrix components. Our preliminary data showed that a population subset of progenitors from hAMEC can be maintained on coated MG in embryonic stem cell culture medium (ESCM) on plastic tissue culture dishes (PL) expressing high amounts of ESC markers, such as Oct4, Nanog, Sox2, and Nestin and CD34+ expression when compared to the control hAMEC cultured in supplemental hormonal epithelial medium on PL in SHEM for 14 days (Xie et al. (2011) *Stem Cells* 29(11):1874-85) (ESCM is made of knockout Dulbecco's modified Eagle medium (DMEM) supplemented with 20% knockout serum, 5 μg/ml insulin, 5 μg/ml transferrin, 5 ng/ml selenium, 1 mM L-glutamine, 0.1 mM β-mercaptoethanol, 1% nonessential amino acid, 50 μg/ml gentamicin, and 1.25 μg/ml amphotericin B; SHEM is made of Dulbecco's Modified Eagle Medium/Ham's F12 nutrient mixture (1:1, v/v) (Invitrogen), 5% (v/v) fetal bovine serum (FBS) (Invitrogen), 0.5% (v/v) dimethyl sulfoxide (DMSO), 2 ng/ml EGF, 5 μg/ml insulin, 5 μg/ml transferrin, 5 ng/ml sodium selenite, 0.5 μg/ml hydrocortisone, 0.1 nM cholera toxin, 50 μg/ml gentamicin, 1.25 μg/ml amphotericin B). Cells expressing CD34 had not previously been identified from MSC expanded from either AM or non-AM tissues. qPCR expression of ESC markers under different culture conditions in adherent and non-adherent cells was further investigated.

Fresh AM sheets were gently peeled off from placenta using forceps and washed three times with Hank's Balanced Salt Solution (HBSS)×1 to remove remaining blood. AM was then transferred to a nylon paper with AM epithelial side up and cut into 5×5 $cm^2$ sheets. The sheets were digested with 10 mg/ml dispase at 37° C. for 30-60 min followed by manual removal of epithelial cells (i.e. hAMEC) by a cement spatula under a dissecting microscope. All epithelial cells were collected and treated with hyaluronidase (HAase; Seikagaku Biobusiness Corporation (Tokyo, Japan)) (200 μg/ml) and collagenase (2 mg/ml) for 2 h at 37° C. and separated into single cells by treatment with TrypLE™ (Invitrogen) for 10 min.

Total hAMECs AM epithelium and stroma cells, respectively, were counted and samples of the cell lysates were collected for protein and RNA analysis. A sample of total hAMECs was subjected to cytospin and immunostaining to determine the % of ES positive cells (FIG. 2).

Figure 4A:
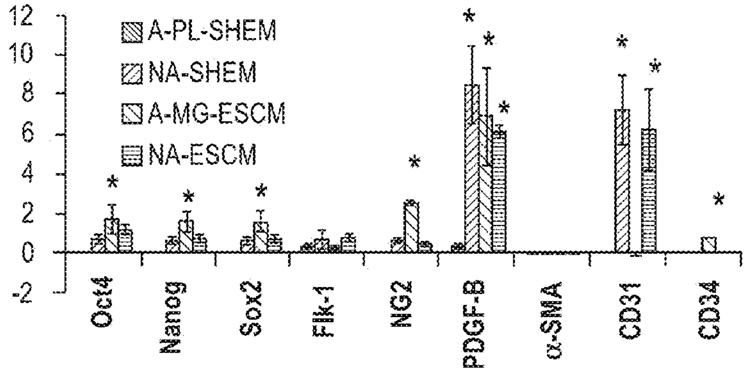
FIG. 4 illustrates the relative expression of ESC and angiogenesis markers and immunostaining in adherent and non-adherent hAMEC with or without 5% coated matrigel. hAMEC were manually scrapped after enzymatic digestion in 10 mg/ml dispase for 3 h. Total hAMEC were seeded at density 5×104/cm2 in SHEM on 6-well plastic (PL) for 72 h, the cell lysate and cytospin of attached (A-PL-SHEM) and non-attached cells (NA-SHEM) cells were collected and labeled as A-PL-SHEM and NA-SHEM. Similarly, hAMEC were seeded directly on 5% MG in ESCM for 72h, the cell lysate and cytospin of attached (A-MG-ESCM) and non-attached cells (NA-ESCM) were collected in similar fashion. Percentage of attachment cells or non-attachment cells of total seeding were calculated (A). Relative RNA expression of ESC and angiogenic markers were compared(B). Immunostaining of ESC markers, Nanog and Oct4.

To test whether the non-adherent cells in SHEM contains cells that express ESC markers and preferentially to adhere on 5% Matrigel (MG), the isolated total hAMEC(a) were seeded at $1\times10^5/cm^2$ in SHEM without (b, B) or with 5% MG (e) and ESCM+EGF(g, D) on coated 5% MG in triplicate of 6 well culture dish for 72 h under a humidified atmosphere of 5% $CO_2$ at 37° C. (A) At 72 h, the non-adherent cells from each culture condition were collected (c, f, h) in which non-adherent cells from SHEM further culture in ESCM+EGF medium on 5% MG (d, C) for additional 72 h. Cell lysates from both adherent and non-adherent cells were harvested for RNA analysis (FIG. 3). Non-adherent cells from (c, f, h) and adherent cells (b, e, g) were collected by cytospin to confirm positive staining of Oct4 and Nanog positive cells are enriched in non-adherent (c) and adherent (b, g) when compare to total cells. Immunostaining of PCK and vimentin staining showed the percentage of hAMECs fraction were 99.6% of PCK+ cells (data not shown) When the percentage of cell attachment was compared, it was found that the number of cells that attached to plastic (PL) in ESCM+EGF was significantly higher than in SHEM. Compare the relative RNA expression of HAEC cells on D0, the adherent hAMEC on either PL in SHEM (FIG. 4A, A-PL-SHEM) exhibited significantly low expression of ESC markers in contrast to the adherent cells on 5% MG in ESCM+EGF (A-MG-ESCM) showed a significantly higher expression of ESC (Oct4, Nanog, Sox2) and pericyte markers (NG2, PDGF-B).(n=3, $p<0.05$). The non-adherence cells in both SHEM(NA-SHEM) and ESMC+EGF (NA-ESCM) showed a significantly higher expression of angiogenic markers indicating that Matrigel and ESCM synergistically promote expression of these markers.

Figure 4B:
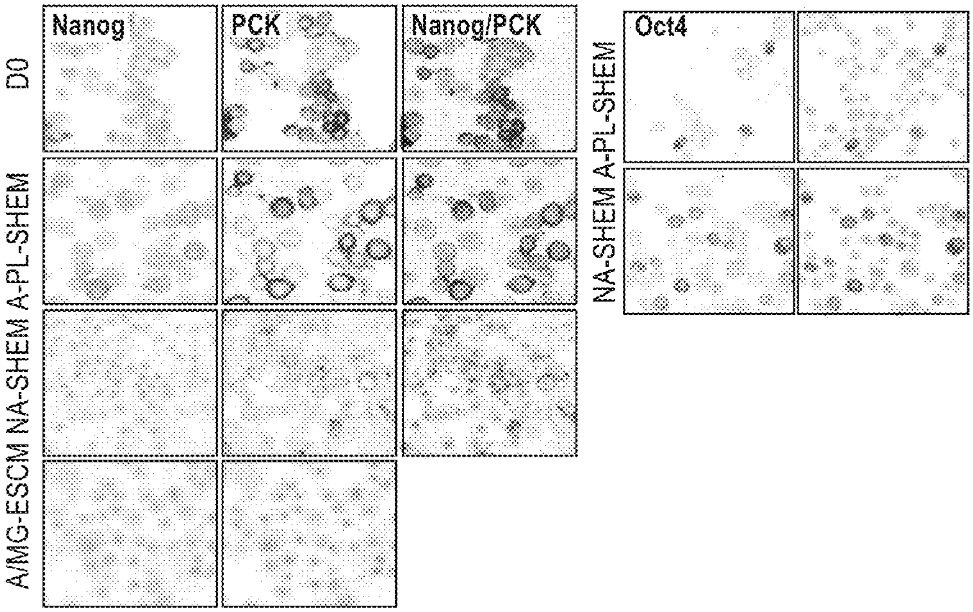
Figure 5A:
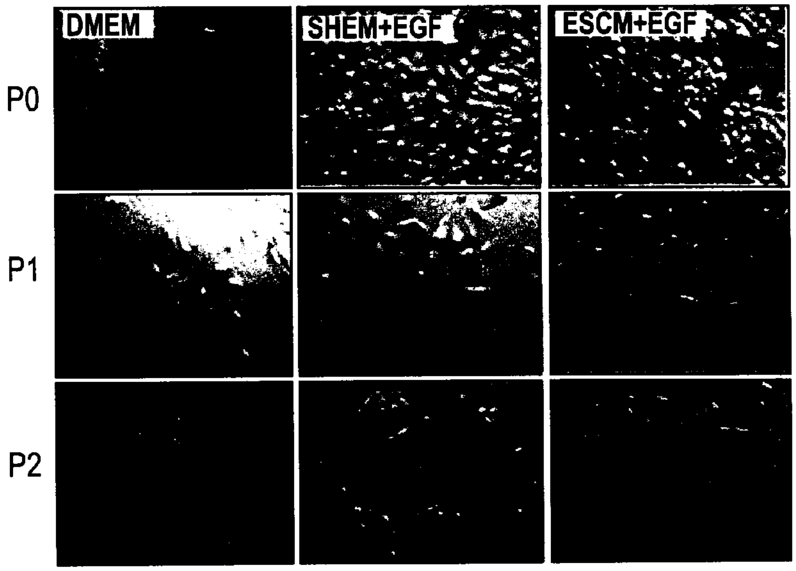
FIG. 5 illustrates the effect of EGF on hAMEC in SHEM and ESCM medium (A) and relative ESC and angiogenic marker expression (B-N).
Figure 5B:
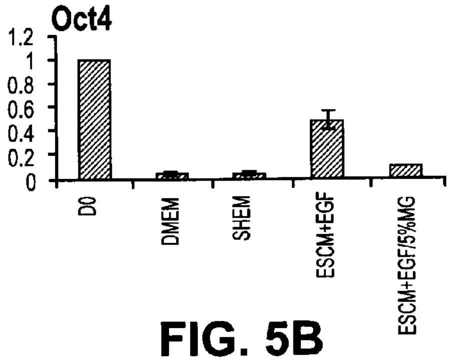
Figure 5C:
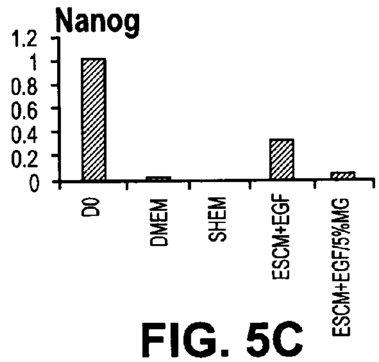
Figure 5D:
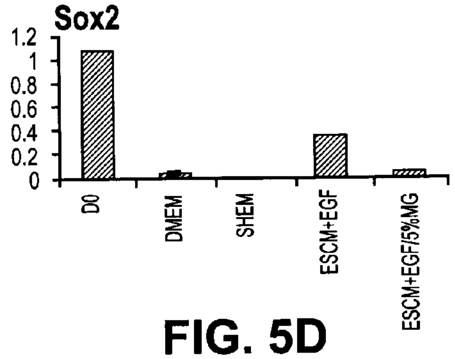
Figure 5E:
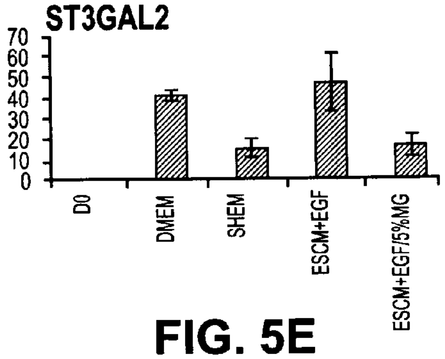
Figure 5F:
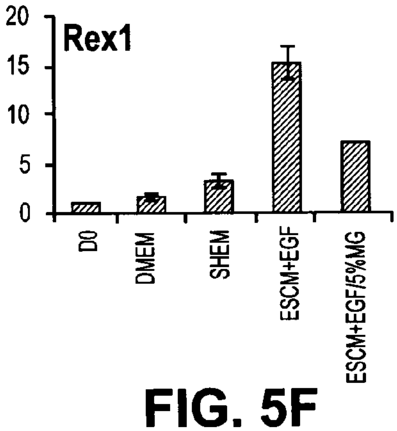
Figure 5G:
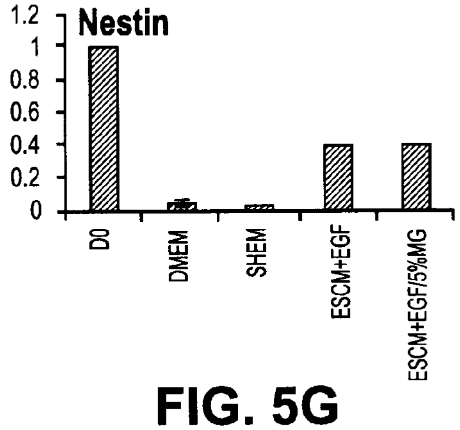
Figure 5H:
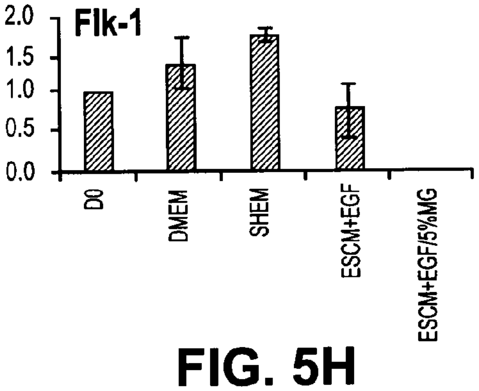
Figure 5I:
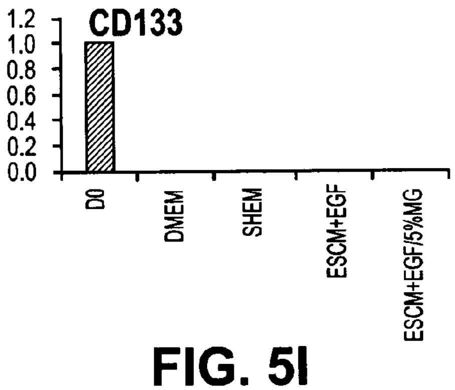
Figure 5J:
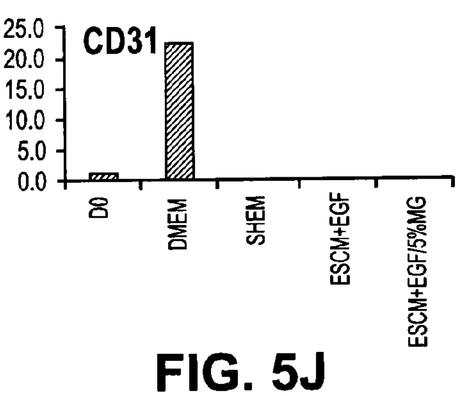
Figure 5K:
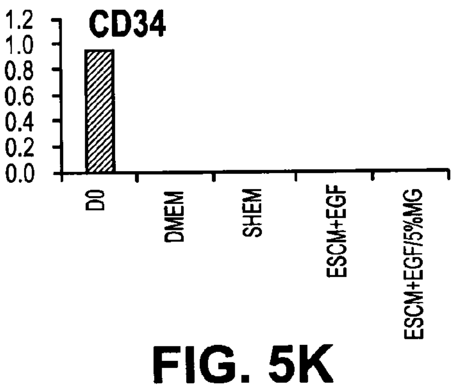
Figure 5L:
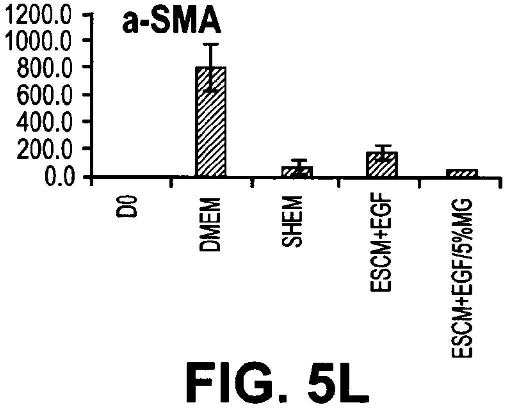
Figure 5M:
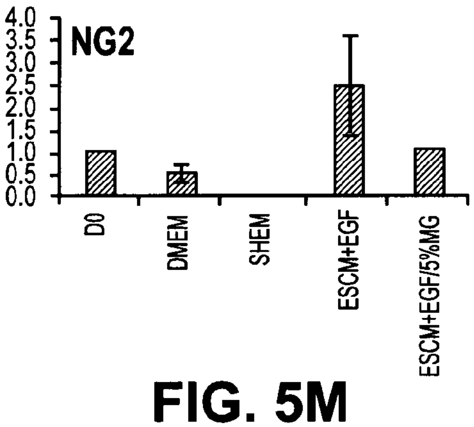
Figure 5N:
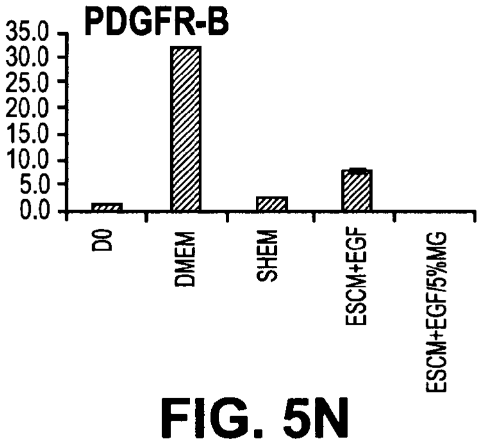

When compared to total hAMEC, A-PL-SHEM preserved expression of CD34, while non-adherent cells maintain expression of the other markers tested (FIG. 4). In addition, compared to A-PL-SHEM, non-adherent hAMEC cultured in SHEM that were subsequently cultured on 5% MG in ESCM consistently showed marked upregulation of the all markers tested except for CD34. These data indicate that non-adherent cells cultured in SHEM on PL can better preserve expression of these markers by subsequent culturing on 5% MG in ESCM. In addition, compared to cells directly seeded on 5% MG in ESCM, non-adherent cells from PL cultured in SHEM that were subsequently seeded on 5% MG in ESCM expressed more of the above markers except for CD34 and NG2, indicating that non-adherent cells on PL in SHEM are a different subpopulation that retains the expression of these markers. Immunostaining of protein expression of Nanog expressed in nucleus and cytoplasm.

When cultured in SHEM on PL (FIG. 4B, A-PL-SHEM), Nanog was expressed in cytosol in adherent cells while the non-adherent cells(NA-SHEM) were expressed in nucleus. Interestingly, Nanog expression was mostly found in nucleus of adherent cells in ESCM on 5% MG (FIG. 4B, A-MG-ESCM) suggesting Nanog expressing cells in nucleus can be isolated from ESCM on 5% MG. When compared to Oct4 expression, A-PL-SHEM contain less Oct4+ cells than in A-MG-ESCM. The expression of Oct4 was preferentially found in cells isolated from non-adherent fraction than adherent fraction in PL-SHEM; enriched of Oct4 expressing cells can be achieved by culture in ESCM on 5% MG.

Example 3

Conventional Adherent Cells on Plastic Promotes Cells to an Angiogenic Phenotype in Serum Containing Medium Use of a reduced level of serum (FBS) and addition of growth factors such as EGF in isolating SC and MSC from non-AM tissues have been shown to extend passage number of the culture. This is consistent with our previous success of expanding hAMEC to P8 in serum-reduced media. In this experiment, the induction of angiogenesis in hAMEC cultured in SHEM media was compared to that in DMEM/10% FBS with EGF (Miki et al. 2005 Stem Cells 23:1549-1559).

Isolation of hAMEC was performed as described in the previous Example. Total isolated hAMEC were seeded at density of $5\times10^5/cm^2$ in 6 well plates in SHEM, DMEM/10% FBS, ESCM+10 ng/ml EGF or ESCM+10 ng/ml EGF on 5% MG. On day 8 of each passage, cell numbers were determined and cumulative numbers of cell doublings (NCD) were calculated by comparing to the cell number at P0. Cells were continually passaged every 8 days until cell number showed no increment of cell doubling times. Medium were changed every 3 days. Samples of cells were collected at day 0 and at each passage for analysis of expression of ESC Markers (Oct4, Nanog, Sox2, Nestin, ST3GAL2 and Rex1), angiogenic markers (Flk-1, CD133, CD31 and CD34, PDGF-R, α-SMA, NG2, and CD146) and MSC markers CD73, CD90, CD105 and CD44 as determined by qPCR. Cell morphology was assayed by phase contrast microscopy at each passage (FIG. 5).

At P0, both SHEM and DMEM/10% FBS cultures generated uniformly monolayer of cobblestone epithelial cells (FIG. 5). The cell size from culturing in DMEM/10% FBS was enlarged during passages; however, the cells ceased proliferation at P2. In contrast, monolayers of small cobblestone epithelial cells were maintained in SHEM until P2. At P3, heterogeneous mesenchymal clones emerged from large cobblestone epithelial cells and turned into more homogenous mesenchymal morphology at P3-P6. These results indicated that SHEM containing EGF and reduced serum promotes prolonged cell passage. In contrast, DMEM/10% FBS may require additional growth factors to promote cell proliferation.

Compared to day 0, the expression of all the ESC markers, except the ST3GAL2 and Rex1, derived from cells cultured in either DMEM/10% FBS or SHEM was significantly less at p1, indicating that neither DMEM/10% FBS nor SHEM promote ESC marker expression at early passage.

Compared to day 0, the expression of angiogenic markers, FLK-1 CD31, α-SMA, PDGFR-B were promoted in the DMEM/10% FBS cultured cells while expression of CD133, CD34 were lost at p1. Thus, DMEM/10% FBS promote angiogenic differentiation; however, the cells could not be passaged beyond p2. In comparison, the expression of angiogenic markers, FLK-1, α-SMA and PDGFR-B were promoted in SHEM cultured cells, while CD133, CD34, CD31, NG2 were lost at early passages. Thus, SHEM also promotes angiogenic differentiation and also can be further passaged until p6.

All ESC markers were significantly upregulated on PL in ESCM+EGF cultured cells compared to serum containing DMEM/10% FBS and SHEM cultured cells. However, ESCM+EGF with 5% MG did not promote ESC marker expression. Thus, ESCM better preserves ESC marker expression on PL compared to serum containing medium, DMEM/10% FBS and SHEM on PL, but not on MG.

When compared to control DMEM/10% FBS without MG on passage 2, all angiogenic markers including, FLK-1, α-SMA, NG2, PDGFR-B were maintained while CD133, CD31, CD34 were significantly diminished. Thus, expression of angiogenic markers better maintained in serum free medium on PL and can be only further passage until p2.

In summary, when hAMEC are cultured in both serum containing media (DMEM/10% FBS or SHEM) on PL, expression of ES markers were significantly decreased with increasing angiogenic markers. When compared to DMEM/10% FBS on PL, ES markers and angiogenic markers in serum free ESCM+EGF can be better maintained. Additional coated MG in ESCM did not improve ES or angiogenic marker expression.

Figure 6A:
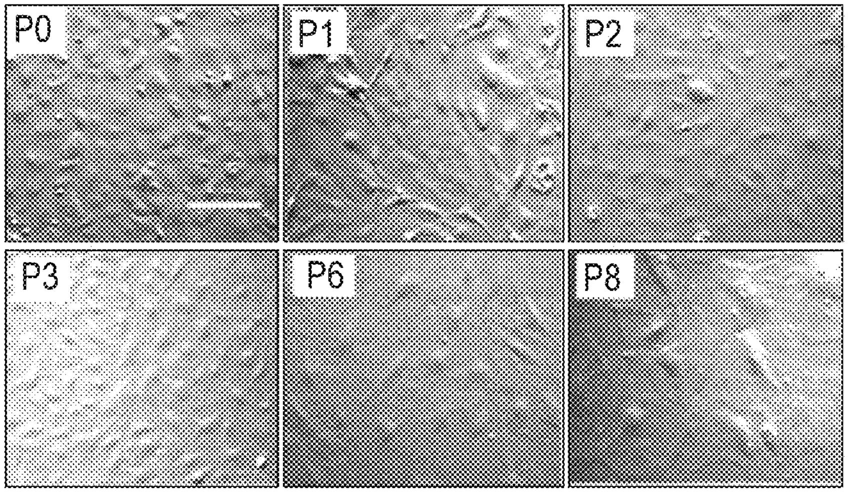
FIG. 6 illustrates cell morphology of hAMEC cultured in SHEM during successive passages and the relative ESC and angiogenic and MSSC marker expression. (A) Phase contrast photographs of hAMEC cultured over successive passages in DMEM/FBS10% on plastic, SHEM on plastic, or ESCM+EGF on plastic, (B) relative expression of ESC and angiogenesis markers as determined by qPCR in hAMEC cultured in DMEM/10% FBS on plastic, SHEM+EGF on plastic, or ESCM+EGF on 5% MG.
Figure 6B:
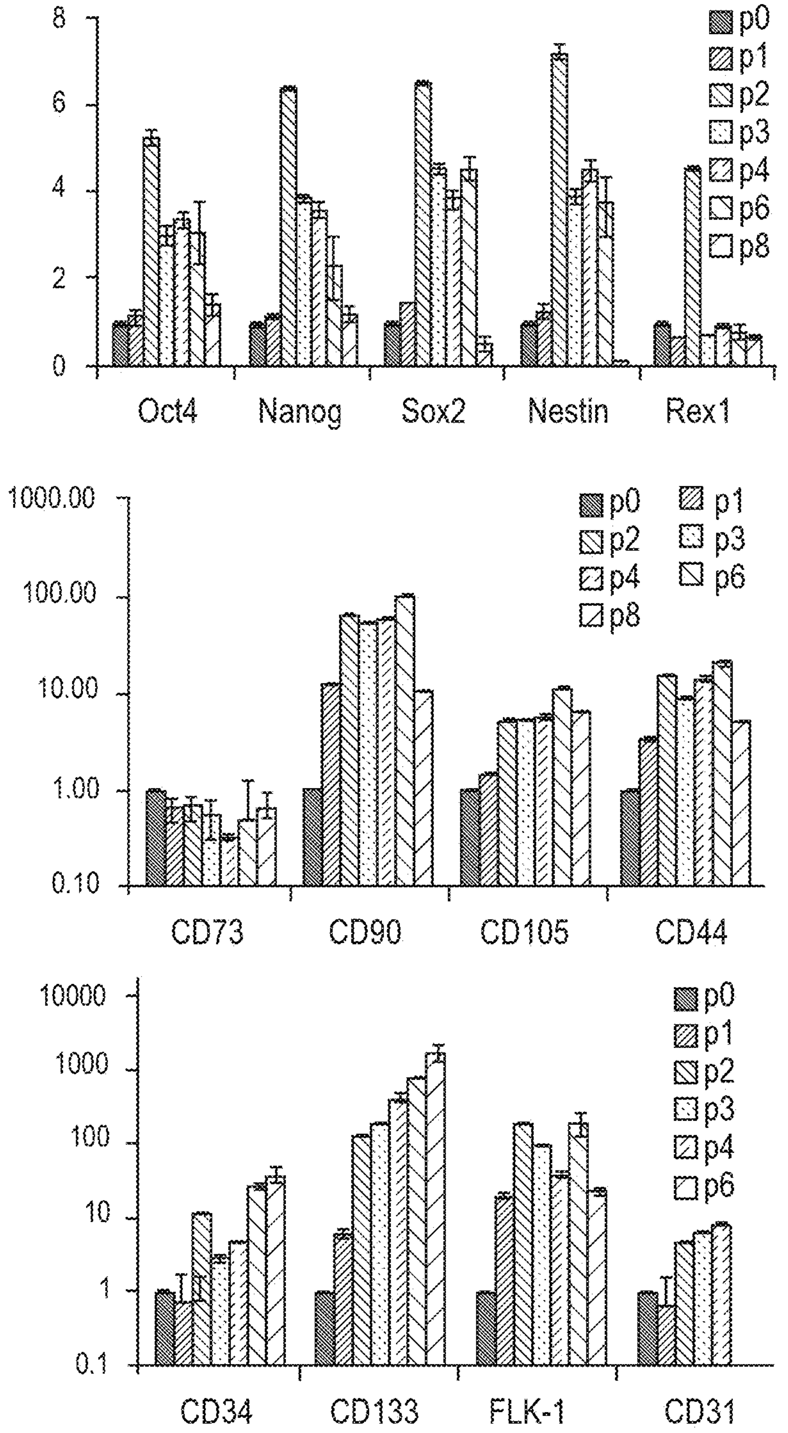
Figure 7A:
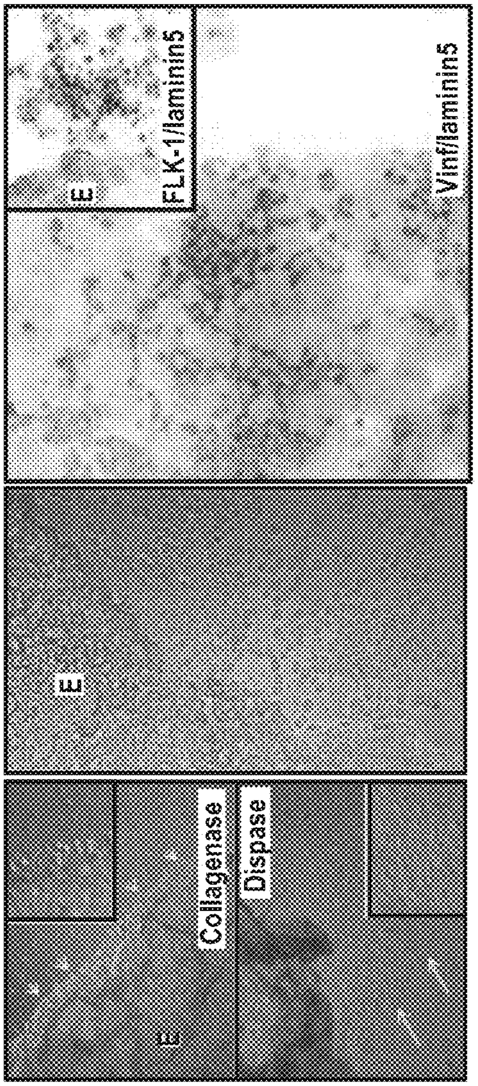
FIG. 7 illustrates immediately isolated cells from collagenase followed by dispase enzymatic digestion (C/D) yields higher percentage of angiogenic progenitors from human amniotic membrane (A-D).
Figure 7B:
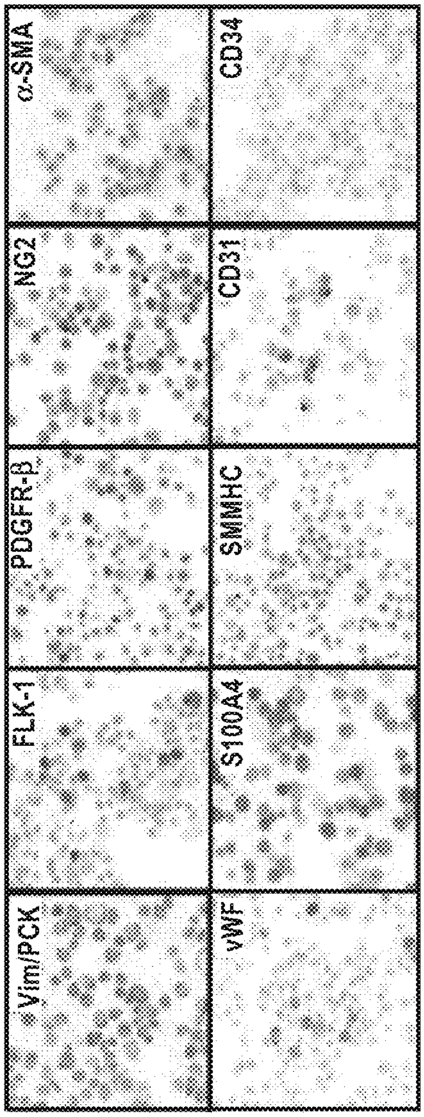
Figure 7C:
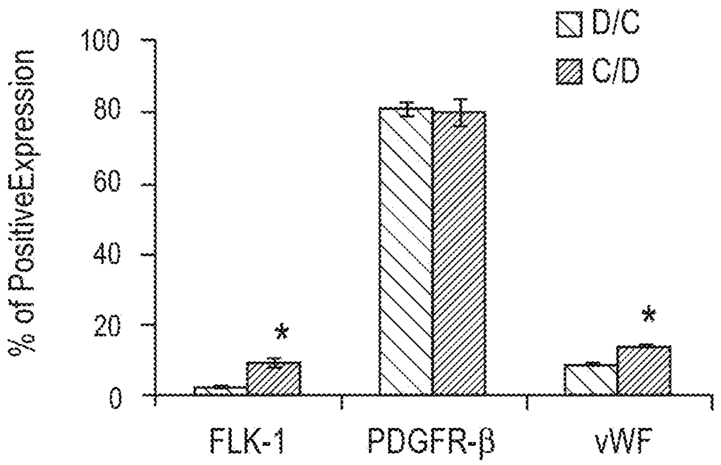
Figure 7D:
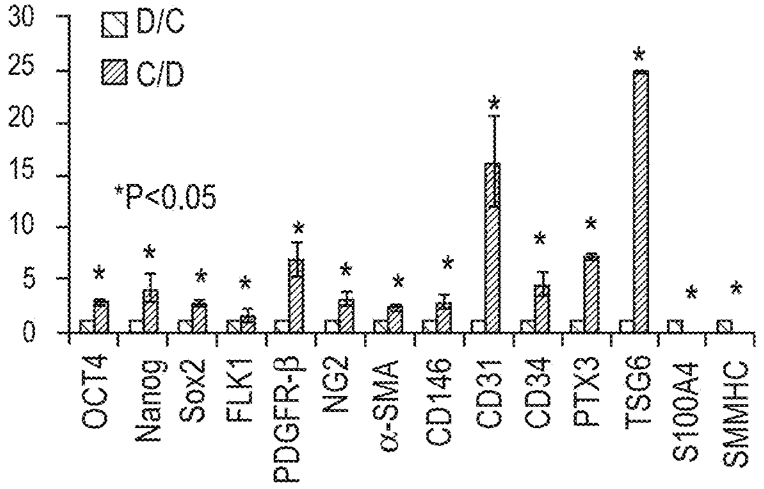
Figure 8A:
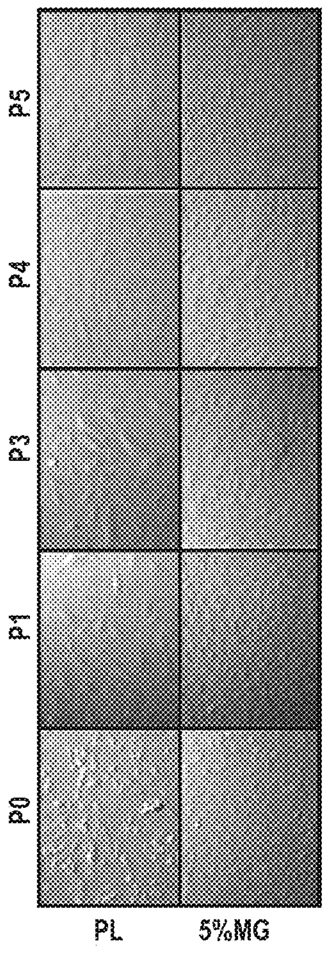
FIG. 8 illustrates that angiogenic progenitors exhibit improved expansion on 5% MG than PL in SHEM (A-D).
Figure 8B:
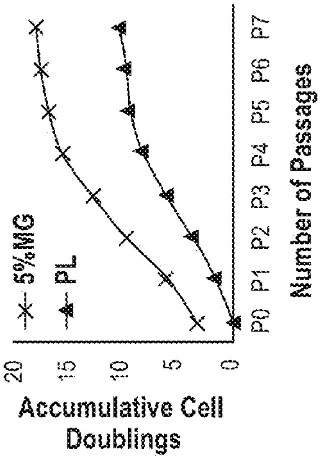
Figure 8C:
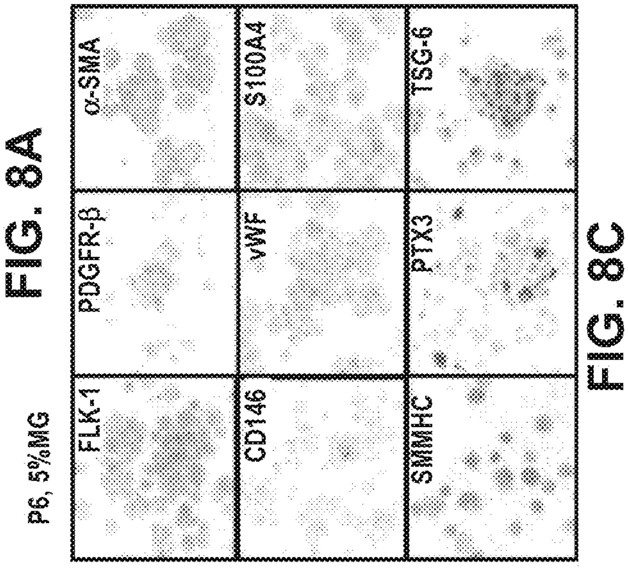
Figure 8D:
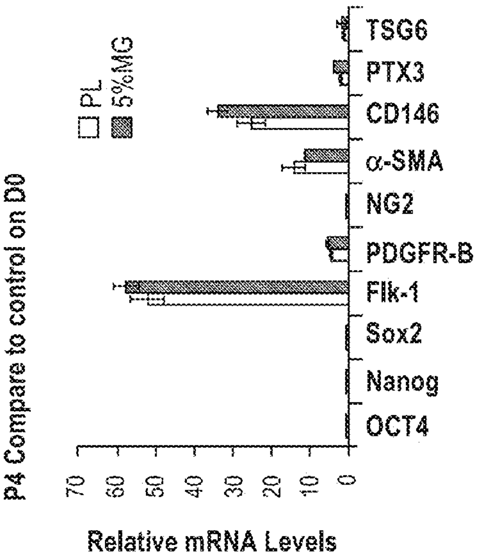
Figure 9A:
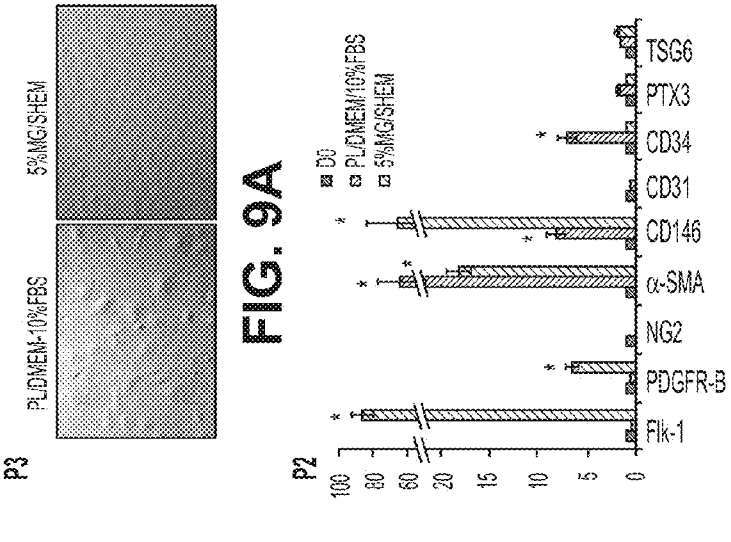
FIG. 9 illustrates that angiogenic progenitors can be expanded on 5% MG in SHEM but cannot be expanded on PL in DMEM/10% FBS (A-D).
Figure 9B:
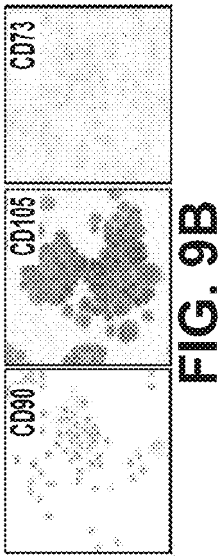
Figure 9C:
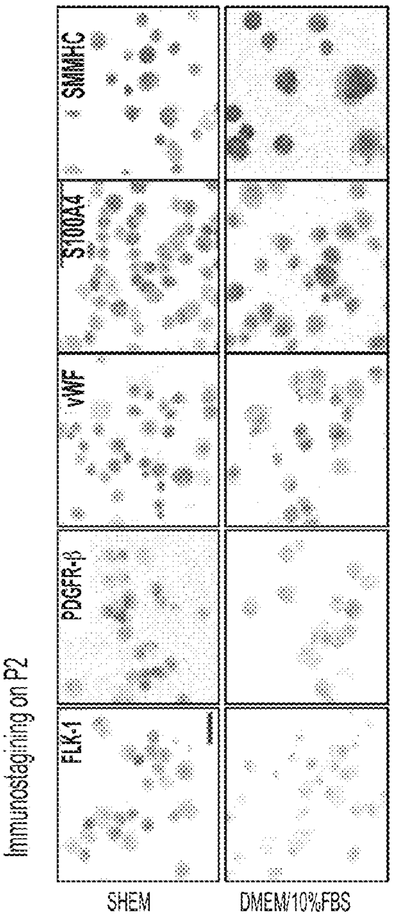
Figure 9D:
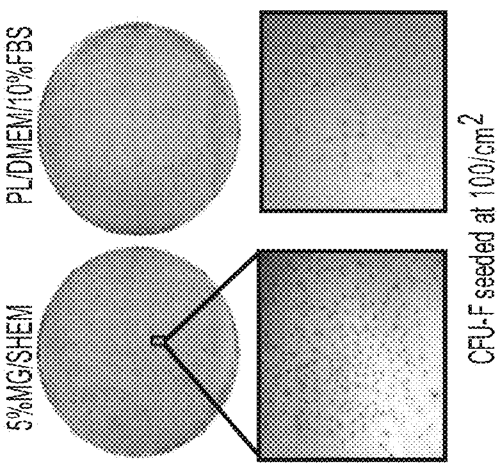

Compared to P0, all ESC markers tested were significantly promoted during serial passages in SHEM on PL (FIG. 6). Compared to P0, all angiogenic markers, except CD31, which ceased after P4, also were significantly upregulated during serial passages in SHEM on PL. Thus, all angiogenic markers are promoted in SHEM on PL although all angiogenic marker expression was significantly lower in adherent cells cultured in SHEM on PL compared to non-adherent cells. The enrichment of mRNA levels in angiogenic markers was greatly increased over successive passages (>20-fold except for NG2, CD31 and CD146). Compared to P0, all MSC markers except CD73 were significantly promoted during serial passages in SHEM on PL, indicating that cells cultured in SHEM on PL are promoted into MSC phenotype.

Compared to P0 in SHEM on PL, all ESC markers were significantly promoted during serial passages. ESC markers can be maintained in SHEM at RNA levels, compared to P0 in SHEM on PL, all angiogenic markers, except CD31, which ceased after P4, were significantly upregulated during serial passages. All angiogenic markers were promoted in SHEM on PL although all angiogenic marker expression was significantly lower adherent cells in SHEM on PL. The enrichment of mRNA levels in angiogenic markers was greatly 20-folded greater except NG2, CD31 and CD146 suggesting positive protein staining by IF may be observed. Compared to P0 in SHEM on PL, all MSC markers except CD73 were significantly promoted during serial In summary adherent non-ES, non-angiogenic expressing hAMECs on PL at p0 can be promoted into angiogenic cells by culturing in SHEM. Such cells also express MSC markers.

Example 4

Expression of Angiogenesis Markers in hAMSC

Mesenchymal stem cells (MSC), a subset of stromal cells present at low frequency in most adult connective tissues, have been extensively studied for their multiple differentiation capabilities. Perivascular pericytes have been regarded as a key source of MSC in different tissues. MSC have been expanded from AM stroma, which is avascular, though it was undetermined whether there are vascular progenitors in hAM stroma. The hAM stroma can be subdivided into a compact layer subjacent to the basement membrane, which contains mostly mesenchymal cells, and a spongy layer with sparse mesenchymal cells. It also was undetermined whether hAMSC derived from these two layers are different. We hypothesized that cells isolated from the compact layer preferentially express angiogenesis markers. In this experiment, the expression of angiogenesis markers in hAMSC was determined.

1×1 $cm^2$ pieces of intact amnion/chorion tissue was embedded and sectioned to 6 μm thickness using standard protocols. The tissues were fixed and analyzed by immunohistochemistry using antibodies against basement membrane components (laminin 5, CoIIIV, FN, keratin sulfate and lumican), ESC markers (Nanog, Sox2, Rex1 and SSEA4) and angiogenic markers (NG2, PDGFR-B, α-SMA, CD133/2, FLK-1, vWF, CD34, CD31 and CD146). The expression of components of the HC-HA complex, which comprises hyaluronan and the heavy chain of inter-α-inhibitor along with TSG-6 and PTX3, also was examined.

AM consists of a single layer of hAMEC and compact and spongy stromal layers. Two rows of mesenchymal cells were noted in the interface between the compact and the spongy layers (FIG. 1A labeled C and S). Double staining of pancytokeratins (PCK) and vimentin (vim) confirmed their coexpression in hAMEC with strong vim+in stromal region. The basement membrane stained by an antibody to laminin 5 separates hAMEC from the remaining stroma, which expressed Vim. Within the AM stroma, the spongy layer preferentially stained from Coll Type IV and fibronectin, while the compact layer preferentially stained for keratin sulfate, express strong lumican in the extracellular matrix and in hAMEC and hAMSC.

hAMSC uniformly expressed ESC markers Sox2 and Rex1 while Oct4, Nanog, Nestin, were weakly expressed in compact layers. Cells in the spongy layer did not express Nanog, SSEA4 or Oct4. For the pericyte markers, NG2 was uniformly expressed, while PDGFR-β and α-SMA were preferentially expressed in the compact but not spongy layer. For the EPC markers, FLK-1, vWF, and CD31 were preferentially expressed in the compact layer. No staining for CD133/2, CD34, CD 144 and CD 146 was observed. For the MSC markers, CD73 and CD 105 were uniformly expressed in compact and spongy layer, while CD90 was preferentially expressed in compact but not spongy layers. For the myofibroblast markers, FSP-1 (s100A4) showed strong uniformly expression in stroma, while no SMMHC expression was found in stromal cells.

For components related to HC-HA, the spongy layer was enriched for HC 1 and Bikunin. The cells between the two layers were strongly positive to TSG-6, while the compact layers were enriched for PTX3.

These data suggest the presence of hAMSC expressing angiogenesis markers between the compact and the spongy layers. These cells preferentially expressed ESC markers, including Sox2 and Rex1, angiogenesis markers, such as NG2, PDGFRβ, α-SMA, FLK-1, vWF, and CD31, and HC-HA components TSG-6 and PTX3.

Example 5

Isolation of AM Stromal Cells Expressing Angiogenesis Markers

The previous study suggested the presence of angiogenesis expressing cells between the compact and the spongy layers of the stroma. To confirm the presence of two different subpopulations of hAMSC, an isolation method was developed to separate the upper region of AM stroma from lower region of spongy layer. The stromal surface of the remaining scraped tissue was scraped for a second time to obtain additional spongy layer. The second scraped sample was digested with collagenase.

Enzymatic Digestion

Samples were prepared by enzymatic digestion. Ten pieces of 5×5 $cm^2$ and three pieces of 1×1 $cm^2$ from fresh hAM were cut. One sample 1×1 $cm^2$ was set aside for IF analysis.

Enzymatic digestion by the D/C method was performed as follows: The intact epithelial sheet was transferred to another dish containing 10 mg/ml dispase at 37° C. for 20 mins. All epithelial cells were collected and treated and rendered into single cells by TrypLE for 10 min. The remaining stroma was then digested with collagenase A (2 mg/ml) and HAase (1:500, 200 ug/ml) in a DMEM/2% FBS at 37° C. for 10 h.

Enzymatic digestion by the C/D method was performed as follows: The intact epithelial sheet was transferred to 2 mg/ml of collagenase and 250 ug/ml of HAase for 8 h. After digestion a floating sheet, which had loose spindle cells at the edge (see FIG. 7 white arrow, inset) was obtained and transferred to a new dish. 10 mg/ml of dispase were added to the dish for another 15-20 mins incubation at 37° C. Immunofluorescence analysis was employed to examine the relative expression of angiogenesis markers (FLK-1, vWF, PDGF-B, α-SMA, CD3 land NG2) by the D/C versus C/D method.

Results

Enzymatic digestion: Collagenase followed by dispase enzymatic digestion (C/D) yielded a high percentage of angiogenic progenitors. After collagenase digestion, some loose cells were observed underneath the epithelial sheet. FIG. 7 shows a phase image a flat mount preparation of an epithelial sheet labeled with Hoechst nucleus 33342 staining (A). While treating with enzymatic dispase digestion, loose cells were gradually released (indicated in white arrow, A). Double staining of laminin 5 showed the loose cells were vim+ and that some of them express FLK-1. Cells were further shown positive stained for angiogenic markers, NG2, PDGFR-β, FLK-1, vWF and α-SMA from C/D (C). Marker expression was confirmed by qPCR.

Double staining of PCK and Vim confirmed that less than 1% of PCK+ cells present HAMSCs isolated from C/D and D/C methods. C/D derived cells exhibited positive expression of angiogenic markers, including FLK-1, PDGFRβ, NG2, α-SMA, vWF, and CD31. Low CD34 positive cells were detected in C/D derived cells. When compared to D/C derived hAMSC, mRNA expression of ES (Oct4, Nanog, Sox2), angiogenic(FLK1, PDGFR-β, NG2, α-SMA, CD146, CD31) were significantly higher in C/D than D/C method. C/D derived cells also showed strong expression of S100A4 (a marker of myofibroblasts), but no expression of SMMHC (a marker of smooth muscle cells). The C/D derived cells also included PTX3 and TSG-6 expressing cells. In summary, these data suggested the avascular AM stroma contains cells with angiogenic potential. These cells can be preferentially isolated from C/D method rather than D/C.

Example 6

Maintenance and Expansion of hAMSC Angiogenic Progenitors Culture in SHEM on Either Coated Matrigel or Plastic In previous experiments, we have successfully isolated and expanded angiogenic progenitor cells on coated Matrigel (MG). These progenitor cells, which are located adjacent to basement membrane, serve as a niche in supporting limbal stem cells (SC). In this experiment, the expansion properties of angiogenic cells derived from the C/D method above on coated MG versus plastic (PL) was examined.

Experimental Design:

Single cells derived from C/D isolated cells were cultured in SHEM on coated 5% MG or plastic (PL). Initial seeding density was $1\times10^4$/cm$^2$. Cells were passaged every 8 days. The expanded cells were subpassaged until the cells diminished proliferation. Samples for mRNA expression and cytospin analysis were collected at each passage.

1) Differentiation of C/D derived cells into mature endothelial cells by Dil-Ac-LDL Uptake Assay:

C/D derived cells previously cultured in SHEM or DMEM/10% FBS cells were seeded at the density of $5\times10^4$ cells per cm$^2$ in 24-well plastic plates for 3 days in the Endothelial Cell Growth Medium 2 (EGM2) supplemented with 10 ng/ml vascular endothelial growth factor-1 (VEGF-A). In parallel, HUVEC (human umbilical vein endothelial cells) were used as the positive control. When the cells reached 80-90% confluence, the cells were incubated with 10 μg/ml Dil-Ac-LDL (Invitrogen, USA) for 4-10 h at 37° C. in the humidified 5% $CO_2$ incubator or fixed with 4% paraformaldehyde for immunofluorescence detection of CD31, vWF, FLK-1 and Dil-Ac-LDL label uptake.

2) Formation of Vascular Tube Like Structures and Ability to Stabilize Vascular Network in C/D Isolated Cells:

Plates were prepared by adding 50 μl of 100% Matrigel into 24 well plates for 30 min before experiment. HUVEC cells were prelabeled with red fluorescent nanocrystals according manufacturer's protocol (Qtracker® cell labeling kits, Invitrogen). C/D cells were prelabeled with green fluorescent nanocrystals or co-culture with HUVEC at ratio of 1:1 at density of $10^5$ cells per cm$^2$ on Matrigel. The cells were cultured in EGM2 supplement with vascular endothelial growth factor-1 (VEGF-A) for 24 hours to elicit vascular tube-like network formation. The stability of vascular network was monitored on Oh, 2 h, 4 h, 6 h, 8 h, 12 h and Day 2.

Results:

Angiogenic Expressing Cells are Preferentially Expanded on 5% MG Rather PL in SHEM.

Single cells from C/D seeded on 5% MG or PL were passaged until p6. Cells derived from coated 5% MG generated smaller cells in size and greater accumulative cell doublings until p5. C/D isolated cells generated total cell expansion to $2.4\times10^6$ cells. Thus, better cell expansion can be achieved when cells seeded on coated 5% MG rather than PL. When cultured on 5% MG at p6 in SHEM, immunostaining suggested the C/D expanded cells expressed strong angiogenic markers FLK-1+, PDGFR-β, vWF, α-SMA and some CD146. Thus, C/D isolated cells expanded on 5% MG in SHEM promote angiogenic cell expansion.

When mRNA of C/D cells cultured on PL vs. 5% MG was compared, cells cultured on PL generated high levels of angiogenic gene expression, similar to 5% MG (FIG. 8). This data suggests that angiogenic expression from C/D can be better expanded on 5% MG rather than PL but does not affect its angiogenic expression.

When C/D cells was compared to MSC, MSC express high levels of PDGFR-β, α-SMA, CD73, CD90 and CD105 but does not express FLK-1. This data suggests that C/D cells may possess angiogenic potential where MSC derived from BM does not possess angiogenic potential.

Analysis of protein expression show positive expression of TSG-6 in nucleus with some spotted PTX3 expressing cells, which is consistent to our previous finding that TSG-6 is constitutively expressed in hAMSC and hAMEC.

Example 7

Expansion of hAMSC on Coated Matrigel in SHEM Compared to DMEM/FBS on PL

Isolation of multi-potent SCs with highest purity and cell numbers from a given tissue is the first step toward cell expansion in vitro. Therefore, the importance in improving cell proliferative capacity without loss of stem cell characteristics is the ultimate goal for cellular therapeutic in clinical application. A MSC conventional expansion method has been developed to expand hAMSC on PL in DMEM/10% FBS; however, poor replication capacity and short proliferative longevity is a recurring problem. Our preliminary data show hAMSC cannot be expanded in serum free medium and we have found the optimal culture medium to expand hAMSC in SHEM. We thus examined whether SHEM medium can be better preserve angiogenic progenitors better than conventional methods of expanding MSC using DMEM/10% FBS on PL.

In the previous Example, we demonstrated the success of isolating enriched angiogenic progenitors from C/D method, separated the upper region of hAM from lower stroma. Because colony forming unit-fibroblasts (CFU-Fs) have previously been demonstrated from MSCs derived from hAM stroma, we examined whether the angiogenic cells enriched by C/D method contribute in generating CFU-Fs or whether such cells may be different from the defined MSC. One way to test this is to measure cells with ability to form CFU-Fs, which where a single derived cell can generate stem like cells Experimental Design:

In this example, we investigated two isolation methods, one is to isolate cells by mechanical scraping and the other will be based on pure enzymatic digestion. In the first method, called method D/C, hAM were treated with 60 mins of trypsin/EDTA follow by additional 30 minutes treatment of 10 mg/ml dispase to release epithelial cells by scraping. The remaining stroma sheet was subjected to 2 mg/ml collagenase with HAse (250 ug/ml) overnight to release total stromal cells (called hAMSC-A). The second method, called method C/D, hAM was digested with collagenase and HAase 6-18 h to release spongy layers of stromal cells (called hAMSC-L) released in the medium. The remaining epithelial sheets were picked out and subjected to 10 mg/ml dispase for 20 mins to release the compact layers stromal cells (called hAMSC-U) associated with the basement membrane.

C/D cells were seeded at density 100 cells/$cm^2$ in 1) DMEM/10% FBS on plastic or 2) SHEM on 5% MG for 12 days. During the expansion, CFU morphology derived from each layer was determined and defined by its clonal size according to the guidelines previously published (Chong et al. (2011) *Cell Stem Cell* 9:527-540). The colony forming efficiency (CFE) was determined by whether the compact fraction generates greater CFU than spongy layers. The resultant of CFU morphology will be stained with crystal violet.

Results

Angiogenic Expressing Cells are Preferred Expanded in SHEM Rather than DMEM/10% FBS (D/F) Medium.

When C/D derived cells cultured on 5% MG in SHEM were compared to conventional culture conditions, cells cultured in DMEM/10% FBS on PL could not be further passaged past p3. At p3, cells cultured in DMEM/10% FBS on PL were enlarged and ceased proliferation. Neither DMEM/10% FBS nor SHEM maintained the ES expressing cells.

Compared to expression in vivo, cells cultured in DMEM/10% FBS showed significantly lower expression in all angiogenic markers, except CD34, α-SMA, CD146 while cells cultured in SHEM on 5% MG, exhibited significant upregulation of FLK-1, PDGFR-β, α-SMA and CD146. Thus, cells expressing angiogenic markers such as FLK-1 and PDGFR-β can be further expanded in SHEM but not DMEM/10% FBS.

Comparison of protein expression by antibody staining confirmed that cells cultured in DMEM/10% FBS expressed significantly less angiogenic markers at p2 compared to cell cultured in SHEM, indicating that SHEM was superior to DMEM/10% FBS for expansion of cells expressing angiogenic markers.

For the CFU-F experiment, it was observed that cells cultured in DMEM/10% FBS on PL did not generate CFU-F. In contrast, cells cultured on 5% MG in SHEM did generate CFU-F (FIG. 9).

Preferential Expansion of hAMSC-U on Coated Matrigel in SHEM

When hAMSC-A were cultured in traditional MSC medium DMEM/10% FBS on PL, the cells quickly enlarged in size, differentiated and reached senescence at p3. In comparison, when hAMSC-A were cultured in SHEM on PL, cells could be passaged up to p8 before reaching senescence. Thus, SHEM medium is better than MSC medium DMEM/10% FBS in expanding hAMSC-A on PL.

When cultured on 5% MG, cells derived from hAMSC-U reached confluence by D6 while cells derived from hAMSC-L remained rounded, indicating the hAMSC-U derived cells are preferentially expanded on 5% MG compared to hAMSC-L. For accumulative doubling time (number of cell doubling (NCD)=$\log_{10}(y/x)/\log_{10}2$, where "y" is the final density of the cells and "x" is the initial seeding density of the cells.). hAMSC-U cultured on PL or 5% MG generated significantly higher accumulated cell doubling times (NCD) 10.43, 18.02, respectively, compared to control hAMSC-A.

qPCR and immunofluorescence data revealed that hAMSC-U expanded cells cultured on 5% MG in SHEM exhibited expression of ES markers Sox2, Rex1 and SSEA4, but were negative for Oct4 and Nanog. hAMSC-U strongly expressed some angiogenic markers, FLK-1, vWR, PDGFR-β, α-SMA, weakly expressed CD146, but were negative for CD31, CD34, CD144 and NG2. These data suggested that angiogenic expressing cells derived from hAMSC-U can be further expanded in vitro on 5% MG in SHEM. Protein expression also showed positive expression of TSG-6 in nucleus with some spotted PTX3 expressing cells, which is consistent with our previous finding that TSG-6 is constitutively expressed in hAMSC and hAMEC.

Example 8

Expression of Markers and Matrix Components of Human Umbilical Cord

Figure 11:
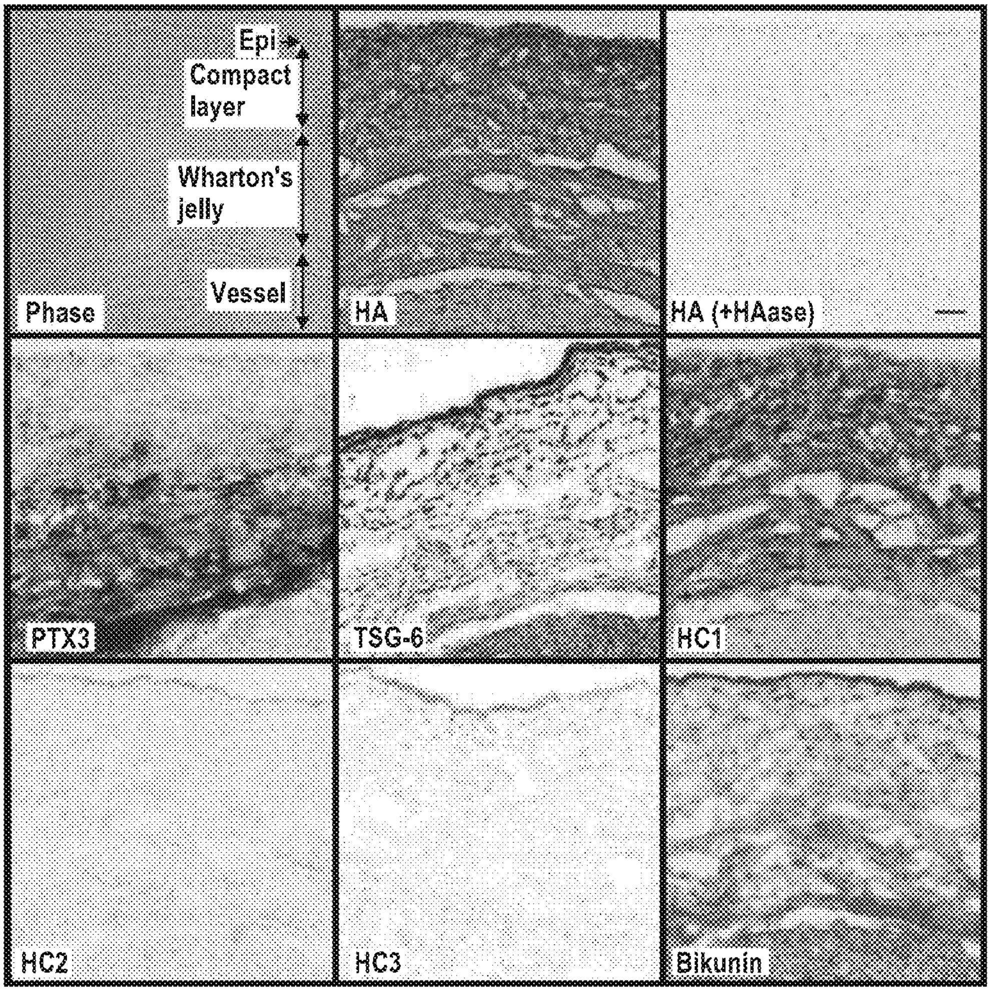
FIG. 11 illustrates a cross section of the anatomy of UC and immunolocalization of HA (hyaluronan), TSG-6 (Tumor necrosis factor α-stimulated gene 6), HC1 (heavy chain of inter-α-inhibitor (IαI)), bikunin and PTX3 (Pentraxin 3) in UC AM. HA, TSG-6, bikunin are expressed from the epithelial layer to vessels, while PTX3 (Pentraxin 3) is expressed more abundantly in zone 3 and 4 of UC (i.e., not in Zone 2). Frozen sections of human AM were probed with biotinylated HABP with or without HAase digestion and with chain-specific antibodies against IαI and PαI components as indicated. Nonimmune rabbit serum was used as a control. Nuclei were counterstained with Hoechst 33342 (blue). Ep, epithelium; St, stroma; Ch, chorion. Scale bar, 25 μm.
Figure 12:
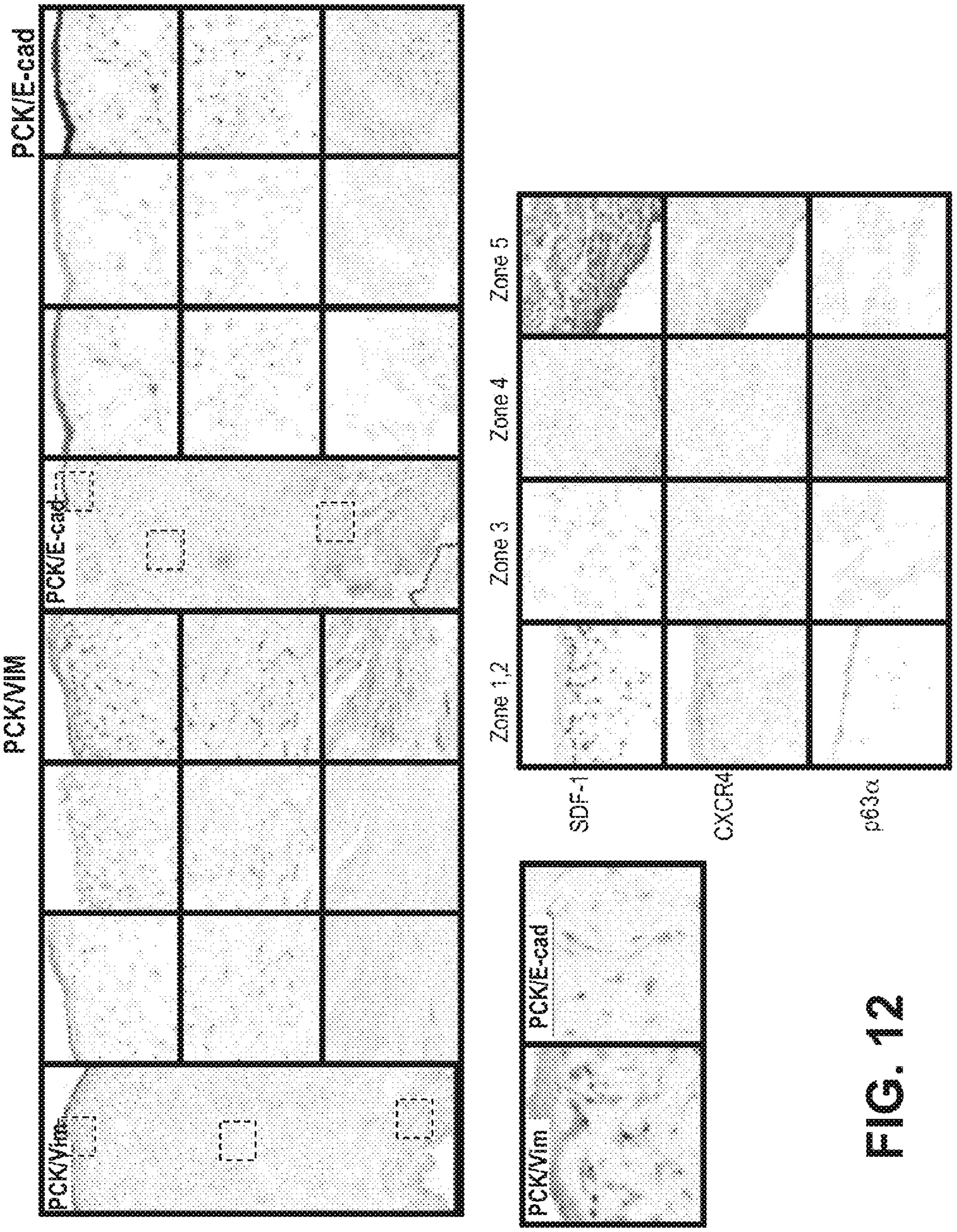
FIG. 12 illustrates a cross section of the anatomy of UC and immunolocalization of vimentin, PCK, E-cadherin, p63 alpha, SDF-1 and CXCR4. Vimentin expressing stromal cells in Zone 2 express epithelial phenotypes such as PCK, E-cadherin and p63 alpha. Those stromal cells also are uniquely expressed both SDF-1 and CXCR4.

In this example, expression of ESC or angiogenesis markers in umbilical cord (UC) tissue was examined by cross section. Hematoxylin and eosin (H&E) staining showed the anatomy of UC is defined consist of five distinct zones (1) amniotic membrane epithelium (zone 1), (2) Sub-amnion cord lining (zone 2) (3) Wharton's Jelly (WJ, zone 3) a surrounding matrix of mucous connective tissue, (4) adventitia (perivascular zone, zone 4), and (5) UC vessels (two arteries and one vein, zone 5)) (FIG. 11). No visible borders can be distinguished from Zone 2 to Zones 3 and 4. However, cell density is the lowest in Zone 3 and the highest in Zone 4. The amniotic membrane and subamnion region of UC (Zones 1 and 2) are the continuation of amniotic membrane and chorion, respectively, from the fetal membrane. A key finding of the study was the presence of small PCK+, E-cad+, p63+, SDF-1+ stromal cells in Zone 2 (FIG. 12). Double immunostaining of PCK and Vimentin (Vim) on a cross section of UC tissue showed Vim+ cells in zone 2 and zone 3 interestingly are heterogeneously coexpress with PCK,E-cadherin and p63 alpha. A higher magnification further suggested that PCK+/E-cad+ stromal cells are a subset of smaller cells in Zone 2, and there are some PCK−/E-cad+ cells.

Double staining of SDF-1 and CXCR4 showed that SDF-1+ cells were uniquely found in Zone 2 and Zone 5 (close to the blood vessels) (FIG. 12). However, CXCR4 was expressed by epithelial cells as well as Zone 2 cells. Hence, stromal cells in Zone 2 also uniquely express both SDF-1 and CXCR4. This result also suggested that double staining of SDF-1+/PCK+ can be used to distinguish stroma cells from SDF-1−/PCK++ epithelial cells in UC.

Figure 10:
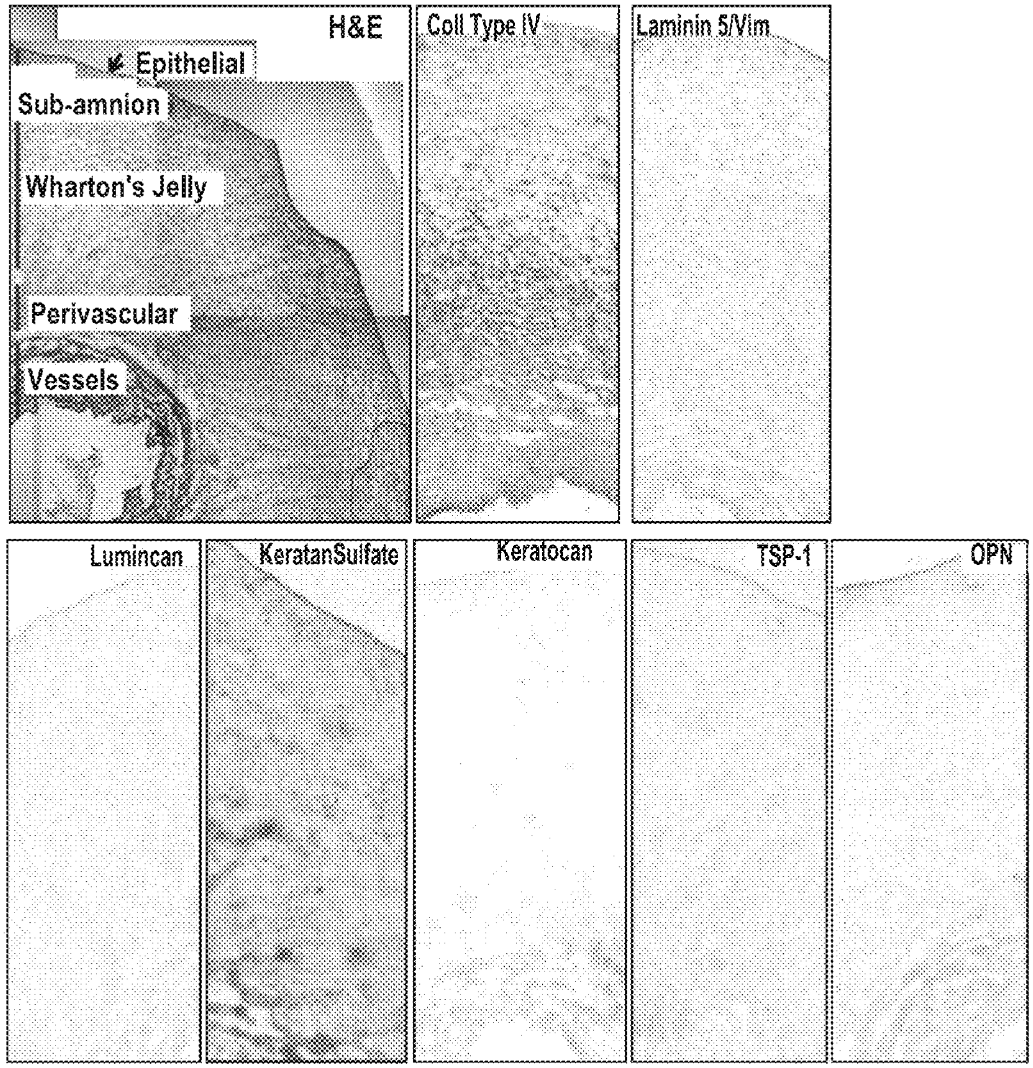
FIG. 10 illustrates cross sections showing the anatomy of the umbilical cord (UC), which consists of five distinct zones and the distribution of basement membrane components and matrix.

Immunostaining further showed the expression of matrix components, Coll IV is abundantly found in the stroma while laminin 5 is only noted in basement membrane between zone 1 and zone 2 (FIG. 10). Keratan sulfate proteoglycans are found in the entire stroma. As reported, little expression of keratocan or lumican is found. TSP-1 is also noted in zone 1 while osteopontin is preferentially found in Zone 1 and 2

Cross sections of the umbilical cord showed abundant expression of HA, TSG6, HC1 and bikunin from the epithelial layer to vessels, except that PTX3 is expressed more abundantly in WJ and the perivascular region of UC (i.e., not in Zone 2), suggesting that other components than HC-HA/PTX3 might be present in Zone 2 (FIG. 11).

Figure 13:
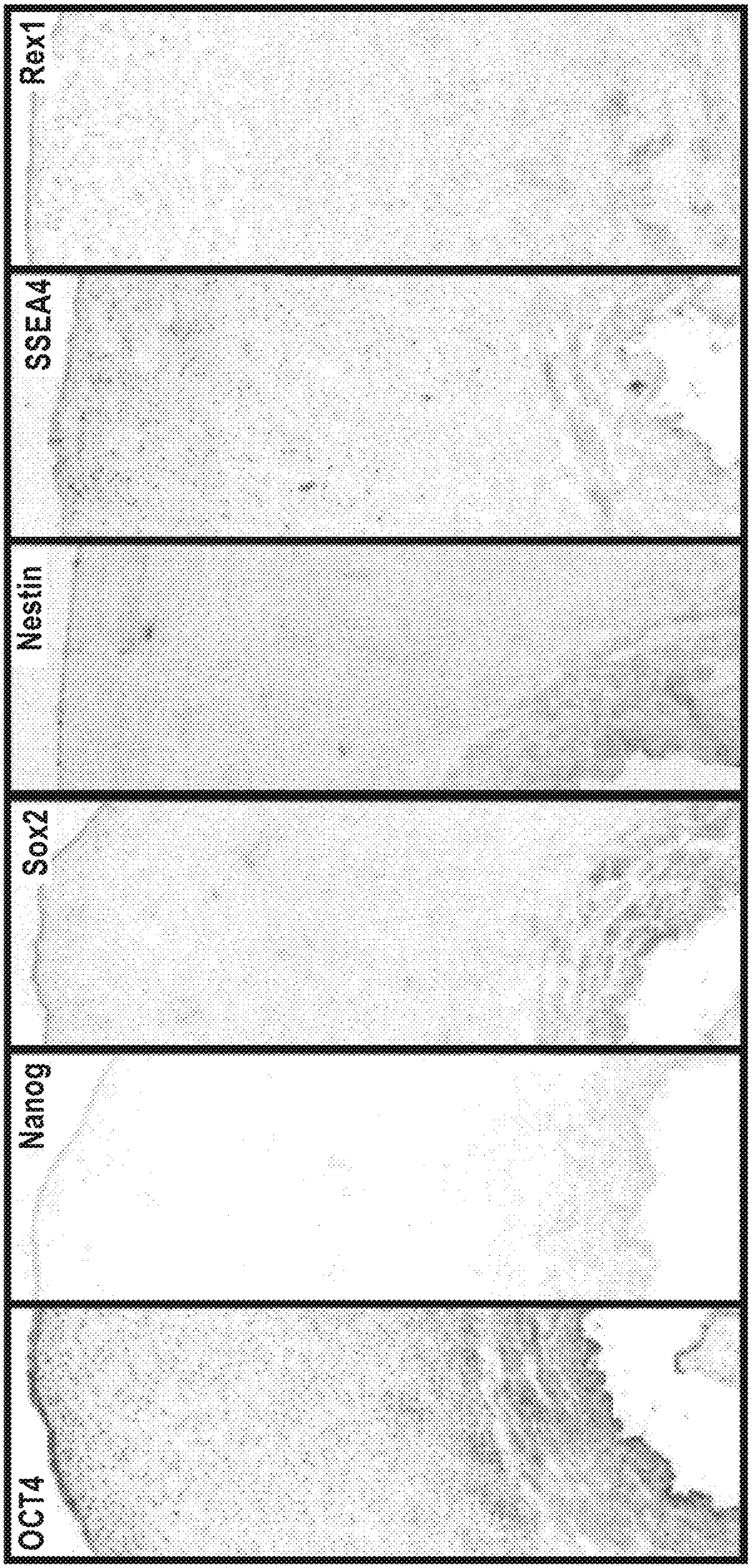
FIG. 13 illustrates a cross section of the anatomy of UC and immunolocalization of ESC markers.
Figure 14:
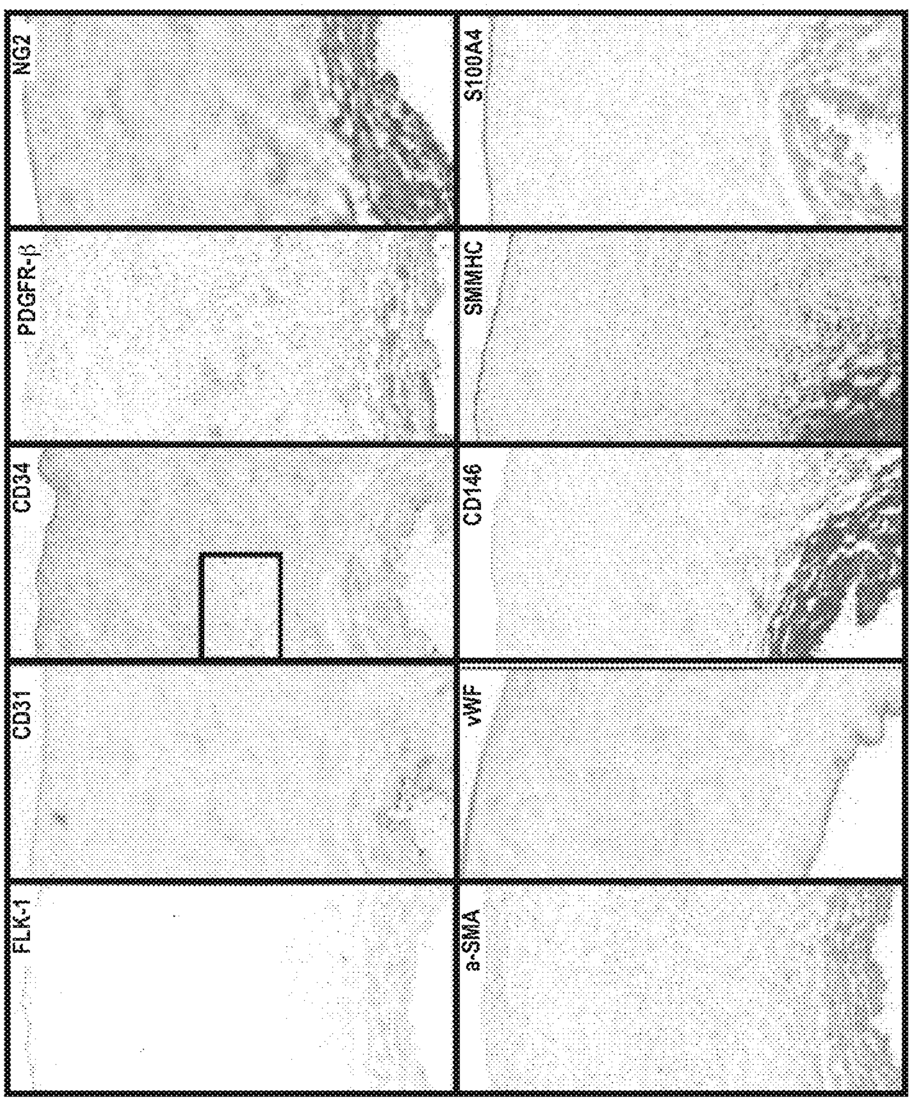
FIG. 14 illustrates a cross section of the anatomy of UC and immunolocalization of angiogenic markers.

Immunostaining further showed expression of ESC markers (Oct4, Sox2, Nanog, SSEA4, Rex1 and Nestin) also noted in UC stromal cells and other angiogenesis progenitor markers (CD34, CD31, FLK-1, PDGFR-β, NG2, α-SMA) (FIGS. 13, 14). Regarding the angiogenic progenitor markers, FLK-1 was not expressed in the UC. CD31 was negative throughout the entire length of the UC except some positive staining of inner wall vessel. CD34 was positive from epithelial to perivascular zones but negative in UC vessels. Pericyte markers, NG2, PDGFR-β, α-SMA were expressed throughout the entire length of the US and strongest expression was observed in vessels. vWF was expressed from epithelial to perivascular zone and strong positive expression only in the inner wall vessel. CD146 was negative in epithelial and subamnion zones but gradually positive in WJ and strongest in vessels. The myofibroblast differentiation markers S100A4 and SMMHC express strongest at zone 1 and 5.

A summary of the expression data is presented in Table 3 and FIG. 15.

TABLE 3

Comparison of Expression ESC and Angiogenic Markers Between AM vs. UC in vivo

| | hAMEC | hAMSC (compact) | hAMSC (spongy) | Zone 1 | Zone 2 | Zone 3 | Zone 4 | Zone 5 |
|---|---|---|---|---|---|---|---|---|
| ECM | | | | | | | | |
| Collagen Type IV | -- | ± | + | + | + | + | ++ | + |
| Lumican | + | + | + | + | ± | ± | ± | ± |
| Keratan Sulfate | -- | + | + | + | + | + | + | + |
| PTX3 | ++ | ++ | + | -- | + | + | ++ | -- |
| TSG6 | ++ | + | + | + | + | + | + | + |
| HA | + | + | + | + | + | + | + | + |
| HC1 | + | + | + | ± | + | + | + | -- |
| HC2 | + | + | + | -- | -- | -- | -- | -- |
| HC23 | + | + | -- | ± | -- | -- | -- | -- |
| Bikunin | + | + | + | + | + | + | + | + |
| PCK | + | -- | -- | ++ | + | + | + | +/- |
| E-cadherin | | | | ++ | + | + | + | +/- |
| Vimentin | + | + | + | + | + | + | + | + |
| ESC | | | | | | | | |
| Oct4 | + | + | -- | + | + | + | + | + |
| Nanog | -- | + | -- | -- | -- | -- | -- | -- |
| Sox2 | + | + | + | + | + | + | + | + |
| Nestin | + | + | + | -- | -- | -- | -- | + |
| SSEA4 | + | -- | -- | + | + | ± | -- | -- |
| Rex1 | + | + | + | + | + | + | + | + |
| Angiogenesis | | | | | | | | |
| FLK1 | + | + | -- | -- | -- | -- | -- | -- |
| CD31 | nd | + | -- | -- | -- | -- | -- | + |
| CD34 | + | -- | -- | + | + | + | ± | -- |
| PDGFR-b | + | + | -- | ± | + | + | + | ++ |
| NG2 | + | + | + | + | + | + | + | ++ |
| a-SMA | -- | + | -- | + | + | + | + | ++ |
| CD146 | -- | -- | + | -- | -- | -- | + | ++ |
| vWF | + | + | -- | + | ± | ± | ± | + |
| S100A4 | ++ | + | -- | + | + | + | + | ++ |
| SMMHC | -- | -- | -- | + | + | + | + | ++ |
| SDF-1 | ++ | -- | -- | -- | ++ | ± | ± | ++ |
| CXCR4 | | | | + | ± | ± | ± | + |

Example 9

Comparison of Collagenase/HAase Digestion Versus Mechanical Stripping for Isolation of Umbilical Cord Multipotent Cells Current Methods of Isolation, Characterization and Expansion of MSCs/SCs from Human Umbilical Cord (Subamniotic Region) and Wharton's Jelly Two conventional ways of isolating MSCs from UC are either by cells generated from explants or by cells dissociated by enzymatic digestion. Because the former does not allow one to clearly identify the zone from which MSCs or SCs are derived from UC, we summarize 11 studies that were reported between 2004 and 2011 using enzymatic isolation (FIGS. 16 and 17).

None of the previous studies have successfully isolated SCs/MSCs from Zones 2 and 3 of the UC. Five studies (Lu et al. (2006) *Haematologica* 91:1017-1026; Koliakos et al. (2011) *Journal of Biological Research-Thessaloniki* 16:194-201, Seshareddy et al. (2008) *Methods Cell Biol* 86:101-119, Schugar et al. (2009) *J Biomed Biotechnol.* 2009:789526, and Tsagias et al. (2011) *Transfus Med.* 21:253-261) did not clearly exclude contamination of amniotic epithelial cells. Three studies (Lu et al. (2006) *Haematologica* 91:1017-1026, Schugar et al. (2009) *J Biomed Biotechnol.* 2009:789526, and Tsagias et al. (2011) *Transfus Med.* 21:253-261) did not exclude blood vessels. Because collagenase cleaves interstitial but not basement membrane collagens, thus leaving aggregates of cells closely associated with the basement membrane, one may lose cells from basement membrane-rich Zones 2 and 3 if trypsin is not used to cleave the basement membrane while filtration is used as shown in studies by Schugar et al. ((2009) *J Biomed Biotechnol.* 2009:789526) and Tong et al. (2011) *Cell Biol Int.* 35:221-226, MSC/SCs. Except Tong (2011), all others may have obtained MSCs along with epithelial cell contamination. Except Weiss et al. (2006) Stem Cells and Montanucci et al. (2011), all used polystyrene surface to culture the MSCs. Weiss 2005 and Montanucci (2011) used HA coated surface and their passage number was high. It is unclear whether HA coated surface is better for isolation and culture of MSCs while preserving their characteristics. DMEM with low serum is used to seed and culture MSCs by all except Sarugaser 2005, who used alpha-MEM with a higher serum concentration. The percentage of serum and glucose concentration is the crucial factor for culturing MSCs. Weiss et al. (2006) and Lu et al. (2006), added growth factors in the culture medium to promote a relatively higher passage number. It is unclear that higher passage number is caused by the use of a medium containing low serum (2-15%) and growth factors. All studies characterized expression of cell markers by flow-cytometry.

Enzymatic digestion is the first step of conventional isolation of MSCs from hUC. Previous isolation methods used the whole UC without removing vessels throughout isolation (Schugar et al. (2009) *J Biomed Biotechnol.* 2009:789526, Koliakos et al. (2011) *Journal of Biological Research-Thessaloniki* 16:194-201, Tsagias et al. (2011) *Transfus Med.* 21:253-261, Lu et al. (2006) *Haematologica* 91:1017-1026) or removing the blood vessels and then performing the enzyme digestion (Wang et al. (2004) *Stem Cells* 22:1330-1337, Weiss et al. (2006) *Stem Cells* 24:781-792), suggesting that collagenase digestion does not remove the entire vessels. In the previous example, we identified a subset of stromal cells expressing a dotted pattern of PCK+ at perinucleus that is different from the cytoplasm expression of PCK in UC epithelial cells. It was unclear whether such PCK expression pattern can be differentiate between stromal cells and UC epithelial cells, and if so, whether stromal PCK+ cells are coexpressed with E-cadherin as well as other ESC markers.

Time-Dependent Collagenase/HAase Digestion Versus Mechanical Stripping for Isolation of Cells from Zones 2 and 3 without Amniotic Epithelial Contamination In this example, it was examined whether it is possible to eliminate epithelial cells contamination by the following two methods: 1) to remove the epithelium mechanically or 2) to follow a modified method reported by Montanucci et al. (2011) *Tissue Eng Part A.* 2011; 17:2651-2661 via injection of collagenase/HAase but with the modification of adding time-dependent digestion 3) directly digest tissue with 2 mg/ml collagenase and 1 mg/ml hyaluronidase (Coll+HA) then pick out the epithelial cells under microscope.

Immediately after procurement, the fresh UC was placed and washed in PBS to remove red blood cells (RBCs). The length and weight of the UC was recorded. The UC was cut into 3-5 cm segments with a sterile blade. The first two (smaller) segments were subjected to (M1) Mechanical Removal of Epithelium using the following steps:

a) A shallow cut was made along the length of the segment by a scalpel.

b) The overlying epithelium was peeled mechanically from its edge. (Additional cuts of the epithelium can be made to achieve this objective).

c) The removed epithelial tissue was cut into several 1×1 cm pieces. One piece was embedded and sectioned for immunohistochemistry. The remaining pieces were subjected to 10 mg/ml collagenase and HAase (250 ug/ml-1000 ug/ml) digestion to generate a epithelial sheet and a digested fraction. Both samples were prepared for cytospin and mRNAs analysis.

d) For the remaining UC, the blood vessels were removed by teasing into WJ and using a forceps. If this could not be accomplished, the second segment went straight to digestion and blood vessels were removed later.

e) The stromal tissue was then digested with collagenase (2 mg/ml) and HAase (200 μg/ml) in DMEM-LG with 2% FBS for up to 16 h at 37° C. in 100 mm dish with periodical microscopic monitoring to determine extent of dissolution of the stromal matrix.

f) At three time points, the mixture was centrifuged in a conical tube at a low speed (e.g., 500×g for 3 min) to remove the undigested portion. The digested solution was neutralized by adding DMEM-LG with 20% FBS and collected for cytospin and mRNA analysis.

g) The undigested matrix remaining in the conical tube was then continuously digested by adding the same enzymatic solution for the next period of time, and centrifuged in the same tube to collect the next fraction of cells for cytospin and mRNA analysis.

The remaining three (large) segments were subjected to (M2) Injection of enzymes into the UC matrix (Montanucci et al. (2011) *Tissue Eng Part A.* 2011; 17:2651-2661) using the following steps:

a) The two ends of the UC segment were ligated with 2-0 silk suture at 0.5 cm away from edge.

b) 12 ml of collagenase (2 mg/ml) and HAase (200 μg/ml) in DMEM-LG with 2% FBS in a 26G syringe were injected into the middle of UC into the Wharton's jelly zone from one end 0.5 cm from the ligation point toward the other end.

c) The injected UC was placed for up to 16 h at 37° C. in a 50 ml conical tube by keeping the injected end up with periodical digital palpation. Attention was given to the extent of dissolution of the stromal matrix, which was determined by the "softness" of the tissue.

d) At three time points, one for each segment, the ligated tube was opened by a scalpel. After removing the blood vessels, the digested matrix was obtained by rinsing with DMEM-LG with 2% FBS. Cells were collected by centrifuging the rinse in a conical tube at a low speed (e.g., 500×g for 3 min). Cells were collected for cytospin and mRNA analysis.

Cells from both methods were subjected to Immunostaining with PCK and SDF-1 to determine epithelial contamination.

For M1 method, epithelium was able to be removed by mechanical peeling of the epithelium from each UC segment, taking roughly 5-10 min for each segment. Vessels were not removed at the time of isolation in this particular example. At 3.5 h, the tissue was visible. Therefore, the stromal tissue underwent enzymatic digestion for 16 h at 37° C. as describe above.

For the M2 method, UC segments were successfully sutured at both ends. After 2 h digestion, the enzymatic liquid started to leak out from the tissue. At 16 h, 37 C, the entire tissue disintegrated.

Because neither method tested removed the blood vessels, cord blood contamination was observed at the time of the isolation. Although the blood vessels can be observed after digestion, blood vessels along with other slimy matrix components are removed, suggesting that some perivascular or WJ components might also be removed. The mixtures from both methods were subjected to 40 um filtration to remove large pieces of epithelial cells.

Figure 18:
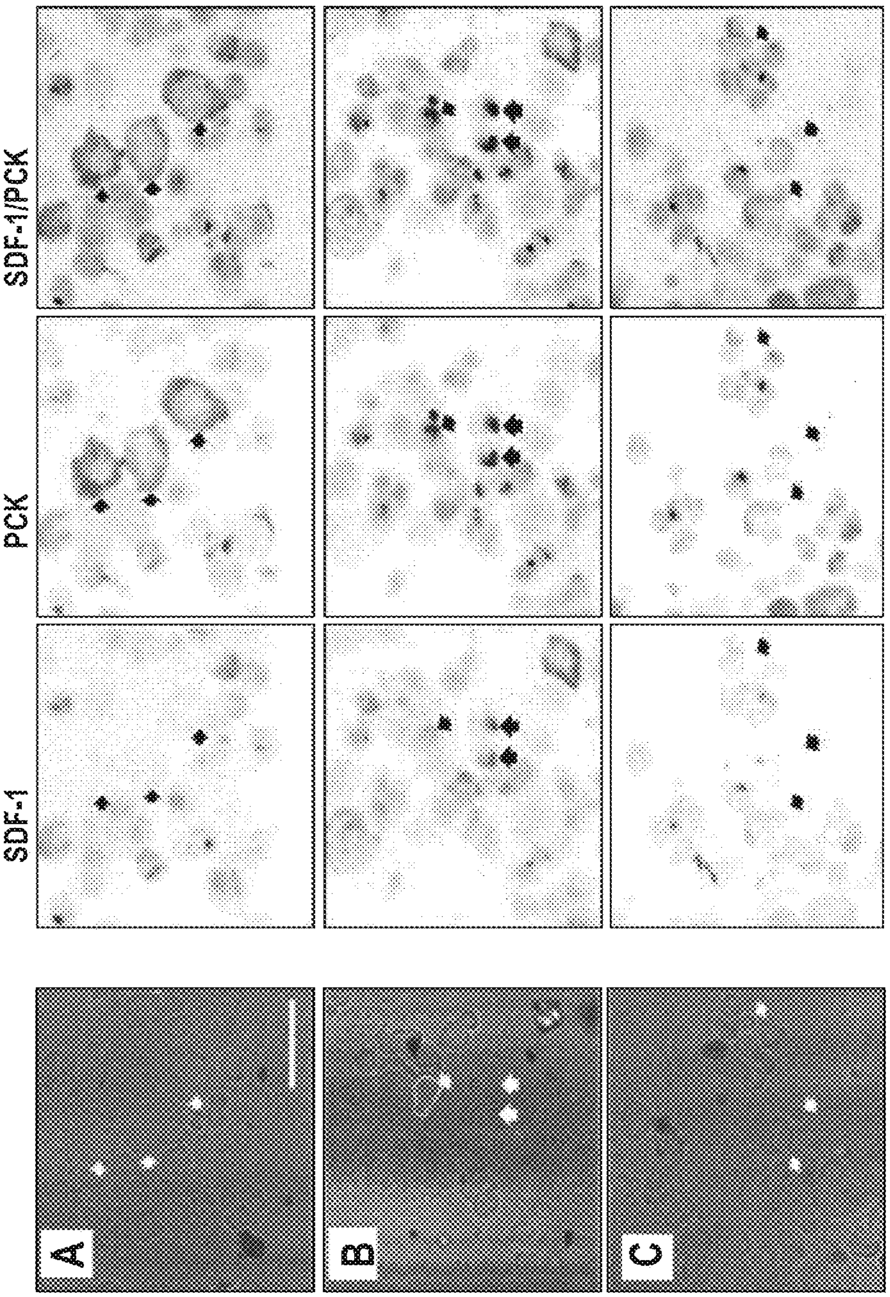
FIG. 18 illustrates immunostaining of SDF-1 and PCK expression in stromal cells isolated from UC.

Double staining of PCK/SDF-1 verified that large $PCK^{bright}$ "epithelial" cells were mostly in the range from 15-30 μm and did not express SDF-1 (FIG. 18). Cell counting analysis further showed the percentage of large $PCK^{bright}$/SDF-1− cells is significantly lower in M1 (1±0.6%, n=1719) than M2 (5.9±2.3%, n=1007) suggesting removal of epithelium prior digestion can significant reduce the contamination of epithelial cells.

Consistent with the previous example, we observed co-localization of $PCK^{bright}$/$SDF\text{-}1^{bright}$+ in perinucleus (FIG. 18, white arrows) and PCK+/SDF-1+ in cytoplasm (FIG. 18B). We also observed a small percentage of very small cells that does not express both PCK and SDF-1 (FIG. 18C, white arrows). These data suggested that stroma cells heterogeneously express PCK and SDF-1; the coexpression of PCK/SDF-1 is expressed in a similar pattern. SDF-1+/PCK+ cells may also co-express with SSEA4 while Oct4 is expressed throughout the entire tissue, suggesting that SDF1+/PCK+/

SSEA4+/Oct4+ cells can be separated from SDF-1−/PCK−/SSEA4−/Oct4 expressing cells.

Example 10

Isolation and Characterization of E-Cadherin+ Stromal Cells from UC by Dyna Beads Previous studies have shown that 3D aggregation formed by MSC derived from UC depends on the expression of E-cadherin (E-cad) (Lee et al. (2012) *Mol. Ther.* 20:1424-1433). Expression of E-cad may signify pluripotency and self-renewal in induced pluripotent stem (iPS) cells (review in Soncin (2011) *Genes* 2(1):229-259). In Examples 8 and 9, we observed a subset of small UC stromal cells uniquely expressing E-cad in Zone 2. In this example, we aim to isolate E-cad+ stromal cells and to compare their expression of p63, SDF-1, CXCR4, ESC (Oct4, SSEA4) and angiogenic (PDGFR, CD34, NG2) and α-SMA to those by E-cad− cells.

Figure 19:
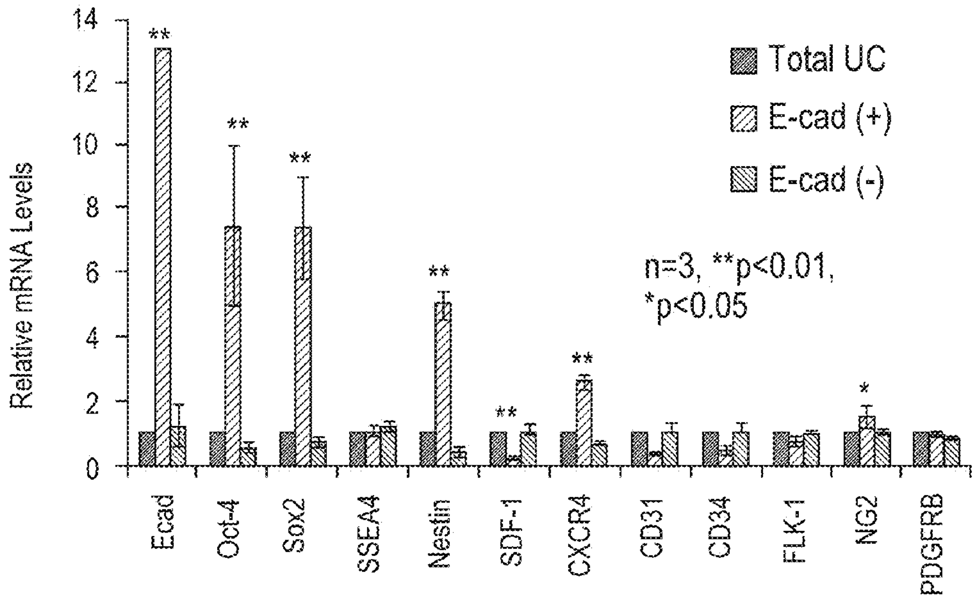
FIG. 19 illustrates of ESC and angiogenic markers in E-cad (+) cells positively selected from digested UC stroma.

Isolation of stromal cells from umbilical cord was performed as described above. In brief, UC was cut into 5 cm segments with a sterile blade. A shallow cut was made along the length of the segment by a scalpel. Umbilical cord tissue was digested with collagenase (2 mg/ml) and HAase (200 mg/ml) in SHEM for up to 16 h at 37° C. in 100 mm dish with periodical microscopic monitoring. Blood vessels and epithelium layer were removed by forceps under a dissecting microscope. All stromal cells were trypsinized into single cells by 0.25% T/E for 10 mins. E-cadherin antibodies were biotinylated with DSB-X. Cells were incubated with E-cadherin/DSB-X antibodies for 20 mins at 4° C. Dynabeads were then added to antibodies bound to E-cadherin positive for positive selection of E-cadherin expressing cells by a magnet. E-cadherin+ cells and E-cadherin—cells (non selected) were collected for further RNA, protein, cytospin analysis.

qPCR results showed E-cadherin positive fraction can be significantly enriched from total UC stromal cells through magnetic isolation. E-cadherin (+) fractions are significantly enriched with ESC markers (Oct4, Sox2, Nestin) and CXCR4 expressing cells than E-cad(−).(n=3) (FIG. 19). In contrast, aside from NG2, E-cad(+) cells contain a significantly less angiogenic markers, CD31, CD34, FLK-1 and SDF-1 than E-cad(−) fraction.

Example 11

Effect of C/D Derived Cells on Human Limbal Epithelial Progenitor Cell (LEPC) Differentiation on 3D Matrigel Limbal native niche cells can be isolated and expanded to support limbal epithelial progenitor cells (LEPC) from differentiation on 3D matrigel (Xie et al. (2011) *Stem Cells* 9(11):1874-85; Xie et al. (2012) *Invest Ophthalmol V is Sci.* 53(1):279-86). Our current data show bone marrow (BM)-derived MSC other than its native niche has similar function (Li et al. (2012) *Invest Ophthalmol V is Sci.* 53(9):5686-97) to prevent LEPC from differentiation. In this experiment, whether cells isolated from C/D of hAMSC has similar function in preventing LEPC from differentiation will be examined.

Single cells derived from dispase-isolated limbal epithelial sheets (LEPC) are mixed at a ratio of 4:1 with candidate niche cells (NCs) according to Table 2. The cells are serially passaged at the total density of $5\times10^4$ per $cm^2$ in 3D Matrigel to generate sphere growth. On D10 in modified embryonic SC medium (MESCM), the resultant spheres are collected by 10 mg/ml dispase digestion at 37° C. for 2 h to dissolve Matrigel. Samples of cells will be collected for further analysis by mRNA, cytospin and protein analysis.

TABLE 2

| Exp Group | Candidate NCs/Medium | SCs source | Growth surface | Medium | Cell density |
|---|---|---|---|---|---|
| 1 | — | LEPC | 3D MG | MESCM | $5\times10^4/cm^2$ |
| 2 | C/D hAMSC/SHEM | LEPC | 3D MG | MESCM | $5\times10^4/cm^2$ |
| 3 | native NCs/MESCM | LEPC | 3D MG | MESCM | $5\times10^4/cm^2$ |
| 4 | MSC/DF | LEPC | 3D MG | MESCM | $5\times10^4/cm^2$ |
| 5 | C/DhAMSC/SHEM | LEPC | 3D MG | MESCM | $5\times10^4/cm^2$ |
| 6 | hAMSC/DF | LEPC | 3D MG | MESCM | $5\times10^4/cm^2$ |

DF: DMEM/10% FBS

Example 12

Isolation of Adipose Stem Cells (ASCs) from Human Orbital Fat

The conventional method of isolating ASCs involves the following steps: (1) Wash adipose tissue 3 times with cold PBS, (2) Cut it into fine pieces, and (3) Subject fine pieces to 1 mg/ml of collagenase I in DMEM/10% FBS for 2 h at 37° C., (4) Centrifuge the digest at 300×g for 10 min to collect the pellet that contains the majority of stromal vascular fraction (SVF) cells, and discard the floating cells that contain mature adipose cells, (5) Resuspend pellet cells in DMEM/10% FBS, (6) Filter the cell suspension via a filter 40-250 μm and collect cell flow through, (7) Lysis of RBC by adding the RBC lysis buffer, (8) Centrifuge at 300×g for 10 min to collect cells for further cell expansion. In this example, a modified method of isolation is presented. The modified method uses modified embryonic SC medium (MESCM) during collagenase digestion and resuspension of cells because it preserves expression of ESC markers. MESCM has the following components: DMEM/F-12 (1:1) supplemented with 10% knockout serum, 5 μg/mL insulin, 5 μg/mL transferrin, 5 ng/mL sodium selenite, 4 ng/mL bFGF, 10 ng/mL hLIF, 50 μg/mL gentamicin, and 1.25 μg/mL amphotericin B.

This example compared the modified method to the conventional method to demonstrate improved properties in preserving the progenitor status during isolation. In addition, cells flowing through the 40-250 μm filter from Step (6) were also compared to those that did not in order to analyze the properties of cells associated with the basement membrane that is not digested by collagenase.

Figure 20:
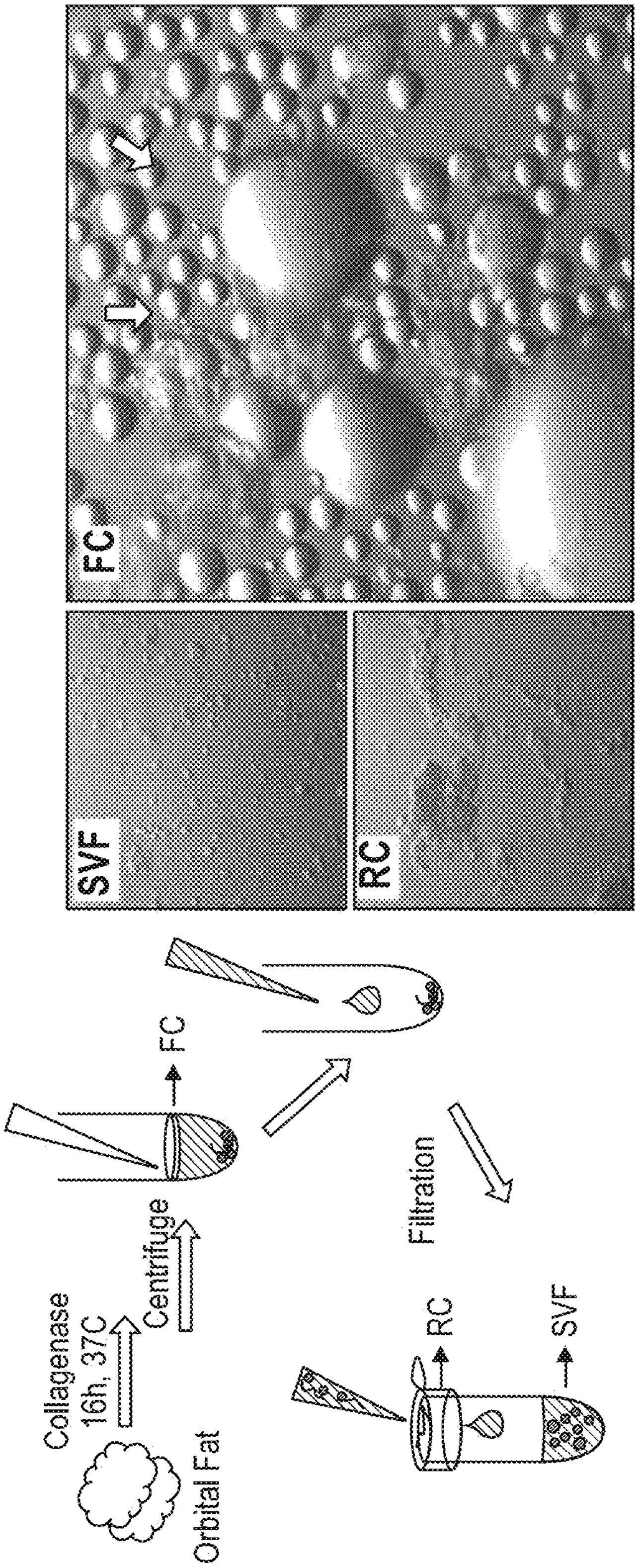
FIG. 20 illustrates an exemplary experimental flow chart for adipose stem cell isolation (left) and phase contrast microscopy images from three fractions derived from human orbital fat following collagenase digestion (right).

Experimental Design:

Orbital adipose tissues obtained from patients after blepharoplasty were digested with 1 mg/ml collagenase A in DMEM/10% FBS or a serum-free modified ESC medium (MESCM) for 16 h at 37° C. After centrifugation at 300×g for 5 min to remove floating cells (FC), the remaining cell pellet was resuspended and filtered through a 250 μm mesh to yield cells retained on the filter (RC) and flowing through (SVF). Single cells from FC, RC and SVF were cultured on 5% coated matrigel or immobilized nHC-HA PTX3 purified from amniotic membrane in MESCM for 8 days (FIG. 20). Expression of ESC markers (Oct4, Nanog, Rex1, Sox2, Nestin, ALP, and SSEA4) and angiogenic markers (CD34, CD31, VWF, α-SMA, PDGFRβ, CD146, and NG-2) was determined by qPCR or immunostaining

TABLE 3

| Exp Group | Digestion Collagenase Medium | Cell Fraction |
|---|---|---|
| 1 | DMEM/10% FBS | FC (floating cells) |
| 2 | DMEM/10% FBS | SVF (flow through) |
| 3 | DMEM/10% FBS | RC (Remaining Cells) |
| 4 | MESCM | FC (floating cells) |
| 5 | MESCM | SVF (flow through and not) |
| 6 | MESCM | RC (Remaining Cells) |

Whether the FC fraction is enriched with cells expressing markers of both ESC and angiogenic progenitors in younger patients compared to older patients also was analyzed. Adipose tissue derived from 3 patients with age of 63, 58, and 49, designated as patient #1, patient #2 and patient #3, were processed according to the above protocol with MESCM used for digestion. Three fractions, i.e., FC, SVF and RC, were collected for qRT-PCR analysis of the following transcripts: ESC (Oct4, Nanog) and other markers such as CD34, CD31, vWF, α-SMA, PDGFRβ, CD146, NG-2 and CD29.

For the experiment, one large brown adipose tissue was cut in half. One half (1×1 $cm^2$) was fixed by 10% formalin for 15 min and embedded for immunostaining for basement membrane (Collagen IV and laminin 5). The other half (1×1 $cm^2$) was digested with 3 ml 1 mg/ml collagenase A to obtain FC, SVF, and RC fractions, which was then dissociated by T/E to generate single cell for cytospin preparation and immunostaining of Collagen IV, Oct4, CD34, and CD31. Fractions that were analyzed are summarized in the table below.

TABLE 4

| Exp Group | Patient Age | Digestion Collagenase Medium | Cell Fraction |
|---|---|---|---|
| 1 | Patient #1 (63) | MESCM | FC (floating cells) |
| 2 | Patient #1 (63) | MESCM | SVF (flow through) |
| 3 | Patient #1 (63) | MESCM | RC (Remaining Cells) |
| 4 | Patient #2 (58) | MESCM | FC (floating cells) |
| 5 | Patient #2 (58) | MESCM | SVF (flow through) |
| 6 | Patient #2 (58) | MESCM | RC (Remaining Cells) |
| 7 | Patient #3 (49) | MESCM | FC (floating cells) |
| 8 | Patient #3 (49) | MESCM | SVF (flow through) |
| 9 | Patient #3 (49) | MESCM | RC (Remaining Cells) |

Figure 21:
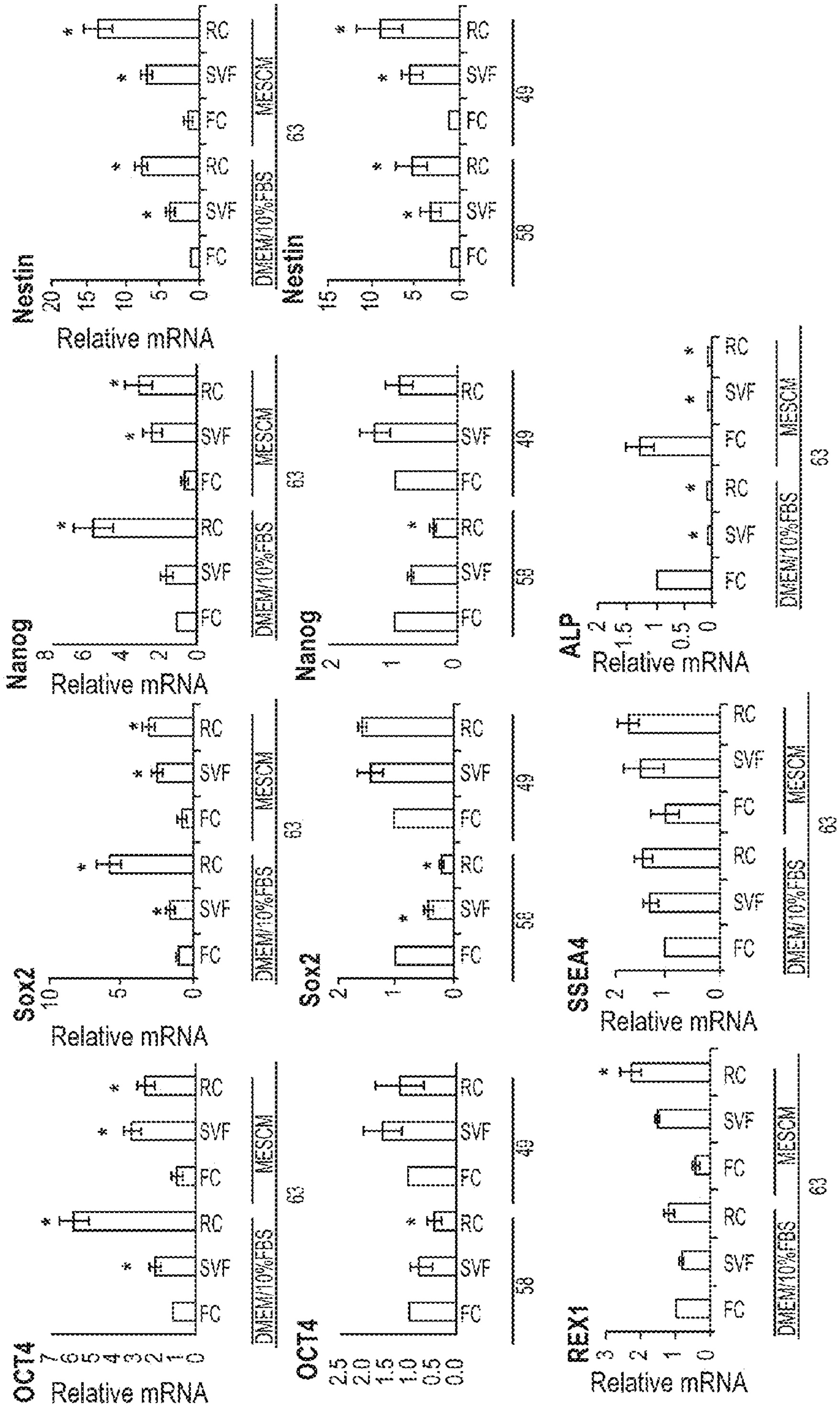
FIG. 21 illustrates expression of ESC markers in RC, FC and SVF fractions derived from human orbital fat following collagenase digestion. Patient #1 (age 63) exhibited an RC fraction that has a significantly higher relative expression of ESC markers than FC or SVF fractions as determined by qPCR when digested in either collagenase in DMEM/10% FBS or MESCM. The FC and SVF fractions also exhibit significantly higher expression of ESC markers in Patient #2 (age 58) and Patient #3 (age 49), respectively.
Figure 21:
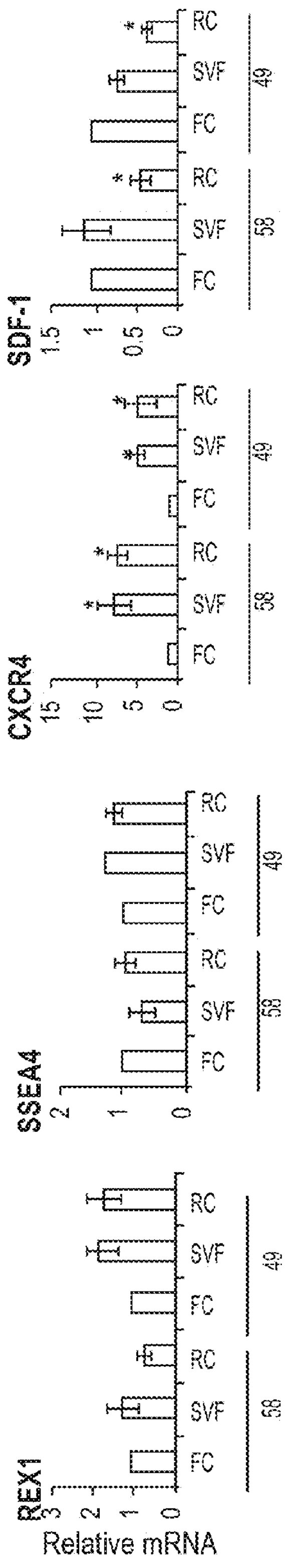

Results:

Regarding expression of ESC markers in patients of different ages, qPCR showed that ESC markers, Oct4, Nanog, and Sox2, were significantly higher in RC in Patient #1, but not statistically significant in Patient #3. In contrast, Patient #2 showed significantly higher expression of Oct4, Nanog, and Sox2 in FC (FIG. 21). Expression of Nestin transcripts was consistently significantly higher in RC than SVF and FC in all 3 patients. The trend of expression of Rex1 and SSEA4 transcripts was also higher in RC except in #2, in which there was no statistical significance between three fractions. Expression of ALP transcript was highest in FC. This data suggested that ESC markers can be enriched in RC or in FC fractions rather than in the SVF fraction, which is the conventional fraction for isolating ASC. The overall expression of Oct4, Sox2 and Nanog transcripts in all fractions digested in DMEM/10% FBS was higher than MESCM, but that of Nestin and Rex1 transcript in MESCM was higher than DMEM/10% FBS.

When compared to the FC fraction, expression of CXCR4 was significantly enriched in RC and SVF fractions. In contrast, cells in FC fractions had a significantly higher SDF-1 expression.

Figure 22:
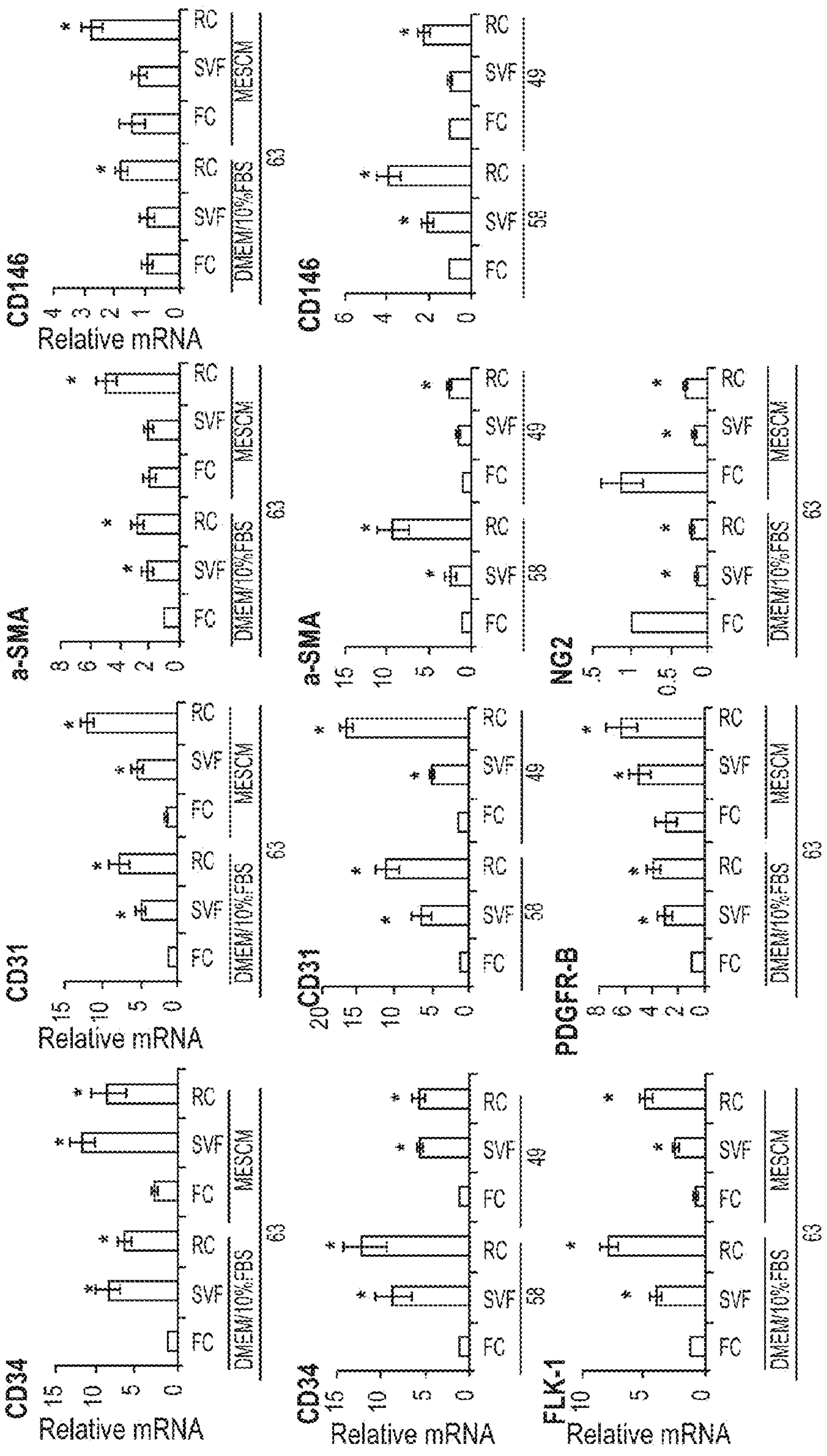
FIG. 22 illustrates that the RC fractions consistently show a significantly higher expression of angiogenic markers as determined by qPCR than FC or SVF fractions among all three patients.
Figure 22:
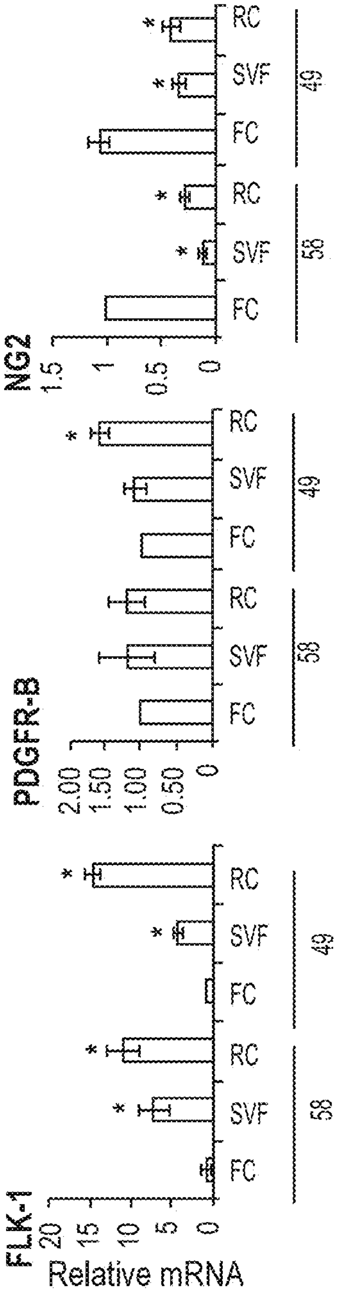

Regarding expression of angiogenesis markers, qPCR showed that RC had a significantly higher expression of CD31, CD34, FLK-1, CD146, α-SMA, and PDGFRβ than SVF and FC in all 3 patients (FIG. 22). Expression of α-SMA and FLK-1 was higher in MESCM than in DMEM/10% FBS, while the expression of CD31, CD34, CD146, PDGFRβ and NG2 was higher in MESCM than in DMEM/10% FBS. These result suggested that cells expressing angiogenic markers in RC may not be the same as cells expressing ESC markers.

Expression of CD34 was the highest in SVF in both media suggesting SVF cells may indeed come from the outer adventitial stromal ring, and in agreement with the published reports they express CD34. The retaining non-flow through (RC) fraction contained high expression of CD31 expressing cells, which usually indicate EPC. Expression of NG2 was the highest in FC in both media and in all patients, suggesting that some pericytes might be around FC. In conclusion, expression of most angiogenesis markers was also significantly higher in RC than SVF in both media and all patients. Collectively, these results supported our hypothesis that RC is a better source than the conventional SVF to provide progenitor cells expressing both ESC and angiogenesis progenitors. The above results also suggested the conventional method can be improved by using RC rather than SVF as the source of generating ASCs.

Figure 23:
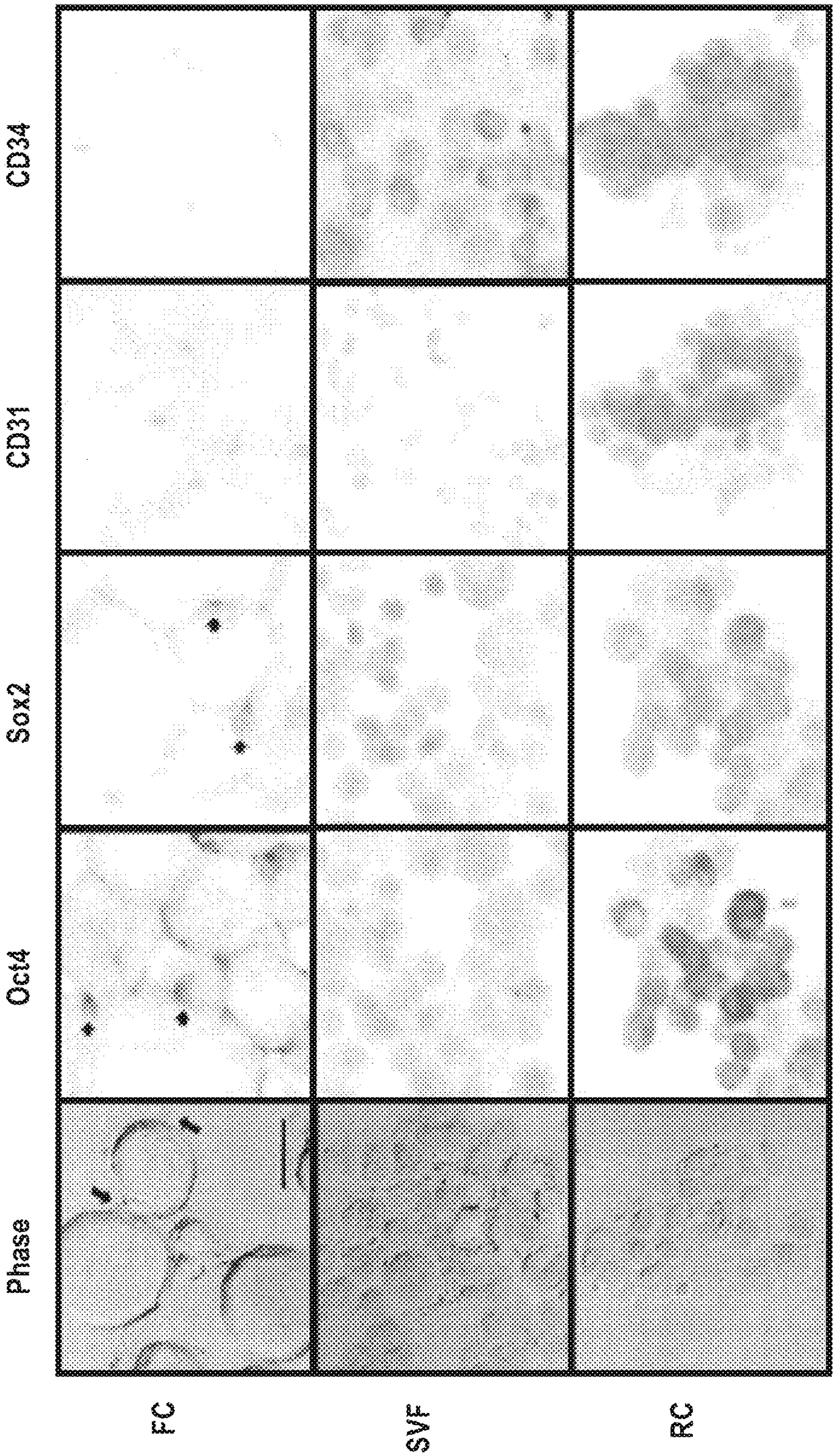
FIG. 23 illustrates phase contrast microscopy and immunofluorescence analysis showing Oct4, Sox2, CD31 and CD34 expression enriched in RC fractions compared to FC or SVF fractions after digestion in collagenase in MESCM. Bars represent 50 μm.

Phase contrast images of the cytospin preparation showed large cells greater than 60 μm and small cells 10 μm in diameter in the FC fraction, of which the latter showed positive staining to Oct4 and Sox2 (FIG. 23). Cells in SVF were overall larger than those in RC fraction. SVF cells contains mixture of positive Oct4 expression in cytoplasm and nucleus while RC cells contain Oct4+ expression in cytoplasm. RC than that of SVF, of which sox2 was expressed in the nucleus. SVF contained cells that expressed highest CD34+/CD31−, while cells in RC coexpressed CD34+/CD31+. FC showed no expression of CD31 and CD34.

In summary, RC contained cells that express the most ESC and angiogenesis progenitor markers than the fraction SVF and the FC fractions when seeded in either DMEM/10% FBS or MESCM. The overall expression of these markers was better preserved in MESCM than DMEM/10% FBS group

Example 13

Method of Expanding ASCs from Orbital Fat Tissues Using RC as the Source on Coated Matrigel in MESCM In the previous example, it was found that the RC fraction retained progenitor cells better than SVF. Because the RC fraction retains the basement membrane that is resistant to collagenase digestion, we further digested the RC fraction by dispase, which cleaves the basement membrane. These cells from this digestion can be further characterized by cytospin and double immunostaining against various markers to determine the homogeneity of cells within such fraction. The ability of ASC to adhere to tissue culture plastic has been commonly used as an enrichment method. This adhesive property of ASC is mediated largely by CD29 (integrin β1), which is a surface marker commonly used to identify ASC.

Experimental Design:

Digestion of adipose tissue with collagenase was performed in DMEM/10% FBS or MESCM and fractionated as described in the previous example. Both SVF and RC fractions were then digested by 10 mg/ml dispase followed by Trypsin EDTA for 10 min for cytospin and double immunostaining Single cells derived from both SVF and RC fractions were also seeded at 2×$10^4$/$cm^2$ on plastic in DMEM/10% FBS or on coated Matrigel in MESCM, and serially passaged while their morphology monitored by phase contrast microscopy. Resultant cells were collected for qPCR analysis of marker expression as performed in the previous example. Cell doubling time and numbers of passage were also determined and compared with the control SVF in DMEM/10% FBS. Samples that were analyzed are summarized in the table below.

TABLE 5

| Exp Group | Digestion Collagenase Medium | Cell Fraction | Substrate |
|---|---|---|---|
| 1 ctrl | DMEM/10% FBS | SVF (flow through) | PL |
| 2 | DMEM/10% FBS | RC (Remaining Cells) | PL or MG |
| 3 | MESCM | SVF (flow through and not) | PL or MG |
| 4 | MESCM | RC (Remaining Cells) | PL or MG |

Figure 24:
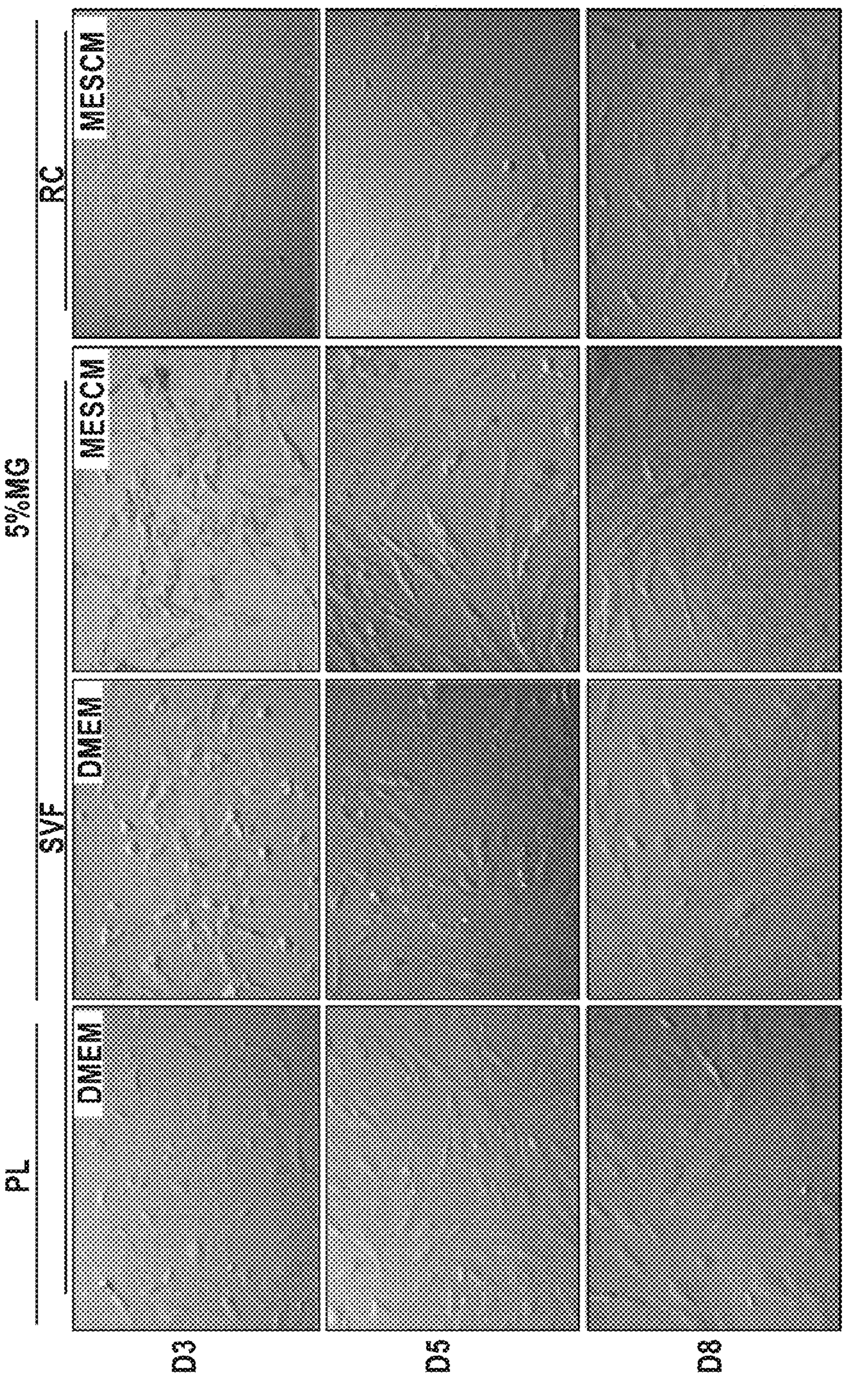
FIG. 24 illustrates phase contrast microscopy of adipose tissue cells of SVF versus RC fractions plated on plastic or 5% Matrigel (MG) at Days 1, 5, and 8 post-seeding.
Figure 25:
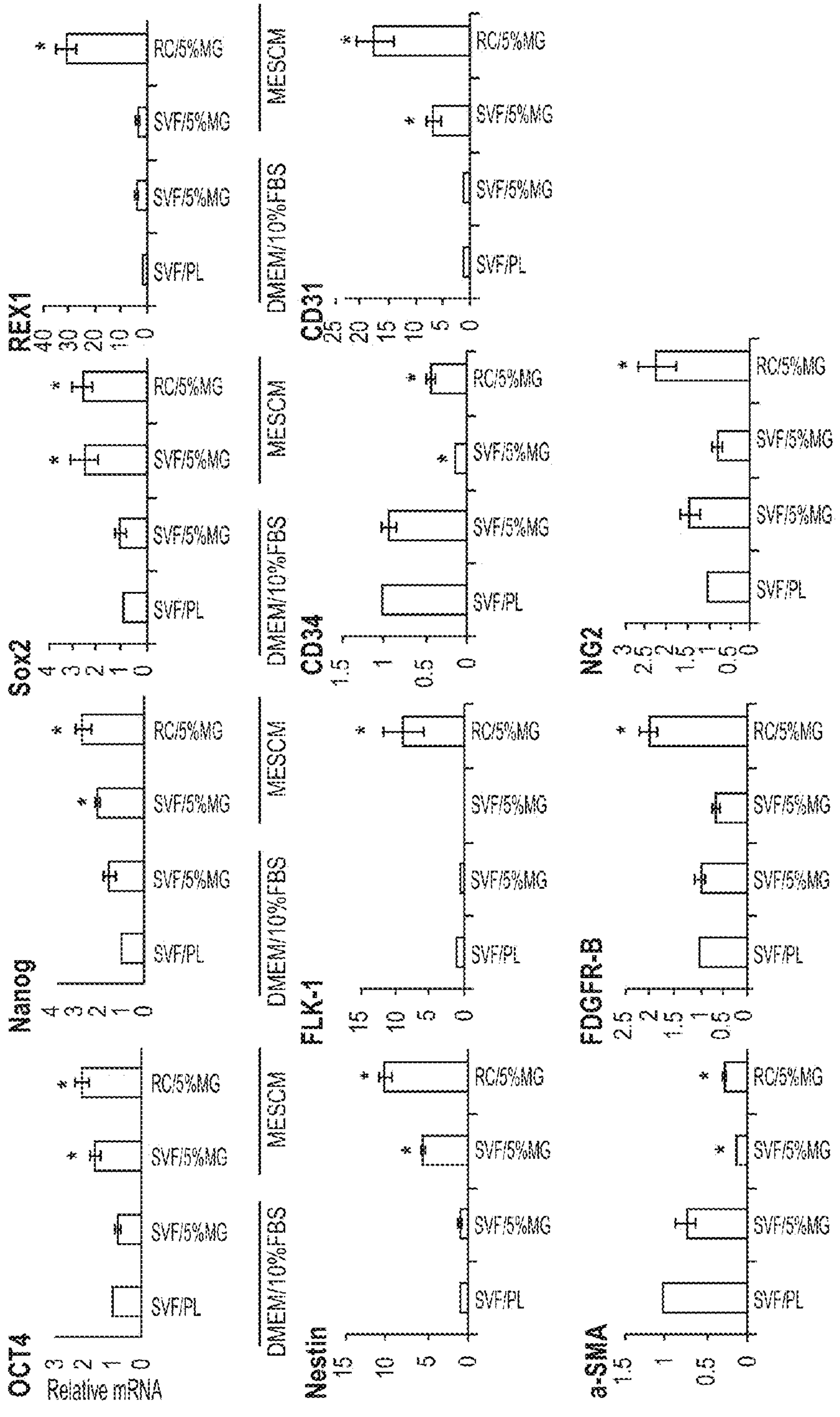
FIG. 25 illustrates that the RC fraction showed a significantly higher expression of ESC or angiogenic markers as determined by qPCR in SVF 5% Matrigel (MG) than on plastic at Days 10 post-seeding

Results:

In the present experiment, due to a small amount of tissue and hence a smaller yield of cells, we were not able to determine the seeding density. By D3, SVF cells on PL in DMEM/10% FBS showed predominant spindle cells, and the same morphology was noted in SVF cells seeded on 5% MG in DMEM/10% FBS (FIG. 24). In contrast, SVF cells on 5% MG in MESCM exhibited two types of morphology. RC cells on 5% MG in MESCM showed many small round cells with few spindle cells, though the overall difference in number of cells may be caused by intrinsic difference in cell density used. No cells were observed from RC on 5% MG in DMEM/10% FBS. By D5, all cells turned into spindle cells except that much smaller spindle cells were noted in RC cells. By day 8, more numbers of cells were noted for each condition except that clonal growth was noted in RC cells.

qPCR consistently showed that RC seeded on 5% MG in MESCM expressed significantly higher Oct4, Nanog, Sox2, Rex1 and Nestin (i.e., ESC markers), than SVF cultured conventionally on PL in DMEM/10% FBS or on 5% MG in DMEM/10% FBS (FIG. 25). SVF cells cultured on 5% MG in MESCM expressed higher levels such markers, but not to the same extent as RC, especially REX1. 5% MG is not as critical as MESCM in promoting ESC expression for SVF.

qPCR also showed that RC cells seeded on 5% MG in MESCM expressed significantly higher angiogenesis markers such as FLK-1, CD31, PDGFR-B and NG2 but not CD34 and α-SMA than SVF cells cultured on either PL or 5% MG in DMEM/10% FBS. Thus, RC cells cultured on 5% MG in MESCM turn into progenitors expressing a pericyte phenotype, a finding similar to what we have observed in human limbal NCs.

On 5% MG and in MESCM, SVF still exhibited significant less expression of FLK-1, CD31, PDGFR-B and NG than RC cells, indicating that RC cells contain more progenitors than SVF and such cells are best maintained on coated Matrigel in MESCM.

In summary, RC derived cells contain younger progenitors than SVF and such progenitors can be better expanded on 5% MG in MESCM with smaller cells and more clonal growth and expressing more ESC and angiogenesis markers.

Example 14

Method of Expanding ASCs from Orbital Fat Tissues by Culturing on Immobilized nHC-HA in MESCM The ability of ASC to adhere to tissue culture plastic has been commonly used as an enrichment method. We have previously demonstrated limbal NCs form aggregates when seeded on immobilized nHC-HA and express ESC and CD31 in MESCM. In this example, a method of expanding ASCs by culturing on immobilized HC-HA in MESCM was examined.

Experimental Design:

Cells were isolated from adipose tissue of human.

Adipose tissue derived from human patients (patient ID #090761 (age 52) and #120254 (age 58)) was digested with collagenase and fractionated into FC, RC, SVF using the protocol described in Example 12, except that the size of filter was changed from 150 μm to 70 μm. Cells in each fraction were then subjected to trypsin/EDTA for 10 min to yield single cells. The cells were then seeded at $4\times10^4$/96 wells on different substrates: plastic or plastic with immobilized HA, 4× nHC-HA/PTX3 water soluble (S; isolated in PBS), and 4× nHC-HA/PTX3 water insoluble (IS; isolated in guanidine) in MESCM (see procedure below). SVF cells were seeded on plastic in DMEM/10% FBS as a control. Cell aggregates were observed at 2 h, 18 h, 2 days, 4 days and 7 day post-seeding. Total RNAs were extracted on day 8 and used for qRT-PCR analysis of the following transcript expression: ESC markers (Oct4, Nanog, Sox2 and Nestin) and other markers such as CD34, CD31, PDGFR-β, vWF and α-SMA. Immunostaining was used to confirm the gene expression.

Immobilization of HA and nHC-HA/PTX3: The covalent coupling of substrates on the surface of Covalink-NH 96 well (Nunc) was similar as described as in He et al. (2009) *J. Biol. Chem.,* 284 (30):20136-20146. In brief, Covalink-NH plates were sterilized in 70% alcohol for 1 h, washed 3 times with distilled water, and added with 100 μl of 0.184 mg/ml Sulfo-NHS and 0.123 mg/ml of EDAC in distilled water containing 20 μg/ml HA or nHC-HA/PTX3 per 96-well plate Control wells contained all reagents except for HA and nHC-HA/PTX3. The plate was incubated at 4° C. overnight or at 25° C. for 2 h before the coupling solution was removed, washed 3 times with PBS containing 2 M NaCl and 50 mM MgSO4, and followed by 3 washes with PBS.

TABLE 6

| | Experimental 96 Well Plate, P0 | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | Medium |
| A | PBS | | | HA | | | nHC-HA/PTX3 (S) Water Soluble | | | nHC-HA/PTX3 (IS) Insoluble | | | |
| B | FC | RC | SVF | FC | RC | SVF | FC | RC | SVF | FC | RC | SVF | |
| C | X | X | X | X | X | X | X | X | X | X | X | X | MESCM |
| D | X | X | X | X | X | X | X | X | X | X | X | X | |
| E | | | X | | | | | | | | | | |
| F | | | X | | | | | | | | | | DMEM/ 10% FBS |
| G | | | | | | | | | | | | | |
| H | | | | | | | | | | | | | |

Total FC: $2.4\times10^5$, RC: $2.4\times10^5$, SVF: $3\times10^5$ cells

Figure 26:
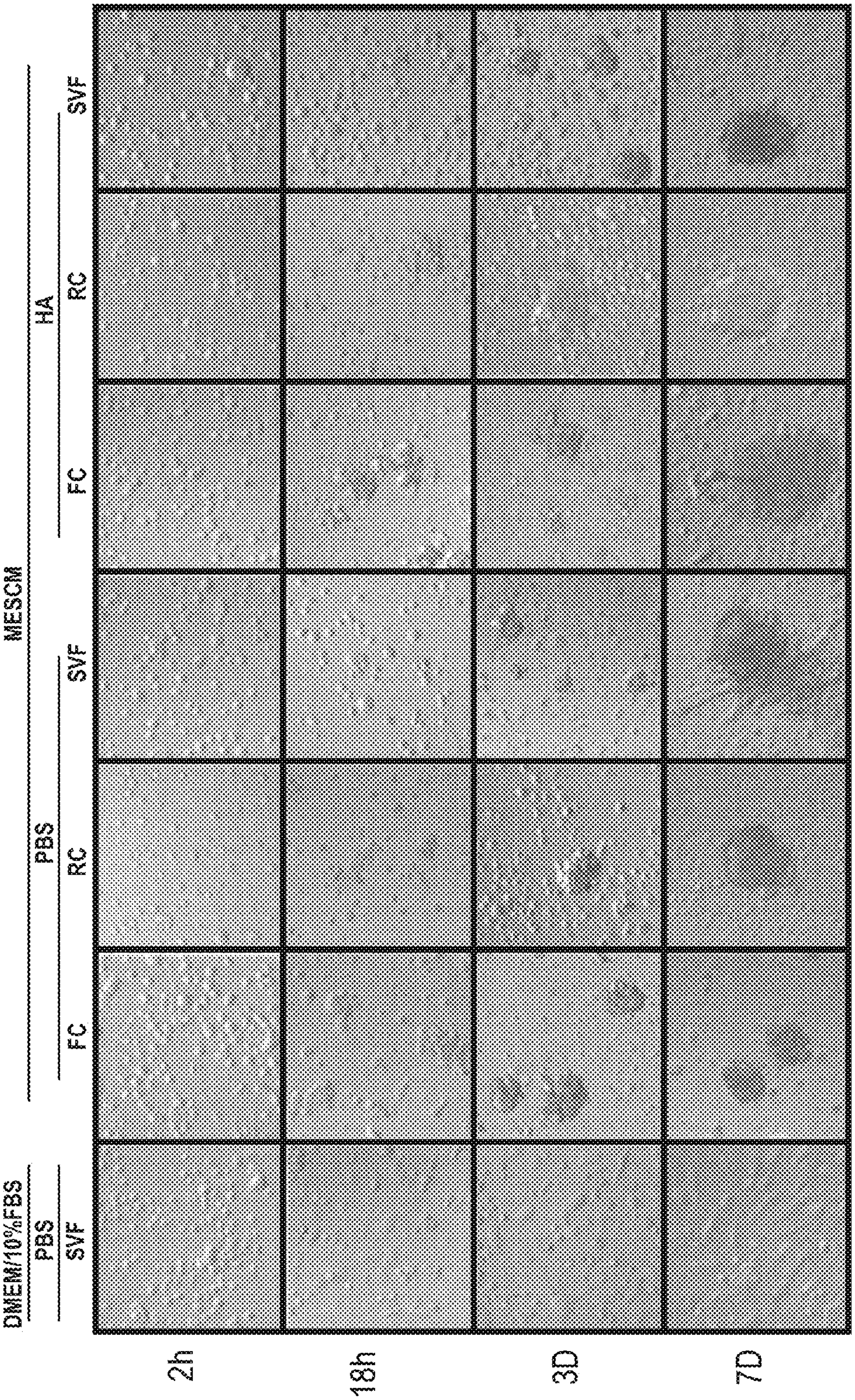
FIG. 26 illustrates phase contrast images of ASCs (adipose stem cells) from FC, RC and SVF fractions after day 9 in culture in MESCM on control PL alone, immobilized HA, immobilized nHC-HA/PTX3 (Water Soluble) or nHC-HA/PTX3 (Water Insoluble) at 2 h, 18 h, 3 days and 7 days. The control SVF fraction seeded in DMEM/10% FBS on PL also is shown.
Figure 26:
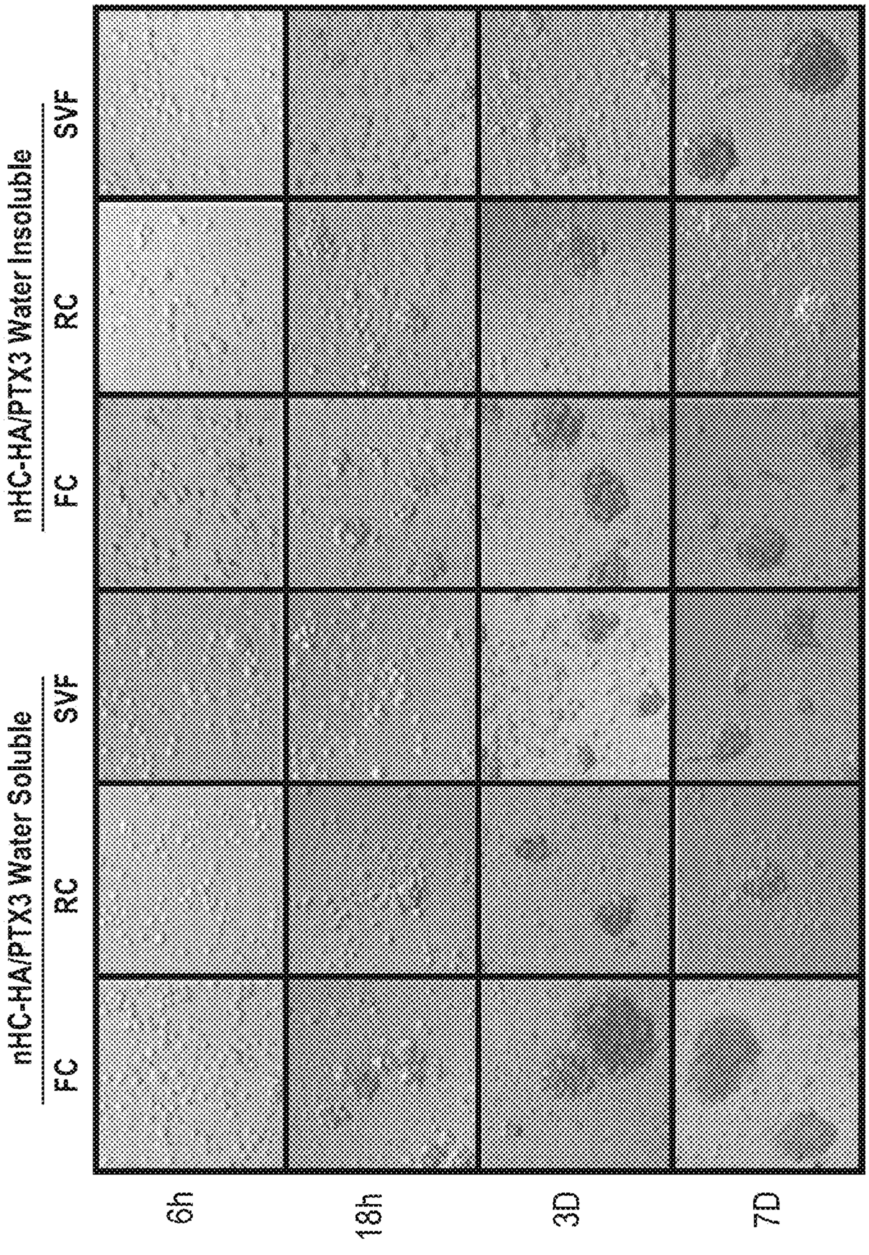
Figure 27:
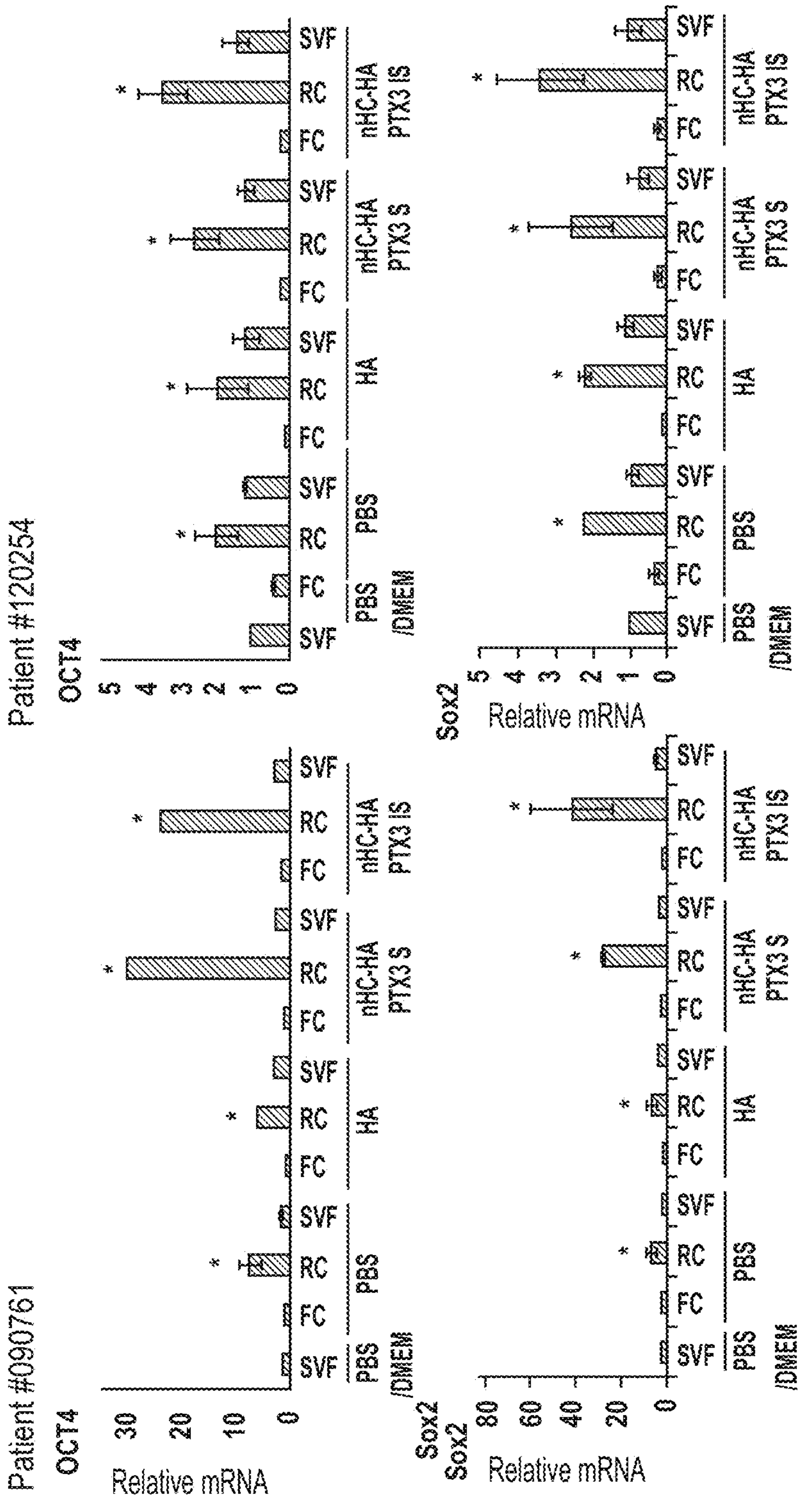
FIG. 27 illustrates relative ESC marker gene expression as determined by qPCR for cells isolated from adipose tissue of patient #090761 (age 52) and #120254 (age 58). Data is shown for cells cultured in MESCM on PL alone, immobilized HA, immobilized nHC-HA/PTX3 (Water Soluble) or nHC-HA/PTX3 (Water Insoluble) at 8 days post seeding. (n=3, * p<0.01).
Figure 27:
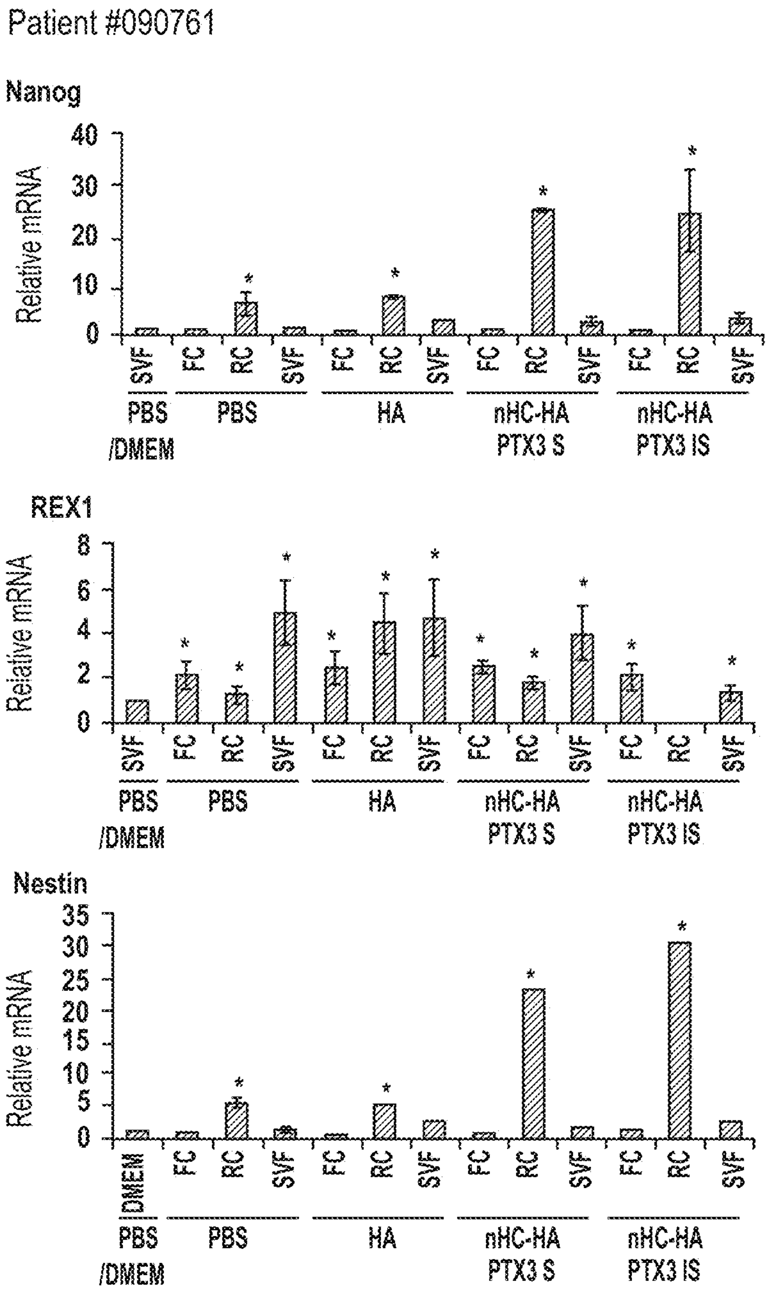

Results:

Phase Image Observations:

At 2 h, all cells from FC, RC, SVF were seeded evenly distributed on plastic (PL), immobilized HA, nHC-HA/PTX3 S, nHC-HA/PTX3 IS (FIG. 26). At 18 h, cell aggregations were observed both patients from FC on PL, immobilized HA, nHC-HA/PTX3 S, nHC-HA/PTX3 IS. At D3 and D7, except in control in DMEM/10% FBS group, all fractions in all immobilized substrates form aggregations. Quantitative counting on cell aggregations showed that both FC and SVF generates high numbers of aggregations while RC generates lowest aggregation count on all immobilized substrates. Aggregates sizes are formed largest in FC and SVF (in patient #120254 only) while smaller sizes were observed in RC. At D7 and D9, cells began to migrate out from aggregates in SVF on immobilized HA and PL as compared to FC and RC fraction. All other fractions on immobilized nHC-HA PTX3 S and nHC-HA PTX3 IS remain aggregated. This result is similar to rabbit inguinal fat data (see Example 15) which showed cell migrations are observed more in PL and HA.

qPCR Comparison:

In both patients, compared to the control SVF in DMEM/10% FBS on plastic, expression of ESC markers, Oct4, Sox2, Nanog, Nestin, were significantly higher in all RC fractions, especially on immobilized nHC-HA PTX3 S and nHC-HA (FIG. 27). In contrast, expression of Rex1 is significantly promoted in SVF on plastic and HA but gradually down regulated in nHC-HA PTX3 S and nHC-HA PTX3 IS. This finding is consistent with D0 finding (Example 12), in which RC fraction contains cells expressing the highest amount of ESC markers. Furthermore, it also suggests that immobilized nHC-HA PTX3 S and nHC-HA PTX3 can further promote their ES expression.

Figure 28:
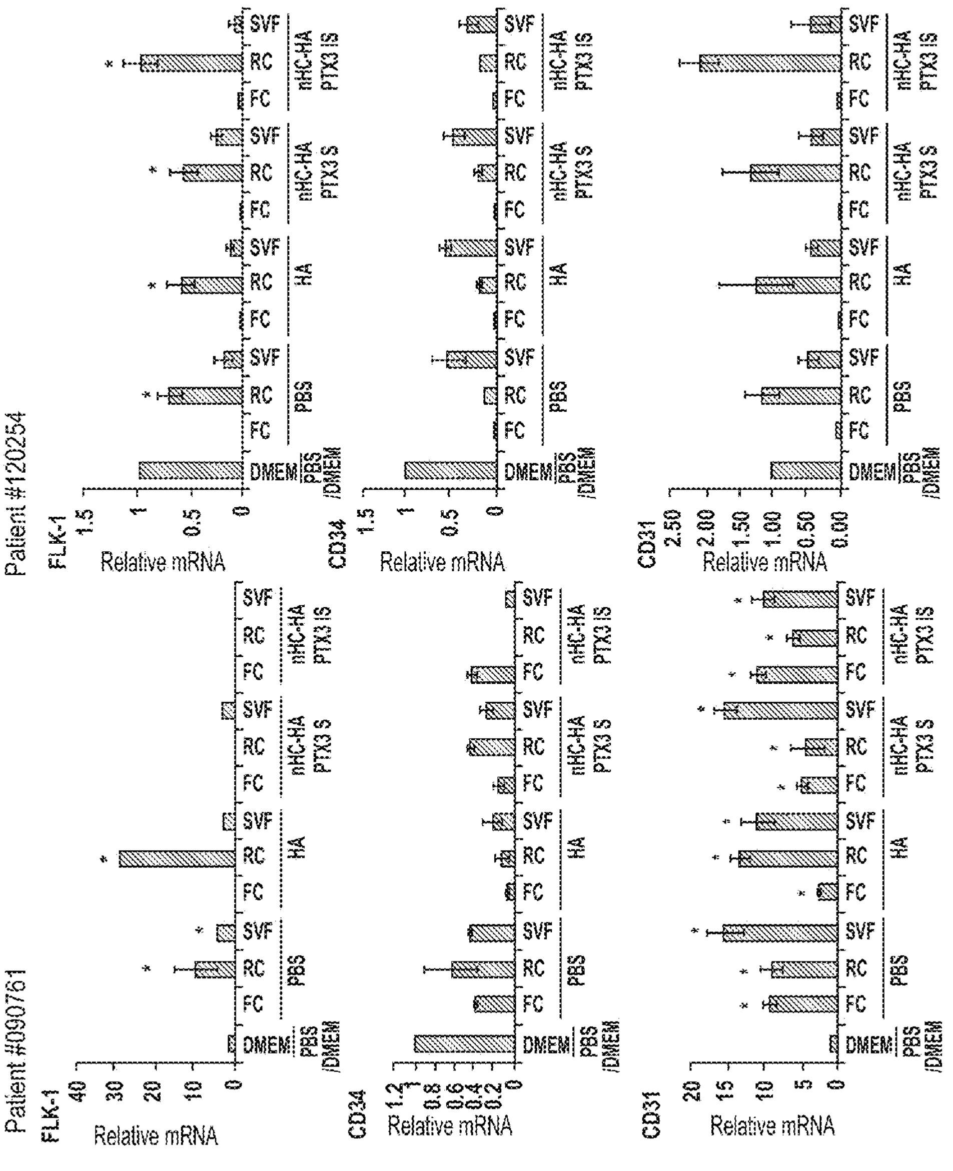
FIG. 28 illustrates angiogenic marker gene expression as determined by qPCR for cells isolated from adipose tissue of patient #090761 (age 52) and #120254 (age 58). Data is shown for cells cultured in MESCM on PL alone, immobilized HA, immobilized nHC-HA/PTX3 (Water Soluble) or nHC-HA/PTX3 (Water Insoluble) at 8 days post seeding. (n=3, * p<0.01).
Figure 28:
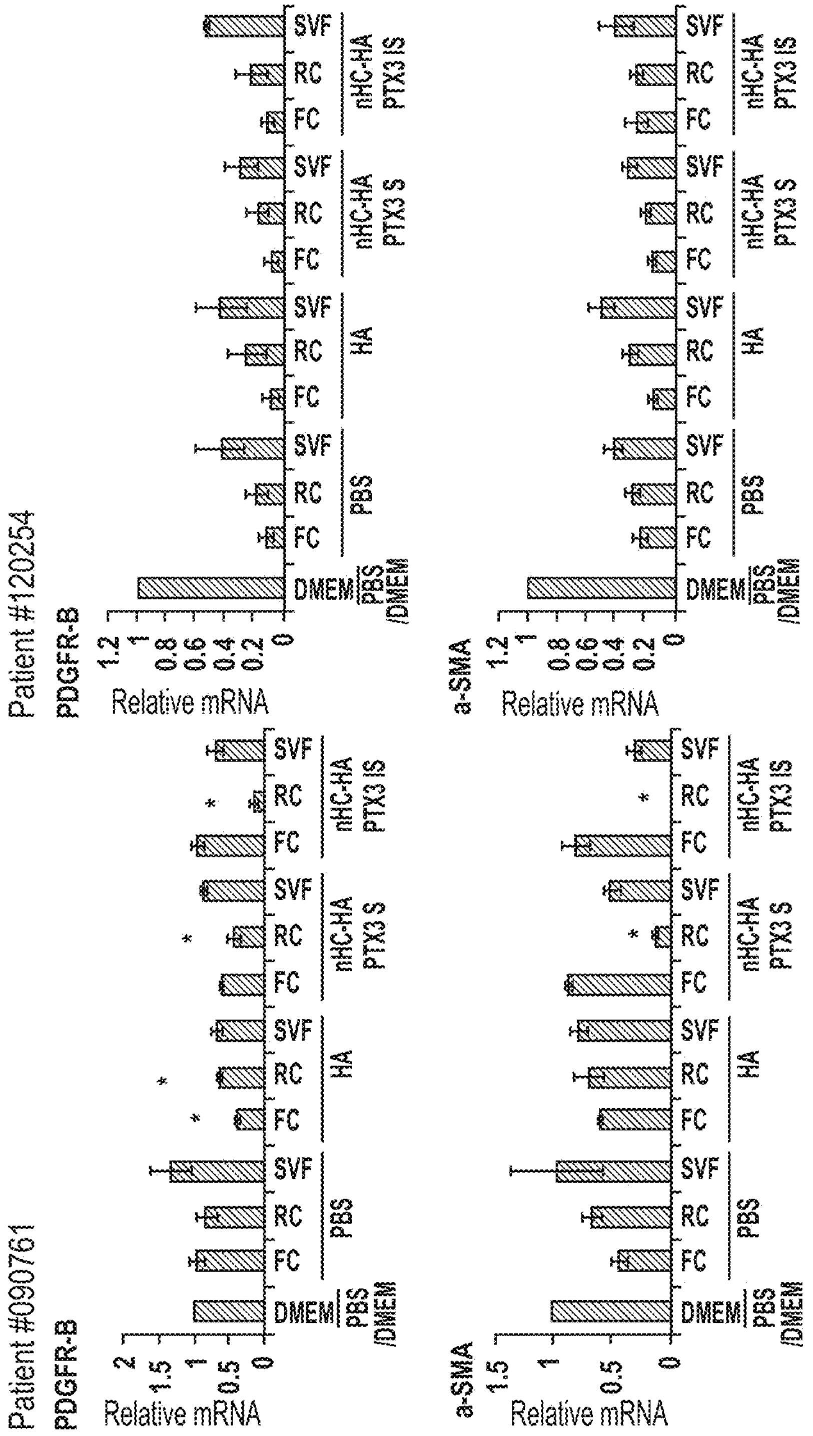

For both patients, SVF in DMEM/10% FBS promote more angiogenic marker expression than respective fraction in MESCM (FIG. 28). In the patient #120254 sample in MESCM, control SVF fraction preferential expressed CD34, PDGFRβ and α-SMA on all substrates. RC preferential expressed FLK-1 and CD31 on all substrate where FC cells exhibited the lowest angiogenic expression. In patient #090761 in MESCM, control SVF contain are preferential express highest angiogenic markers than RC and FC on plastic and HA. When seeded on immobilized nHC-HA PTX3 S and IS, both RC and SVF were significantly down regulated. Overall, immobilized HA contain mixture appeared to promote angiogenic action but downregulated CD34 expression. nHC-HA PTX3 S down regulated angiogenic expression in RC and FC while nHC-HA PTX3 IS downregulated angiogenic expression in RC and SVF.

Figure 29:
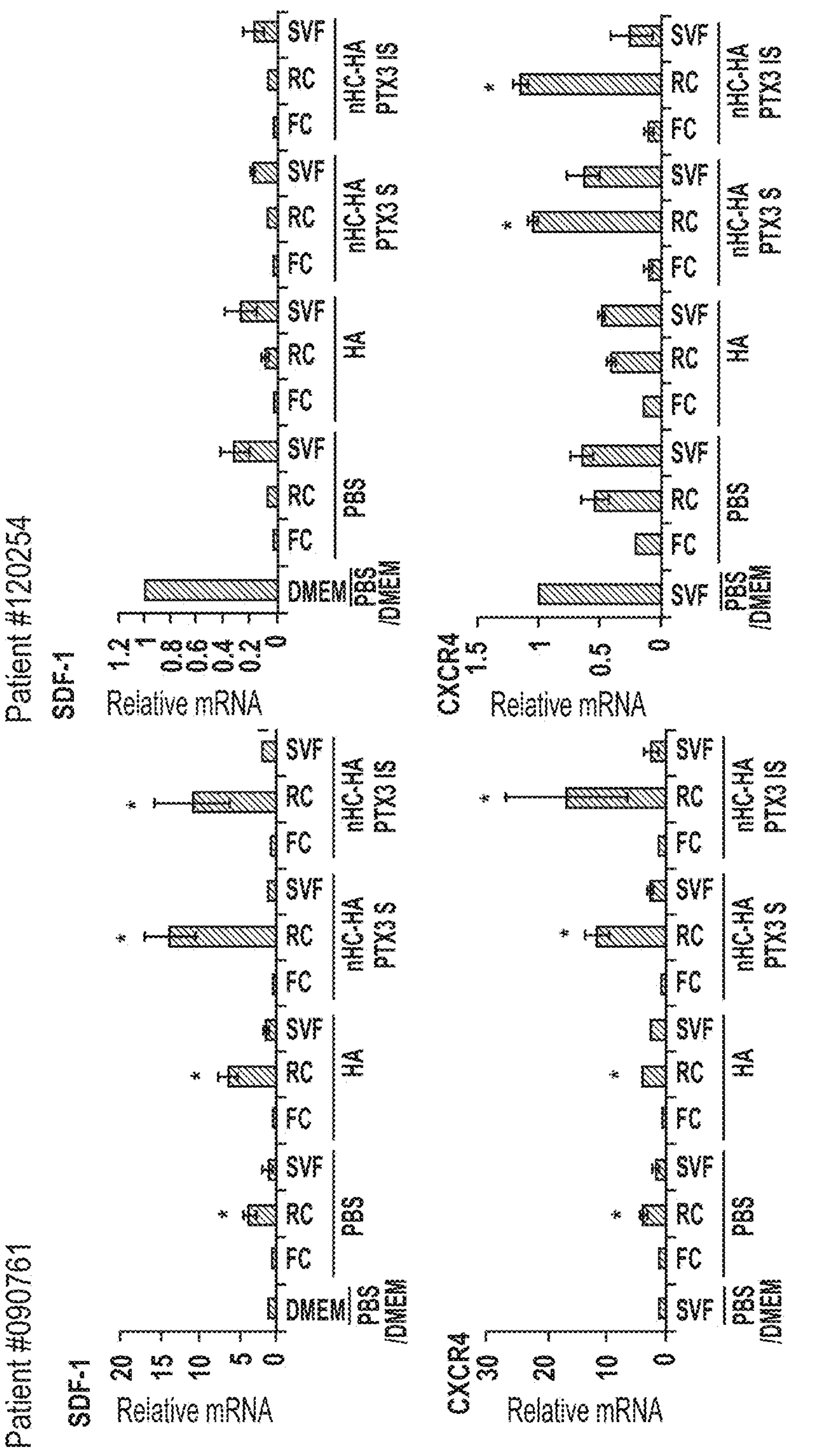
FIG. 29 illustrates marker gene expression as determined by qPCR for cells isolated from adipose tissue of patient #090761 (age 52) and #120254 (age 58). Immobilized HA, immobilized nHC-HA/PTX3 (Water Soluble) or nHC-HA/PTX3 (Water Insoluble) promote RC expression of relative SDF-1 and CXCR4 marker gene expression for cells isolated from adipose tissue of patient #090761 and #120254. Data is shown for cells cultured in MESCM on PL alone, immobilized HA, immobilized nHC-HA/PTX3 (Water Soluble) or nHC-HA/PTX3 (Water Insoluble) at 8 days post seeding. (n=3, * p<0.01).

Two patients displayed different SDF-1 and CXCR4 expression in the cell fractions (FIG. 29). In the age 52 patient sample, RC has the highest SDF-1 and CXCR4 expression, and both markers were significantly increased on nHC-HA PTX3 S and IS. In the age 58 patient sample, the SVF fraction on plastic in DMEM/10% FBS had highest SDF-1 expression when compared to SVF in MESCM. In MESCM, SDF-1 expression was highest in SVF than RC and SVF. CXCR4 expression was highest in SVF on plastic and HA, and was significantly promoted in RC when seeded on immobilized nHC-HAPTX3 S and IS. Overall, nHC-HA PTX3S and IS can promote SDF-1 and CXCR4 expression in RC but not SVF or FC.

Figure 30:
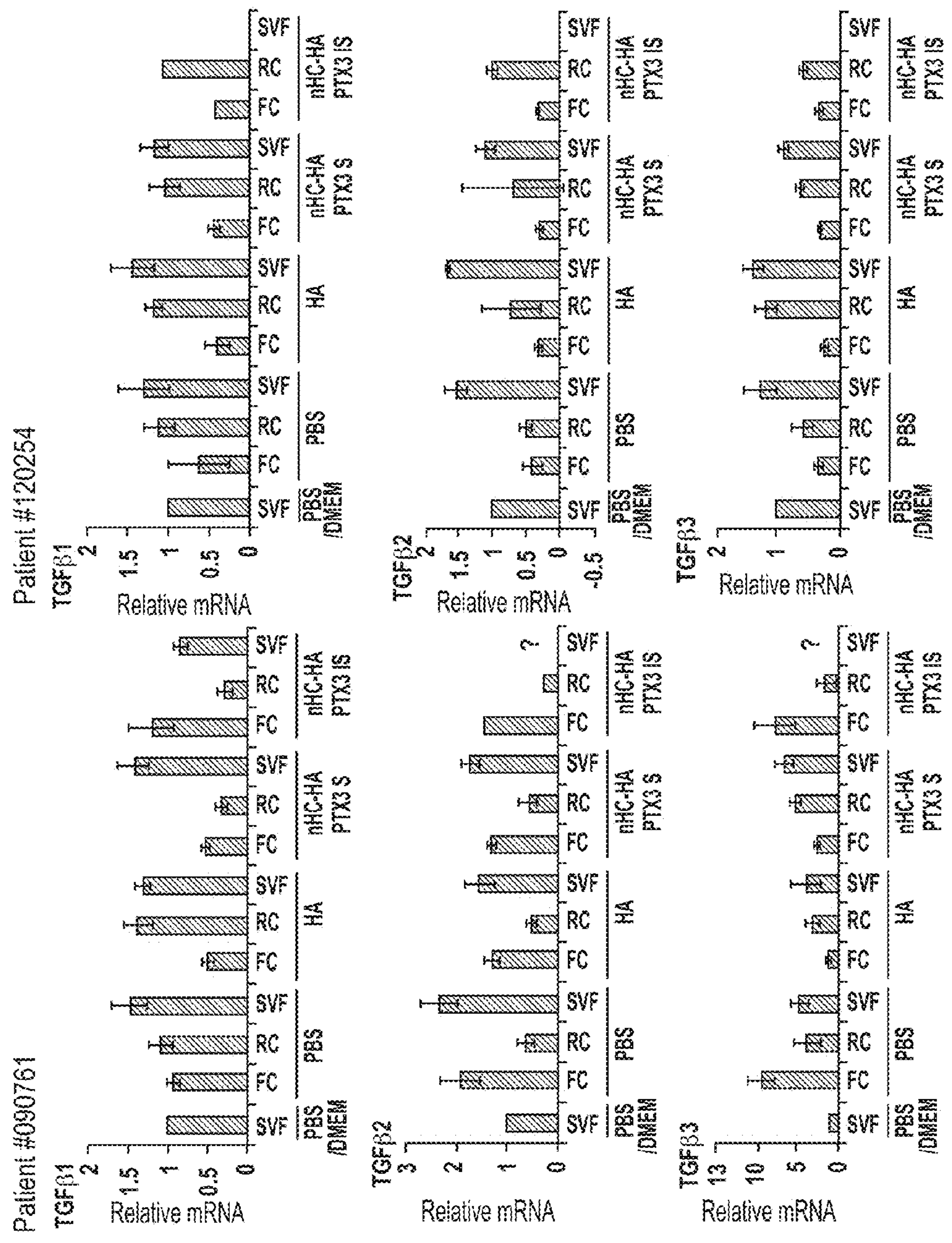
FIG. 30 illustrates relative TGFβ1, TGFβ2 and TGFβ3 marker gene expression as determined by qPCR for cells isolated from adipose tissue of patient #090761 (age 52) and #120254 (age 58). Data is shown for cells cultured in MESCM on PL alone, immobilized HA, immobilized nHC-HA/PTX3 (Water Soluble) or nHC-HA/PTX3 (Water Insoluble) at 8 days post seeding. (n=3, * p<0.01).

When compared to the control SVF on plastic in DMEM/10% FBS, SVF exhibited significantly higher expression of TGFβ1, TGFβ2 and TGFβ3 than RC and FC on plastic (FIG. 30). No significant differences in substrates was observed.

Figure 31:
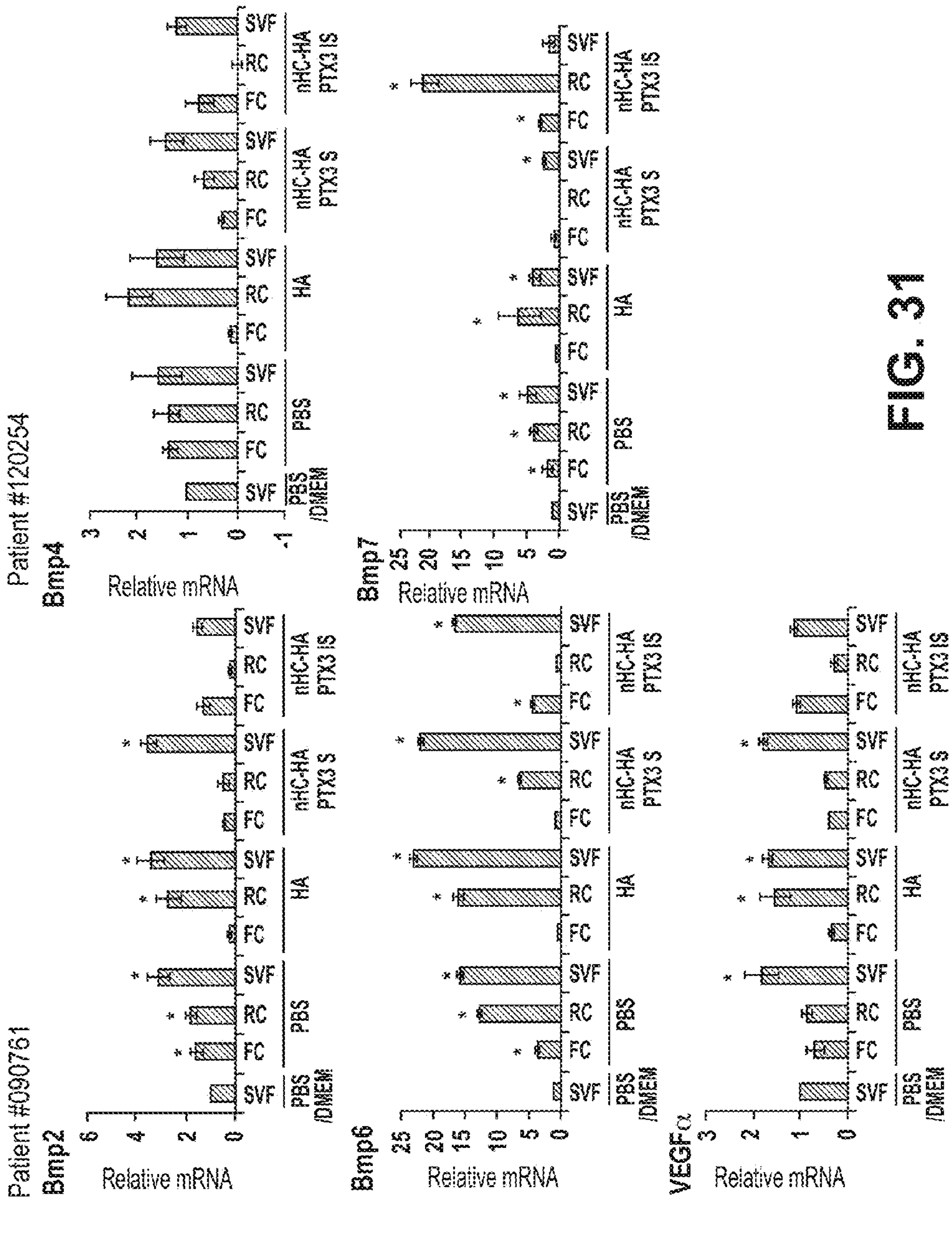
FIG. 31 illustrates relative BMP2, BMP4, BMP6, BMP7 and VEGFα marker gene expression as determined by qPCR for cells isolated from adipose tissue of patient #090761 (age 52). Data is shown for cells cultured in MESCM on PL alone, immobilized HA, immobilized nHC-HA/PTX3 (Water Soluble) or nHC-HA/PTX3 (Water Insoluble) at 8 days post seeding. (n=3, * p<0.01).

When compared to the control SVF fraction cultured on plastic in DMEM/10% FBS, cells cultured on plastic in MESCM significantly promoted expression BMP2, 4, 6 and 7 in all fractions (FIG. 31). This suggested that MESCM can promote expression of BMP2, 4, 6 and 7 even when cells were seeded on different substrates.

Compared to each fraction cultured on plastic, cells cultured on immobilized HA downregulated all BMPs from FC, but upregulated all BMPs from RC and SVF. Similarly, cells from SVF but not FC and RC, showed similar upregulation of all BMPs when cultured on immobilized nHC-HA PTX3 S and nHC-HA PTX3 IS, except BMP7, which was promoted in RC. It has been previously report that BMP7 increases the production of "good" brown fat cells, while keeping their levels of the normal white fat cells constant. In addition, BMP-7 triggers commitment of mesenchymal progenitor cells to brown adipocyte lineage in vitro and in vivo.

Figure 32:
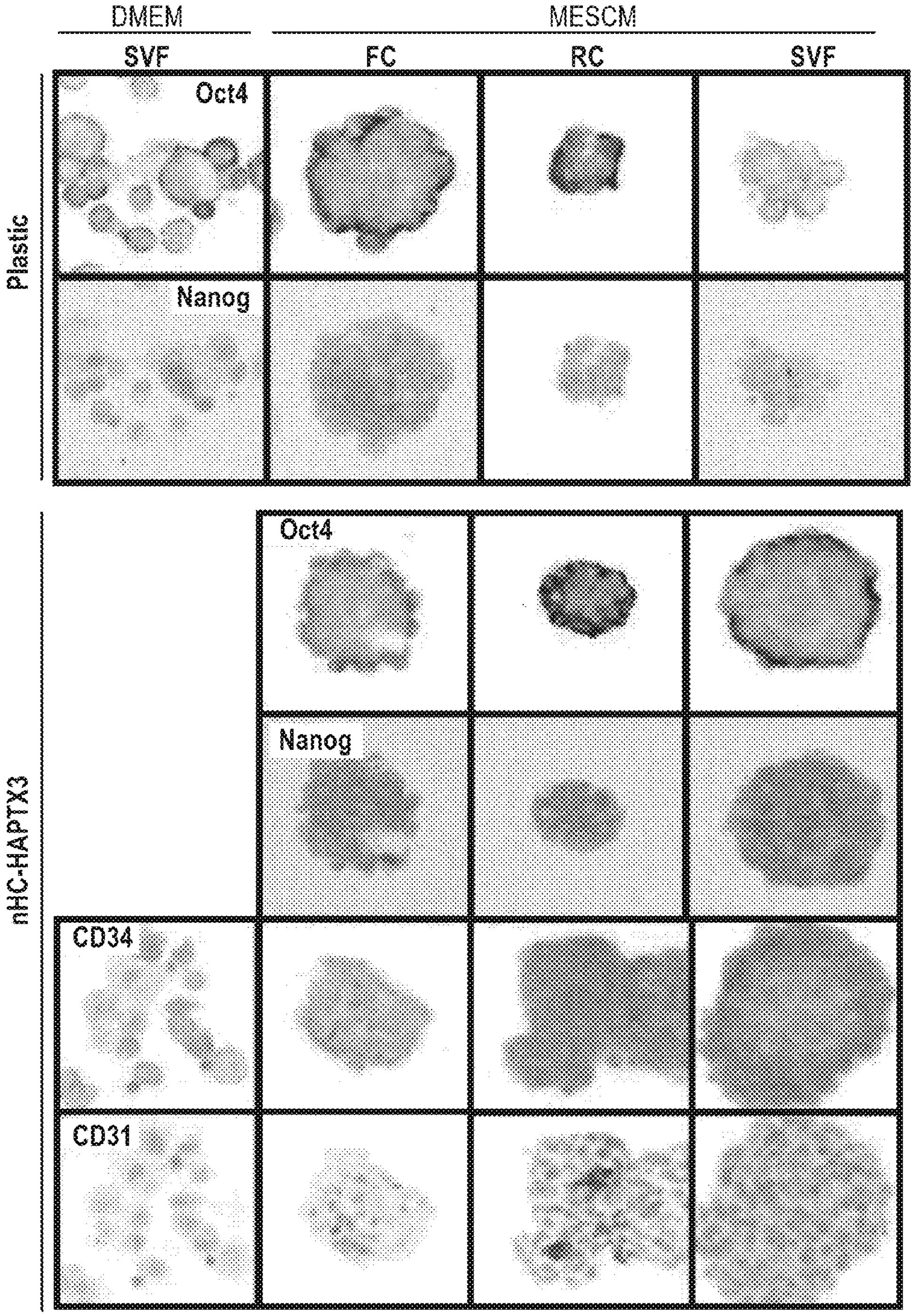
FIG. 32 illustrates immunofluorescence of Oct4, Nanog, CD34 and CD in cells cultured on plastic versus nHC-HA/PTX3 in DMEM or MESCM.

Immunostaining of human adipose cells on nHC-HA PTX3 or control PL/SVF in DMEM from Patient #120254 demonstrated that most cells derived from express Oct4, Nanog. Oct4 was strongly expressed in RC than in FC and SVF. In RC, the Oct4 expression was the strongest on nHC-HA PTX3 compared to PL. In FC, the Oct4 expression was the strongest on PL/FC compared to nHC-HA PTX3. This is consistent with the PCR data which showed that Oct4 is expressed more in RC than SVF and FC. No significant differences of Nanog expression were observed between substrates. Immunostaining of expression angiogenesis markers and CD31, demonstrated expression in the center of clusters where CD34 are weakly expressed in vitro (FIG. 32).

Example 15

Modified Method of Isolating Progenitor Cells from Rabbit Inguinal Fat Pads

In this example, methods of isolating and expanding ASCs from adipose tissues from Rabbit inguinal fats pads was examined.

Experimental Design:

Inguinal white fat pads (identified as WAT) derived from rabbits were minced into 2 $mm^2$ pieces to achieve a homogenous sampling in a 150 $cm^2$ large petri dish. They were then subdivided into two parts, and digested in 1 mg/ml of collagenase A in either DMEM/10% FBS and or MESCM for 18 h at 37° C. Actual weights of the samples used were as follows:

Female Rabbit 1: 39.7 g fat pad, 8.3 g aliquot used for each tube, 2 tubes for either DMEM or MESCM containing 10 ml solution, each 0.83 g/ml.

Female Rabbit 2: 29.4 g fat pad, 6.2 g aliquot used and split, 2tubes DMEM, 2 tubes MESCM containing 10 ml solution, 0.62 g/ml.

Female Rabbit 3: 25.0 g fat pad, 6.9 g aliquot used and split, 2tubes DMEM, 2 tubes MESCM containing 10 ml solution, 0.69 g/ml.

Male Rabbit 4: 1×1 cm of fat pieces weighted at 5.4 g and digested in 22 mls MESCM+Coll (~0.4 g/ml)

Male Rabbit 5: 1×1 cm of fat pieces weighted at 6.3 g and digested in 23 mL of MESCM+Coll (~0.3 g/ml)

Figure 33:
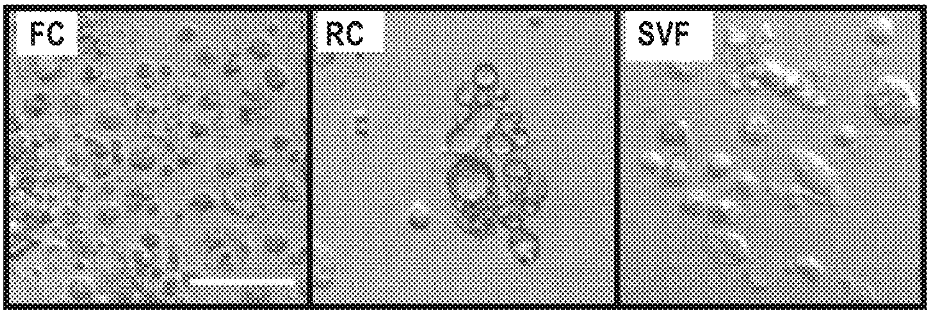
FIG. 33 illustrates phase contrast microscopy of cells of FC, SVF or RC fractions from rabbit adipose tissue digested in collagenase in MESCM (Bar indicates 50 μm).

After digestion, the cell suspensions were gently pipetted and centrifuged at 300×g for 10 min to collect floating fat cells (FC) and cell pellet. The cell pellets were resuspended in either DMEM/10% FBS (the first part) or MESCM (the second part), respectively. The suspension was then filtered via a 250 μm mesh to collect cells flowing through (designated as SVF) and those not (designated as RC). RBC lysis buffer was then added to the SVF fraction and centrifuged at 300×g for 10 min to collect cells. For the FC fraction, the cell suspension was subdivided into two, one was labeled as FC1. The other half was subjected to 10 mg/ml of dispase digestion in MESCM for 2 h at 37° C. The cell suspensions were then centrifuged at 300×g and the collected cell pellet (designated as FC2). For the above cell fractions, i.e., SVF, FC1, FC2 and RC, total RNAs were extracted and used for qRT-PCR analysis of the following transcript expression: ESC markers (Oct4, Nanog, Sox2 and Nestin) and other marker such as CD34, CD31, vWF and α-SMA. FIG. 33 shows phase contract microscopy of the fractions.

TABLE 7

| Exp Group | Digestion Collagenase Medium | Cell Fraction |
|---|---|---|
| 1 | DMEM/10% FBS | SVF (flow through) |
| 2 | DMEM/10% FBS | RC |
| 3 | DMEM/10% FBS | FC (floating cells) |
| 4 | MESCM | SVF (flow through and not) |
| 5 | MESCM | RC |
| 6 | MESCM | FC (FC1 or FC2) |

Figure 34:
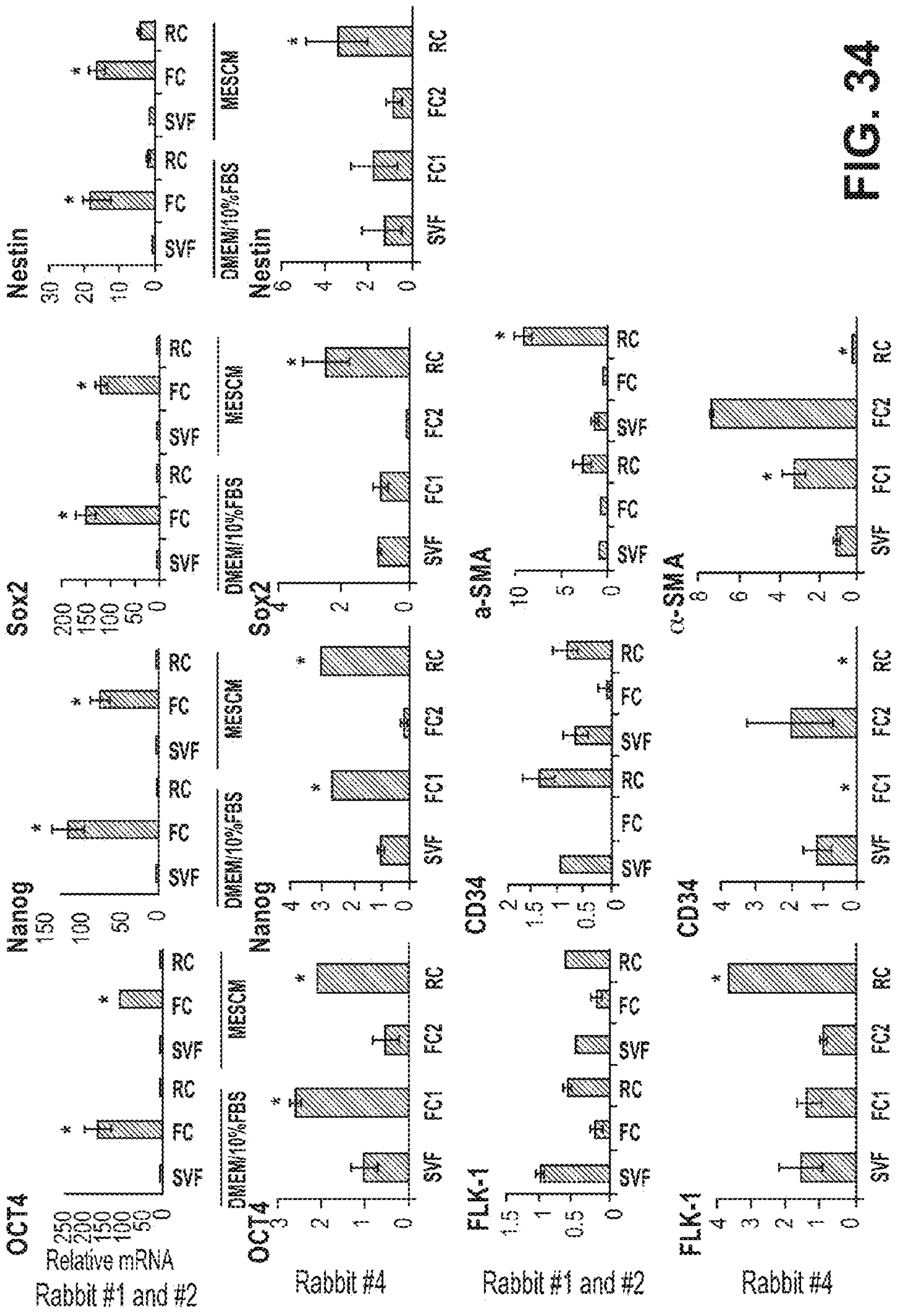
FIG. 34 illustrates relative expression of ESC markers and angiogenic markers in FC, SVF or RC fractions as determined by qPCR for Rabbit adipose tissue samples digested in collagenase in DMEM/10% FBS versus MESCM.

Results:

Unlike human adipose tissues (Example 14), we noted that little tissue was obtained from the RC fraction after filtration in rabbit #1, #2. Also unlike human adipose tissues, qPCR showed that the FC fraction has significantly higher expression of Oct4, Nanog, Sox2, and Nestin than SVF and RC fractions (FIG. 34). The overall expression of Oct4, Nanog, and Sox2 in FC was significantly higher in DMEM/10% FBS than that in MESCM, but no difference was noted in expression of Nestin transcript. Regarding the expression of angiogenic markers, similar to human adipose tissues, qPCR showed that the transcripts of FLK-1, CD34, and α-SMA were preferentially retained in RC fraction. The same result was found in Rabbit #1 and Rabbit #3. Overall, in WAT with very few blood vessels, most ESC markers can be obtained from FC fraction while the RC fraction retains cells expressing angiogenesis markers. This result is different from human adipose tissues. We did not note any significant difference of gene expression in these two different media during isolation.

In addition, adipose tissue from Rabbit #4 were derived from vascular fat zone without mincing, the result showed similar to human adipose tissue, some vessels like tissue were observed after filtration. Similarly, qPCR showed the transcript of Oct4, Nanog, Sox2 and Nestin were significantly higher in both RC and FC. FLK-1 was significantly higher in RC but not in FC1 and FC2 fraction. CD34 was preferentially expressed in SVF fraction and in FC2 but not in FC1 and RC fraction. α-SMA is significantly enriched in FC1 and FC2 but not RC. Overall, in WAT containing blood vessels, ESC expressing cells can be found in both RC and FC1. Such cells cannot be further isolated by dispase, FC2. CD34 cells can be consistently isolated from SVF where other angiogenic markers such FLK-1 or α-SMA are enriched more in RC or FC fraction suggesting the some ESC expressing progenitor can be isolated from other fractions rather than SVF.

Example 16

Expanding ASCs from Inguinal Fat Tissues by Culturing on Immobilized nHC-HA in MESCM In this example, a method of expanding rabbit ASCs from inguinal fat tissue by culturing on immobilized HC-HA in MESCM was examined.

Experimental Design:

Inguinal white fat pads (identified as WAT) derived from rabbits were obtained and subjected to digestion and fractionation of FC, RC, SVF procedures as described in Example 15. Cells were treated with trypsin/EDTA for 10 minutes to separate cells into single cells.

Weight and digestion medium ratio were calculated as following:

Female Rabbit #6(labeled rabbit #1): 11.2 g in 22.4 ml of Coll/MESCM,

Female Rabbit #7(labeled rabbit #2): 10.7 g in 21.4 ml of Coll/MESCM.

Both Rabbit #6, #7 samples were digested in 2 mg/ml of collagenase 16 h, 37° C. During the filtration step, we decreased the filter size to 70 μm. When we retrieved the RC fraction, Rabbit #7 exhibited many vessels retained on the filter compared Rabbit #6. Total cell counts derived from each fraction of Rb#7 was calculated as RC: $7.5\times10^{6}$ cells and SVF $12.2\times10^{6}$ cells.

Cells derived from FC, RC and SVF fractions were seeded in at density of $2\times10^{4}$/96 on different substrates: plastic or plastic with immobilized HA, 4× nHC-HA/PTX3 water soluble (S), and 4× nHC-HA/PTX3 water insoluble (IS) in MESCM (see procedure below). SVF cells were seeded on plastic in DMEM/10% FBS as a control. Cell aggregates were observed at 6 h, 24 h, 4 days and 7 days post-seeding. Total RNAs were extracted on day 4 and day 7 and used for qRT-PCR analysis of the following transcript expression: ESC markers (Oct4, Nanog, Sox2 and Nestin) and other markers such as CD34, CD31, PDGFR-β, vWF and α-SMA. Immunostaining was used to confirm the gene expression. Immobilization of HA and nHC-HA/PTX3 to culture plates is described above (Example 14).

TABLE 8

| | Experimental 96 Well Plate, P0 | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | Medium |
| A | PBS | | | HA | | | nHC-HA/PTX3 (S) Water Soluble | | | nHC-HA/PTX3 (IS) Insoluble | | | |
| B | FC | RC | SVF | FC | RC | SVF | FC | RC | SVF | FC | RC | SVF | |
| C | X | X | X | X | X | X | X | X | X | X | X | X | MESCM |
| D | X | X | X | X | X | X | X | X | X | X | X | X | |
| E | X | X | X | X | X | X | X | X | X | X | X | X | |
| F | | | X | | | | | | | | | | DMEM/ 10% FBS |
| G | | | X | | | | | | | | | | |
| H | | | X | | | | | | | | | | |

Total FC: $2.4\times10^{5}$, RC: $2.4\times10^{5}$, SVF: $3\times10^{5}$ cells

Figure 35:
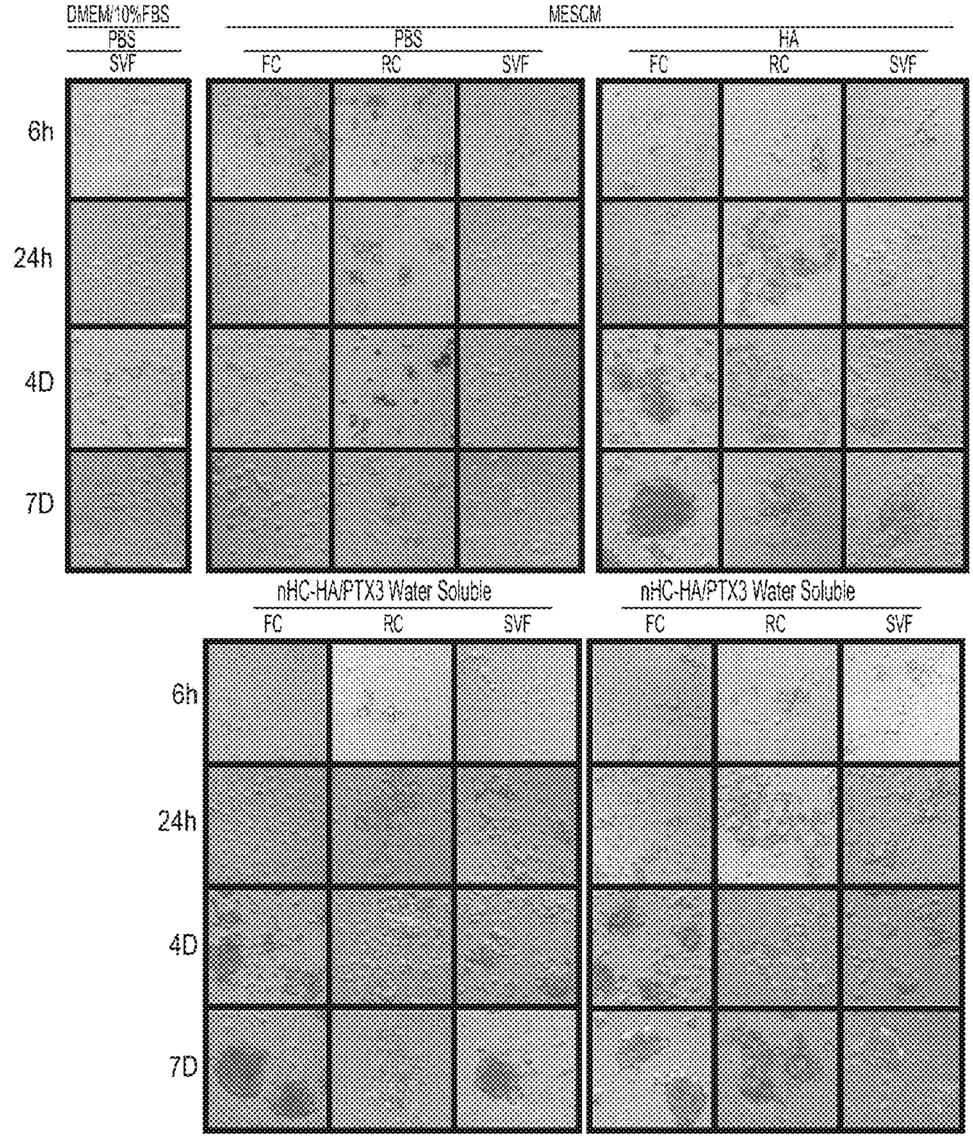
FIG. 35 illustrates phase images of cells of FC, SVF or RC fractions plated in DMEM/10% FBS or MESCM on PL or immobilized HA

Results:

Cell size and morphology of each fraction, FC, RC, SVF are presented in FIG. 35. RC cells contains mixture of large and small cells in size and cell surface appear to be smooth with bright oil-like cluster. Like RC, FC cells also contain mixture of large and small sizes while SVF cells are mostly uniform.

Compared to control SVF cells in DMEM/10% FBS at 6 h, FC, RC, SVF cells in MESCM are observed evenly distributed on plastic, immobilized HA, nHC-HA/PTX3 (S), and nHC-HA/PTX3 (IS). At 24 h, with exception on plastic in DMEM and MESCM, cell aggregations were first observed in all RC and SVF cells on HA, nHC-HA/PTX3 (S), and nHC-HA/PTX3 (IS), and more profoundly on D4 and D7. FC cells did not form aggregates on plastic throughout culture but began to form aggregates on D4 on immobilized HA, nHC-HA/PTX3 (S), nHC-HA/PTX3 (IS). At D7, cell spreading was observed in all RC and SVF cells on PL and HA. The cell spreading is more prominently in SVF than in RC, and more in PBS than in HA. All cells on nHC-HA/PTX3 (S), nHC-HA/PTX3 (IS) remained as aggregates. For FC cells, nHC-HA/PTX3 (S), nHC-HA/PTX3 (IS) promote cell aggregation and prevents cells from spreading.

Figure 36:
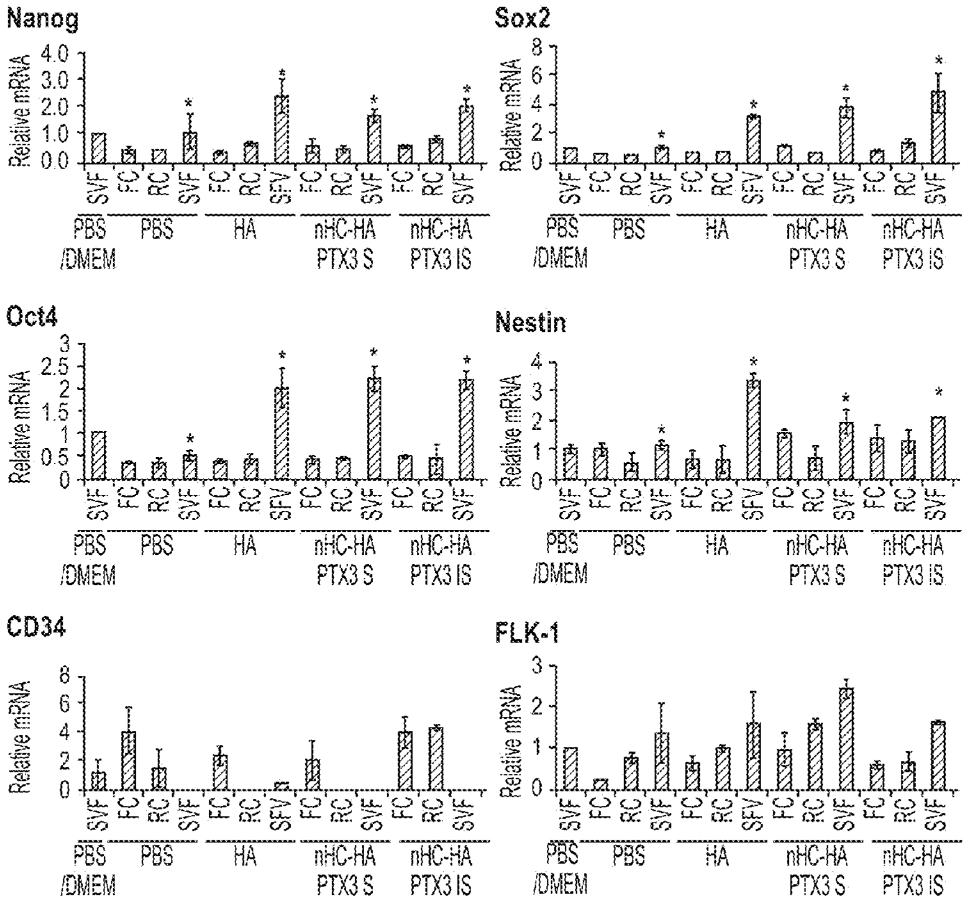
FIG. 36 illustrates relative ESC and angiogenic marker gene expression as determined by qPCR for cells isolated from Rabbit adipose tissue. Data is shown for cells cultured in MESCM on PL alone, immobilized HA, immobilized nHC-HA/PTX3 (Water Soluble) or nHC-HA/PTX3 (Water Insoluble) at 8 days post seeding.

Overall, RC, SVF cells on plastic did not form aggregated cells. Instead, the cells began to spread and proliferate. FC cell did not exhibit cell spreading in MESCM. All cells on immobilized HA, nHC-HA/PTX3 (S), and nHC-HA/PTX3 (IS) exhibit aggregation, but only on immobilized HA did cells begin spreading and proliferating on D7. The above data suggested in normal rabbit adipose, both nHC-HA/PTX3 (S) and (IS) promote cell aggregations in all FC, RC SVF fractions. qPCR data for stem cell marker expression is presented in FIG. 36.

Example 17

Effect of AMD3100 Treatment on Expression of Embryonic SC Markers and SDF-1/CXCR4-VEGF/BMP Signaling Our previous study demonstrated that disruption of reunion between PCK+ and Vim+ cells by AMD3100 added on Day 0 resulted in more spheres with a smaller size, but did not perturb their expression of Sox2 and Nanog as well as that of SDF-1 and CXCR4 (Xie et al. (2011) *Stem Cells* 9(11): 1874-85). In addition, the resultant spheres became more differentiated as evidenced by less DNp63a and CK15 transcripts, and more CK12 transcript and proteins, and by the absence of holoclone formation on 3T3 fibroblasts (Xie et al. (2011) *Stem Cells* 9(11):1874-85). Our results above indicate that 4×HC-HA activates SDF1/CXCR4—VEGF/BMP and integrin signaling. This experiment examined how signal pathways may be linked. We used a disrupting agent of SDF1/CXCR4 signaling AMD3100 to determine which signaling molecule is upstream or downstream of SDF1/CXCR4 signaling and whether AMD3100 affects the expression of those molecules, as well as SDF1, CXCR4, and ESC markers.

Experimental Design:

Experimental groups: plastic (control), 3D Matrigel (control), immobilized nHC-HA (positive control), and immobilized nHC-HA+AMD3100 (experimental, added at 0 -day and 5-day of culture). Limbal niche cells (LNCs) were cultured in MESCM for 10 days on immobilized HC-HA with or without AMD3100 for 10 days (20 ug/ml, added on day 0 and day 5) (Xie et al. (2011) *Stem Cells* 9(11):1874-85). Cells cultured on matrigel were digested with dispase on D10.

The samples were collected for determination of mRNA levels by qPCR. Specifically, mRNA was collected from $10^5$ cells, and qPCR was performed for SDF1, CXCR4, Nanog, Oct-4, Rex-1, Sox-2, CD31, VEGF, BMP-2, BMP-4, BMP-7, IGF-1, ICAM, and HIF-1β. Cell morphology was observed by phase contrast microscopy.

Figure 37:
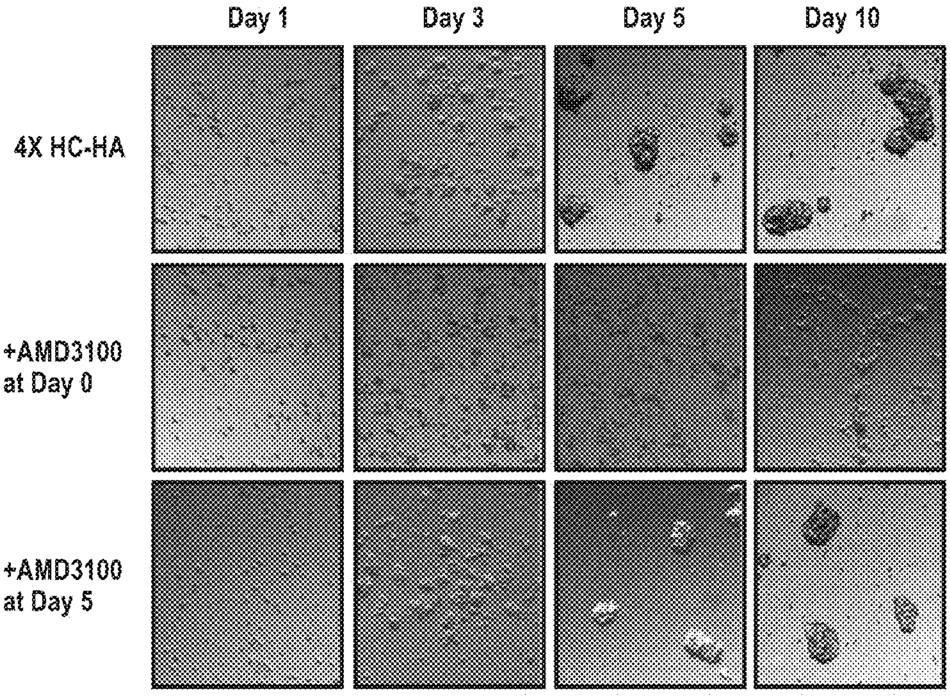
FIG. 37 illustrates phase images of limbal niche cells treated with the CXCR4 chemokine receptor antagonist AMD3100. AMD3100 inhibits initiation of aggregation on Day 0 but not affect on cell aggregation on Day 5.

Results:

The cell morphology results indicated that the sphere formation could be altered by inhibiting SDF1-CXCR4 signaling by a specific CXCR4 antagonist AMD3100 on Day 0 but not on Day 5 (FIG. 37). The results also indicated that AMD3100 added on Day 0 but not day 5 resulted in more spheres with a smaller size.

Figure 38:
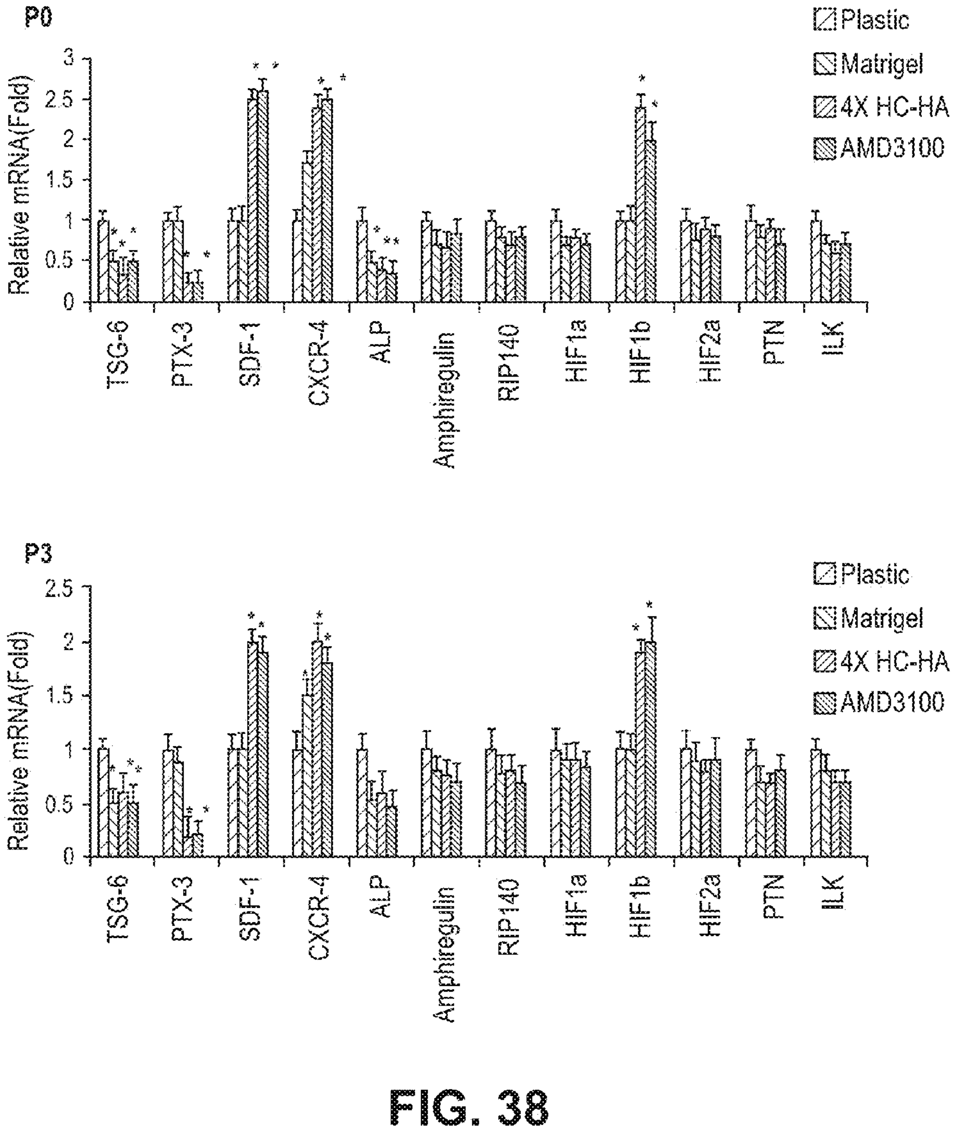
FIG. 38 illustrates marker gene expression of limbal niche cells treated with AMD3100. AMD3100 did not affect expression of SDF-1/CXCR4 signaling in limbal niche cells cultured from passage 0 or passage 3 on plastic only, Matrigel, immobilized HA, or immobilized HC-HA complexes purified from AM (2nd or 4th fraction)

From the qPCR analysis, it was observed that interrupting SDF1/CXCR4 signaling by AMD3100 treatment did not affect increased gene expression of SDF-1 and CXCR-4 induced by 4×HC-HA in LNCs (p0), indicating that disruption of SDF-1/CXCR-4 signaling does not affect gene expression of SDF-1 and CXCR-4. (FIG. 38 upper $*p<0.05$ when compared to the plastic control). Similarly, interrupting SDF1/CXCR4 signaling by AMD3100 treatment also did not affect increased gene expression of SDF-1 and CXCR-4 induced by 4×HC-HA in LNCs (p3), indicating that disruption of SDF-1/CXCR-4 signaling does not affect gene expression of SDF-1 and CXCR-4 (FIG. 38 lower; $*p<0.05$).

Figure 39:
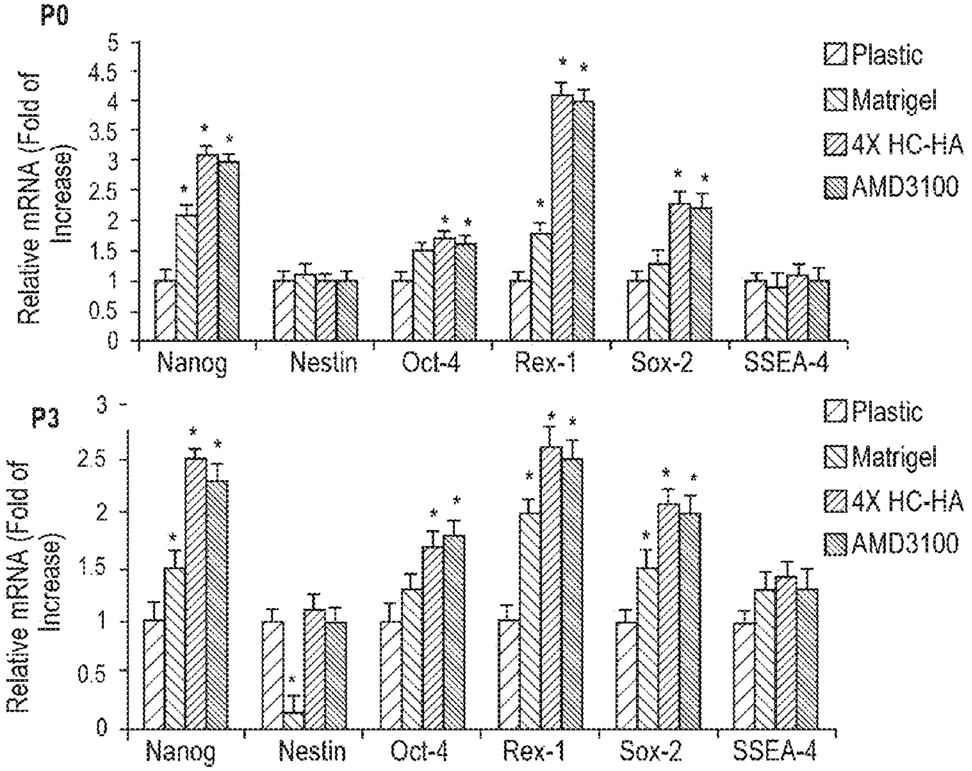
FIG. 39 illustrates marker gene expression of limbal niche cells treated with AMD3100. AMD3100 did not inhibit expression of ESC markers in limbal niche cells cultured from passage 0 or passage 3 on plastic only, Matrigel, immobilized HA, or immobilized HC-HA complexes purified from AM (2nd or 4th fraction).

In addition, AMD3100 did not affect increased gene expression of Nanog, Oct-4, Rex-1, Sox-2 induced by 4×HC-HA in LNCs (p0) (FIG. 39 upper; $*p<0.05$). AMD3100 also did not affect increased gene expression of Nanog, Oct-4, Rex-1, Sox-2 induced by 4×HC-HA in LNCs (p3) (FIG. 39 lower).

Figure 40:
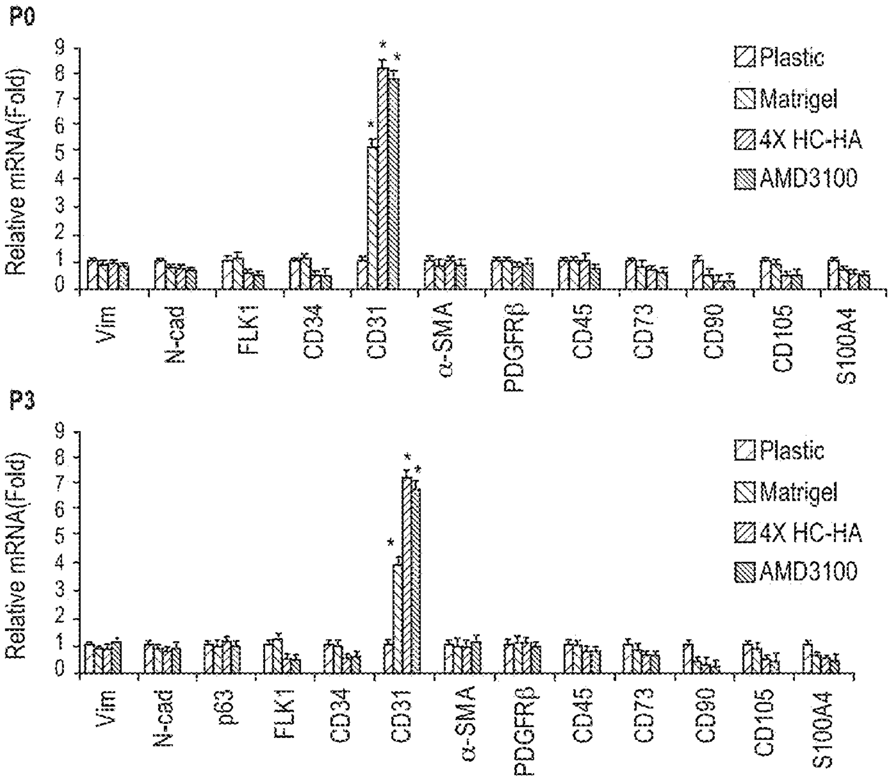
FIG. 40 illustrates marker gene expression of limbal niche cells treated with AMD3100. AMD3100 did not inhibit expression of CD31 in limbal niche cells cultured from passage 0 or passage 3 on plastic only, Matrigel, immobilized HA, or immobilized HC-HA complexes purified from AM (2nd or 4th fraction).

The qPCR results also indicated that expression of CD31 was notably upregulated by 4×HC-HA in LNCs (p0) and in LNCs (p3), which is consistent previous data from reseeding the cells on 3D Matrigel (Li et al. (2012) *Invest Ophthalmol V is Sci.* 53(7):3357-67). Addition of AMD3100 did not affect expression of CD31, indicating that CD31 is not downstream of SDF-1/CXCR-4 signaling (FIG. 40; $*p<0.05$).

Figure 41:
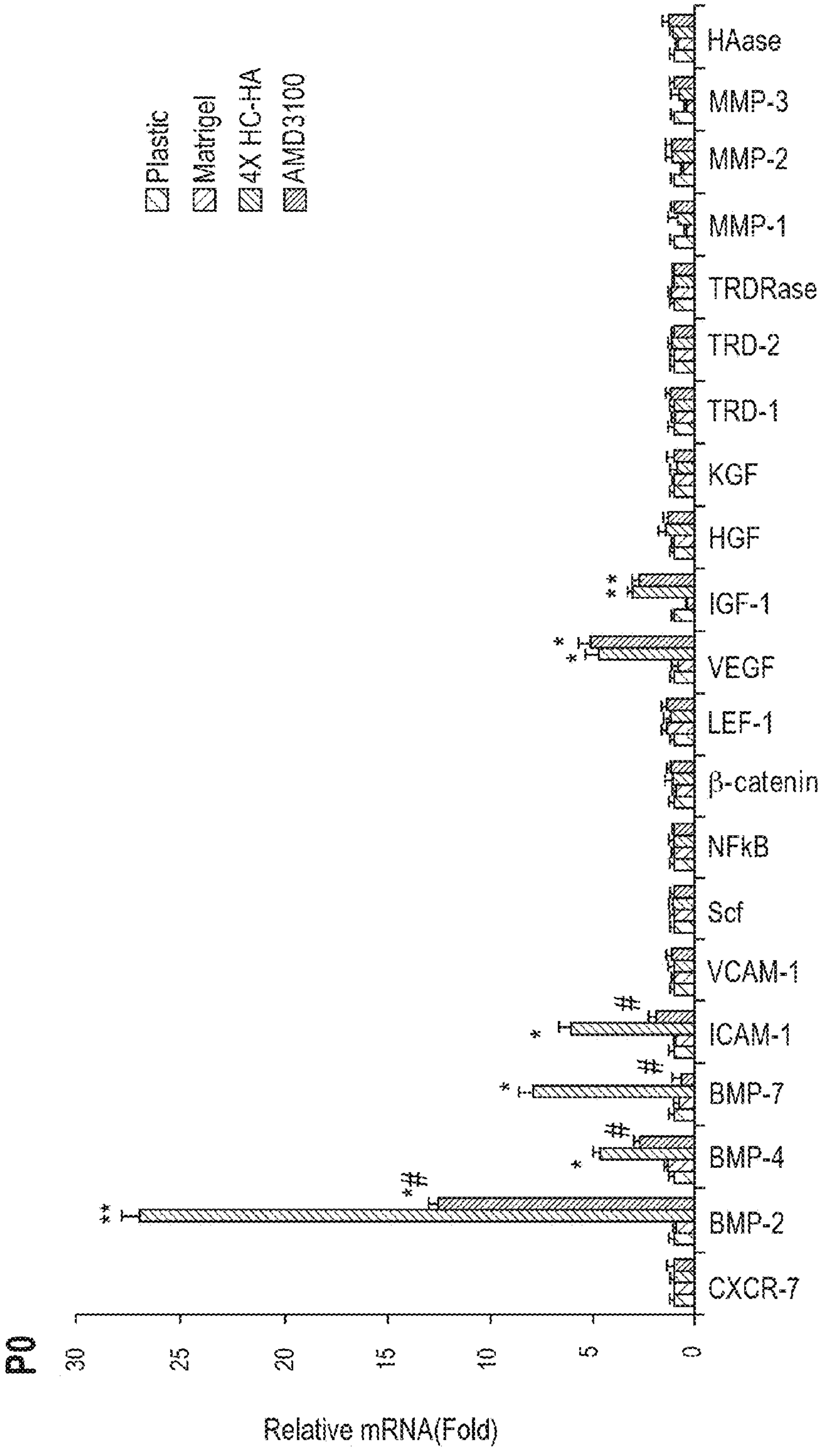
FIG. 41 illustrates marker gene expression of limbal niche cells treated with AMD3100. AMD3100 significantly downregulated expression of BMPs and ICAM, but not that of VEGF and IGF-1 in limbal niche cells from passage 0 or passage 3 on immobilized 4×HC-HA.
Figure 41:
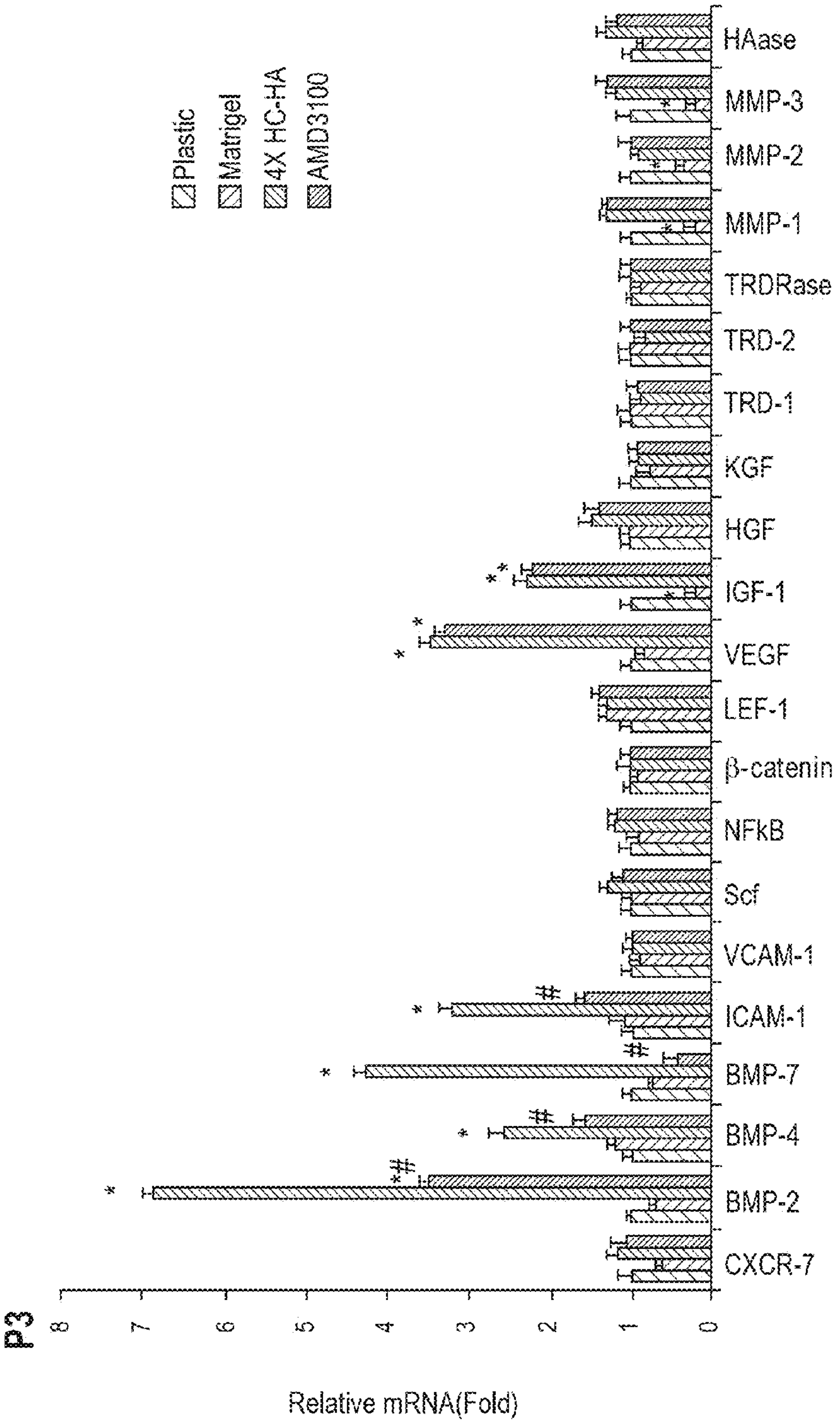

The results also indicated that addition of AMD3100 to the cultures of LNCs (p0) on immobilized 4×HC-HA significantly downregulated expression of all BMPs (BMP-2, BMP-4 and BMP-7) and ICAM, but not that of VEGF and IGF-1 induced by 4×HC-HA, indicating that BMPs and ICAM are downstream of SDF-1/CXCR-4 signaling (FIG. 41 upper; $*p<0.05$, $p<0.01$ when compared to the plastic control, $\#p<0.05$ when compared to the 4×HC-HA control). Similar results were observed for the cultures of LNCs (p3) (FIG. 41** lower; $*p<0.05$ when compared to the plastic control, $\#p<0.05$ when compared to the 4×HC-HA control). These results suggest that activation of SDF-1 and CXCR-4 signaling is through BMPs network, similar to a report demonstrating that cardiogenic induction of pluripotent stem cells is through the SDF-1/VEGF/BMP2 network (Chiriac et al. (2010) *PLoS One* 5:e9943), and that integrin signaling is downstream of SDF-1/CXCR-4 signaling, that is, integrin signaling is controlled by SDF-1/CXCR-4 signaling. Since expression of VEGF and IGF-1 is not affected by AMD3100, this suggests that VEGF and IGF-1 signaling are not downstream of SDF-1 and CXCR-4 signaling.

In summary, interruption of SDF1/CXCR4 signaling by AMD3100 did not affect increased gene expression of SDF-1 and CXCR-4 induced by 4×HC-HA in LNCs, indicating that disruption of SDF-1/CXCR-4 signaling does not affect gene expression of SDF-1 and CXCR-4. Similarly, AMD3100 did not affect increased gene expression of Nanog, Oct-4, Rex-1, Sox-2 induced by 4×HC-HA in LNCs. Expression of CD31 was notably upregulated by 4×HC-HA, indicating that 4×HC-HA promotes angiogenesis since CD31 is the key marker of EPC and mature VEC, operating as a regulator of adhesion, migration, and activation (Feng et al. (2004) *J*

*Histochem Cytochem.* 52:87-101). Addition of AMD3100 did not affect expression of CD31, indicating that CD31 is not downstream of SDF-1/CXCR-4 signaling. Addition of AMD3100 to the cultures of LNCs (p3) on immobilized 4×HC-HA significantly downregulated expression of all BMPs (BMP-2, BMP-4 and BMP-7) and ICAM, but not that of VEGF and IGF-1 induced by 4×HC-HA, indicating that BMPs and ICAM are likely downstream of SDF-1/CXCR-4 signaling. The results also suggest that activation of SDF-1 and CXCR-4 signaling is through BMPs network, similar to a report demonstrating that cardiogenic induction of pluripotent stem cells is through the SDF-1/VEGF/BMP2 network (Chiriac et al. (2010) *PLoS One* 5:e9943). Our results also indicated that ICAM or integrin signaling is downstream of SDF-1/CXCR-4 signaling, and controlled by SDF-1/CXCR-4 signaling. Since expression of VEGF and IGF-1 is not affected by AMD3100, VEGF and IGF-1 signaling are likely upstream or independent of SDF-1 and CXCR-4 signaling.

Example 18

Detection of MMP1, MMP3, TSG-6 and PTX3 Expression in Cell Lysates and Culture Media of CCh Fibroblast Cultured on Immobilized nHC-HA Conjunctivochalasis (CCH) is a common eye surface disease characterized by the presence of excess folds of the conjunctiva located between the globe of the eye and the eye-lid margin. The loose, excess conjunctiva may mechanically irritate the eye and disrupt the tear film and its outflow, leading to dry eye and excess tearing. It has been thought that inflammation may play a pathogenic role in CCH development, because a elevated levels of such pro-inflammatory cytokines as TNF-α, IL-1β, IL-6, and IL-8 are found in CCH patients (Acera et al. (2008) *Ophthalmic Res.* 40:315-321; Erdogan-Poyraz et al. (2009) *Cornea* 28:189-193; Ward et al. (2010) *Invest Ophthalmol Vis Sci.* 51:1994-2002). Our previous work found that conjunctival fibroblasts from CCH overexpress extracellular matrix-degrading enzymes MMP-1 and MMP-3 (Li et al. (2000) *Invest Ophthalmol V is Sci.* 41:404-410), and that such overexpression of MMP-1 and MMP-3 is further upregulated by TNF-α and IL-1β (Meller et al. (2000) *Invest Ophthalmol V is Sci.* 41:2922-2929). Others have used immunohistochemical staining to reveal a significantly higher number of cells positive for MMP-3 and MMP-9 in CCH patients. These data indicate that CCH manifests excessive degradation of conjunctival matrix and Tenon capsule.

We detected higher TSG-6 and PTX3 expression in subconjunctival stroma and Tenon in CCH patients. Furthermore, there is a higher level of MMP1 and MMP3 transcripts and proteins, and a higher level of actMMP1 expressed by CCH conjunctival fibroblasts, and their expression is further promoted by TSG-6 or PTX3 siRNA (Guo et al. (2012) *Invest Ophthalmol V is Sci.* 53(7):3414-23). Of note is that knockdown TSG-6 or PTX3 by specific siRNA led to more conversion of proMMP1 to actMMP1, and more apoptosis of normal and CCH conjunctival fibroblasts. It remains unknown how TSG-6 and PTX3 might be involved in transcriptional control of MMP-1 and MMP-3 as well as activation of MMP-1.

Immobilized 4th nHC-HA decreased PTX3 expression, but increased TSG-6 transcript level in CCh fibroblasts, and also decreased the increasing extent of MMP1, MMP3, TSG-6 and PTX3 mRAN stimulated by IL-1β, but whether their protein expressions have the same changes as their mRNA was not known. In this example, we determined the protein level in cell lysates and culture medium of CCh fibroblasts cultured on 4th nHC-HA by Western blot.

Experimental Design

CCh fibroblasts were obtained as described in Guo et al. (2012) *Invest Ophthalmol V is Sci.* 53(7):3414-23. The cells were cultured in DMEM+0.5% FBS on tissue cultures dishes containing no substrate (control) or immobilized HA, 2nd HC-HA or 4th HC-HA (see Example 19). Samples of the tissue culture media were obtained at passage 0 and passage 2, concentrated, and analyzed for expression of proMMP1, actMMP1, proMMP3 and PTX3 by Western blot.

Results

Figure 42:
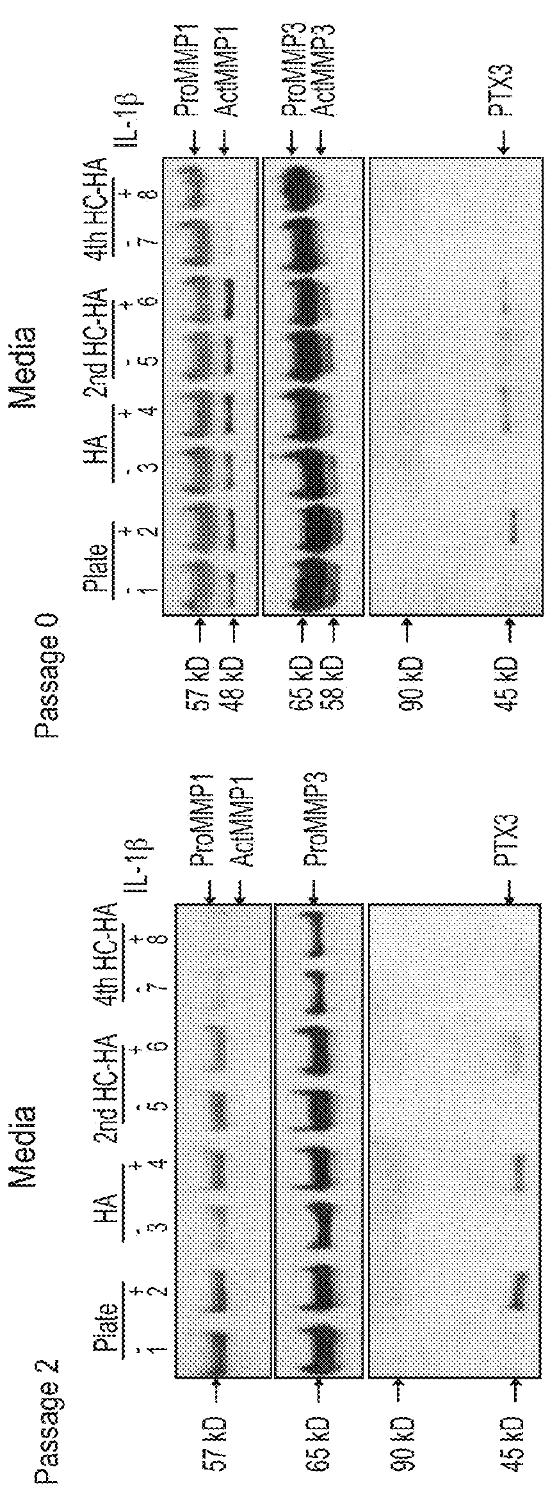
FIG. 42 illustrates marker gene expression of limbal niche cells treated with AMD3100. Immobilized 4th HC-HA decreases proMMP1, proMMP3 and PTX3 protein level in culture medium of CCh Fibroblasts.

Immobilized 4Th HC-HA Decreased proMMP1, proMMP3 and PTX3 Protein Level in Culture Medium of CCh Fibroblasts For MMP1 and MMP3, Western blot analysis of CCh fibroblast culture media showed that both p2 and p0 control (Plate) rest CCh fibroblasts expressed proMMP1 and proMMP3 protein and released them to culture media, while both active MMP1 and MMP3 proteins were detected in P0 CCh fibroblasts in culture media but only active MMP3 in p2 culture media (FIG. 42).

IL-1β did not induce more pro- and active-MMP1 and MMP3 in p2 culture, but p0 medium showed increased active MMP 1 level. Prior studies reported more active MMP 1 were detected than proMMP1 in culture medium upon IL-1β stimulation (Guo et al. (2012) *Invest Ophthalmol V is Sci.* 53(7):3414-23). Immobilized HA decreased pro-MMP1 and MMP3 level in p2 medium and no effect in p0 medium, but IL-1β still induced more pro-MMP1 and MMP3 in p2 medium and active-MMP1 in p0 medium. Without IL-1β, immobilized 2nd HC-HA have the similar result as immobilized HA, but IL-1β did not increase proMMP1 and proMMP3 compared with control in p2 but increase active-MMP1 in p0. Immobilized 4th HC-HA significantly decreased pro- and active-MMP1 and MMP3 proteins level regardless IL-1β stimulation.

For PTX3, control rest p2 CCh fibroblasts expressed low level of 45 kD PTX3 protein and p0 CCh fibroblasts expressed both 45 kD and 90 kD PTX3 at low level. IL-1β stimulated more 45 kD PTX3 protein expression, and a 90 kD PTX3 was also appeared in p2 but decreased in p0, consistent with previous results in the case of p2 cells (Guo et al. (2012) *Invest Ophthalmol V is Sci.* 53(7):3414-23). When cells were cultured on HA and 2nd HC-HA, PTX3 was not detectable, and the inducible expression level by IL-1β were decreased gradually. Importantly, 4th HC-HA diminished PTX3 protein expression with or without IL-1β stimulation. These results suggested that immobilized 4th HC-HA downregulates MMP1, MMP3 and PTX3 protein expression. No TSG-6 protein was detected in both p0 and p2 culture medium. In addition, immobilized 4th HC-HA promoted primary CCh fibroblasts to aggregate and form spheres, while immobilized 2nd HC-HA and HA did not.

Example 19

Constitutive Expression of Inter-α-Inhibitor (IαI) Family Proteins and Tumor Necrosis Factor-Stimulated Gene-6 (TSG-6) by Human Amniotic Membrane Epithelial and Stromal Cells Supporting Formation of the Heavy Chain-Hyaluronan (HC-HA) Complex In our previous studies, we reported HC-HA, a covalent complex formed between heavy chains (HCs) of inter-α-inhibitor (IαI) and hyaluronan (HA) by the catalytic action of tumor necrosis factor (TNF)-stimulated gene-6 (TSG-6), is responsible for human amniotic membrane (AM) anti-inflammatory, anti-scarring, and anti-angiogenic actions. The study presented in this example showed that AM epithelial and stromal cells and stromal matrix all stained positively for HA, HC 1, 2, and 3, bikunin, and TSG-6. TSG-6 mRNA and protein were constitutively expressed by cultured AM epithelial and stromal cells without being up-regulated by TNF. In serum-free conditions, these cells expressed IαI, leading to the formation of HC-HA complex that contained both HC1 and HC2. In contrast, only HC1 was found in the HC-HA complex purified from AM. Local production of IαI, the HC-TSG-6 intermediate complex, and HC-HA were abolished when cells were treated with siRNA to HC1, HC2, bikunin (all of which impair the biosynthesis of IαI), or TSG-6 but not to HC3. Collectively, these results indicate that AM is another tissue in addition to the liver to constitutively produce IαI and that the HC-HA complex made by this tissue is different from that found at inflammatory sites (e.g. in asthma and arthritis) and in the matrix of the cumulus oocyte complex.

Materials

Guanidine hydrochloride, cesium chloride, EDTA, anhydrous alcohol, potassium acetate, sodium acetate, sodium chloride, sodium hydroxide, Tris, Triton X-100, 3-(N,N-dimethyl palmityl ammonio) propanesulfonate (Zwittergent3-16), protease inhibitor mixture (including 4-(2-aminoethyl)-benzenesulfonyl fluoride hydrochloride, aprotinin, bestatin hydrochloride, E-64, leupeptin, and pepstatin A) and phenylmethanesulfonyl fluoride were obtained from Sigma-Aldrich. Streptomyces hyaluronidase (HAase), chondroitinase ABC, and biotinylated HA-binding protein (HABP) were from Seikagaku Biobusiness Corporation (Tokyo, Japan). DMEM, Ham's F12 nutrient mixture, FBS, Hanks' balanced salt solution, gentamicin, amphotericin B, and radioimmune-precipitation assay buffer were purchased from Invitrogen. Slide-A-Lyzer dialysis cassettes (3.5K MWCO) were from Fisher Scientific. The BCA protein assay kit was from Pierce. The HA Quantitative Test kit was from Corgenix (Westminster, CO). 4-15% gradient acrylamide ready gels and nitrocellulose membranes were from Bio-Rad. IαI and urinary trypsin inhibitor (i.e. bikunin) were prepared in our laboratory from human plasma and urine, respectively, according to the published methods. Recombinant human TNF and human/mouse TSG-6 mAb (MAB2104) were from R&D Systems (Minneapolis, MN). Mouse anti-human ITIH1 polycolonal antibody against full-length ITIH1 and rabbit anti-human bikunin polyclonal antibody against full-length bikunin were from Abcam (Cambridge, MA). The recombinant human TSG-6 protein (TSG-6Q) and rabbit antisera against the C-terminal peptide of human TSG-6 (RAH-1, TSTGNKNFLAGRFSHL (SEQ ID NO: 1)), the N-terminal peptides of human HC2 (SLPGESEEMM (SEQ ID NO: 2)) and HC3 (SLPEGVANGI (SEQ ID NO: 3)), and the C-terminal peptide of human HC2 (ESTPPPHVMRVE (SEQ ID NO: 4)) were as described previously. PepMuteTM siRNA Transfection Reagent was from SignaGen Laboratories (Rockville, MD). The RNeasy Mini RNA isolation kit, small interfering RNA (siRNA) oligonucleotides for targeting endogenous human HC1 (UAAUGUUCUGAGGAGUCACTT (SEQ ID NO: 5)) and HC3 (UUGACUAUCUGCACGUUGCCA (SEQ ID NO: 6)), and nontargeting siRNA control oligonucleotides (scrambled RNA) were from Qiagen (Valencia, CA). siRNA oligonucleotide for targeting endogenous human TSG-6 (GGUUUCCAAAUCAAAUAUGUUGCAA (SEQ ID NO: 7)), HC2 (GGAUCAAAUAGAGAGCGUUAUCACG (SEQ ID NO: 8)), and bikunin (GGUAUUUCUAUAAUGGUACAUCCAT (SEQ ID NO: 9)) were from OriGene Technologies (Rockville, MD). Western Lighting™ Chemiluminesence Reagent was from PerkinElmer Life Sciences. The ultracentrifuge (LM8 model, SW41 rotor) was from Beckman Coulter.

Cell Cultures

Human tissue was handled according to the Declaration of Helsinki. The fresh human placenta was obtained from healthy mothers after elective cesarean deliveries in the Baptist Hospital (Miami, Fla.) via an approval (Protocol 03-028) by the Baptist Health South Florida Institutional Review Board. Primary human AM epithelial and stromal cells (designated as AMECs and AMSCs, respectively) were isolated from fresh placenta and cultured in supplemental hormonal epithelial medium (SHEM, which consisted of DMEM/F12 (1:1, v/v), 5% (v/v) FBS, 0.5% (v/v) dimethyl sulfoxide, 2 ng/ml EGF, 5 μg/ml insulin, 5 μg/ml transferrin, 5 ng/ml sodium selenite, 0.5 μg/ml hydrocortisone, 0.1 nm cholera toxin, 50 μg/ml gentamicin, 1.25 μg/ml amphotericin B) under a humidified atmosphere of 5% CO2 at 37° C. The culture medium was changed every 2 days. At subconfluence, cells were incubated in SHEM containing 20 ng/ml TNF for 4 or 24 h prior to RT-PCR or Western blot analysis. In experiments for TSG-6 detection, AMECs, AMSCs, and human skin fibroblasts were cultured in DMEM/F12 containing 10% FBS medium (i.e. to prevent the influence of other components such as EGF in SHEM on TSG-6 expression). To exclude serum IαI, serum-free cultures were established with secondary cultures. After seeding and attachment, cells were washed three times with Hanks' balanced salt solution and switched to fresh SHEM without serum, and the serum-free medium was changed every 2 days until experimental manipulation.

siRNA Transfection

AMECs and AMSCs were cultured in serum-free SHEM in 6-well plates until 50-60% confluence, when cells were transfected with PepMute™ siRNA Transfection Reagent with or without 10 nm HC1 siRNA, HC2 siRNA, bikunin siRNA, HC3 siRNA, or scrambled (sc) RNA. After 48 h, cells were harvested and subjected to RT-PCR and Western blot analysis. For TSG-6 detection, AMECs and AMSCs were cultured in DMEM/F12 containing 10% FBS medium and transfected with TSG-6 siRNA or scRNA.

Purification of HC-HA Complex from AM and Serum-Free Cultures by Ultracentrifugation HC-HA complex was purified from AM and serum-free cultures. For purification of HC-HA complex from AM, cryopreserved human AM, obtained from Bio-tissue (Miami, Fla.), was sliced into small pieces, frozen in liquid nitrogen, and ground to fine powder by a BioPulverizer. The powder was mixed with cold PBS at 1:1 (g/ml). The mixture was kept at 4° C. for 1 h with gentle stirring and then centrifuged at 48,000×g for 30 min at 4° C. The supernatant (designated as AM extract) was then mixed with a 8 m guanidine HCl/PBS solution (at 1:1 ratio of v/v) containing 10 mm EDTA, 10 mm aminocaproic acid, 10 mm N-ethylmaleimide, and 2 mm PMSF. For purification of HC-HA complex from serum-free cultures, cells were washed three times with Hanks' balanced salt solution and extracted with 6 m guanidine HCl, 0.2 m Tris-HCl (pH 8.0), 0.1% (w/v) Zwittergent3-16 containing protein inhibitors (10 mm EDTA, 10 mm aminocaproic acid, 10 mm N-ethylmaleimide, and 2 mm PMSF). The cell extract was kept at 4° C. overnight with gentle stirring before removing the insoluble materials by centrifuging at 14,000×g for 30 min at 4° C. The above extracts were adjusted to a density of 1.35 g/ml (AM extract) or 1.40 g/ml (cell extract) with cesium chloride, respectively, and subjected to isopycnic centrifugation at 35,000 rpm, 15° C., for 48 h. The resultant density gradients were fractioned into 12 tubes (1 ml/tube), in which the contents of HA and proteins were measured using HA Quantitative Test kit and BCA protein assay kit, respectively. Fractions from the first ultracentrifugation, which contained most HA, were pooled, brought to a density of 1.40 g/ml (AM extract) or 1.45 g/ml (cell extract) by addition of CsCl, ultracentrifuged, and fractionated in the same manner as described above. Fractions from the second ultracentrifugation, which contained HA but no detectable proteins, were pooled and dialyzed in distilled water and then precipitated twice with 3 volumes of 95% (v/v) ethanol containing 1.3% (w/v) potassium acetate at 0° C. for 1 h. After centrifugation at 15,000×g, the pellet was briefly dried by air, stored at −80° C., and designated as AM HC-HA complex and cell HC-HA complex, respectively.

Immunofluorescence Analysis

Human fetal membrane containing AM and chorion was cryosectioned to 5 μm thickness, fixed with 4% paraformaldehyde at room temperature for 15 min, and permeabilized with 0.2% (v/v) Triton X-100 in PBS for 20 min. After blocking with 0.2% (w/v) BSA in PBS for 1 h, sections were incubated with biotinylated HABP (for HA, 5 μg/ml) or different primary antibodies specific for HC1, HC2, HC3, bikunin, and TSG-6 (all diluted 1:200 in blocking solution) overnight in a humidity chamber at 4° C. For HC2, we used an anti-N-terminal HC2 antibody throughout unless mentioned otherwise. For TSG-6, we used MAB2104 throughout unless mentioned otherwise. After washing with PBS, they were incubated with Alexa Fluor 488 streptavidin (for HA, diluted 1:100), or respective secondary antibodies (i.e. FITC-conjugated anti-mouse IgG, or FITC-conjugated anti-rabbit IgG) for 1 h at room temperature. Isotype-matched nonspecific IgG antibodies were used as a control. Alternatively, sections were treated with 50 units/ml *Streptomyces* HAase at 37° C. for 4 h before fixation. Nuclei were stained by Hoechst 33342, and images were obtained using a Zeiss LSM700 confocal laser scanning microscope (Zeiss, Germany).

RT-PCR

Total RNA was extracted from AM tissue and cell cultures using a RNeasy Mini RNA isolation kit. The cDNA was reverse-transcribed from 1 μg of total RNA using a Cloned AMW First-Strand cDNA synthesis kit with gene-specific antisense primer (for HC1-3 and bikunin) (Table 9) or oligo (dT) primer (for TSG-6). First-strand cDNAs were amplified by PCR using AmpliTaq Gold Fast PCR Master Mix and the specific gene primers (Table 9). Glyceraldehyde-3-phosphate dehydrogenase (GAPDH) gene expression was used to normalize the amounts of the amplified products. The PCR products were electrophoresed on a 2% (w/v) agarose gel with ethidium bromide staining, photographed using the UVP BioImaging system, and analyzed using the ImageJ software (Java).

TABLE 9

PCR Primers

| Protein | Sense/ antisense | Primer sequence | Production size bp |
|---|---|---|---|
| HC1 | Sense | 5'-CCACCCCATCGGTTTTGAAGTGTCT-3' (SEQ ID NO: 10) | 138 |
| | Antisense | 5'-TGCCACGGGTCCTTGCTGTAGTCT-3' (SEQ ID NO: 11) | |
| HC2 | Sense | 5'-ATGAAAAGACTCACGTGCTTTTTC-3' (SEQ ID NO: 12) | 127 |
| | Antisense | 5'-ATTTGCCTGGGGCCAGT-3' (SEQ ID NO: 13) | |
| HC3 | Sense | 5'-TGAGGAGGTGGCCAACCCACT-3' (SEQ ID NO: 14) | 318 |
| | Antisense | 5'-CGCTTCTCCAGCAGCTGCTC-3' (SEQ ID NO: 15) | |
| Bikunin | Sense | 5'-GTCCGGAGGGCTGTGCTACC-3' (SEQ ID NO: 16) | 294 |
| | Antisense | 5'-GATGAAGGCTCGGCAGGGGC-3' (SEQ ID NO: 17) | |
| TSG-6 | Sense | 5'-CCAGGCTTCCCAAATGAGTA-3' (SEQ ID NO: 18) | 284 |
| | Antisense | 5'-TTGATTTGGAAACCTCCAGC-3' (SEQ ID NO: 19) | |
| GAPDH | Sense | 5'-ACCACAGTCCATGCCATCAC-3' (SEQ ID NO: 20) | 452 |
| | Antisense | 5'-TCCACCACCCTGTTGCTGTA-3' (SEQ ID NO: 21) | |

Western Blotting

Culture supernatants were collected, and cell lysates were obtained by washing cells six times with cold PBS followed by incubating in radioimmuneprecipitation assay buffer at 4° C. for 1 h with gentle stirring and centrifugation at 14,000×g for 30 min at 4° C. Protein concentrations in culture supernatants and cell lysates were quantified with a BCA protein assay kit. For alkaline treatment of AM extract, samples were incubated in 50 mm NaOH for 1 h at 25° C. For HAase digestion of the HC-HA complex, samples were dissolved in 0.1 m sodium acetate buffer (pH 6.0) and incubated at 60° C. for 1 h with or without 20 units/ml *Streptomyces* HAase. The above samples were resolved by SDS-PAGE on 4-15% (w/v) gradient acrylamide ready gels under denaturing and reducing conditions and transferred to a nitrocellulose membrane. The membrane was then blocked with 5% (w/v) fat-free milk in 50 mm Tris-HCl (pH 7.5) buffer containing 150 mm NaCl and 0.05% (v/v) Tween 20 followed by sequential incubation with different primary antibodies followed by their respective HRP-conjugated secondary antibodies. Immunoreactive proteins were visualized by Western Lighting™ Chemiluminescence reagent.

Results

Immunolocalization of HA, HCs, Bikunin, and TSG-6 in Human AM

To address whether the AM could produce its own IαI to form HC-HA complex, we first investigated whether the required components, i.e. HA, each individual HC, bikunin, and TSG-6, were actually present in human AM in vivo. Frozen sections of the fetal membrane revealed AM consisting of a simple epithelium and an avascular stroma and subjacent cell-rich chorion (FIG. 11, Phase). Consistent with what has been reported previously, strong positive HA immunostaining was noted in AM stroma and relatively weak staining in AM epithelium using a biotinylated HABP (FIG. 11, HA). This staining was lost when the tissue section was predigested by HAase (FIG. 11, HA(+HAase)) indicating that HA staining is specific. Immunostaining of each individual HC using specific antibodies also revealed a positive staining in AM epithelium, stromal cells, and/or stromal matrix (FIG. 11, HC1, HC2, and HC3). Positive bikunin immunostaining was found in the apical surface of the epithelium, the basement membrane zone, and the stroma (FIG. 11, Bikunin). TSG-6 immunostaining with two different anti-TSG-6 antibodies, i.e. MAB2104 (FIG. 11, TSG-6) and RAH-1 (data not shown) showed the same pattern with positive staining associated with AMECs, AMSCs, and stromal matrix. The lack of immunoreactivity by nonimmune control serum indicates that the staining described above is specific. Collectively, these results suggested the presence of all components in AM required for forming IαI, PαI, and HC-HA.

Presence of Individual HCs, Bikunin, TSG-6, PαI, and IαI in AM-Soluble Extract

Figure 43:
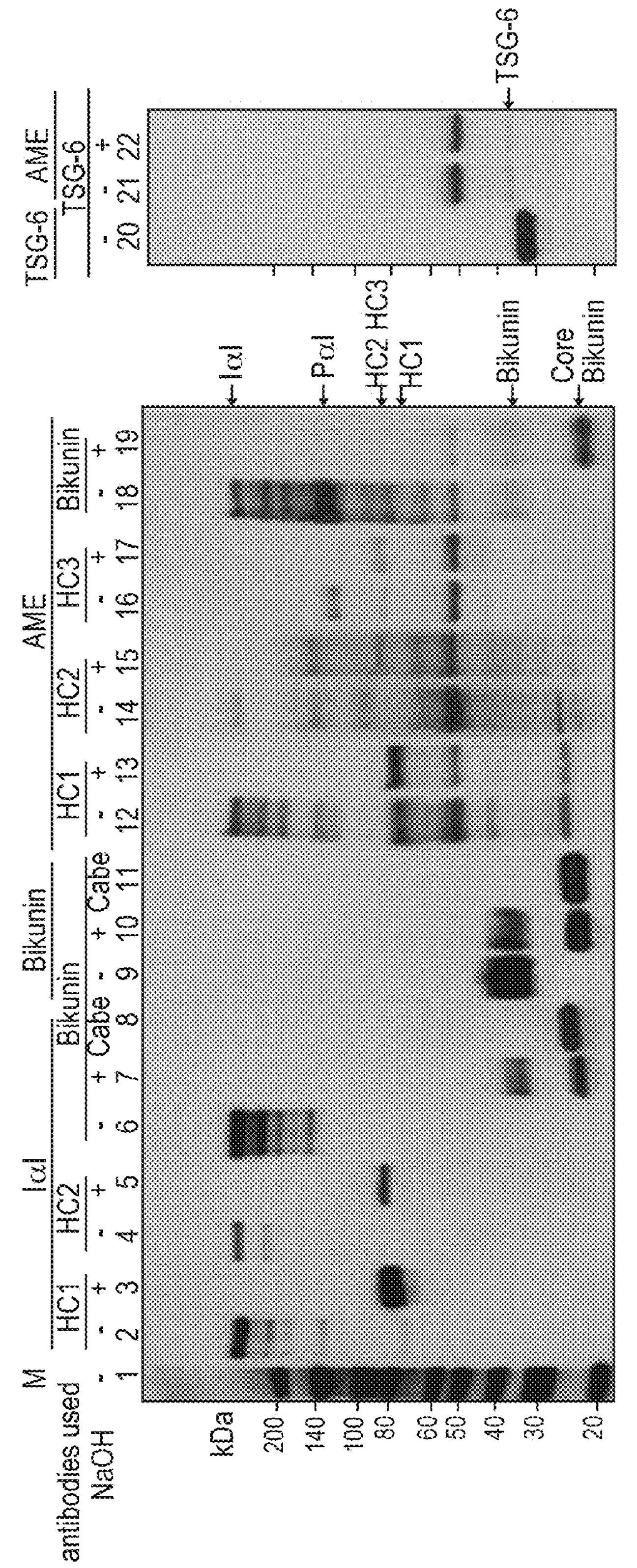
FIG. 43 illustrates presence of IαI, PαI, individual HCs, bikunin, and TSG-6 in AM extract. Purified IαI, urinary trypsin inhibitor (i.e. bikunin), TSG-6, and AM extract (AME) were treated with or without 50 mm NaOH at 25° C. for 1 h or chondroitinase ABC (Cabc) at 37° C. for 2 h before Western blotting using antibodies as indicated. Individual HC1, HC2, HC3, bikunin, and TSG-6 species were found in AM extract. M, protein ladder markers.

To investigate further the presence of the above components in AM, we performed Western blotting analyses of proteins extracted by an isotonic salt buffer before and after 50 mm NaOH treatment to cleave ester bonds. Using anti-HC1, HC2, or bikunin antibodies, purified IαI was found to contain a major 250-kDa species corresponding to intact IαI and several weak species of smaller molecular mass most likely representing intermediate species (FIG. 43, lanes 2, 4, and 6), including a free HC1 species of 75 kDa (lane 2). NaOH treatment of the IαI preparation released HC1 (75 kDa, lane 3), HC2 (80 kDa, lane 5), and bikunin as 35-kDa and 22-kDa species (lane 7). The latter two species likely correspond to bikunin with and without an attached CS chain. When purified IαI was treated with chondroitinase ABC lyase, only the 22-kDa species was observed with the anti-bikunin antibody (lane 8). Purified bikunin, which appeared as a 35-kDa species (lane 9), yielded both 35-kDa and 22-kDa species after the same NaOH treatment (lane 10), but gave rise to only the 22-kDa species after chondroitinase ABC treatment (lane 11). These results confirmed that both 35-kDa and 22-kDa bikunin species formed after mild NaOH treatment of IαI (i.e. with partial release of the CS chain). Based on the profile generated by both IαI and bikunin controls, we detected the 250-kDa IαI species and its components, HC1, HC2, and bikunin in AM-soluble extract (lanes 12, 14, and 18). The anti-bikunin antibody also reacted with a 130-kDa species (lane 18), which was likely PαI because it was detected by an anti-HC3 antibody that also recognized a free HC3 species of 80 kDa (lane 16). The identity of IαI and PαI was further verified by the NaOH treatment, which released corresponding HCs and bikunin species that were detected by the various chain-specific antibodies (lanes 13, 15, 17, and 19). A similar result was also obtained with an anti-IαI antibody (data not shown). Because IαI/PαI chain-specific antibodies and the anti-IαI antibody all reacted with a 50-kDa species, which was also detected by normal mouse or rabbit serum (data not shown), we concluded that this 50-kDa species was nonspecific.

Analysis of the AM extract with an anti-TSG-6 antibody (MAB2104) revealed a species of ~35 kDa (lane 21), which corresponds to the expected size of native TSG-6, which is slightly larger than the size of recombinant TSG-6 (TSG-6Q, 32 kDa) (lane 20) that has a lower level of glycosylation. This antibody also detected a major 50-kDa species, where neither this nor the ~35-kDa species was affected by NaOH treatment (i.e. in agreement with our previous report using three different anti-TSG-6 antibodies). Again, the detection of the 50-kDa species is likely nonspecific. Taken together, these results demonstrated that the soluble AM extract indeed contained IαI, PαI, HC1, HC2, HC3, bikunin, and TSG-6.

Figure 44A:
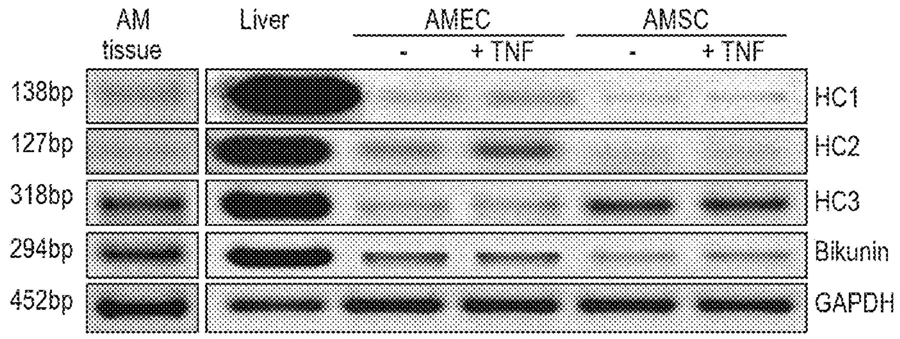
FIG. 44 illustrates constitutive expression of HC1, HC2, HC3, and bikunin mRNA and proteins by AMECs and AMSCs. RNA and protein were extracted from AM tissue and both AMECs and AMSCs cultured in SHEM with or without 20 ng/ml TNF for 4 h (for RT-PCR) or 24 h (for Western blotting). Expression of HC1, HC2, HC3, and bikunin transcripts was compared with liver total RNA using GAPDH as the loading control (A), whereas that of HC1, HC2, HC3, and bikunin proteins was compared with control IαI and serum using β-actin as the loading control (B, C, D, and E, respectively).
Figure 44B:
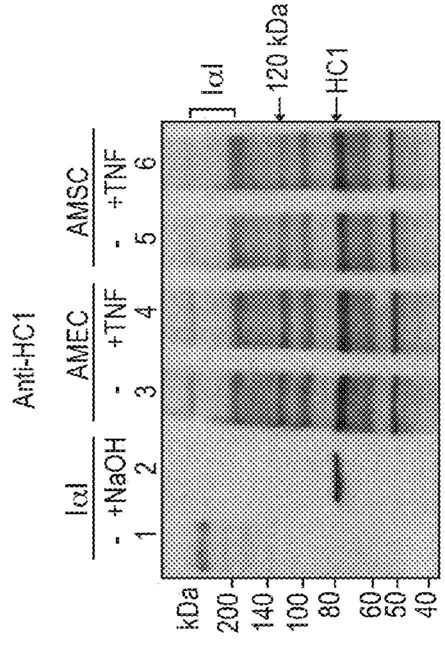
Figure 44C:
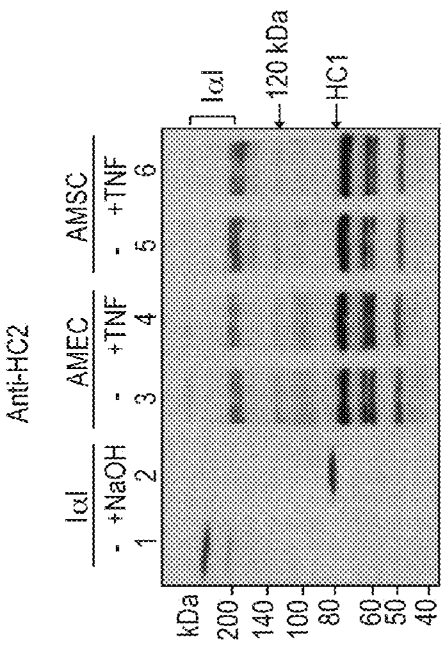
Figure 44D:
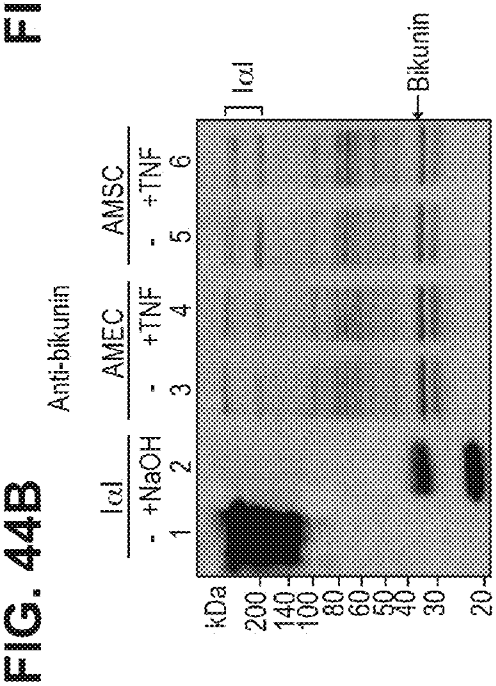
Figure 44E:
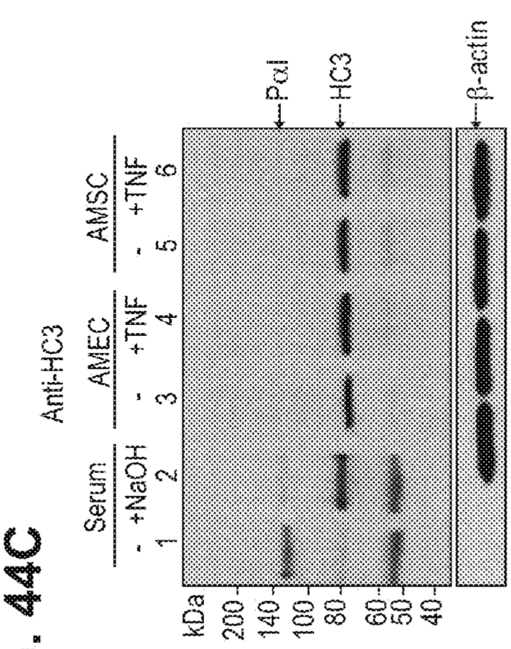

Constitutive Expression of HC1, HC2, HC3, and Bikunin mRNA and Proteins by AMECs and AMSCs in Serum-containing Media To provide data on the cellular sources of HC1, HC2, HC3, and bikunin, we established primary cultures of AMECs and AMSCs in SHEM, which was found to be the optimal medium in our prior study, and extracted total RNA for RT-PCR and proteins for Western blot analysis. The positive control of human liver RNA yielded PCR products with the expected sizes of 138 bp (HC1), 127 bp (HC2), 318 bp (HC3), and 294 bp (bikunin) (FIG. 44A). These four RT-PCR products were all present in AM tissue as well as both AMECs and AMSCs. The expression of HCs and bikunin transcripts was not greatly up-regulated by TNF in AMECs and AMSCs. Western blotting of AMEC and AMSC lysates showed that a 265-kDa and a 200-kDa species were recognized by the chain-specific antibodies against HC1, HC2, and bikunin (FIG. 44, B, C, and D) but not by anti-HC3 (FIG. 44E), suggesting that these two species were IαI-related. Anti-HC1, anti-HC2, and anti-HC3 antibodies all recognized ~75-kDa species (FIG. 44, B, C, and E); the anti-bikunin antibody detected a 35-kDa species (FIG. 44D). Thus, based on our comparison with purified IαI and a serum control (as a source of PαI), and with published data, AMECs and AMSCs can be concluded to express HC1, HC2, HC3, and bikunin proteins. In addition, both anti-HC1 (FIG. 44B) and anti-HC2 antibodies (FIG. 44C) also recognized 120-kDa species that are likely HC1-TSG-6 and HC2-TSG-6 complexes, respectively. Based on prior reports, the 100-kDa species revealed by anti-HC1, anti-HC2, and anti-HC3 antibodies were likely HC1, HC2, and HC3 precursors, respectively. Approximately 45-90-kDa species revealed by anti-bikunin are likely to be bikunin precursor (i.e. al-microglobuin/bikunin tandem protein) with or without glycosaminoglycan attached, a finding also observed in primary rat hepatocytes. The identities of HC1- and HC2-positive species at 65 and 50 kDa (FIG. 44, B and C) and the faint HC3-positive species at 50 kDa (FIG. 44E) are not clear because these species were also present in serum-free AMEC and AMSC lysates (see below); they were likely not derived from serum. Interestingly, the intensities of the various HC and IαI species were not notably affected by addition of TNF. Overall, these results indicate that AMEC and AMSC produce individual HC1, HC2, and bikunin chains that are assembled into IαI proteins.

Production of IαI Family Proteins in Serum-Free AMEC and AMSC Cultures

Figure 45A:
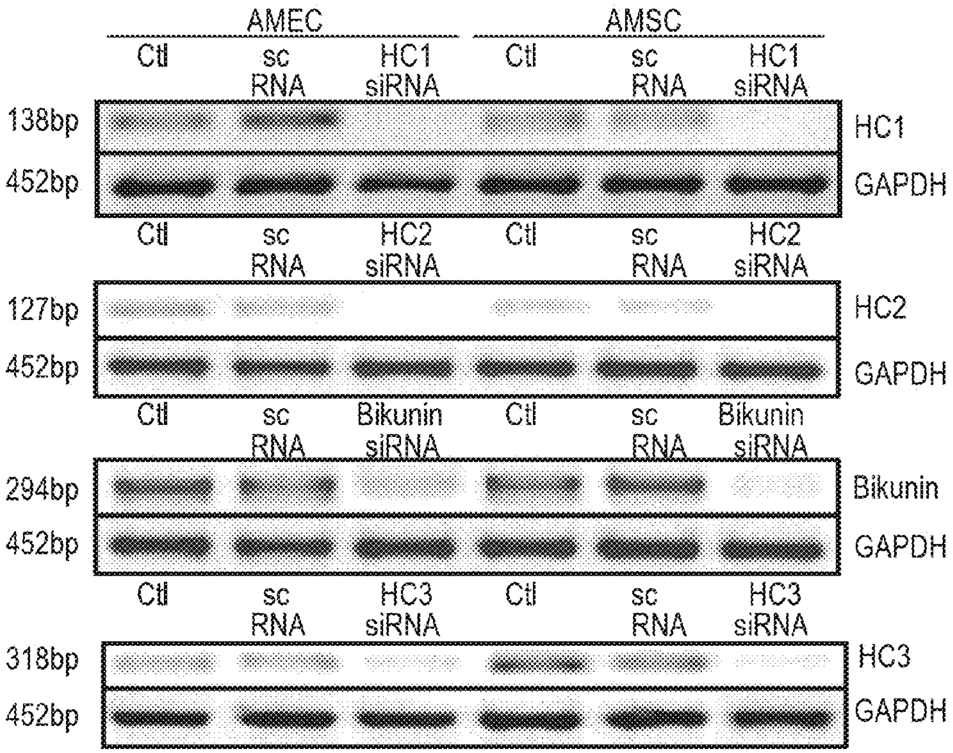
FIG. 45 illustrates expression of IαI family proteins in serum-free AMECs and AMSCs. Primary AMECs and AMSCs were cultured in serum-free SHEM with or without siRNA to HC1, HC2, bikunin, or HC3. mRNA expression was quantified by RT-PCR using GAPDH as the loading control (A). Total proteins were extracted and subjected to Western blot analysis using antibodies against human HC1, HC2, bikunin (B) and HC3 (C) as indicated. Ctl, control.
Figure 45B:
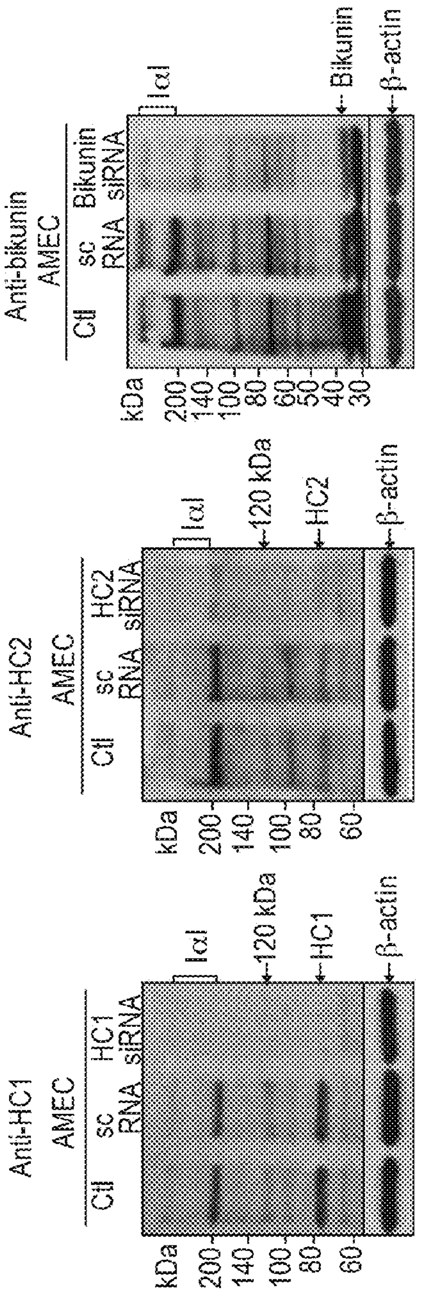
Figure 45C:
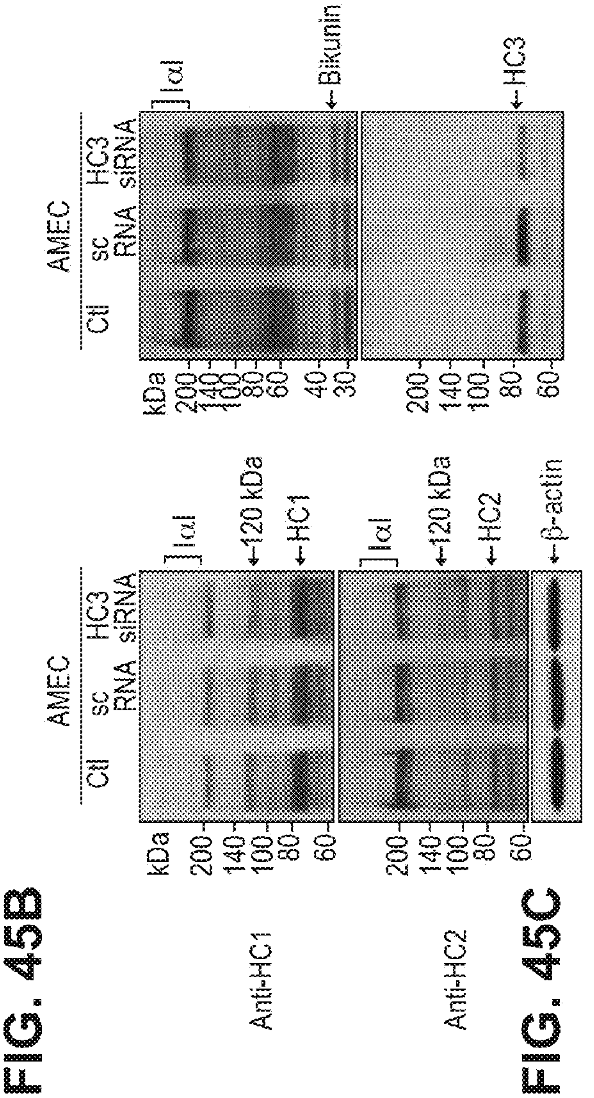

To avoid undue influence by serum IαI and to provide further evidence for the cellular production of IαI family proteins by AMECs and AMSCs, we harvested cell lysates from their respective serum-free cultures. We also treated these two serum-free cultures with HC1 siRNA, HC2 siRNA, and bikunin siRNA (i.e. because HC1, HC2, and bikunin are components of IαI); as a comparison, we also treated cells with HC3 siRNA because HC3 is not a part of IαI. RT-PCR analysis confirmed the efficiency of these siRNAs to down-regulate their respective transcripts in these two cultures (FIG. 45A). Western blot analysis showed that the 265-kDa and 200-kDa species were significantly reduced by HC1 siRNA, HC2 siRNA, and bikunin siRNA (FIG. 45B), but not by HC3 siRNA (FIG. 45C). The production of HC1, HC2, and bikunin (and their putative precursors) was notably down-regulated by their respective siRNA (FIG. 45B). In addition, the 120-kDa species recognized by anti-HC1 and anti-HC2 antibodies that likely corresponded to respective HC1-TSG-6 and HC2-TSG-6 complexes was decreased by HC1 siRNA and HC2 siRNA, respectively (FIG. 45B). The HC3 siRNA decreased the HC3 species but did not affect the aforementioned species (FIG. 45C), consistent with the inhibitory effects of the siRNAs against HC1, HC2, and bikunin, shown in FIG. 45B, being specific. Essentially the same results were obtained using AMSCs (data not shown). These results collectively provided further evidence that AMECs and AMSCs produced HC1, HC2, and bikunin proteins, which assemble to form IαI.

Constitutive Expression of TSG-6 mRNA and Protein by AMECs and AMSCs

Figure 46A:
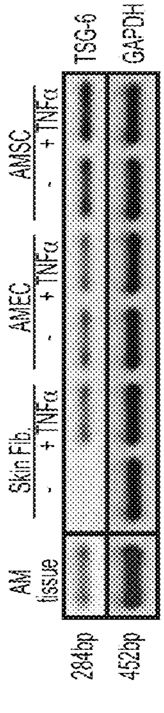
FIG. 46 illustrates constitutive expression of TSG-6 mRNA and protein by AMECs and AMSCs. RNA and protein were extracted from AM tissue, human skin fibroblasts (Skin Fib.), and both AMECs and AMSCs cultured in DMEM/F12 plus 10% FBS with or without 20 ng/ml TNF for 4 h (for RT-PCR) or 24 h (for Western blotting). Expression of TSG-6 mRNA (A) and protein in cell lysates (B) and supernatants (C) was compared. TSG-6 siRNA transfection was performed to verify the expression of TSG-6 in AMECs and AMSCs (D and E). Ctl, control.
Figure 46B:
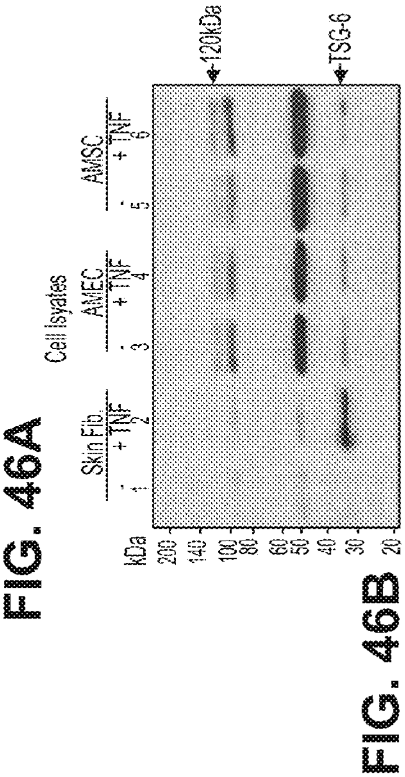
Figure 46C:
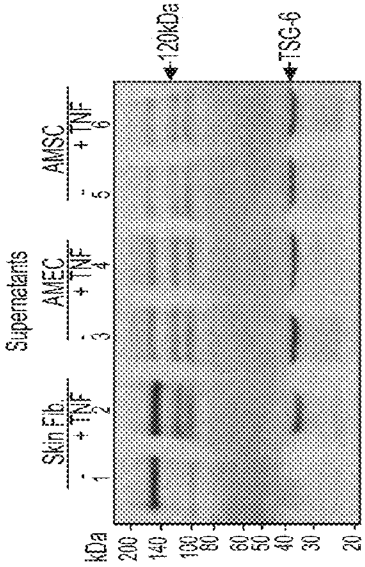

Previous studies have shown that adult skin fibroblasts and peripheral blood mononuclear cells, myeloid dendritic cell, renal tubular epithelial cells, articular chondrocytes, as well as cervical smooth muscle cells express TSG-6 mRNA and protein only under the stimulation of pro-inflammatory cytokine such as TNF and IL-1. To provide further evidence for the cellular sources of TSG-6, we cultured AMECs and AMSCs in DMEM/F12 with 10% FBS to prevent the influence of other components such as EGF in SHEM on TSG-6 expression. As expected, expression of TSG-6 mRNA by human skin fibroblasts was negative but significantly up-regulated by 20 ng/ml TNF (FIG. 46A). In contrast, there was constitutive expression of TSG-6 mRNA by AMECs and AMSCs without being affected by TNF (FIG. 46A). TSG-6 mRNA was also detected in RNAs extracted from fresh AM tissue (FIG. 46A). Western blot analyses of lysates detected four species, i.e. 35, 50, 100, and 120 kDa, in both AMECs and AMSCs, but only 35 kDa and two faint species of 50 and 100 kDa in skin fibroblasts (FIG. 46B). Addition of TNF did not change any species in AMECs and AMSCs, but up-regulated the 35-kDa species (but not the 50- or 100-kDa species) in skin fibroblasts (FIG. 46B). In supernatants, we detected 35-, 100-, 120-, and 150-kDa species (but not 50 kDa) in skin fibroblasts (FIG. 46C); after TNF stimulation, the 100- and 150-kDa species did not change, but 35- and 120-kDa species became intensified. All of these species were also detected in AMEC and AMSC supernatants, where 35- and 120-kDa species were unaffected by TNF.

Figure 46D:
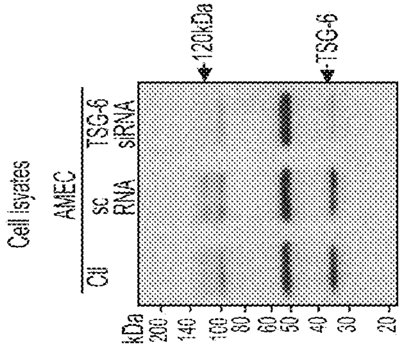
Figure 46E:
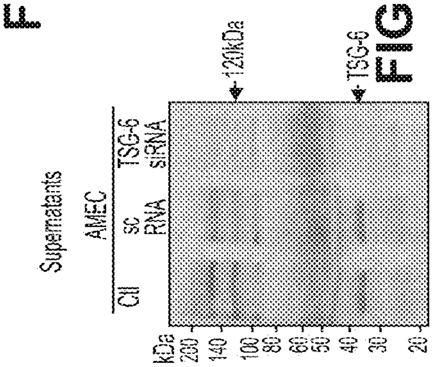

TSG-6 siRNA transfection greatly reduced both 35- and 120-kDa species in both lysates and supernatants of AMEC but did not affect the 50- and 100-kDa species in cell lysates (FIG. 46D) or the 100- and 150-kDa species in supernatants (FIG. 46E). The same result was observed in AMSCs (data not shown). From these experiments we concluded that the 35-kDa species corresponded to TSG-6 secreted by AMECs and AMSCs, where its production was induced by TNF in skin fibroblasts but was constitutive in AMECs and AMSCs. On the basis of earlier reports, the 120-kDa species likely corresponded to the covalent complexes of TSG-6 with HCs. Because the 50-, 100-, and 150-kDa species were not affected by TSG-6 siRNA and because the amounts of these species were not altered by TNF in skin fibroblasts, they were concluded to be nonspecific.

Cellular Production of HC-HA Complex Containing Both HC1 and HC2 Whereas AM HC-HA Complex Contains Only HC1

Previous studies have shown that HC1 and HC2 of IαI and HC3 of PαI can covalently bind to HA in vivo and in vitro to form HC-HA complex. Our prior study showed that a HC-HA complex can be purified from the AM-soluble extract. However, it remained unclear whether bikunin or TSG-6 was also present and which HC isotypes were present in AM HC-HA complex. Because AMECs and AMSCs were found here to synthesize their own IαI and TSG-6 proteins (FIGS. 43 and 44), we aimed to determine further whether they could also produce their own HC-HA complex.

Figure 47A:
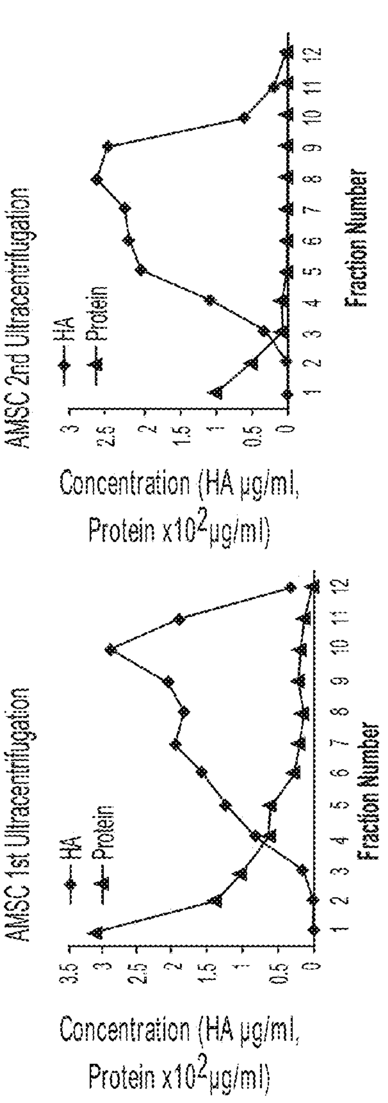
FIG. 47 illustrates production of HC-HA complex in serum-free cultures. Primary AMECs and AMSCs cultured in serum-free SHEM were treated with or without HC1 siRNA or TSG-6 siRNA. Guanidine-HC1 extract of AM cells was subjected to two successive ultracentrifugations with CsCl density gradient and 6 m guanidine HC1 (A). The HA-rich and protein-absent fractions were pooled essentially as reported previously for isolation of HC-HA complex from AM extract. Cell HC-HA complex and AM HC-HA complex with or without HAase digestion were analyzed by Western blotting using anti-HC1, anti-HC2 (N-terminal and C-terminal) and anti-IαI antibodies (B); purified IαI with or without NaOH treatment was included as a control.
Figure 47B:
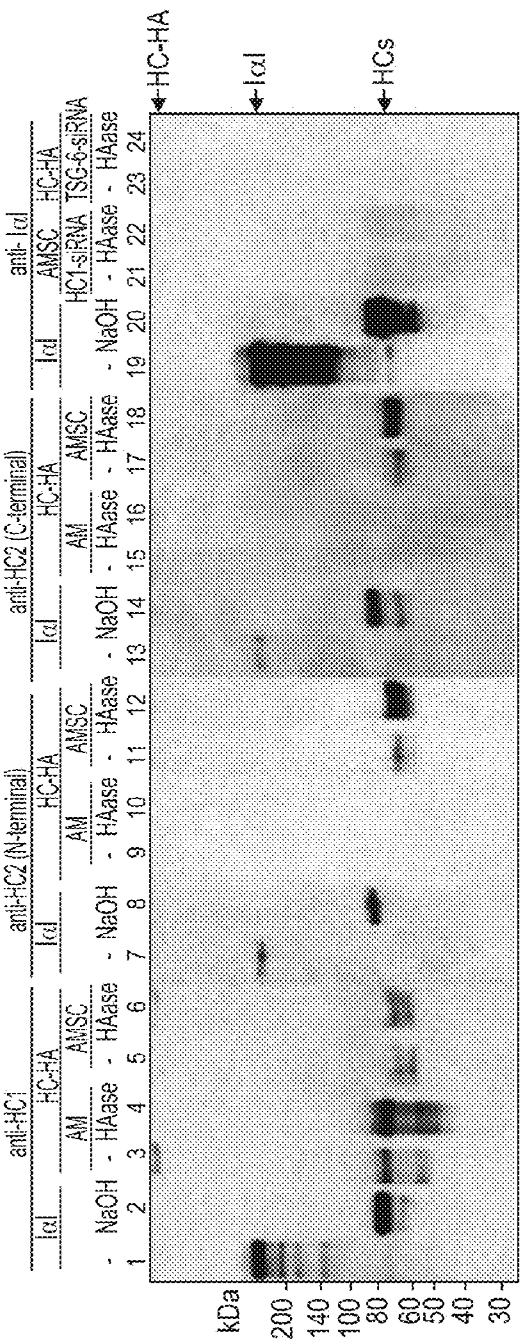

We used two successive ultracentrifugations to isolate the HC-HA complex from the AM extract as reported previously and from both cellular extracts (FIG. 47A). Western blot analysis using the anti-HC1 antibody showed that AM HC-HA complex presented as a high molecular mass species at the bottom of the loading well and free HC1 (FIG. 47B, lane 3) by comparison with purified IαI treated with NaOH (FIG. 47B, lanes 1 and 2). HAase digestion completely eliminated the high molecular mass species, resulting in a notable increase in the intensity of the HC1 species (FIG. 47B, lane 4), confirming that the high molecular mass species represented a HC-HA complex. The presence of free HC1 in the AM HC-HA complex might be due to the degradation of HA that lead to release of some HC1 during purification and storage of the complex. Interestingly, the anti-HC2 antibody (raised against the N-terminal peptide) did not detect any species in the AM HC-HA complex with or without HAase digestion (FIG. 47B, lanes 9 and 10) but did detect a HC2 species in IαI (FIG. 47B, lane 8). The same result was obtained using an alternative anti-HC2 antibody raised against the C-terminal peptide (FIG. 47B, lanes 13-16). Preliminary mass spectrometric analysis of the AM HC-HA complex following digestion with HAase and trypsin detected peptides from HC1 but not from HC2 consistent with the absence of HC2 in AM HC-HA complex.4 Furthermore, by Western blotting we did not find HC3, bikunin, or TSG-6 in the AM HC-HA complex (data not shown); the absence of bikunin and TSG-6 in the HC-HA complex is in agreement with our previous data.

Overall, the above results indicate that the HC-HA complex from AM only contains HC1. However, Western blot analysis of the aforementioned cell HC-HA revealed the presence of both HC1 and HC2 after HAase digestion of material purified from both AMSCs (FIG. 47B, lanes 5, 6, 11, 12, 17, and 18) and AMECs (data not shown) although the amount increased for HC1 was not as dramatic as HC2. These results indicated that both cells primarily make HC2—HA. We also did not detect HC3, bikunin, and TSG-6 in the cell HC-HA complex (data not shown). The formation of this HC-HA complex was abolished when cells were treated by HC1 siRNA (FIG. 47B, lanes 21 and 22) and TSG-6 siRNA (FIG. 47B, lanes 23 and 24). Available evidence suggests that the covalent coupling of HCs to the CS chain of bikunin to form intact IαI is a prerequisite for the subsequent transfer of HCs to HA. We found that HC1-siRNA was specific for HC1 but did not affect HC2 and bikunin mRNA expression and their protein synthesis in AMEC and AMSC (data not shown), but prevented the formation of intact IαI. So, HC1-siRNA treatment prevents any type of HC-HA formation due to the inhibition of IαI biosynthesis caused by HC1 knockdown.

Example 20

Effect of HC-HA Purified from AM on Expression of ESC, MSC, Pericyte and Angiogenesis Markers in Native Limbal Niche Cells Cryopreserved human amniotic membrane (AM) has been applied to surgical or injury sites to reduce the inflammation and scarring. Application of human AM as a temporary graft induces rapid regression of corneal stromal edema and inflammation. Our studies also have demonstrated that amniotic membrane extract (AME) and HC-HA purified from AM retains anti-inflammatory and anti-scarring activities of AM, and HC-HA exerts a more potent antiangiogenic action than does HA by inhibiting viability, proliferation, migration, and differentiation without promoting the detachment or death of cultured HUVECs. In this experiment, the effect of HC-HA complexes isolated from AM on gene expression of markers for cell angiogenesis and differentiation was examined.

To characterize the effect of HC-HA complexes on ESC, EPC, MSC and angiogenesis markers, passage 4 of limbal niche cells were cultured on plastic, plastic coated with 5% matrigel, HA, 2nd purified HC-HA and 4th purified HC-HA (see Example 19 for HC-HA extract purification). Limbal NCs cells (P4/3D) and limbal epithelial progenitor cells (LEPC) were seeded in 96 well plastic plates at a density of 5000/well in modified embryonic SC medium (MESCM), culture for 4 days, and the morphology of the cells was monitored by phase contrast microscopy and photographed daily. At Day 4, the cells were rinsed and mRNA was isolated for qPCR for the expression of markers ESC, EPC, MSC and angiogenesis.

Figure 48:
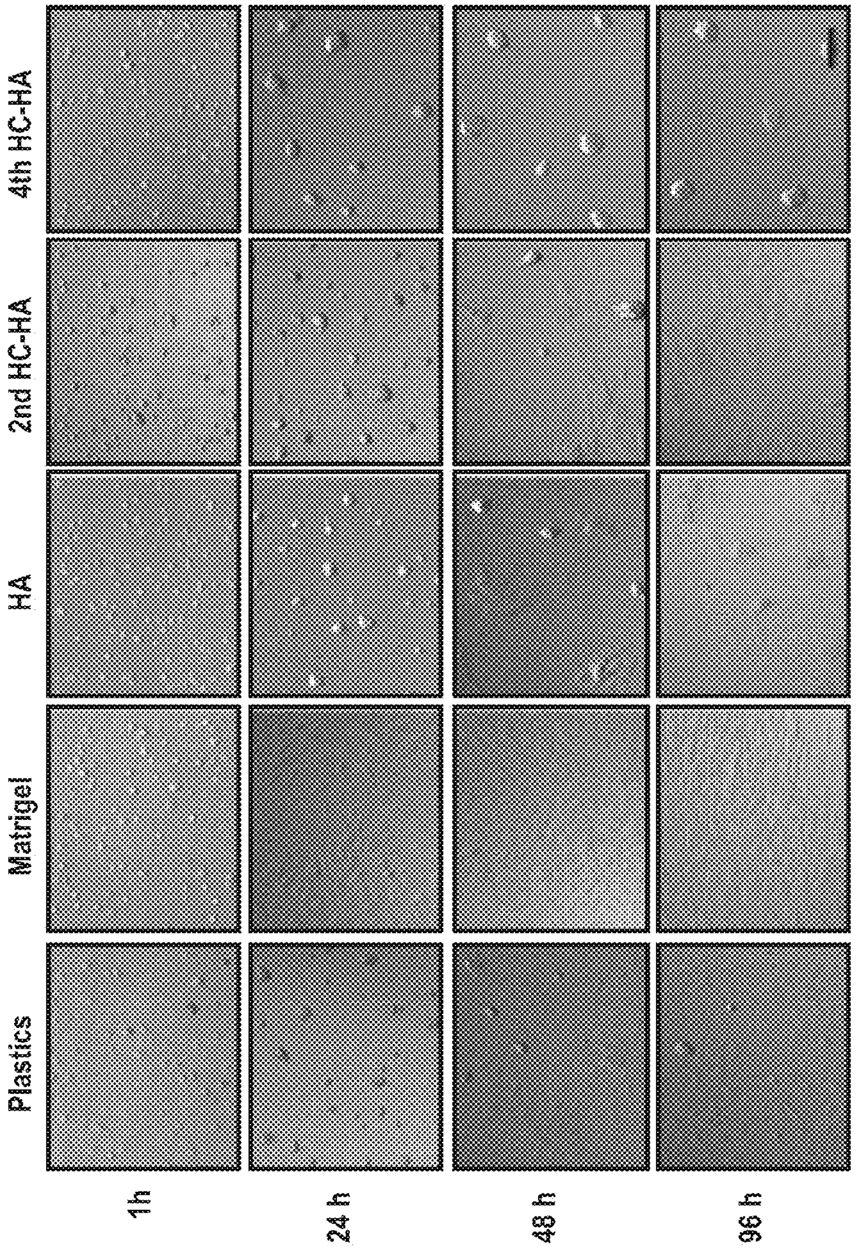
FIG. 48 illustrates effect of Matrigel and immobilized HC-HA on cell morphology and differentiation of native limbal niche cells. Cells were cultured on plastic only, Matrigel, immobilized HA, or immobilized HC-HA complexes purified from AM ($2^{nd}$ or $4^{th}$ fraction) and observed at 1, 24, 48, and 96 h after seeding by phase contrast microscopy.

It was observed that 4th HC-HA, not 2nd HC-HA and HA, promotes aggregation of limbal niche cells (FIG. 48). In addition, it was demonstrated that HA and HC-HA promoted expression of ESC, EPC and angiogenesis progenitor markers in limbal niche cells, but not differentiation in limbal niche cells.

Figure 49:
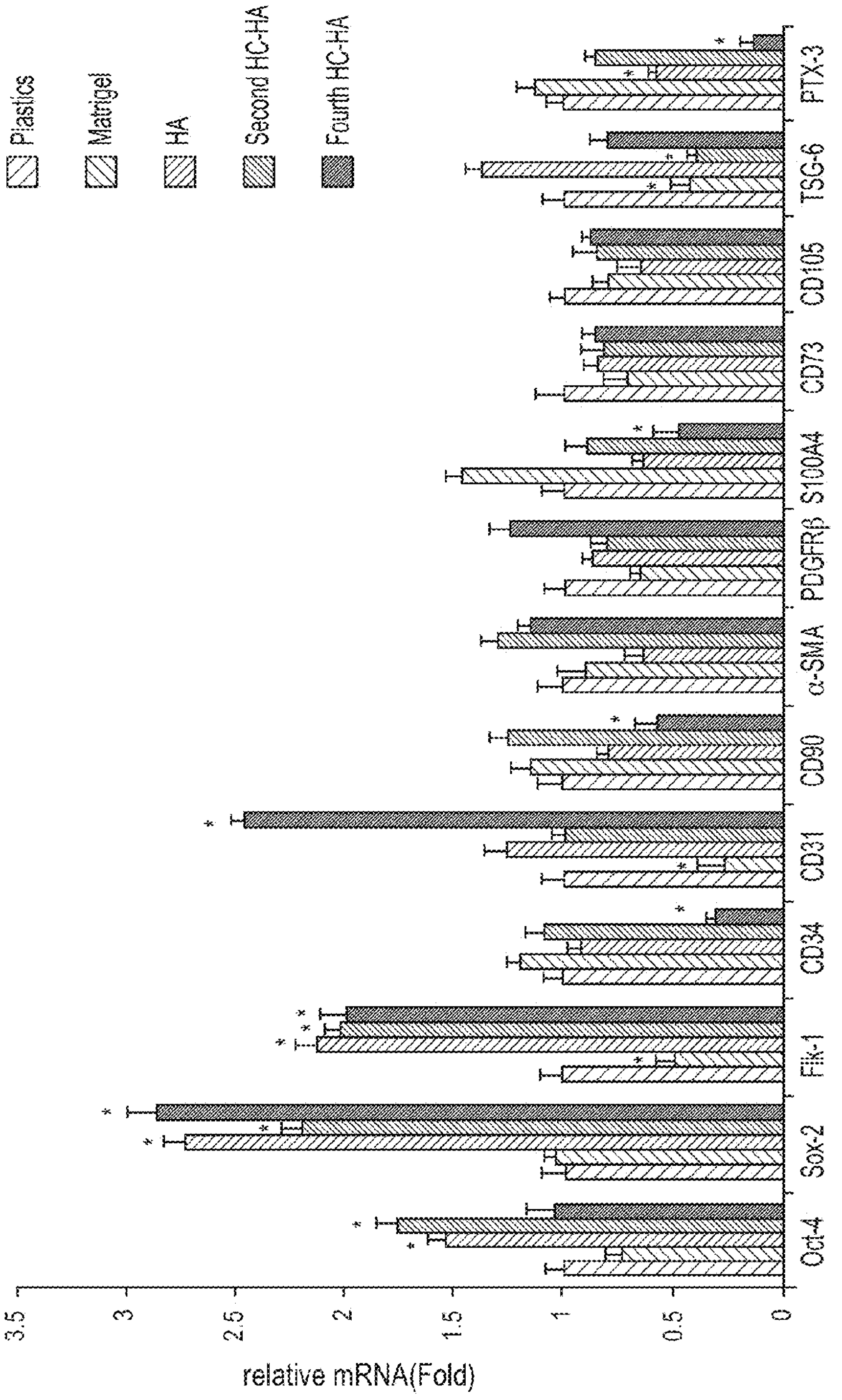
FIG. 49 illustrates relative ESC and angiogenesis marker expression as determined by qPCR in native limbal niche cells cultured on plastic only, Matrigel, immobilized HA, or immobilized HC-HA complexes purified from AM ($2^{nd}$ or $4^{th}$ fraction).

After 96 h of culture, the cells cultured in HA, 2nd HC-HA and 4th HC-HA expressed 2-3 times more Sox-2, Flk-1 and CD 31 (in case of 4th HC-HA), the markers of ESC, EPC and angiogenesis progenitors, indicating that HA and HC-HA promote anti-inflammatory and anti-scaring properties by altering the phenotype of the niche cells (FIG. 49). The cells cultured on 4th HC-HA expressed 2.5 times higher CD31, indicating that 4th HC-HA is the most effective form of HA. There is no detectable SMMHC in all groups of cells, indicating that the differentiation of the cells were not promoted by HA and HC-HA. 4th HC-HA inhibited the expression of PTX-3 by ~80%, indicating that downregulation of PTX3 by 4th HC-HA may be related to its anti-inflammatory and anti-scaring effect.

Figure 50:
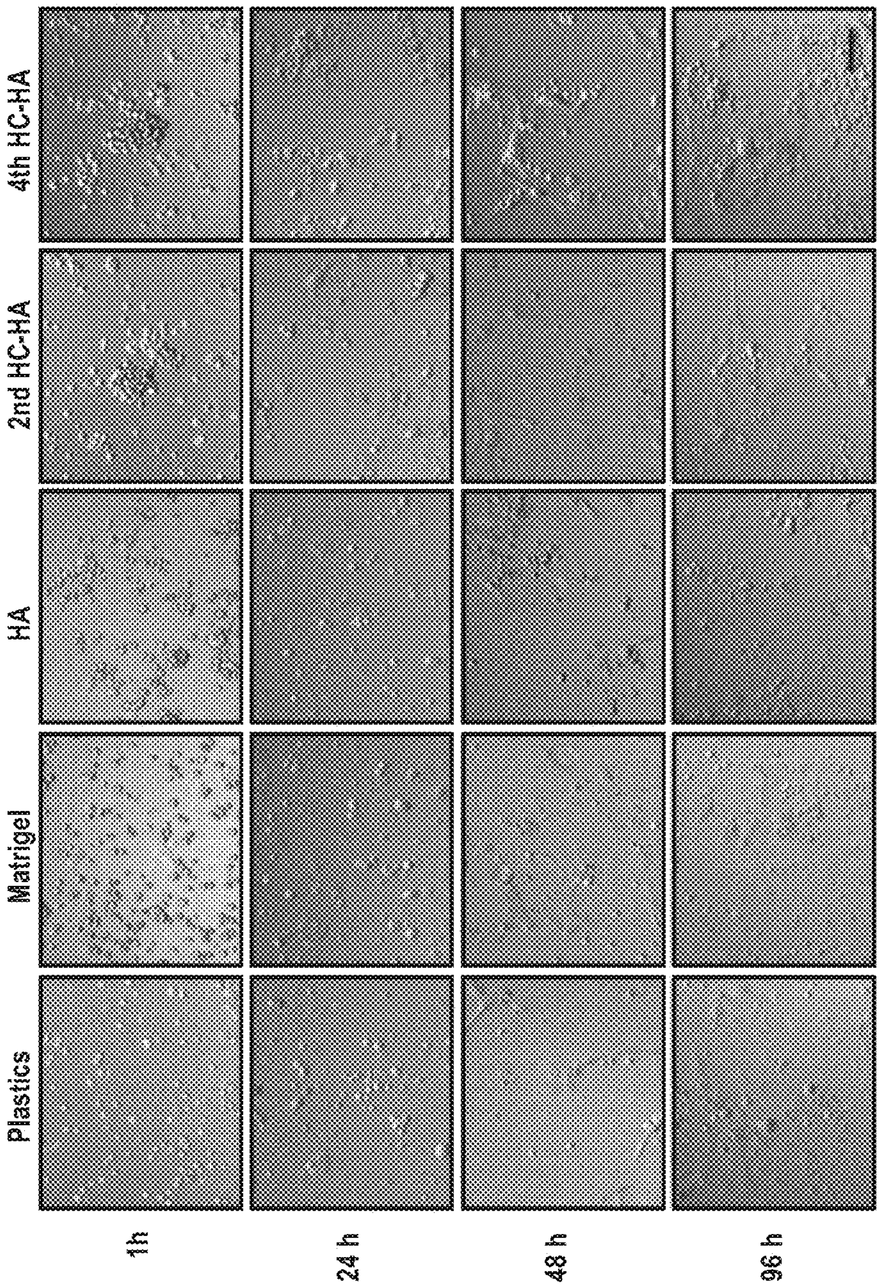
FIG. 50 illustrates effect of Matrigel and immobilized HC-HA on cell morphology and differentiation of limbal epithelial progenitor cells (LEPC). Cells were cultured on plastic only, Matrigel, immobilized HA, or immobilized HC-HA complexes purified from AM ($r^{nd}$ or $4^{th}$ fraction) and observed at 1, 24, 48, and 96 h after seeding by phase contrast microscopy.

The attachment and growth of LEPC on plastic or plastic coated with Matrigel were poor, and HA and HC-HA did not support the attachment and growth of LEPC (FIG. 50). The cells were mostly rounded at the beginning of 24 h of culture. After 48 h of culture, a small portion of the cells began to grow in a spindle and fibroblastic-like shape. The addition of HA and HC-HA did not improve the attachment and growth of LEPC on plastic for the 96 h duration of the test.

Figure 51:
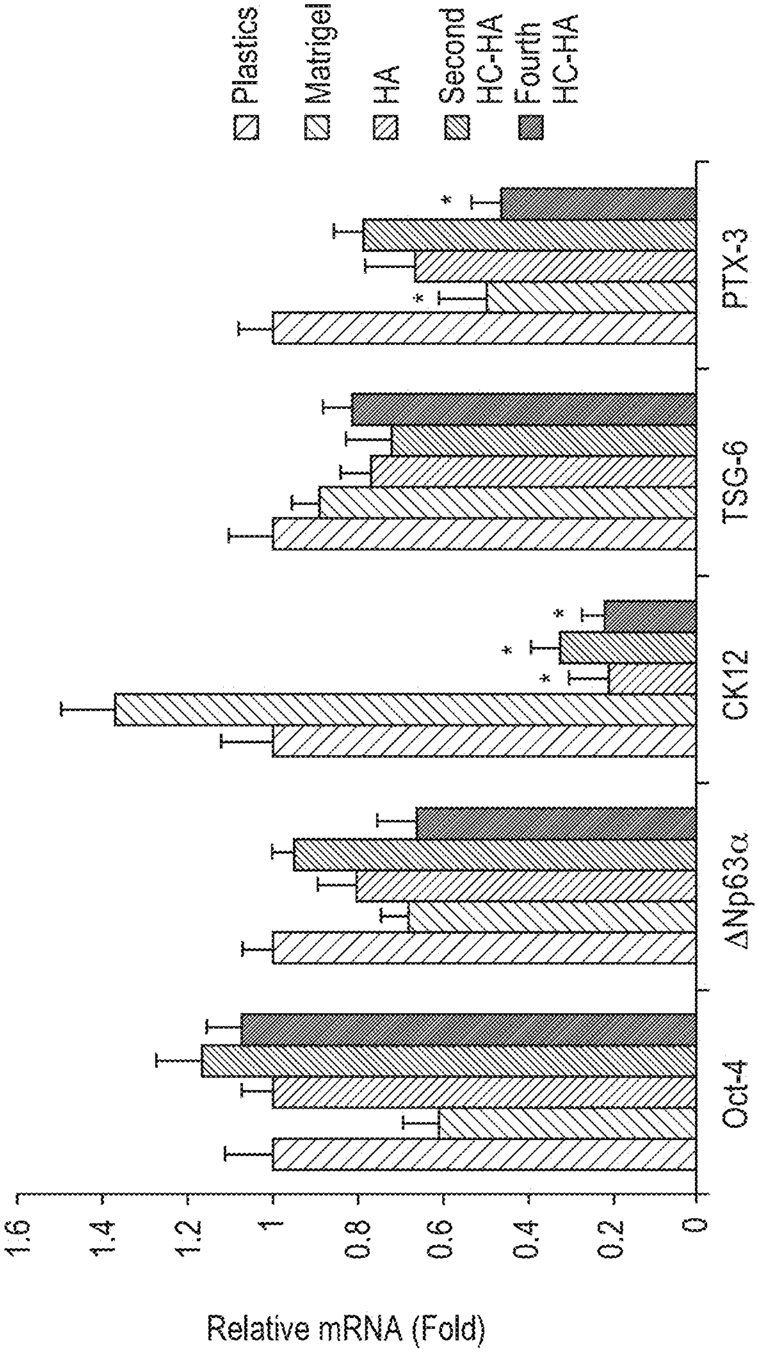
FIG. 51 illustrates relative ESC and angiogenesis marker expression as determined by qPCR in limbal epithelial progenitor cells (LEPC) cultured on plastic only, Matrigel, immobilized HA, or immobilized HC-HA complexes purified from AM ($2^{nd}$ or $4^{th}$ fraction).

HA and HC-HA also did not affect expression of epithelial stem cell markers of Oct-4 and ΔNp63α, but decreased expression of epithelial marker CK12. 4th HC-HA also induced a less significant reduction of PTX-3 (by 60%) (FIG. 51).

Example 21

Effect of HC-HA Purified from AM on Expression of ESC, MSC, Pericytes and Angiogenesis Markers from Conjunctivochalasis Fibroblasts Derived from Diseased Patients In this example, the ability of HC-HA to induced a stem cell like phenotype in fibroblasts was examined. Conjunctivochalasis (CCh) fibroblasts were obtained as described in Guo et al. (2012) *Invest Ophthalmol V is Sci.* 53(7):3414-23. The cells were cultured in DMEM+0.5% FBS on tissue cultures dishes containing no substrate (control) or immobilized HA, 2nd HC-HA or 4th HC-HA (see Example 20). The cell were cultured for 48 hours and added with or without 20 ng/mL IL-1β for 4 or 24 hours before being harvested for total RNAs or proteins, respectively.

1. Effects of Immobilized HC-HA Complex on CCh Fibroblasts Morphology

Figure 52:
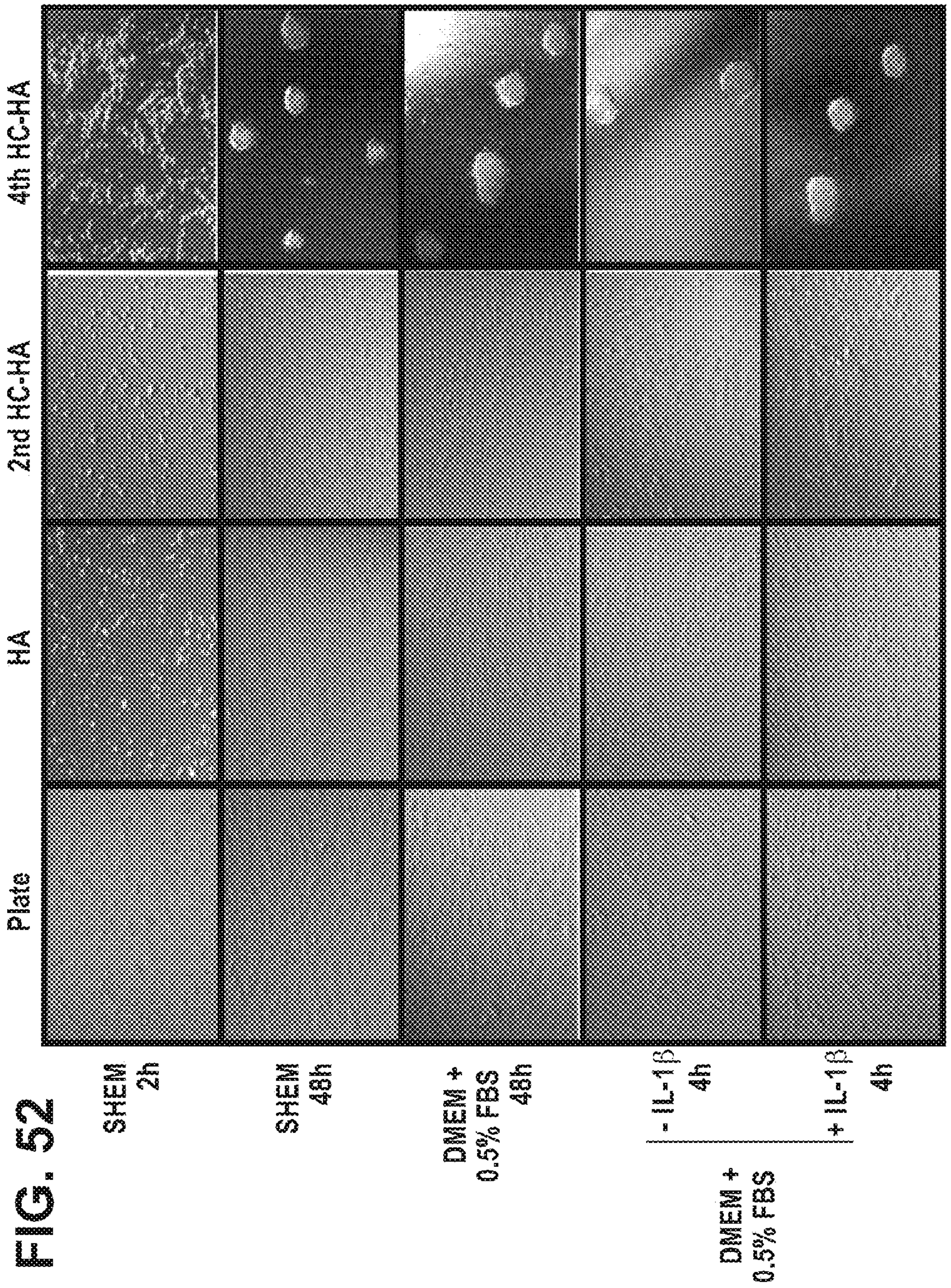
FIG. 52 illustrates effect of HC-HA on cell morphology and differentiation of conjunctivochalasis (CCh) fibroblasts. Cells were cultured on plastic only, immobilized HA, or immobilized HC-HA complexes purified from AM ($2^{nd}$ or $4^{th}$ fraction) in either SHEM, DMEM/0.5% FBS, or DMEM/0.5% FBS+IL1β and observed over 2, 4 and/or 48 after seeding by phase contrast microscopy.

Immobilized 4th HC-HA promoted CCh fibroblasts to aggregate and form spheres (FIG. 52). The cells maintained this morphology even with IL-1β treatment after cultured in DMEM+0.5% FBS for 48 h, but the control, immobilized HA and 2nd HC-HA did not. These results indicated that 4th HC-HA promoted cells back into quiet state, and possibly into stem cell-like state and decreased cell sensitivity to stimulation.

Figure 53A:
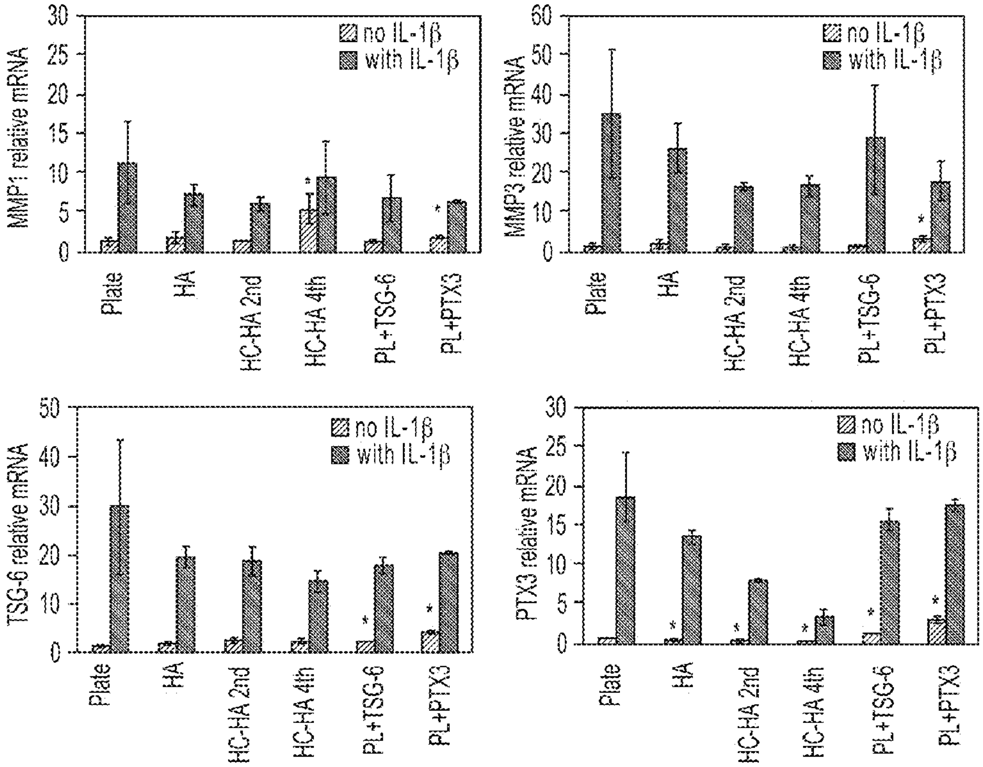
FIG. 53 illustrates relative expression of MMP1, MMP3, TFG-6 and PTX3 as determined by qPCR in CCh fibroblasts cultured on plastic only, immobilized HA, or immobilized HC-HA complexes purified from AM ($2^{nd}$ or $4^{th}$fraction) (A, B).
Figure 53B:
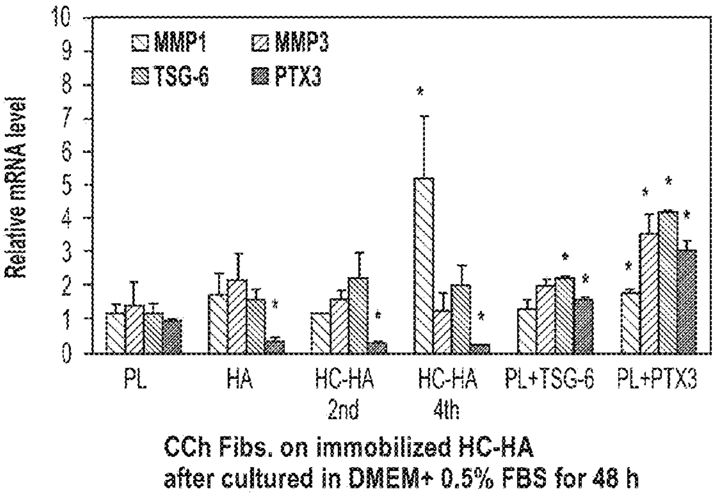

2. Effects of Immobilized HC-HA Complex on the Expression of MMP1, MMP3, TSG-6 and PTX3 mRNA in CCh Fibroblasts The 4th HC-HA decreased PTX3 expression in CCh fibroblasts, and down-regulated MMP1, MMP3, TSG-6 and PTX3 expression under inflammatory cytokine stimulation (FIG. 53).

Figure 54:
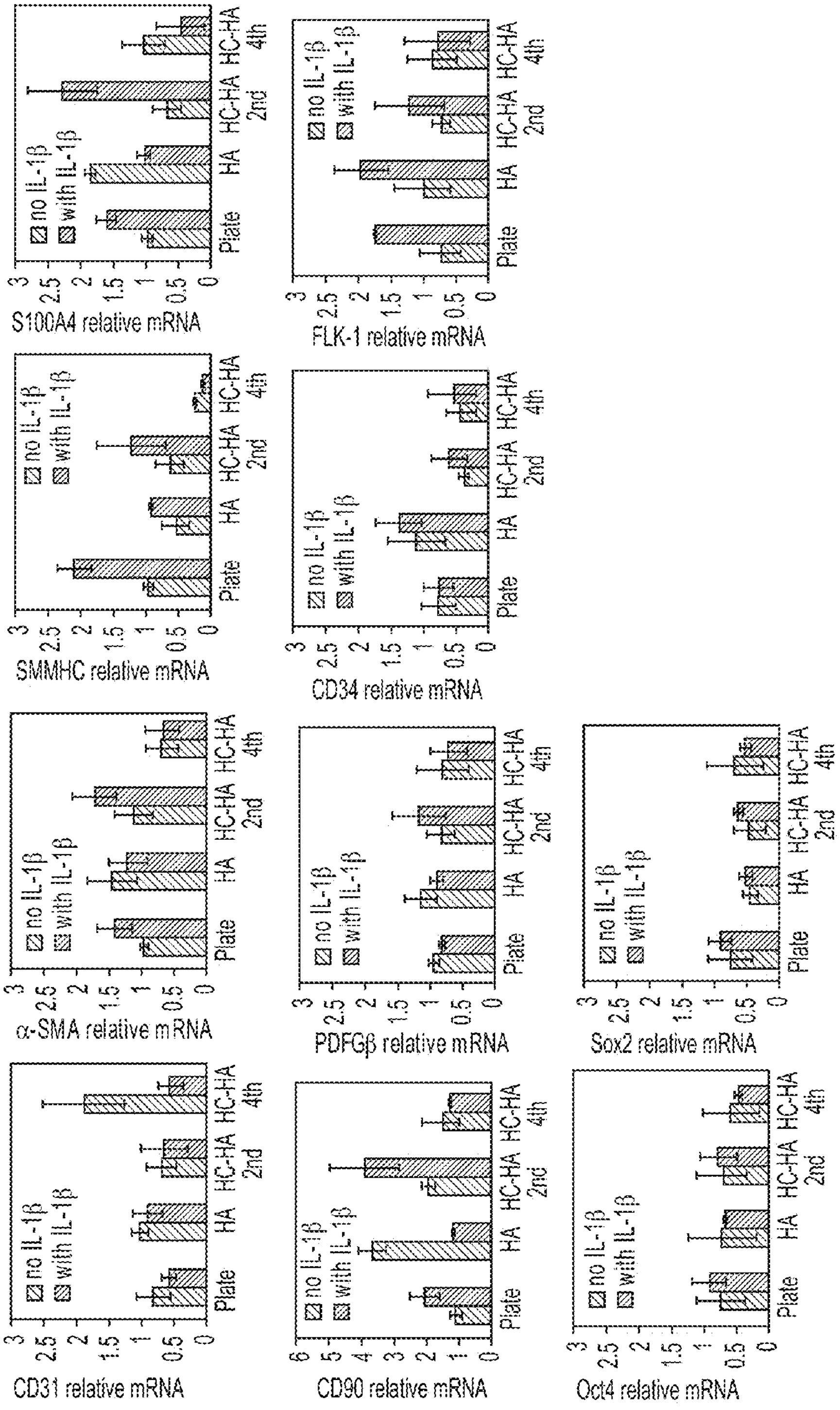
FIG. 54 illustrates relative expression of ESC and angiogenesis markers as determined by qPCR in CCh fibroblasts cultured DMEM/0.5% FBS, or DMEM/0.5% FBS+IL113 on plastic only, immobilized HA, or immobilized HC-HA complexes purified from AM ($2^{nd}$ or $4^{th}$ fraction).

3. Effects of Immobilized HC-HA Complex on Expression of Stem Cell Markers in CCh Fibroblasts 4th HC-HA increased EPC marker CD31 expression but decreased α-SMA, SMMHC expression, suggesting 4th HC-HA likely promoted CCh fibroblasts into an endothelial progenitor state, consistent with the cell morphology results (FIG. 54). The ESC markers, MSC markers and other EPC markers did not show any significant difference among these conditions.

Example 22

Angiogenic Potential of C/D Derived Cells

To confirm that C/D isolated cells expressing FLK-1+, vWF+ and CD31− are indeed cells that possess angiogenic potential, that ability of angiogenic progenitor to differentiate into mature vascular endothelial cells is examined. Previous studies reported that defined endothelial progenitor cells (EPCs) should follow differential potential by demonstrating (1) positive expression of FLK-1, CD31 and vWF when cultured on plastic in EGM2 with VEGF, bFGF (Park et al. (2010) *Int J. Cardiol.* 145:261-262) 2) ability to uptake Dil-Ac-LDL(Voyta et al. (1984) *J. Cell Biol.* 99:2034-2040), and 3) form temporary vascular network on 100% Matrigel (Gargett et al. (2000) *Hum Reprod.* 15:293-301; Ieronimakis et al. (2008) *PLoS One* 3:e0001753; Park et al. (2010) *Int J. Cardiol.* 145:261-262). Because previous studies reported pericyte and/or its progenitors stabilize vessel and function through paracrine and cell-cell contact with endothelial cells Song (2005) *Chin Med J* (Engl) 118:927-935; Traktuev et al. (2008) *Circ Res.* 102:77-85; Stratman et al. (2009) *Blood*

114:5091-5101). C/D derived cells (see examples 5 and 6) expressing pericyte-like markers were examined for similar function.

Figure 55:
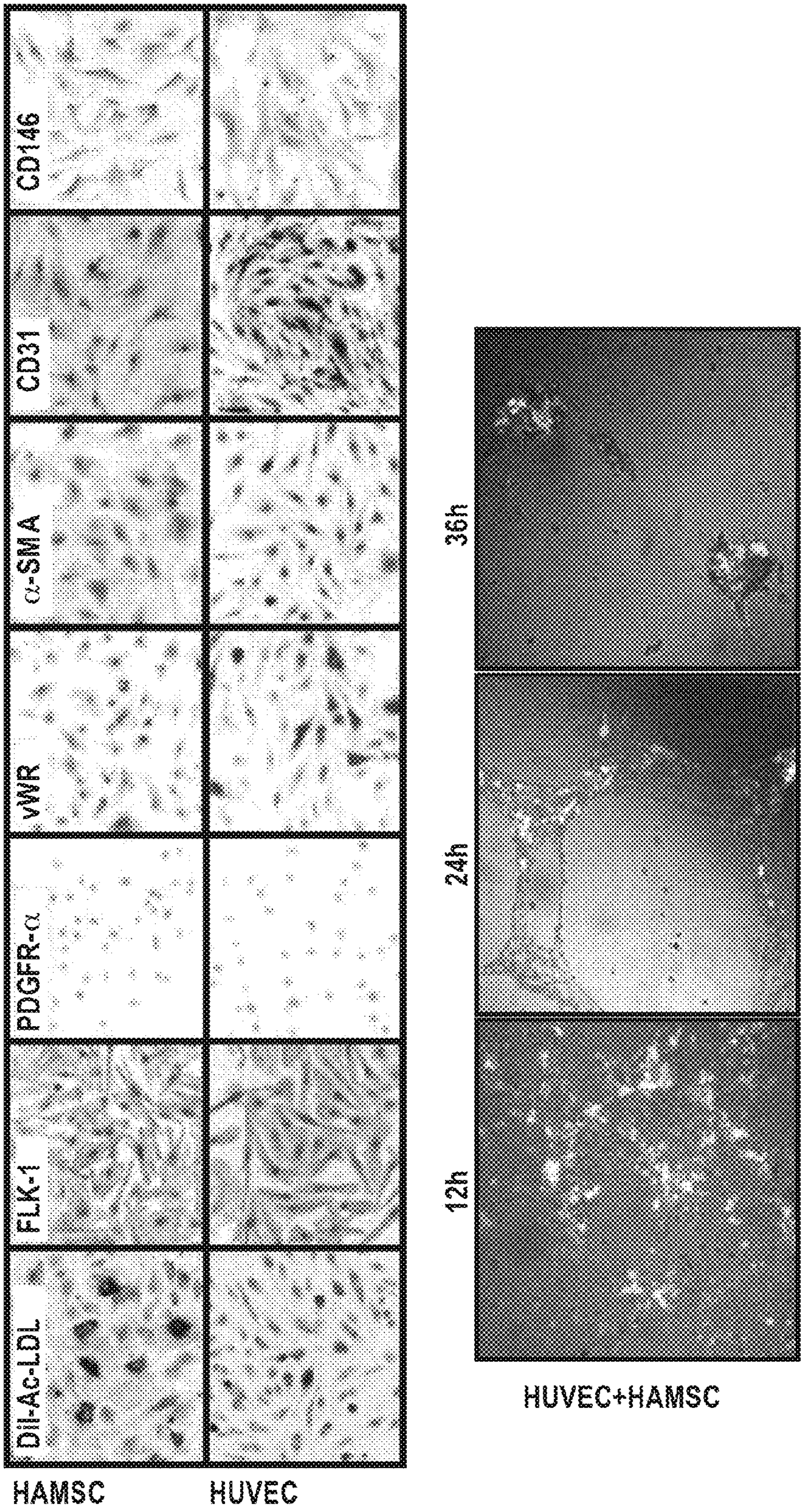
FIG. 55 illustrates relative expression of ESC and angiogenesis markers by immunofluorescence in hAMSC and vascular network formation on 100% matrigel.

Results in FIG. 55 show that C/D isolated hAMSC at P3 culture in EGM with VEGF, bFGF medium, exhibit angiogenic potential and can be differentiated into mature vascular endothelial cells with ability to uptake Dil-Ac-LDL. These hAMSC also demonstrate similar expression of the mature vascular endothelial phenotype (FLK-1, vWR, α-SMA, CD31 and CD146). Similar to human umbilical vascular endothelial cells (HUVEC), hAMSCs were able to form network formation on 100% matrigel within 24 hours but the network formation diminished after 36 hours.

Example 23

Presence of Small Leucine-Rich Proteoglycans (SLRPs) in Native HC-HA Complexes Isolated from Amniotic Membrane and Umbilical Cord The small leucine-rich proteoglycans (SLRPs) are a family of proteins that are present in the extracellular matrix. This family includes decorin (36 kD), biglycan (38 kD), fibromodulin (42 kD), lumican (38 kD), keratocan (40 kD), epiphycan (Pg-Lb), osteoglycin (25 kD), PRELP (55-62 kD), and osteoadherin (60 kD). All members of the SLRP family consist of a protein core with multiple leucine-rich repeats and one or more glycosaminoglycan side chains, which include chondroitin sulfate, dermatan sulfate or keratan sulfate. SLRPs appear to interact in many cases with collagen, modifying the deposition and arrangement of collagen fibers in the extracellular matrix, and also with cells and with soluble growth factors like TGF-beta regulating cell function. Previously, we have purified lumican from human AM and demonstrated that AM contains abundant lumican that appeared as a non-keratan sulfated glycoprotein (50 kD) in both soluble and insoluble forms, which is different from that in cornea, where it present as a keratan sulfate proteoglycan (MW 70-90 kDa). Decorin and biglycan have also been found in human AM as chondroitin sulfate proteoglycans by Western blotting and immunostaining. These findings suggested that AM produces SLRPs.

In HC-HA 4th purified from an guanidine HC1 extract of AM, we detected a broad and strong 140 kDa band and relatively weaker 705 kDa, doublet 55 kDa and 20 kDa bands that were not found in 4×HC-HA purified from PBS extract of AM. Because the 140 kDa band is not sharp suggesting the content of sugar moieties, we speculated that they were proteoglycans. We have detected positive immunostaining of keratan sulfate in AM, especially localized in the stromal compact layer, a similar distribution pattern as PTX3 in AM. We also found positive immunostaining of keratan sulfate in UC subamnion and Wharton's jelly. In this example, the presence of SLRPs in HC-HA complexes purified by extraction in PBS or guanidine HC1 were compared.

AM, CH and UC Extraction by PBS.

According to the method described in He et al. (2009) *J Biol. Chem.* 284(30):20136-46, amniotic membrane (AM) and umbilical cord (UC) tissues were homogenized with a blender in cold PBS at 1:1 (g/ml) for AM or 1:1.5 (g/ml) for UC, and mixed at 4° C. for 1 h. The mixture was centrifuged at 48,000 g at 4° C. for 30 min. The supernatants of PBS extract were designated as AME, and UCE, respectively. In addition, a Wharton's jelly mixture from UC was also extracted by PBS and such extract was named UJE. Ultracentrifugation was performed on the extracted samples as described above to obtain nHC-HA $4^{th}$ complexes for analysis. The sample were lyophilized and stored at −20° C.

AM and UC Extraction by GnHCl after PBS Extraction.

The insoluble pellet of AM, UC and UC jelly mixture after PBS extract were further extracted by 4 M GnHCl buffer (100 mM sodium acetate, pH 5.8, 4M GnHCl, 10 mM EDTA, 1% Triton X-100) at 4° C. for 24 h. After centrifugation at 48,000 g, at 4° C. for 30 min, the supernatants were collected and named AMGnE, UCGnE and UJGnE, respectively. The HA and protein concentrations in each extraction were detected by HA ELISA and BCA assay, respectively. Ultracentrifugation was performed on the extracted samples as described above to obtain nHC-HA $4^{th}$ complexes for analysis. The sample were lyophilized and stored at −20° C.

Deglycosylation Treatment of HC-HA Samples:

(1) Chemical deglycosylation with TFMSA: Lyophilized HC-HA complexes (containing 30 μg HA) were incubated with 50 μA TFMS and 20 μA anisole on ice for 3 h. TFMS was neutralize with 125 μA N-ethylmorpholine. The sample was then precipitated with 5-10 volumes of acetone overnight at −20° C. or for 1 h at −80 C. The samples were centrifuged and dried. The dried pellets were dissolved in SDS sample loading buffer for electrophoresis.

(2) Enzymatic deglycosylation with keratanase (Endo-β-galactosidase) to remove keratan sulfate chain and N-linked oligosaccharides, or with Chondroitinase (Cabc) to remove chondroitin sulfate chain: HC-HA complexes (containing 30 μg HA) were incubated with 0.1 U/ml keratanase in 50 mM sodium acetate, pH 5.8, at 37 C for 2 h, or incubated with 5 U/ml Cabc in PBS at 37 C for 2 h.

Samples were analyzed SDS-Page and Western blotting for Keratan sulfate, osteoadherin, Keratocan, PRELP, and osteoglycin.

Results:

For the AM HC-HA samples, it was found that keratan sulfate and osteoadherin are present in AM GnHCl HC-HA, but not in PBS HC-HA. AM GnHCl HC-HA contains abundant decorin and biglycan that are bound to HC-HA, but PBS HC-HA contains only faint decorin and no biglycan. AM GnHCl HC-HA also contains osteoadherin and keratan sulfate-containing species, while PBS HC-HA does not. In addition, a small amount of decorin and biglycan in AM GnHCl HC-HA contains chondroitin sulfate chain. No fibromodulin, lumican, keratocan, PRELP, osteoglycin, epiphycan, periostin, TSG-6 or Bikunin was detected in AM GnHCl HC-HA.

For the UC HC-HA samples, it was found that decorin and biglycan are abundantly present in UC GnHCl HC-HA, but not in PBS HC-HA. Decorin and biglycan in UC GnHCl HC-HA further appear to be attached to a chondroitin sulfate chain. Osteoadherin and bikunin are also present in UC GnHCl HC-HA, but not in PBS HC-HA. Keratan sulfate was present in GnHCl HC-HA and PBS HC-HA. No fibromodulin, lumican, keratocan, PRELP, osteoglycin, epiphycan, periostin or TSG-6 was detected in UC GnHCl HC-HA.

While preferred embodiments have been shown and described herein, it will be obvious to those skilled in the art that such embodiments are provided by way of example only. Numerous variations, changes, and substitutions may now occur. It should be understood that various alternatives to the embodiments described herein may be employed in practicing the described methods. It is intended that the following claims define the scope of the embodiments and that methods and structures within the scope of these claims and their equivalents be covered thereby.

The invention claimed is:

1. A method for isolating an E-cadherin positive stem cell, comprising:

(a) removing all epithelial cells from an isolated mixed cell population comprising one or more stem cells and one or more non-stem cells; and (b) after removal of all of the epithelial cells contacting the remaining cells of the mixed cell population with an agent that binds to E-cadherin, thereby isolating an E-cadherin positive stem cell from the mixed cell population.

2. The method of claim 1, wherein the agent that binds to E-cadherin is an antibody.

3. The method of claim 1, further comprising isolating the E-cadherin positive stem cell by fluorescence activated cell sorting or magnetic activated cell sorting.

4. The method of claim 1, wherein the mixed cell population comprises an embryonic stem cell, an adult stem cell, a fetal stem cell, or an induced pluripotent stem cell.

5. The method of claim 1, wherein the mixed cell population comprises a limbal stromal niche cell, an umbilical cord stem cell, an amniotic membrane stem cell or an adipose stem cell.

6. The method of claim 1, further comprising isolating the isolated mixed cell population from an umbilical cord.

7. The method of claim 6, wherein the umbilical cord is a human, non-human primate, cow or pig umbilical cord.

8. The method of claim 6, further comprising:

(a) mechanically or enzymatically removing all epithelial cells from the umbilical cord, thereby producing epithelial free-umbilical cord tissue; and (b) contacting the epithelial free-umbilical cord tissue with collagenase for a period of time sufficient to release one or more stem cells from other bound cells and components of the stromal matrix of the epithelial free-umbilical cord tissue, thereby producing the isolated mixed cell population.

9. The method of claim 8, further comprising removing an umbilical cord blood vessel from the epithelial free-umbilical cord tissue prior to contacting the epithelial free-umbilical cord tissue with collagenase.

10. The method of claim 1, further comprising isolating the isolated mixed cell population from adipose tissue.

11. The method of claim 10, further comprising digesting the adipose tissue with collagenase, thereby producing collagenase-digested adipose tissue, thereby producing the isolated mixed cell population.

12. The method of claim 11, further comprising digesting the adipose tissue with collagenase in modified ESC medium.

13. The method of claim 11, further comprising fractionating the collagenase-digested adipose tissue by centrifugation, thereby producing a floating cell fraction (FC) and a sedimented stromal vascular fraction (SVF).

14. The method of claim 13, further comprising selecting the FC as the isolated mixed cell population.

15. The method of claim 13, further comprising selecting the sedimented SVF as the isolated mixed cell population.

16. The method of claim 13, further comprising filtering the sedimented SVF on a mesh filter, thereby producing a filtered SVF and a remaining cell fraction (RC).

17. The method of claim 16, further comprising selecting the filtered SVF as the isolated mixed cell population.

18. The method of claim 16, further comprising selecting the RC as the isolated mixed cell population.

19. The method of claim 16, wherein the filter has a pore size of about 40 μm to about 250 μm.

20. The method of claim 1, further comprising isolating the isolated mixed cell population from amniotic membrane.

21. The method of claim 20, further comprising:

(a) contacting the amniotic membrane with collagenase, thereby producing collagenase-digested amniotic membrane; and (b) contacting the collagenase-digested amniotic membrane with dispase, thereby producing the isolated mixed cell population.

22. The method of claim 20, further comprising:

(a) contacting the amniotic membrane with dispase, thereby producing dispase-digested amniotic membrane; and (b) contacting the dispase-digested amniotic membrane with collagenase, thereby producing the isolated mixed cell population.

23. A method for isolating an E-cadherin positive stem cell, comprising contacting an isolated mixed cell population comprising one or more stem cells and one or more non-stem cells with an agent that binds to E-cadherin, thereby isolating an E-cadherin positive stem cell from the mixed cell population, wherein the isolated mixed cell population is free of epithelial cells.

24. The method of claim 23, wherein the mixed cell population comprises a limbal stromal niche cell, an umbilical cord stem cell, an amniotic membrane stem cell or an adipose stem cell.

* * * * *